(12) United States Patent
Karp

(10) Patent No.: US 6,303,783 B1
(45) Date of Patent: Oct. 16, 2001

(54) 1-(3-HETEROCYCLYLPHENYL) ISOTHIOUREA, -ISOUREA, -GUANIDINE AND -AMIDINE HERBICIDAL AGENTS

(75) Inventor: Gary Mitchell Karp, Princeton Junction, NJ (US)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/368,340

(22) Filed: Aug. 4, 1999

Related U.S. Application Data

(60) Provisional application No. 60/096,448, filed on Aug. 13, 1998.

(51) Int. Cl.[7] .......................... C07D 239/02; A01N 43/54
(52) U.S. Cl. .......................... 544/319; 544/309; 544/311; 544/315; 544/316; 504/136
(58) Field of Search ..................... 544/309, 311, 544/315, 316, 319; 504/136

(56) References Cited

U.S. PATENT DOCUMENTS

| | | | |
|---|---|---|---|
| 3,287,466 | 11/1966 | Klopping | 260/306.7 |
| 4,854,961 | * 8/1989 | Wellinga et al. | 71/88 |

FOREIGN PATENT DOCUMENTS

| | | | |
|---|---|---|---|
| 3505432 | 2/1985 | (DK) | |
| 270138 | * 8/1979 | (EP) | |
| 3640 | * 8/1979 | (EP) | |
| 0 270 138 | 8/1979 | (EP) | C07D/417/12 |
| 0 745 599 A2 | 12/1996 | (EP) | C07D/403/10 |
| 07304759 | 5/1994 | (JP) | |

OTHER PUBLICATIONS

Chem. Abst., vol. 85, 21211q (1976), Achary et al.: "Synthesis of bis(thiazolidone) and bis(thiohydantoin) and their derivatives from m–phenylenediamine" p. 678.

Chem. Abst., 70, 37695b, (1969), Chaudhary et al.: "m–Bis (4–oxothiazolidin–2–ylideneamino) benzene and 4,4'–bis (4–oxothiazolidin–2–ylideneamino) –3,3'–dimethylbiphenyl and their derivatives", p. 340.

Chem Abstr., 81, 3810x, (1974), Rao et al.: "4–Thiazolidinones. XVIII. 3–aryl–2–(arylimino)–4–thiazolidiones derived from sym–diarylthioureas", p. 309.

Chem. Abstr., 86, 29921n, (1977), Singh et al.: "4–Thiazolidinones: synthesis and fungicidal activityof 5–methyl–3–aryl–2–arylimino–4–thiazolidinones", p. 381.

Chem. Abstr., 108, 150356h, (1988), Vladzimirskaya et al.: Synthesis of physiologically active thiazolidine derivatives of m–phenylenediamine, p. 736.

* cited by examiner

Primary Examiner—Mukund J. Shah
Assistant Examiner—Sudhaker B. Patel
(74) Attorney, Agent, or Firm—Barbara V. Maurer

(57) ABSTRACT

There are provided 1-(3-heterocyclyphenyl)isothio-urea, -isourea, -guanidine and -amidine compounds of formula I

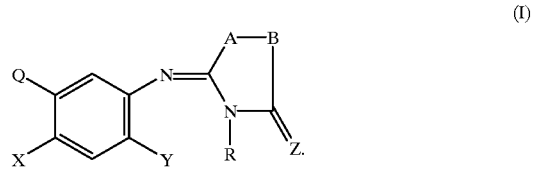

(I)

Further provided are compositions and methods comprising those compounds for the control of undesirable plant species.

30 Claims, No Drawings

1-(3-HETEROCYCLYLPHENYL) ISOTHIOUREA, -ISOUREA, -GUANIDINE AND -AMIDINE HERBICIDAL AGENTS

This application claims priority from copending provisional application(s) Ser. No. 60/096,448, filed on Aug. 13, 1998,

BACKGROUND OF THE INVENTION

Weeds cause tremendous global economic losses by reducing crop yields and lowering crop quality. In the United States alone, agronomic crops must compete with hundreds of weed species.

In spite of the commercial herbicides available today, damage to crops caused by weeds still occurs. Accordingly, there is ongoing research to create new and more effective herbicides.

JP 07304759-A and DE 3505432-A describe certain iminothiazolone derivatives which are useful as herbicidal agents. However, none of the compounds described in those applications are substituted with the 3-heterocyclylphenyl group of the present invention.

U.S. Pat. No. 3,287,466 describes certain 3-alkyl-4-imino-5-(arylimino)-2-thiazolidinone compounds which are useful as herbicidal agents. However, the arylimino groups of those compounds are not substituted with the heterocyclyl groups of this invention.

It is therefore an object of the present invention to provide compounds which are highly effective for controlling undesirable plant species.

It is also an object of the present invention to provide methods for controlling undesirable plant species.

These and other objects of the present invention will become more apparent from the detailed description thereof set forth below.

SUMMARY OF THE INVENTION

The present invention describes 1-(3-heterocyclylphenyl) isothiourea, -isourea, -guanidine and -amidine compounds which are useful as herbicidal agents.

The 1-(3-heterocyclylphenyl)isothiourea, -isourea, -guanidine and -amidine compounds of the present invention have the structural formula I

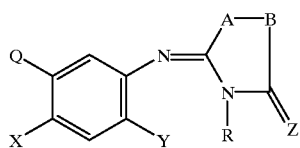

(I)

wherein
X and Y are each independently hydrogen, halogen, nitro, cyano, $C_1$–$C_4$alkyl, $C_1$–$C_4$haloalkyl or $S(O)_m R_1$;
R is hydrogen,
a $C_1$–$C_8$alkyl, $C_3$–$C_7$cycloalkyl, $C_3$–$C_8$alkenyl, $C_5$–$C_7$-cycloalkenyl or $C_3$–$C_8$alkynyl group, wherein each group is optionally substituted with any combination of one to six halogen atoms, one or two cyano groups, one or two nitro groups, one or two $C(W)R_2$ groups, one or two $C(W)OR_3$ groups, one or two $C(W)NR_4R_5$ groups, one or two $P(V)(OR_6)_2$ groups, one or two $OR_7$ groups, one or two $SR_8$ groups, one or two $NR_9R_{10}$ groups, one or two $OC(W)R_{11}$ groups, one or two $NR_{12}S(O)_n R_{13}$ groups, one or two $C(W)NR_{12}S(O)_n R_{13}$ groups,
one 4- to 10-membered heterocyclic ring optionally substituted with any combination of one or two oxo groups, one or two thioxo groups, one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$-alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups, one or two $NR_{15}S(O)_p R_{16}$ groups or one or two $C(W)NR_{15}S(O)_p R_{16}$ groups, or
one phenyl group optionally substituted with any combination of one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$-haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups one or two $NR_{15}S(O)_p R_{16}$ groups or one or two $C(W)NR_{15}S(O)_p R_{16}$ groups,
a 4- to 10-membered heterocyclic ring optionally substituted with any combination of one or two oxo groups, one or two thioxo groups, one to three halogen atoms, one to three nitro groups, one to three cyano groups, one to three $C_1$–$C_4$-alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$-alkylcarbonylalkyl groups, one to three $C_3$–$C_6$haloalkylcarbonylalkyl groups, one or two $NR_{15}S(O)_p R_{16}$ groups or one or two $C(W)NR_{15}S(O)_p R_{16}$ groups,
phenyl optionally substituted with any combination of one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups, one or two $NR_{15}S(O)_p R_{16}$ groups or one or two $C(W)NR_{15}S(O)_p R_{16}$ groups,
$OR_{17}$,
$NR_{18}R_{19}$,
$NR_{20}S(O)_q R_{21}$, NR$_{22}$C(V)R$_{23}$,
NR$_{24}$P(V)(OR$_{25}$)$_2$,
C(V)NR$_{20}$S(O)$_q$R$_{21}$,
cyano,
S(O)$_q$R$_{26}$,
P(V)(OR$_{27}$)$_2$,
C(V)R$_{28}$ or
C(V)OR$_{29}$;

W is O, S, NR$_{30}$, NOR$_{31}$ or NNR$_{32}$R$_{33}$;

V and Z are each independently O or S;

R$_1$ and R$_{14}$ are each independently C$_1$–C$_4$alkyl or C$_1$–C$_4$haloalkyl;

R$_2$ is hydrogen, C$_1$–C$_6$alkyl, C$_3$–C$_7$cycloalkyl, C$_1$–C$_6$haloalkyl, C$_3$–C$_6$alkenyl, C$_3$–C$_6$alkynyl, C$_2$–C$_6$alkoxyalkyl, C$_2$–C$_6$haloalkoxyalkyl, C$_3$–C$_6$alkoxycarbonylalkyl,
  phenyl optionally substituted with any combination of one to three halogen atoms, one to three C$_1$–C$_4$alkyl groups, one to three C$_1$–C$_4$haloalkyl groups, one to three C$_1$–C$_4$alkoxy groups, one to three C$_1$–C$_4$haloalkoxy groups, one or two C$_2$–C$_6$alkoxyalkyl groups, one or two C$_2$–C$_6$haloalkoxyalkyl groups, one or two nitro groups, one or two cyano groups, one NR$_{15}$S(O)$_p$R$_{16}$ group, one C$_2$–C$_6$alkoxycarbonyl group, one C$_2$–C$_6$haloalkoxycarbonyl group, one C$_2$–C$_6$alkylcarbonyl group, one C$_2$–C$_6$haloalkylcarbonyl group, one C$_3$–C$_6$alkoxycarbonylalkyl group, one C$_3$–C$_6$haloalkoxycarbonylalkyl group, one C$_3$–C$_6$alkylcarbonylalkyl group or one C$_3$–C$_6$haloalkylcarbonylalkyl group,
  a 4- to 10-membered heterocyclic ring optionally substituted with any combination of one or two oxo groups, one or two thioxo groups, one to three halogen atoms, one to three C$_1$–C$_4$alkyl groups, one to three C$_1$–C$_4$haloalkyl groups, one to three C$_1$–C$_4$alkoxy groups, one to three C$_1$–C$_4$haloalkoxy groups, one or two C$_2$–C$_6$alkoxyalkyl groups, one or two C$_2$–C$_6$haloalkoxyalkyl groups, one or two nitro groups, one or two cyano groups, one NR$_{15}$S(O)$_p$R$_{16}$ group, one C$_2$–C$_6$alkoxycarbonyl group, one C$_2$–C$_6$haloalkoxycarbonyl group, one C$_2$–C$_6$alkylcarbonyl group, one C$_2$–C$_6$haloalkylcarbonyl group, one C$_3$–C$_6$alkoxycarbonylalkyl group, one C$_3$–C$_6$haloalkoxycarbonylalkyl group, one C$_3$–C$_6$alkylcarbonylalkyl group or one C$_3$–C$_6$haloalkylcarbonylalkyl group,
  C$_1$–C$_4$alkyl substituted with one phenyl group wherein the phenyl group is optionally substituted with any combination of one to three halogen atoms, one or two nitro groups, one or two cyano groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups, or
  C$_1$–C$_4$alkyl substituted with one 4- to 10-membered heterocyclic ring wherein the heterocyclic ring is optionally substituted with any combination of one to three halogen atoms, one or two nitro groups, one or two cyano groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups;

R$_3$ is hydrogen, C$_1$–C$_6$alkyl, C$_1$–C$_6$haloalkyl, C$_3$–C$_7$cycloalkyl, C$_3$–C$_6$alkenyl C$_3$–C$_6$alkynyl, C$_2$–C$_6$alkoxyalkyl, C$_2$–C$_6$haloalkoxyalkyl, C$_3$–C$_6$alkoxycarbonylalkyl,
  phenyl optionally substituted with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups,
  benzyl optionally substituted on the phenyl ring with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups,
  furfural optionally substituted with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups, or
  an alkali metal, alkaline earth metal, manganese, copper, zinc, cobalt, silver, nickel, ammonium or organic ammonium cation;

R$_4$ and R$_5$ are each independently hydrogen, C$_1$–C$_6$alkyl, C$_1$–C$_6$haloalkyl, C$_3$–C$_7$cycloalkyl, C$_1$–C$_6$alkoxy, hydroxy, C$_3$–C$_6$alkenyl, C$_3$–C$_6$haloalkenyl, C$_3$–C$_6$alkynyl, C$_3$–C$_6$haloalkynyl, C$_3$–C$_6$alkylcarbonylalkyl, C$_3$–C$_6$haloalkylcarbonylalkyl, C$_3$–C$_6$alkoxycarbonylalkyl, C$_3$–C$_6$haloalkoxycarbonylalkyl, C$_2$–C$_6$hydroxycarbonylalkyl, C$_2$–C$_6$alkylsulfonylalkyl, C$_2$–C$_6$haloalkylsulfonylalkyl, S(O)$_p$R$_{16}$,
  phenyl optionally substituted with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups,
  benzyl optionally substituted on the phenyl ring with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups, or
  furfural optionally substituted with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups,
  provided that only one of R$_4$ and R$_5$ can be hydroxy or C$_1$–C$_6$alkoxy, and
  when R$_4$ and R$_5$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

R$_6$, R$_{25}$ and R$_{27}$ are each independently hydrogen, C$_1$–C$_6$alkyl, C$_1$–C$_6$haloalkyl,
  phenyl optionally substituted with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_7$, and $R_8$ and $R_{17}$ are each independently hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $C_2$–$C_6$haloalkoxyalkyl, $C_2$–$C_6$alkylcarbonylalkyl, $C_2$–$C_6$haloalkylcarbonylalkyl, $C_2$–$C_6$alkoxycarbonylalkyl, $C_2$–$C_6$haloalkoxycarbonylalkyl, $C_2$–$C_6$alkylsulfonylalkyl, $C_2$–$C_6$haloalkylsulfonylalkyl, $C_2$–$C_6$hydroxycarbonylalkyl, $C(V)NR_{12}S(O)_nR_{13}$, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_9$, $R_{10}$, $R_{18}$, $R_{19}$, $R_{32}$ and $R_{33}$ are each independently hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, $C_2$–$C_6$hydroxycarbonylalkyl, $C_2$–$C_6$alkylsulfonylalkyl, $C_2$–$C_6$haloalkylsulfonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_9$ and $R_{10}$ or $R_{18}$ and $R_{19}$ or $R_{32}$ and $R_{33}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{11}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $C_2$–$C_6$haloalkoxyalkyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, $C_2$–$C_6$hydroxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{12}$, $R_{15}$, $R_{20}$ and $R_{24}$ are each independently hydrogen, $C_1$–$C_6$alkyl, $C_1$–$C_6$haloalkyl, $C_3$–$C_6$alkenyl or $C_3$–$C_6$alkynyl;

$R_{13}$, $R_{21}$, $R_{22}$, $R_{23}$, $R_{26}$, $R_{28}$ and $R_{29}$ are each independently hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two nitro groups, one or two cyano groups, one $C_3$–$C_6$alkoxycarbonylalkyl group, one $C_3$–$C_6$haloalkoxycarbonylalkyl group, one $C_3$–$C_6$alkylcarbonylalkyl group, one $C_3$–$C_6$haloalkylcarbonylalkyl group or one $C_2$–$C_6$hydroxycarbonylalkyl group, a 4- to 10-membered heterocyclic ring optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two nitro groups, one or two cyano groups, one $C_3$–$C_6$alkoxycarbonylalkyl group, one $C_3$–$C_6$haloalkoxycarbonylalkyl group, one $C_3$–$C_6$alkylcarbonylalkyl group, one $C_3$–$C_6$haloalkylcarbonylalkyl group or one $C_2$–$C_6$hydroxycarbonylalkyl group, benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{16}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, phenyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{30}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$alkynyl, $C_2$–$C_6$alkoxyalkyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $C_2$–$C_6$alkoxyalkyl group, one $C_2$–$C_6$haloalkoxyalkyl group, one $NR_{15}S(O)_nR_{16}$ group, one $C_2$–$C_6$alkoxycarbonyl group, one $C_2$–$C_6$alkylcarbonyl group, one $C_3$–$C_6$alkoxycarbonylalkyl group, one $C_3$–$C_6$alkylcarbonylalkyl group, one $C_3$–$C_6$haloalkoxycarbonylalkyl group or one $C_3$–$C_6$haloalkylcarbonylalkyl group, a 4- to 10-membered heterocyclic ring optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $C_2$–$C_6$alkoxyalkyl group, one $C_2$–$C_6$haloalkoxyalkyl group, one $NR_{15}S(O)_nR_{16}$ group, one $C_2$–$C_6$alkoxycarbonyl group, one $C_2$–$C_6$alkylcarbonyl group, one $C_3$–$C_6$alkoxycarbonylalkyl group, one $C_3$–$C_6$alkylcarbonylalkyl group, one $C_3$–$C_6$haloalkoxycarbonylalkyl group or one $C_3$–$C_6$haloalkylcarbonylalkyl group, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$ haloalkoxy groups, or furfural optionally substituted with any combination of one to three halogen atoms, one or two cyano groups, one or two nitro groups one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{31}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $C_2$–$C_6$haloalkoxyalkyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, $C_2$–$C_6$alkylsulfonylalkyl, $C_2$–$C_6$haloalkylsulfonylalkyl, $C_2$–$C_6$hydroxycarbonylalkyl, $C(V)NR_{12}S(O)_nR_{13}$, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, a 4- to 10-membered heterocyclic ring optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

A is —O—, —S(O)$_r$—, —NR$_{34}$— or —CR$_{35}$R$_{36}$—;

B is —CR$_{37}$R$_{38}$(CR$_{39}$R$_{40}$)$_s$—, —C(=T)— or —C(=CR$_{41}$R$_{42}$)—;

$R_{34}$, $R_{35}$, $R_{36}$, $R_{37}$, $R_{38}$, $R_3$ and $R_{40}$ are each independently hydrogen, halogen, $C_1$–$C_6$alkyl optionally substituted with one to three halogen atoms, one or two cyano groups, one or two nitro groups, one or two $C(W)R_2$ groups, one or two $C(W)OR_3$ groups, one or two $C(W)NR_4R_5$ groups, one or two $P(V)(OR_6)_2$ groups, one or two $OR_7$ groups, one or two $SR_8$ groups, one or two $NR_9R_{10}$ groups or one or two $OC(W)R_{11}$ groups, $C_3$–$C_7$cycloalkyl,
$C_3$–$C_6$alkenyl,
$C_3$–$C_6$haloalkenyl
$C_3$–$C_6$alkynyl,
$C_3$–$C_6$haloalkynyl,
$C(V)NR_{12}S(O)_nR_{13}$, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two nitro groups, one or two cyano groups, one $NR_{15}S(O)_pR_{16}$ group, one $C_2$–$C_6$alkoxycarbonyl group, one $C_2$–$C_6$haloalkoxycarbonyl group, one $C_2$–$C_6$alkylcarbonyl group, one C₂–C₆haloalkylcarbonyl group, one C₃–C₆alkoxycarbonylalkyl group, one C₃–C₆haloalkoxycarbonylalkyl group, one C₃–C₆alkylcarbonylalkyl group or one C₃–C₆haloalkylcarbonylalkyl group, a 4- to 10-membered heterocyclic ring optionally substituted with any combination of one to three halogen atoms, one to three C₁–C₄alkyl groups, one to three C₁–C₄haloalkyl groups, one to three C₁–C₄alkoxy groups, one to three C₁–C₄haloalkoxy groups, one or two C₂–C₆alkoxyalkyl groups, one or two C₂–C₆haloalkoxyalkyl groups, one or two nitro groups, one or two cyano groups, one NR₁₅S(O)ₚR₁₆ group, one C₂–C₆alkoxycarbonyl group, one C₂–C₆haloalkoxycarbonyl group, one C₂–C₆alkylcarbonyl group, one C₂–C₆haloalkylcarbonyl group, one C₃C₆alkoxycarbonylalkyl group, one C₁–C₆haloalkoxycarbonylalkyl group, one C₃–C₆alkylcarbonylalkyl group or one C₃–C₆haloalkylcarbonylalkyl group, C₁–C₄alkyl substituted with one phenyl group wherein the phenyl group is optionally substituted with any combination of one to three halogen atoms, one to three C₁–C₄alkyl groups, one to three C₁–C₄haloalkyl groups, one to three C₁–C₄alkoxy groups, one to three C₁–C₄haloalkoxy groups, one or two C₂–C₆alkoxyalkyl groups, one or two C₂–C₆haloalkoxyalkyl groups, one C₂–C₆alkoxycarbonyl group, one C₂–C₆haloalkoxycarbonyl group, one C₂–C₆alkylcarbonyl group, one C₂–C₆haloalkylcarbonyl group, one C₃–C₆alkoxycarbonylalkyl group, one C₃–C₆haloalkoxycarbonylalkyl group, one C₃–C₆alkylcarbonylalkyl group, one C₃–C₆haloalkylcarbonylalkyl group, one C₃–C₈alkoxycarbonylalkoxy group or one C₂–C₈hydroxycarbonylalkoxy group, or C₁–C₄alkyl substituted with one 4- to 10-membered heterocyclic ring wherein the heterocyclic ring is optionally substituted with any combination of one to three halogen atoms, one to three C₃–C₄alkyl groups, one to three C₁–C₄haloalkyl groups, one to three C₁–C₄alkoxy groups, one to three C₁–C₄haloalkoxy groups, one or two C₂–C₆alkoxyalkyl groups, one or two C₂–C₆haloalkoxyalkyl groups, one C₂–C₆alkoxycarbonyl group, one C₂–C₆haloalkoxycarbonyl group, one C₂–C₆alkylcarbonyl group, one C₂–C₆haloalkylcarbonyl group, one C₃–C₆alkoxycarbonylalkyl group, one C₃–C₆haloalkoxycarbonylalkyl group, one C₃–C₆alkylcarbonylalkyl group or one C₃–C₆haloalkylcarbonylalkyl group, and when R₃₅ and R₃₆ or R₃₇ and R₃₈ or R₃₉ and R₄₀ are taken together with the atom to which they are attached, they represent a ring in which R₃₅R₃₆ or R₃₇R₃₈ or R₃₉R₄₀ is a C₂–C₆alkylene group;

T is O, S, NR₃₀, NOR₃₁ or NNR₃₂R₃₃;

R₄₁ and R₄₂ are each independently hydrogen, C₁–C₆alkyl, C₁–C₆haloalkyl, C₃–C₇cycloalkyl, C₃–C₆alkenyl, C₃–C₆haloalkenyl, C₃–C₆alkynyl, C₃–C₆haloalkynyl, C₂–C₆alkylcarbonyl, C₃–C₆haloalkylcarbonyl, C₂–C₆alkoxycarbonyl, C₂–C₆haloalkoxycarbonyl, hydroxycarbonyl, C₃–C₆alkylcarbonylalkyl,
C₃–C₆haloalkylcarbonylalkyl,
C₁–C₆alkoxycarbonylalkyl,
C₃–C₆haloalkoxycarbonylalkyl,
C₂–C₆hydroxycarbonylalkyl,
C₂–C₆alkylsulfonylalkyl,
C₂–C₆haloalkylsulfonylalkyl, phenyl optionally substituted with any combination of one to three halogen atoms, one or two cyano groups, one or two nitro groups, one to three C₁–C₄alkyl groups, one to three C₁–C₄haloalkyl groups, one to three C₁–C₄alkoxy groups, one to three C₁–C₄haloalkoxy groups or one C₃–C₈alkoxycarbonylalkoxy group, benzyl optionally substituted on the phenyl ring with any combination of one to three halogen atoms, one or two cyano groups, one or two nitro groups, one to three C₁–C₄alkyl groups, one to three C₁–C₄haloalkyl groups, one to three C₁–C₄alkoxy groups or one to three C₁–C₄haloalkoxy groups, or furfural optionally substituted with any combination of one to three halogen atoms, one or two cyano groups, one or two nitro groups, one to three C₁–C₄alkyl groups, one to three C₁–C₄haloalkyl groups, one to three C₁–C₄alkoxy groups or one to three C₁–C₄haloalkoxy groups, and when R₄₁ and R₄₂ are taken together with the atom to which they are attached, they represent a three- to seven-membered saturated or unsaturated ring optionally interrupted with one group selected from O, S(O)ᵣ or NR₃₁, and optionally substituted with one to three methyl groups or one or more halogen atoms;

m and r are each independently an integer of 0, 1 or 2;

n, p and q are each independently an integer of 1 or 2;

s is an integer of 0 or 1;

Q is selected from

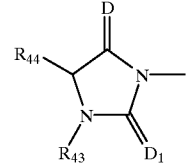

Q1

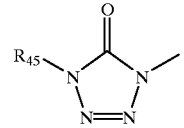

Q2

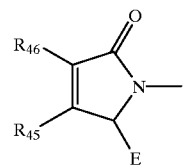

Q3

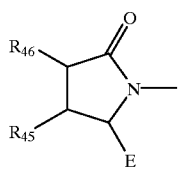
Q4
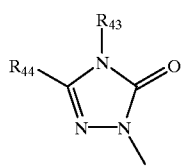
Q5
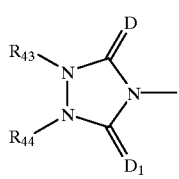
Q6
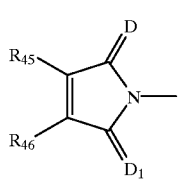
Q7
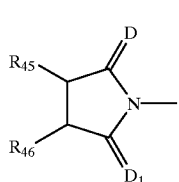
Q8
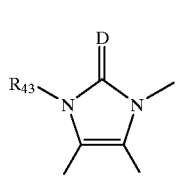
Q9
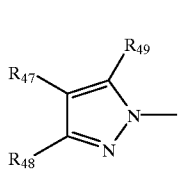
Q10
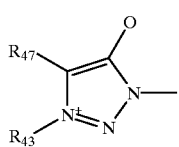
Q11
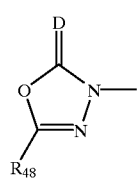
Q12
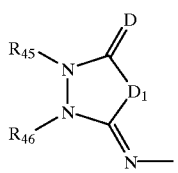
Q13
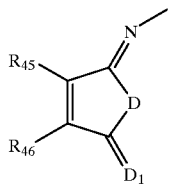
Q14
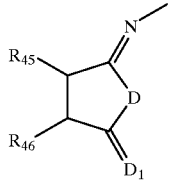
Q15
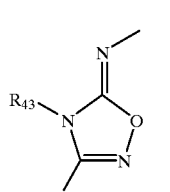
Q16
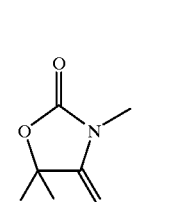
Q17
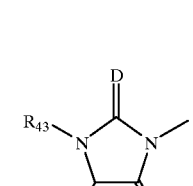
Q18
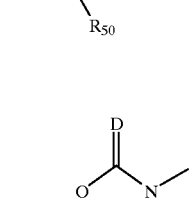
Q19
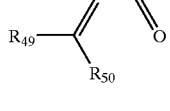

-continued
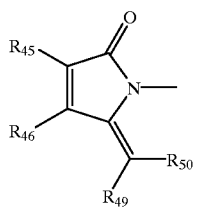 Q20
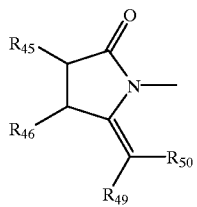 Q21
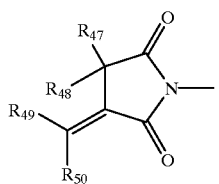 Q22
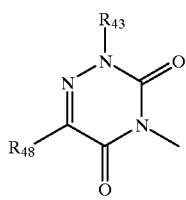 Q23
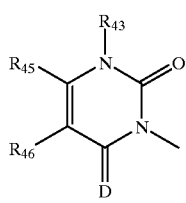 Q24
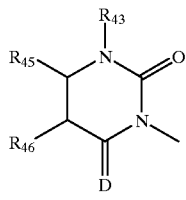 Q25
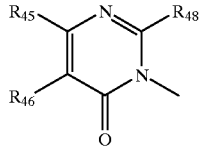 Q26
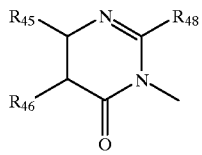 Q27
-continued
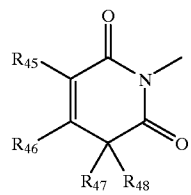 Q28
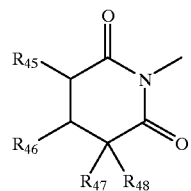 Q29
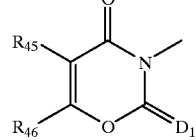 Q30
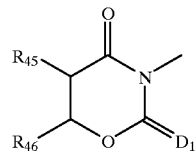 Q31
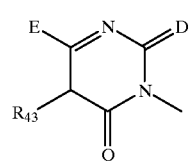 Q32
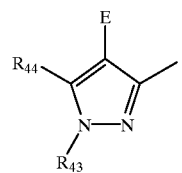 Q33
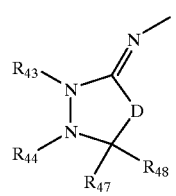 Q34
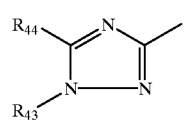 Q35

-continued

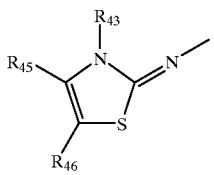
Q36

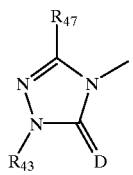
Q37

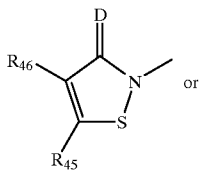
Q38

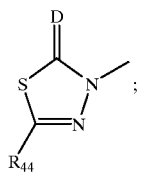
Q39

D and $D_1$ are each independently O or S;

E is hydroxy, halogen, $C_1$–$C_4$alkoxy or $C_1$–$C_4$alkylthio;

$R_{43}$ and $R_{44}$ are each independently hydrogen, halogen, $C_1$–$C_6$ alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, cyano, amino, hydroxy or benzyl, and when $R_{43}$ and $R_{44}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{45}$ and $R_{46}$ are each independently hydrogen, halogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $OR_{51}$, $S(O)_tR_{52}$ or $NR_{53}R_{54}$, and when $R_{45}$ and $R_{46}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{47}$, $R_{49}$ and $R_{50}$ are each independently hydrogen, halogen or $C_1$–$C_6$alkyl;

$R_{48}$ is hydrogen, halogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $OR_{51}$ or $SR_{52}$;

$R_{51}$ and $R_{52}$ are each independently hydrogen, $C_1$–$C_4$alkyl, $C_1$–$C_4$haloalkyl, $C_3$–$C_7$cycloalkyl, $C_1$–$C_4$cyanoalkyl, $C_3$–$C_6$alkenyl, $C_3$–$C_6$haloalkenyl, $C_3$–$C_6$alkynyl, benzyl or
phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_3$–$C_4$haloalkoxy groups;

$R_{53}$ is hydrogen, $C_1$–$C_4$alkyl, benzyl or
phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{54}$ in hydrogen, $C_1$–$C_4$alkyl, $C_3$–$C_6$alkenyl, $C_3$–$C_7$cycloalkyl, benzyl, $S(O)_tR_{52}$ or
phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups; and t is an integer of 0, 1 or 2; and the agriculturally acceptable salts thereof.

This invention also relates to compositions containing those compounds and methods for using those compounds and compositions. Advantageously, it has been found that the compounds of the present invention, and compositions containing them, are useful for the control of undesirable plant species

DETAILED DESCRIPTION OF THE INVENTION

The present invention provides a method for the control of undesirable plant species which comprises applying to the foliage of said plants or to the soil or water containing seeds or other propagating organs thereof, a herbicidally effective amount of a formula I, 1-(3-heterocyclylphenyl)isothiourea, -isourea, -guanidine or -amidine compound.

The 1-(3-heterocyclylphenyl)isothiourea, -isourea, -guanidine and -amidine compounds of the present invention have the structural formula I

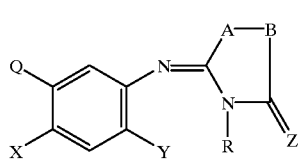
(I)

wherein A, B, Q, R, X, Y and Z are as defined above for formula I.

Preferred formula I compounds of this invention are those wherein

X is hydrogen or halogen;

Y is hydrogen, halogen, nitro or cyano;

R is hydrogen,
a $C_1$–$C_8$alkyl, $C_3$–$C_7$cycloalkyl, $C_3$–$C_8$alkenyl, $C_5$–$C_7$cycloalkenyl or $C_3$–$C_6$alkynyl group, wherein each group is optionally substituted with any combination of one to six halogen atoms, one or two cyano groups, one or two nitro groups, one or two $C(O)R_2$ groups, one or two $C(O)OR_3$ groups, one or two $C(O)NR_4R_5$ groups, one or two $P(O)(OR_6)_2$ groups, one or two $OR_7$ groups, one or two $SR_8$ groups, one or two $NR_9R_{10}$ groups, one or two $OC(O)R_{11}$ groups, one or two $NR_{12}S(O)_nR_{13}$ groups, one or two $C(O)NR_{12}S(O)_nR_{13}$ groups, one 4- to 10-membered heterocyclic ring optionally substituted with any combination of one or two oxo groups, one or two thioxo groups, one to three halogen atoms, one to three nitro groups, one to three cyano groups, one to three $C_1$–$C_4$alkyl groups, one to three $C_1$–$C_4$haloalkyl groups, one to three $C_{1-4}$alkoxy groups, one to three $C_{1-4}$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonyalkyl groups, one to three $C_3$–$C_6$haloalkylcarbonylalkyl groups, one or two $NR_{15}S(O)_pR_{16}$ groups or one or two $C(O)NR_{15}S(O)_pR_{16}$ groups, or one phenyl group optionally substituted with any combination of one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups, one or two $NR_{15}S(O)_pR_{16}$ groups or one or two $C(O)NR_{15}S(O)_pR_{16}$ groups, phenyl optionally substituted with any combination of one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_1$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups or one or two $NR_{15}S(O)_pR_{16}$ groups, $OR_{17}$,
$NR_{18}R_{19}$,
$NR_{20}S(O)_qR_{21}$,
$NR_{22}C(O)R_{23}$,
$C(O)NR_{20}S(O)_qR_{21}$,
$S(O)_qR_{26}$,
$C(O)R_{28}$ or
$C(O)OR_{29}$;

Z is O;

$R_{14}$ is $C_1$–$C_4$alkyl or $C_1$–$C_4$haloalkyl;

$R_2$ is hydrogen, $C_1$–$C_6$alkyl, $C_3$–$C_7$cycloalkyl, $C_1$–$C_6$haloalkyl, $C_2$–$C_6$alkoxyalkyl, $C_3$–$C_6$alkoxycarbonylalkyl, or phenyl optionally substituted with any combination of one to three halogen atoms, one to three $C_1$–$C_4$alkyl groups, one to three $C_1$–$C_4$alkoxy groups, one or two $C_2$–$C_6$alkoxyalkyl groups, one $C_2$–$C_6$alkoxycarbonyl group, one $C_3$–$C_6$alkoxycarbonylalkyl group or one $C_3$–$C_6$haloalkoxycarbonylalkyl group;

$R_3$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$alkynyl, $C_2$–$C_6$alkoxyalkyl, $C_2$–$C_6$haloalkoxyalkyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or an alkali metal, alkaline earth metal, manganese, copper, zinc, cobalt, silver, nickel, ammonium or organic ammonium cation;

$R_4$ and $R_5$ are each independently hydrogen, $C_1$–$C_6$alkyl, $C_3$–$C_7$cycloalkyl, $C_1$–$C_6$alkoxy, hydroxy, $C_3$–$C_6$alkenyl, $C_3$–$C_6$alkylcarbonylalkyl, $C_3$–$C_6$alkoxycarbonylalkyl, $C_2$–$C_6$alkylsulfonylalkyl, $C_2$–$C_6$haloalkylsulfonylalkyl, $S(O)_pR_{16}$, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, provided that only one of $R_4$ and $R_5$ can be hydroxy or $C_1$–$C_6$alkoxy, and when $R_4$ and $R_5$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_6$ is hydrogen, $C_1$–$C_6$alkyl, $C_1$–$C_6$haloalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_7$ and $R_8$ are each independently hydrogen, $C_1$–$C_6$alkyl, $C_2$–$C_6$alkoxycarbonylalkyl or $C_2$–$C_6$hydroxycarbonylalkyl;

$R_{17}$ is hydrogen, $C_1$–$C_6$alkyl, $C_3$–$C_7$cycloalkyl, $C_3$–$C_6$alkenyl, $C_3$–$C_6$alkynyl, $C_2$–$C_6$alkoxyalkyl, $C_1$–$C_6$haloalkoxyalkyl, $C_3$–$C_6$alkylcarbonylalkyl, $C_1$–$C_6$haloalkylcarbonylalkyl,
$C_3$–$C_6$alkoxycarbonylalkyl,
$C_1$–$C_6$hydroxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_6$haloalkyl groups, one to three $C_1$–$C_4$alkoxy groups or one to three $C_1$–$C_4$haloalkoxy groups;

$R_9$ and $R_{10}$ are each independently hydrogen, $C_1$–$C_6$alkyl, $C_3$–$C_6$alkylcarbonylalkyl, $C_3$–$C_6$alkoxycarbonylalkyl, $C_2$–$C_6$hydroxycarbonylalkyl, or phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_9$ and $R_{10}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{18}$ and $R_{19}$ are each independently hydrogen, $C_1$–$C_6$alkyl, $C_3$–$C_6$alkoxycarbonylalkyl, $C_3$–$C_6$haloalkoxycarbonylalkyl, $C_2$–$C_6$hydroxycarbonylalkyl, $C_2$–$C_6$alkylsulfonylalkyl, $C_2$–$C_6$haloalkylsulfonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_1$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_{18}$ and $R_{19}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{11}$ is hydrogen, $C_1$–$C_6$alkyl or $C_1$–$C_6$haloalkyl;

$R_{12}$, $R_{15}$ and $R_{20}$ are each independently hydrogen or $C_1$–$C_6$alkyl;

$R_{13}$, $R_{16}$, $R_{21}$ and $R_{26}$ are each independently $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, or benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{22}$ is hydrogen or $C_1$–$C_6$alkyl;

$R_{23}$ is hydrogen, $C_1$–$C_6$alkyl, $C_1$–$C_6$haloalkyl, $C_3$–$C_7$cycloalkyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{28}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$alkynyl, $C_3$–$C_6$alkoxycarbonylalkyl, or phenyl optionally substituted with any combination of one to three halogen atoms, one to three $C_1$–$C_4$alkyl groups, one to three $C_2$–$C_4$haloalkyl groups, one to three $C_1$–$C_4$alkoxy groups or one to three $C_1$–$C_4$haloalkoxy groups;

$R_{29}$ is hydrogen, $C_1$–$C_6$alkyl or benzyl;

A is —O—, —S(O)$_r$—, or —NR$_{34}$—;

B is —CR$_{37}$R$_{38}$—, —C(O)— or —C(=CR$_{41}$R$_{42}$)—;

$R_{34}$ is hydrogen, $C_1$–$C_6$alkyl optionally substituted with one to three halogen atoms, one or two cyano groups, one or two nitro groups, one or two C(O)R$_2$ groups, one or two C(O)OR$_3$ groups, one or two C(O)NR$_4$R$_5$ groups, one or two P(O)(OR$_6$)$_2$ groups, one or two OR, groups, one or two SR$_8$ groups, one or two NR$_9$R$_{10}$ groups or one or two OC(O)R$_{11}$ groups, $C_3$–$C_7$cycloalkyl,
$C_3$–$C_6$alkenyl,
$C_3$–$C_6$alkynyl,
C(O)NR$_{12}$S(O)$_n$R$_{13}$, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two nitro groups, one or two cyano groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group, or $C_1$–$C_4$alkyl substituted with one phenyl group wherein the phenyl group is optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group;

$R_{37}$ and $R_{38}$ are each independently hydrogen, halogen

C$_1$–C$_6$alkyl optionally substituted with one to three halogen atoms, one or two cyano groups, one or two nitro groups, one or two C(O)R$_2$ groups, one or two C(O)OR$_3$ groups, one or two C(O)NR$_4$R$_5$ groups, one or two P(O)(OR$_6$)$_2$ groups, one or two OR$_7$ groups, one or two SR$_8$ groups, one or two NR$_9$R$_{10}$ groups or one or two OC(O)R$_{11}$ groups, C$_3$–C$_7$cycloalkyl, C$_3$–C$_6$alkenyl, C$_3$–C$_6$haloalkenyl C$_3$–C$_6$alkynyl, C$_3$–C$_6$haloalkynyl, C(O)NR$_{12}$S(O)$_n$R$_{13}$, phenyl optionally substituted with any combination of one to three halogen atoms, one to three C$_1$–C$_4$alkyl groups, one to three C$_1$–C$_4$haloalkyl groups, one to three C$_1$–C$_4$alkoxy groups, one to three C$_1$–C$_4$haloalkoxy groups, one or two C$_2$–C$_6$alkoxyalkyl groups, one or two nitro groups, one or two cyano groups, one C$_2$–C$_6$alkoxycarbonyl group, one C$_2$–C$_6$alkylcarbonyl group, one C$_3$–C$_6$alkoxycarbonylalkyl group or one C$_3$–C$_6$alkylcarbonylalkyl group, or C$_1$–C$_4$alkyl substituted with one phenyl group wherein the phenyl group is optionally substituted with any combination of one to three halogen atoms, one to three C$_{1-4}$alkyl groups, one to three C$_1$–C$_4$haloalkyl groups, one to three C$_1$–C$_4$alkoxy groups, one to three C$_1$–C$_4$haloalkoxy groups, one or two C$_2$–C$_6$alkoxyalkyl groups, one C$_2$–C$_6$alkoxycarbonyl group, one C$_2$–C$_6$alkylcarbonyl group, one C$_3$–C$_6$alkoxycarbonylalkyl group or one C$_3$–C$_6$alkylcarbonylalkyl group, and when R$_{37}$ and R$_{38}$ are taken together with the atom to which they are attached, they represent a ring in which R$_{37}$R$_{38}$ is a C$_2$–C$_6$alkylene group;

R$_{41}$ and R$_{42}$ are each independently hydrogen, C$_1$–C$_6$alkyl, C$_2$–C$_6$alkylcarbonyl, C$_2$–C$_6$alkoxycarbonyl, hydroxycarbonyl, C$_3$–C$_6$alkylcarbonylalkyl, C$_3$–C$_6$alkoxycarbonylalkyl, C$_2$–C$_6$hydroxycarbonylalkyl, phenyl optionally substituted with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups, benzyl optionally substituted on the phenyl ring with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups, or furfural optionally substituted with any combination of one to three halogen atoms, one or two cyano groups, one or two nitro groups, one to three C$_1$–C$_4$alkyl groups, one to three C$_1$–C$_4$haloalkyl groups, one to three C$_1$–C$_4$alkoxy groups or one to three C$_1$–C$_4$haloalkoxy groups, and when R$_{41}$ and R$_{42}$ are taken together with the atom to which they are attached, they represent a three- to seven-membered saturated or unsaturated ring optionally interrupted with one group selected from O, S(O)$_r$ or NR$_{31}$, and optionally substituted with one to three methyl groups or one or more halogen atoms;

r is an integer of 0, 1 or 2;

n, p and q are each independently an integer of 1 or 2;

Q is selected from

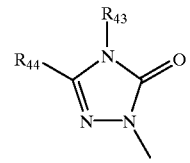
Q5

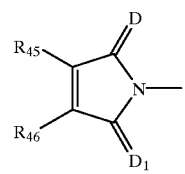
Q7

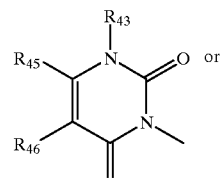
Q24

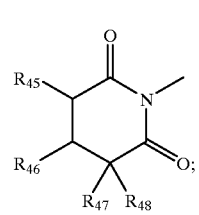
Q29

D and D$_1$ are each independently O or S;

R$_{43}$ and R$_{44}$ are each independently hydrogen, C$_1$–C$_6$alkyl, C$_1$–C$_6$haloalkyl, C$_3$–C$_7$cycloalkyl, C$_3$–C$_6$alkenyl, C$_3$–C$_6$haloalkenyl, C$_3$–C$_6$alkynyl, amino, or benzyl;

R$_{45}$ and R$_{46}$ are each independently hydrogen, halogen, C$_1$–C$_6$alkyl, C$_1$–C$_6$haloalkyl, C$_3$–C$_7$cycloalkyl, C$_3$–C$_6$alkenyl, C$_3$–C$_6$haloalkenyl or C$_3$–C$_6$alkynyl, and when R$_{45}$ and R$_{46}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms; and R$_{47}$ and R$_{48}$ are each independently hydrogen, halogen or C$_1$–C$_6$alkyl.

More preferred formula I herbicidal agents of the present invention are those wherein X is hydrogen, fluorine or chlorine;

Y is fluorine, chlorine, nitro or cyano;

R is hydrogen,

C$_1$–C$_8$alkyl optionally substituted with any combination of one to six halogen atoms, one or two cyano groups, one or two nitro groups, one or two C(O)R$_2$ groups, one or two C(O)OR$_3$ groups, one or two C(O)NR$_4$R$_5$ groups, one or two P(O)(OR$_6$)$_2$ groups, one or two OR$_7$ groups, one or two SR$_8$ groups, one or two NR$_9$R$_{10}$ groups, one or two C(O)NR$_{12}$S(O)$_n$R$_{13}$ groups, one furyl group optionally substituted with any combination of one to three $C_1$–$C_4$alkyl groups, one to three $C_1$–$C_4$alkoxy groups, one or two $C(O)OR_{14}$ groups or one or two $C(O)R_{14}$ groups, one pyridyl group optionally substituted with any combination of one to three $C_1$–$C_4$alkyl groups, one to three $C_1$–$C_4$alkoxy groups, one or two $C(O)OR_{14}$ groups or one or two $C(O)R_{14}$ groups, or one phenyl group optionally substituted with any combination of one to three $C_1$–$C_4$alkyl groups, one to three $C_1$–$C_4$alkoxy groups, one or two $C(O)OR_{14}$ groups or one or two $C(O)R_{14}$ groups, phenyl optionally substituted with any combination of one to three $C_1$–$C_4$alkyl groups, one to three $C_1$–$C_4$alkoxy groups, one or two $C_2$–$C_6$alkoxyalkyl groups, one or two $C(O)OR_{14}$ groups, one or two $C(O)R_{14}$ groups, one to three $C_3$–$C_6$alkoxycarbonylalkyl groups or one or two $NR_{15}S(O)_pR_{16}$ groups, $C_3$–$C_8$alkenyl,
$C_3$–$C_6$alkynyl,
$OR_{17}$,
$NR_{18}R_{19}$,
$C(O)R_{28}$ or
$C(O)OR_{29}$;

Z is O;

$R_{14}$ is $C_1$–$C_4$alkyl;

$R_2$ is hydrogen, $C_1$–$C_6$alkyl, $C_2$–$C_6$alkoxyalkyl or $C_3$–$C_6$alkoxycarbonylalkyl;

$R_3$ is hydrogen, $C_1$–$C_6$alkyl, $C_1$–$C_6$haloalkyl, $C_3$–$C_6$alkenyl, $C_3$–$C_6$alkynyl, $C_2$–$C_6$alkoxyalkyl, $C_2$–$C_6$haloalkoxyalkyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_4$ and $R_5$ are each independently hydrogen, $C_1$–$C_6$alkyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_4$ and $R_5$ are taken together with the atom to which they are attached, they represent a ring in which $R_4R_5$ is a $C_2$–$C_6$alkylene group;

$R_6$ is hydrogen, $C_1$–$C_6$alkyl or benzyl;

$R_7$ and $R_8$ are each independently hydrogen, $C_1$–$C_6$alkyl, $C_2$–$C_6$alkoxycarbonylalkyl or $C_2$–$C_6$hydroxycarbonylalkyl;

$R_{17}$ is hydrogen, $C_1$–$C_6$alkyl, $C_3$–$C_6$alkenyl, $C_3$–$C_6$alkynyl, $C_2$–$C_6$alkoxyalkyl, $C_3$–$C_6$alkoxycarbonylalkyl, $C_2$–$C_6$hydroxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_9$ and $R_{10}$ are each independently hydrogen, $C_1$–$C_6$alkyl or $C_3$–$C_6$alkoxycarbonylalkyl, and when $R_9$ and $R_{10}$ are taken together with the atom to which they are attached, they represent a ring in which $R_9R_{10}$ is a $C_2$–$C_6$alkylene group; $R_{18}$ and $R_{19}$ are each independently hydrogen, $C_1$–$C_6$alkyl, $C_3$–$C_6$alkoxycarbonylalkyl, $C_2$–$C_6$hydroxycarbonylalkyl, $C_2$–$C_6$alkylsulfonylalkyl, $C_2$–$C_6$haloalkylsulfonylalkyl, or phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_{18}$ and $R_{19}$ are taken together with the atom to which they are attached, they represent a ring in which $R_{18}R_{19}$ is a $C_2$–$C_6$alkylene group;

$R_{12}$ and $R_{15}$ are each independently hydrogen or $C_1$–$C_6$alkyl;

$R_{13}$ and $R_{16}$ are each independently $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, or benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{28}$ is hydrogen, $C_1$–$C_6$alkyl, $C_1$–$C_6$haloalkyl, $C_3$–$C_6$alkenyl $C_3$–$C_6$alkynyl, $C_3$–$C_6$alkoxycarbonylalkyl, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{29}$ is hydrogen, $C_1$–$C_6$alkyl or benzyl;

A is —O—, —S(O)$_r$—, or —NR$_{34}$—;

B is —CR$_{37}$R$_{38}$— or —C(=CR$_{41}$R$_{42}$)—;

$R_{34}$ is hydrogen, $C_1$–$C_6$alkyl optionally substituted with one or two $C(O)OR_3$ groups or one or two $C(O)NR_4R_5$ groups, $C_3$–$C_6$alkenyl,
$C_3$–$C_6$alkynyl, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two nitro groups, one or two cyano groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group, or benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{37}$ and $R_{38}$ are each independently hydrogen, halogen, $C_1$–$C_6$alkyl optionally substituted with one or two cyano groups, one or two $C(O)R_2$ groups, one or two $C(O)OR_3$ groups, one or two $C(O)NR_4R_5$ groups, one or two $P(O)(OR_6)_2$ groups, one or two $OR_7$ groups or one or two $NR_9R_{10}$ groups, $C_3$–$C_7$cycloalkyl,
$C_3$–$C_6$alkenyl,
$C_3$–$C_6$alkynyl,
$C(O)NR_{12}S(O)_nR_{13}$, or benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group, and when $R_{37}$ and $R_{38}$ are taken together with the atom to which they are attached, they represent a ring in which $R_{37}R_{38}$ is a $C_2$–$C_6$alkylene group;

$R_{41}$ and $R_{42}$ are each independently hydrogen, $C_1$–$C_6$alkyl, $C_2$–$C_6$alkylcarbonyl, $C_2$–$C_6$alkoxycarbonyl, hydroxycarbonyl, or phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

r is an integer of 0, 1 or 2;
n and p are each independently an integer of 2; and
Q is selected from

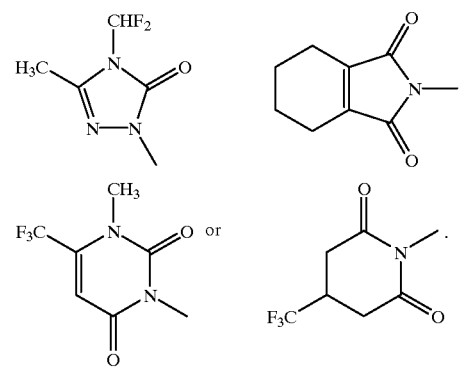

Most preferred formula I herbicidal agents of this invention are those wherein
X is fluorine;
Y is chlorine;

R is $C_1$–$C_8$alkyl optionally substituted with any combination of one or two $C(O)OR_3$ groups, one or two $C(O)NR_4R_5$ groups, one or two $P(O)(OR_6)_2$ groups, one or two $OR_7$ groups, one or two $SR_8$ groups, one or two $NR_9R_{10}$ groups, one or two $C(O)NR_{12}S(O)_nR_{13}$ groups or one phenyl group optionally substituted with any combination of one to three $C_1$–$C_4$alkyl groups or one to three $C_1$–$C_4$alkoxy groups, phenyl optionally substituted with any combination of one to three $C_1$–$C_4$alkyl groups, one to three $C_1$–$C_4$alkoxy groups, one or two $C_2$–$C_6$alkoxyalkyl groups, one or two $C_3$–$C_6$alkoxycarbonylalkyl groups or one or two $NR_{15}S(O)_pR_{16}$ groups, $C_3$–$C_8$alkenyl or
$C_3$–$C_8$alkynyl;

Z is O;

$R_3$ is hydrogen, $C_1$–$C_6$alkyl, $C_1$–$C_6$haloalkyl, $C_3$–$C_6$alkenyl, $C_3$–$C_6$alkynyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_4$ and $R_5$ are each independently hydrogen or $C_1$–$C_6$alkyl, and when $R_4$ and $R_5$ are taken together with the atom to which they are attached, they represent a ring in which $R_4R_5$ is a $C_2$–$C_6$alkylene group;

$R_6$ is hydrogen or $C_1$–$C_6$alkyl;

$R_7$ and $R_8$ are each independently hydrogen, $C_1$–$C_6$alkyl $C_2$–$C_6$alkoxycarbonylalkyl or $C_2$–$C_6$hydroxycarbonylalkyl;

$R_9$ and $R_{10}$ are each independently hydrogen, $C_1$–$C_6$alkyl or
$C_3$–$C_6$alkoxycarbonylalkyl, and when $R_9$ and $R_{10}$ are taken together with the atom to which they are attached, they represent a ring in which $R_9R_{10}$ is a $C_2$–$C_6$alkylene group;

$R_{12}$ and $R_{15}$ are hydrogen;

$R_{13}$ and $R_{16}$ are each independently $C_1$–$C_6$alkyl, $C_1$–$C_6$haloalkyl, $C_3$–$C_6$alkenyl, $C_3$–$C_6$alkynyl, or
benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

A is —O— or —S(O)$_r$—;
B is —$CR_{37}R_{38}$— or —$C(=CR_{41}R_{42})$—;

$R_{37}$ and $R_{38}$ are each independently hydrogen, halogen, $C_1$–$C_6$alkyl optionally substituted with one or two $C(O)OR_3$ groups, one or two $C(O)NR_4R_5$ groups, one or two $OR_7$ groups or one or two $NR_9R_{10}$ groups, or benzyl optionally substituted on the phenyl ring with any combination of one to three $C_1$–$C_4$alkyl groups, one to three $C_1$–$C_4$alkoxy groups or one $C_3$–$C_6$ alkoxycarbonylalkyl group, and when $R_{37}$ and $R_{38}$ are taken together with the atom to which they are attached, they represent a ring in which $R_{37}R_{38}$ is a $C_2$–$C_6$alkylene group;

$R_{41}$ and $R_{42}$ are each independently hydrogen, $C_1$–$C_6$alkyl, $C_2$–$C_6$alkylcarbonyl, $C_2$–$C_6$alkoxycarbonyl or hydroxycarbonyl;

r is an integer of 0, 1 or 2;

n and p are each independently an integer of 2; and

Q is selected from

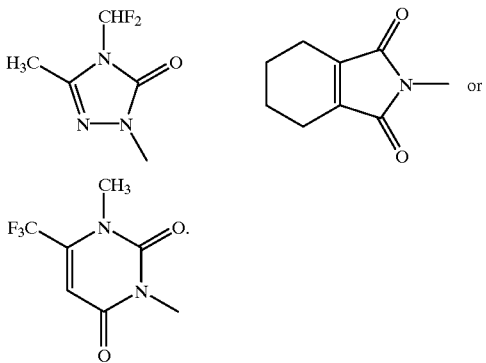

Formula I compounds of the present invention which are particularly effective herbicidal agents include N-{4-chloro-2-fluoro-5-[(3-methyl-4-oxo-2-thiazolidinylidene)amino]phenyl}-1-cyclohexene-1,2-dicarboximide;

3-{4-chloro-2-fluoro-5-[3-methyl-4-oxo-2-thiazolidinylidene)amino]phenyl}-1-methyl-6-(trifluoromethyl)-2,4(1H,3H)-pyrimidinedione;

ethyl 2-{{(2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-(carboxymethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-delta5,alpha-thiazolidineacetic acid, diethyl ester;

ethyl 5-{{(2-chloro-5-[3,6-dihydro-3-methyl-2,6-dioxo-4-(trifluoromethyl)-1(2H)-pyrimidinyl]-4-fluorophenyl}imino}-7-oxo-4-thia-6-azaspiro[2.4]heptane-6-acetate;

2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidineacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-oxazolidineacetate;

α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, L-;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinedlacetic acid, 3-ethyl methyl ester;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl isopropyl ester;

ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

ethyl 2-{{2-chloro-5-[3,6-dihydro-3-methyl-2,6-dioxo-4-(trifluoromethyl)-1(2H)-pyrimidinyl]-4-fluorophenyl}imino}-5-[(methylcarbamoyl)methyl]-4-oxo-3-thiazolidineacetate;

2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl (2-propynyl) ester;

methyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

isopropyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl 2-fluoroethyl ester;

2-fluoroethyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-5-(hydroxyethyl)-4-oxo-3-thiazolidineacetate;

allyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacecate;

isopropyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{4-chloro-2-fluoro-5-[(3-furfuryl-4-oxo-2-thiazolidinylidene)amino]phenyl}-1-methyl-6-(trifluoromethyl)-2,4(1H,3H)-pyrimidinedione;

cyclopropylmethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

ethyl 5-chloro-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{4-chloro-5-[(3-cyclopropyl-4-oxo-2-thiazolidinylidene)amino]-2-fluorophenyl}-1-methyl-6-(trifluoromethyl)-2,4(1H,3H)-pyrimidinedione;

3-{4-chloro-2-fluoro-5-{[3-(2-methoxyethyl)-4-oxo-2-thiazolidinylidene]amino}phenyl}-1-methyl-6-(trifluoromethyl)-2,4(1H,3H)-pyrimidinedione;

3-{4-chloro-2-fluoro-5-{[3-(1-methyl-2-propynyl)-4-oxo-2-thiazolidinylidene]amino}phenyl}-1-methyl-6-(trifluoromethyl)-2,4(1H,3H)-pyrimidinedione;

ethyl 5-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{5-[(3-benzyl-4-oxo-2-thiazolidinylidene)amino]-4-chloro-2-fluorophenyl}-1-methyl-6-(trifluoromethyl)-2,4(1H,3H)-pyrimidinedione;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinepropionate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, D-;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-α-(p-nitrobenzyl)-3-thiazolidineacetate, L-;
ethyl α-benzyl-2-{{2-chloro-5-[3,6-dihydro-3-methyl-2,6-dioxo-4-(trifluoromethyl)-1(2H)-pyrimidinyl]-4-(fluorophenyl}imino}-4-oxo-3-thiazolidineacetate, L-; and
methyl α-(p-chlorobenzyl)-2-{{-2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, DL-, among others.

Exemplary of halogen hereinabove are fluorine, chlorine, bromine and iodine. The terms haloalkyl, halocycloalkyl, haloalkoxy, haloalkenyl, halocycloalkenyl and haloalkynyl as used in the specification and claims designate an alkyl group, a cycloalkyl group, an alkoxy group, an alkenyl group, a cycloalkenyl group and an alkynyl group substituted with one or more halogen atoms, respectively. In formula I above, alkali metals include: sodium, potassium and lithium. Alkaline earth metals of formula I include magnesium and calcium. Further, the term organic ammonium is defined as a group consisting of a positively charged nitrogen atom joined to from one to four aliphatic groups, each containing from one to sixteen carbon atoms.

In formula I above, 4- to 10-membered heterocyclic rings include, but are not limited to, 1,2,4-triazole, 1,3,4-thiadiazole, 1,3,5-triazine, 2-thiazoline, benzimidazole, benzofuran, benzothiophene, coumarin, furan, imidazole, imidazoline-2-thione, indole, isatoic anhydride, isoquinoline, isoxazole, morpholine, oxazole, piperazine, piperidine, purine, pyrazine, pyrazole, pyridazine, pyridine, pyrimidine, pyrrole, pyrrolidine, quinoline, tetrahydrofuran, tetrahydrothiophene, thiazole and thiophene rings, wherein each ring is optionally substituted as described hereinabove for formula I.

The formula I compounds of the present invention are effective herbicidal agents useful for the control of a wide variety of undesirable plant species. Those compounds are effective for controlling weeds native to both dry land and wet land areas. The compounds are effective in controlling the above-said plants when applied to the foliage thereof or to the soil or water containing seeds or other propagating organs thereof such as stolons, tubers or rhizomes, at rates of from about 0.01 kg/ha to 4 kg/ha and preferably from about 0.01 kg/ha to 1 kg/ha.

The compounds of this invention are best suited for use as broad spectrum herbicides. However, certain compounds of this invention are selective in soybeans and/or cereal crops such as corn, wheat and rice when applied as preemergence and/or postemergence treatments.

In addition, it has been found that the formula I compounds of this invention may be used for the selective control of undesirable plant species in transplanted rice culture by applying a herbicidally effective amount of a formula I compound to the soil or water containing seeds or other propagating organs of said undesirable plant species after the rice has been transplanted.

Formula I compounds of this invention which are especially useful for the selective control of undesirable plant species in the presence of corn include
N-{4-chloro-2-fluoro-5-[(3-methyl-4-oxo-2-thiazolidinylidene)amino]phenyl}-1-cyclohexene-1,2-dicarboximide;
ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;
2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl methyl ester;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl isopropyl ester;
ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl (2-propynyl) ester;
isopropyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;
methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl 2-fluoroethyl ester;
2-fluoroethyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate; and
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-oxazolidinediacetic acid, 3-ethyl ester, among others.

Formula I compounds of the present invention which are particularly useful for the selective control of undesirable plant species in the presence of wheat include
3-(carboxymethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-delta5,alpha-thiazolidineacetic acid, diethyl ester;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl methyl ester;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl isopropyl ester;
ethyl 5-(carbamoylmethyl)-2-{{2-chloro-5-[3,6-dihydro-3-methyl-2,6-dioxo-4-(trifluoromethyl)-1( 2H)-pyrimidinyl]-4-fluorophenyl}imino}-4-oxo-3-thiazolidineacetate;
ethyl 2-{{2-chloro-5-[3,6-dihydro-3-methyl-2,6-dioxo-4-(trifluoromethyl)-1(2H)-pyrimidinyl]-4-fluorophenyl}imino}-5-[(methylcarbamoyl)methyl]-4-oxo-3-thiazolidineacetate;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl (2-propynyl) ester;
isopropyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl 2-fluoroethyl ester;

2-fluoroethyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-5-(hydroxyethyl)-4-oxo-3-thiazolidineacetate; and cyclopropylmethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, among others.

Formula I compounds of this invention which are particularly useful for the selective control of undesirable plant species in the presence of transplanted rice include ethyl 5-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{5-[(3-benzyl-4-oxo-2-thiazolidinylidene)amino]-4-chloro-2-fluorophenyl}-1-methyl-6-(trifluoromethyl)-2,4(1H,3H)-pyrimidinedione;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinepropionate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;

methyl α-benzyl-2-{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, D-;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-α-(p-nitrobenzyl)-3-thiazolidineacetate, L-;

ethyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-; and methyl α-(p-chlorobenzyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, DL-, among others.

Formula I compounds of this invention which are particularly useful for the selective control of undesirable plant species in the presence of soybeans include ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl 2-fluoroethyl ester;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 3-ethyl ester;

allyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate; and 3-{4-chloro-2-fluoro-5-[(3-furfuryl-4-oxo-2-thiazolidinylidene)amino]phenyl}-1-methyl-6-(trifluoromethyl)-2,4(1H,3H)-pyrimidinedione, among others.

While the compounds of this invention are effective for controlling undesirable plant species when employed alone, they may also be used in combination with or in conjunction with one or more other biological chemicals, including herbicides.

The compounds of this invention may be applied to the foliage of undesirable plant species or to the soil or water containing seeds or other propagating organs thereof in the form of a solid or liquid herbicidal composition, comprising a herbicidally effective amount of the desired compound dispersed or dissolved in an agronomically acceptable, inert solid or liquid carrier. The compositions may be applied as preemergence or postemergence treatments.

The formula I compounds of the present invention may be formulated as emulsifiable concentrates, wettable powders, granular formulations, suspension concentrates, flowable concentrates and the like.

Formula I compounds wherein Q is Q1, Q2, Q3, Q5, Q6, Q7, Q9, Q10, Q11, Q12, Q13, Q14, Q16, Q17, Q18, Q19, Q20, Q22, Q24 and Q25 may be prepared from 1-(3-aminophenyl)-isothiourea, -isourea, -guanidine and -amidine compounds of formula II

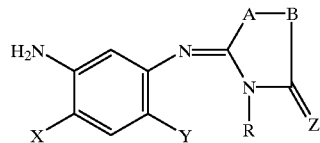

(II)

wherein A, B, R, X, Y and Z are as described hereinabove, using essentially the same procedures as described in U.S. Pat. No. 5,523,278.

Formula I compounds wherein Q is Q8 may be prepared by reacting an amine of formula II with a substituted tetrahydrofuran of formula III as shown below in Flow Diagram I.

FLOW DIAGRAM I

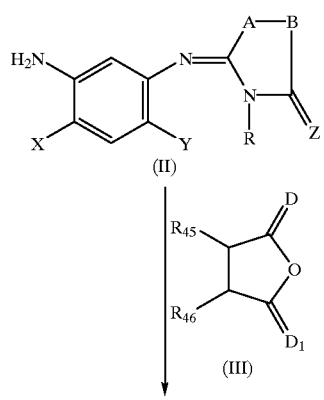

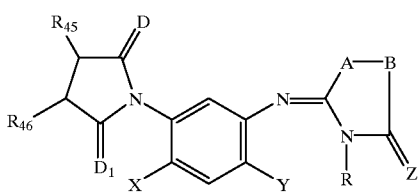

Formula I compounds wherein Q is Q4 may be prepared from formula I compounds wherein Q is Q8 using essentially the same procedures used to prepare formula I compounds wherein Q is Q3 from formula I compounds wherein Q is Q7.

Compounds of formula I wherein Q is Q15 may be prepared by reacting an amine of formula II with a substituted tetrahydrofuran of formula III to form an acid-amide of formula IV, and dehydrating the acid-amide with a dehydrating agent such as 1,3-dicyclohexylcarbodiimide. The reaction scheme is shown below in Flow Diagram II.

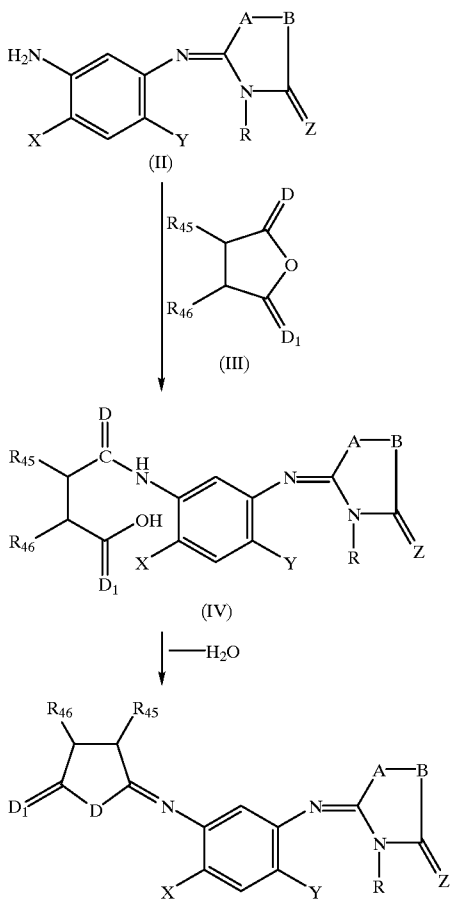

Formula I compounds wherein Q is Q21 may be prepared from formula I compounds wherein Q is Q8 using essentially the same procedure used to prepare formula I compounds wherein Q is Q20 from formula I compounds wherein Q is Q7.

Compounds of formula I wherein Q is Q23 may be prepared by converting an amine of formula II to its corresponding isocyanate of formula V using standard methods such as phosgene in an inert solvent or palladium chloride and carbon monoxide, reacting the formula V compound with a substituted hydrazine of formula VI to form an intermediate compound of formula VII, and reacting the formula VII compound with an ester of formula VIII. The reaction scheme is shown in Flow Diagram III.

FLOW DIAGRAM III

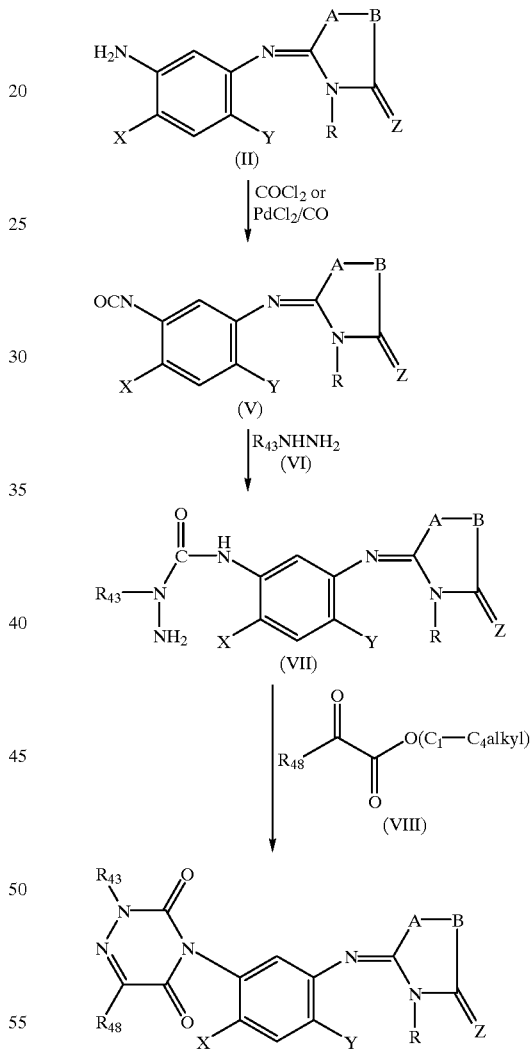

Formula I compounds wherein Q is Q26 may be prepared by reacting an amine of formula II with a β-aminoacrylic acid chloride of formula IX to form an intermediate compound of formula X, and reacting the intermediate compound with an acid chloride of formula XI. The reaction scheme is shown in Flow Diagram IV.

FLOW DIAGRAM IV

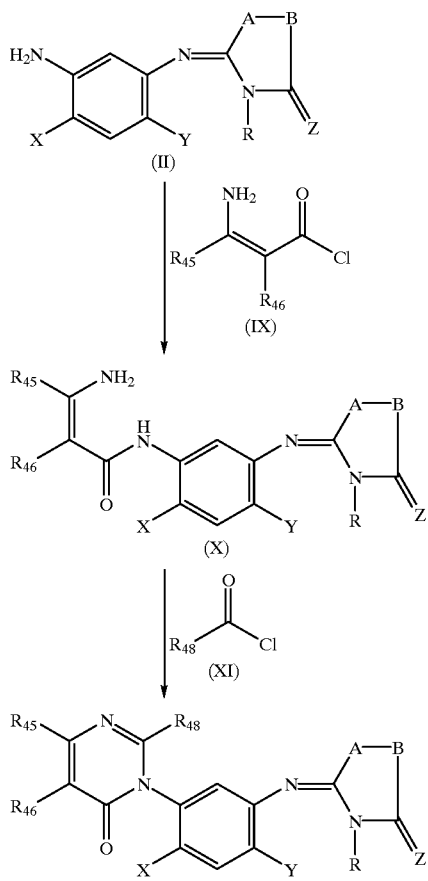

Compounds of formula I wherein Q is Q27 may be prepared by reacting an amine of formula II with an acid chloride of formula XII to form an intermediate compound of formula XIII, and reacting the intermediate compound (after deprotection) with an acid chloride of formula XI. The reaction sequence is shown below in Flow Diagram V.

FLOW DIAGRAM V

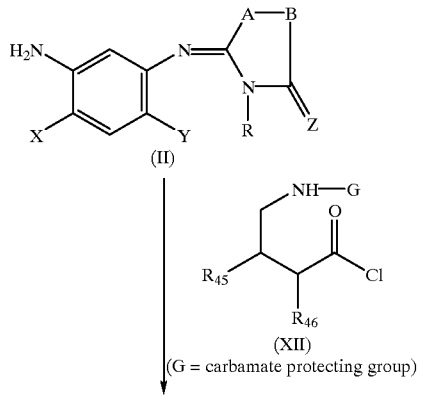

(G = carbamate protecting group)

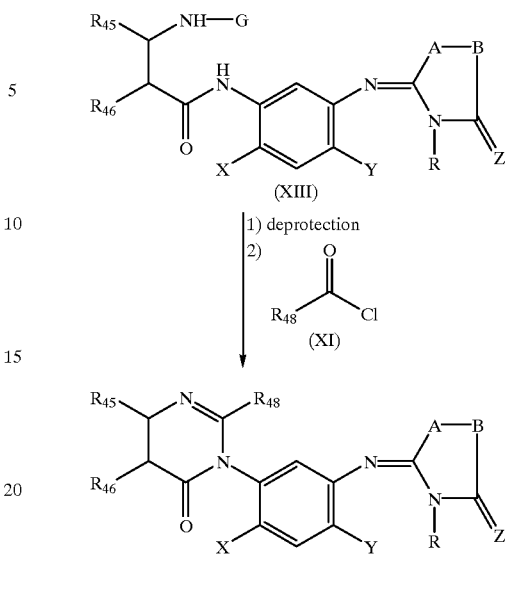

Formula I compounds wherein Q is Q28 may be prepared by reacting an amine of formula II with an unsaturated lactone of formula XIV as shown below in Flow Diagram VI.

FLOW DIAGRAM VI

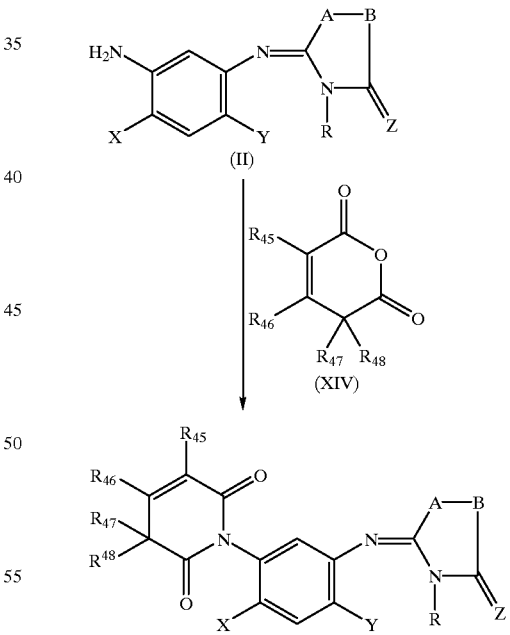

Similarly, formula I compounds wherein Q is Q29 may be prepared by reacting an amine of formula II with a lactone of formula XV. The reaction scheme is shown in Flow Diagram VII.

FLOW DIAGRAM VII

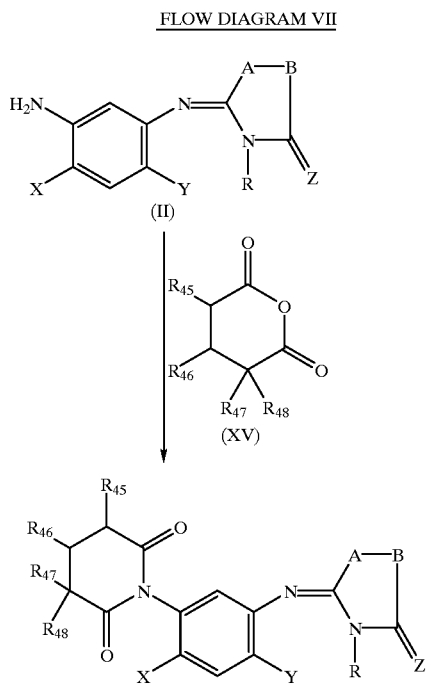

Compounds of formula I wherein Q is Q30 may be prepared, as shown in Flow Diagram VIII, by reacting an isocyanate or isothiocyanate of formula XVI with an unsaturated lactone of formula XVII at an elevated temperature.

FLOW DIAGRAM VIII

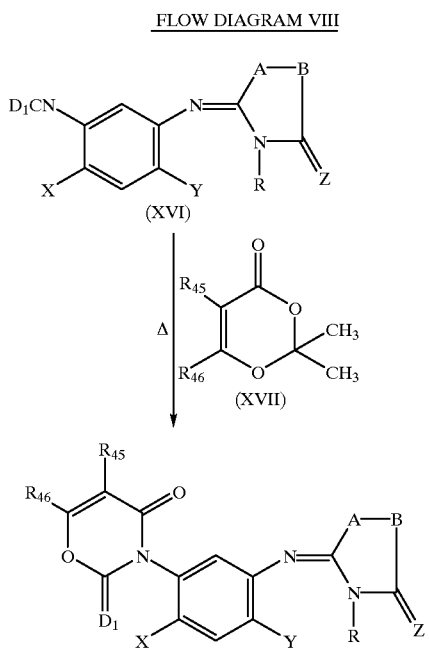

Similarly, formula I compounds wherein Q is Q31 may be prepared by reacting an isocyanate or isothiocyanate of formula XVI with a lactone of formula XVIII at an elevated temperature. The reaction scheme is shown in Flow Diagram IX.

FLOW DIAGRAM IX

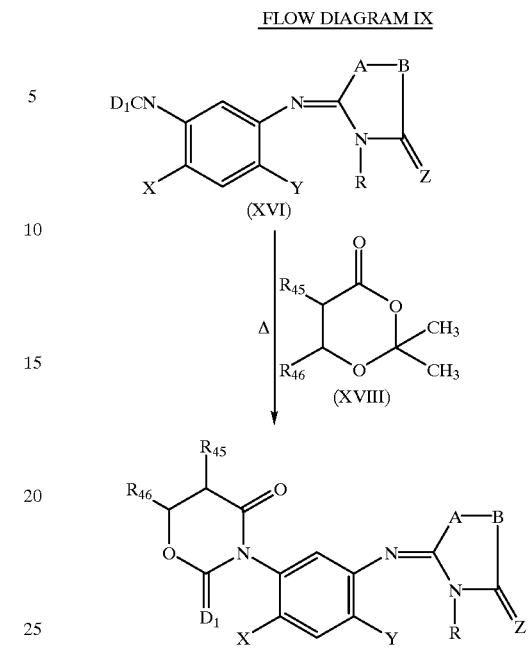

Formula I compounds wherein Q is Q32 may be prepared, as shown in Flow Diagram X, by reacting an amine of formula II with sodium isocyanate or sodium isothiocyanate to form a urea of formula XIX, reacting the urea with a malonic acid diester of formula XX to form an intermediate compound of formula XXI, and reacting the intermediate compound with a phosphorus oxyhalide to form a formula I compound wherein Q is Q32 and E is halogen, and optionally reacting the formula I compound wherein Q is Q32 and E is halogen with a $C_1$–$C_4$alkyl sulfide or a $C_1$–$C_4$alkoxide to form a formula I compound wherein Q is Q32 and E is $C_1$–$C_4$alkylthio or $C_1$–$C_4$alkoxy, respectively.

FLOW DIAGRAM X

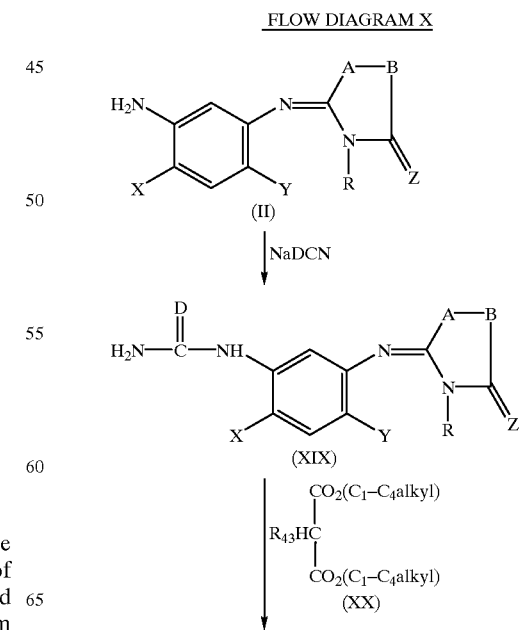

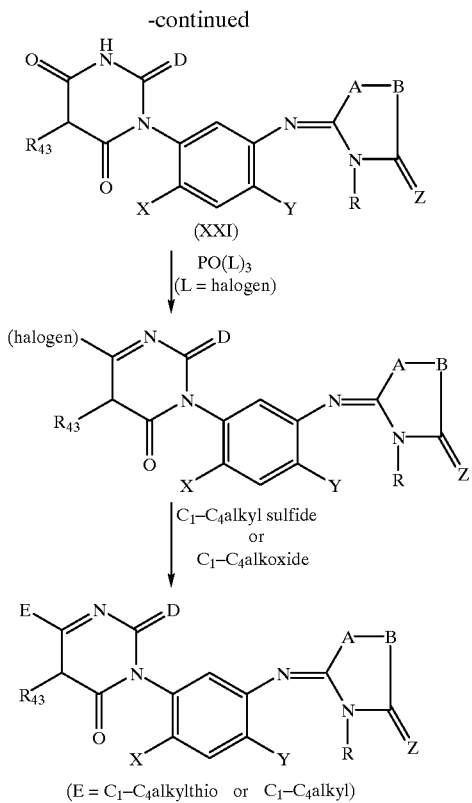

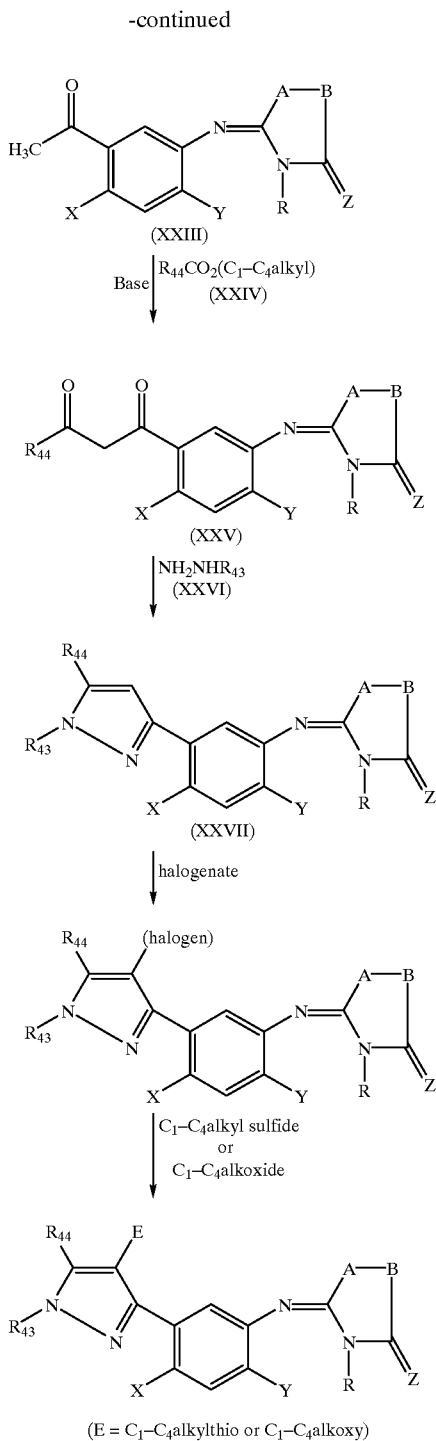

Compounds of formula I wherein Q is Q33 may be prepared, as shown in Flow Diagram XI, by acylating a compound of formula XXII with acetyl chloride and aluminum chloride to form an acetophenone of formula XXIII, reacting the acetophenone compound with an ester of formula XXIV in the presence of a base to form a diketone compound of formula XXV, reacting the formula XXV compound with a substituted hydrazine of formula XXVI to form an intermediate compound of formula XXVII, and halogenating the formula XXVII compound with a halogenating agent such as phosphorus oxychloride to form a formula I compound wherein Q is Q33 and E is halogen, and optionally reacting the formula I compound wherein Q is Q33 and E is halogen with a $C_1$–$C_4$alkyl sulfide or a $C_1$–$C_4$alkoxide to form a formula I compound wherein Q is Q33 and E is $C_1$–$C_4$alkylthio or $C_1$–$C_4$alkoxy, respectively.

FLOW DIAGRAM XI

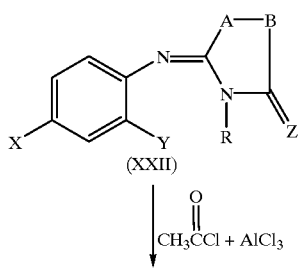

Formula I compounds wherein Q is Q34 may be prepared, as shown in Flow Diagram XII, by reacting an isocyanate or isothiocyanate of formula XVI with a substituted hydrazine of formula XXVIII to form an intermediate compound of formula XXIX, and reacting the formula XXIX compound with an acetal of formula XXX at an elevated temperature.

FLOW DIAGRAM XII

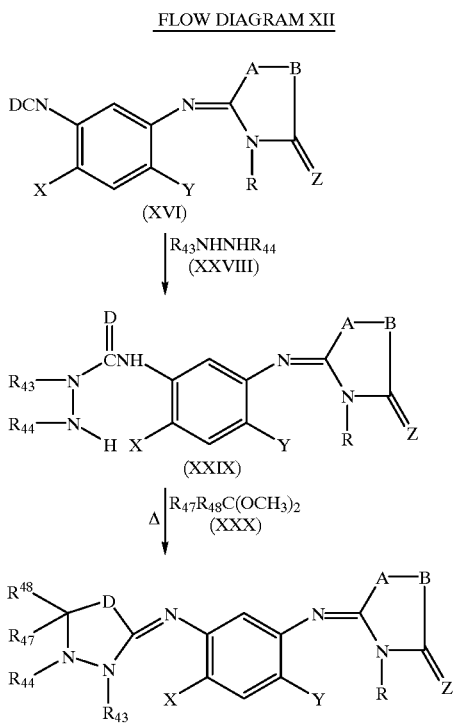

Compounds of formula I wherein Q is Q35 may be prepared by reacting a cyano compound of formula XXXI with a substituted hydrazine of formula XXVI to form an intermediate compound of formula XXXII, and reacting the intermediate compound with an acid chloride of formula XXXIII. The reaction scheme is show in Flow Diagram XIII.

FLOW DIAGRAM XIII

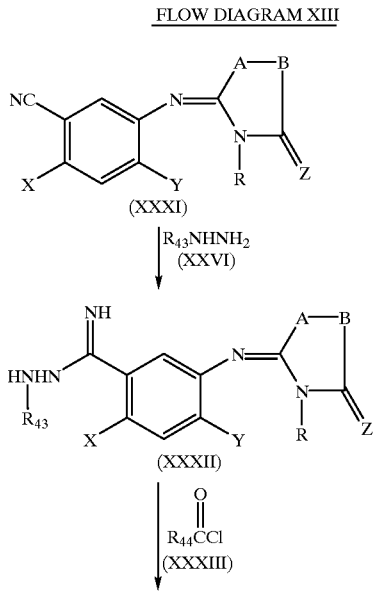

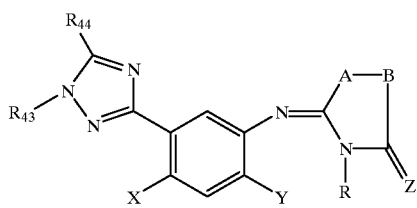

Formula I compounds wherein Q is Q36 may be prepared, as shown in Flow Diagram XIV, by reacting an isothiocyanate of formula XXXIV with an amine of formula XXXV to form a thiourea of formula XXXVI, and reacting the thiourea with an a-haloketone of formula XXXVII.

FLOW DIAGRAM XIV

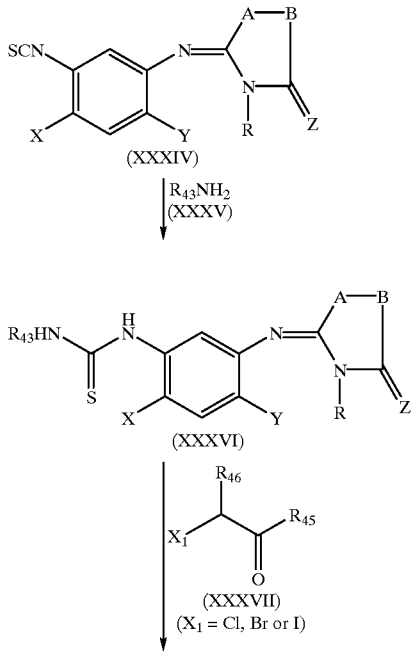

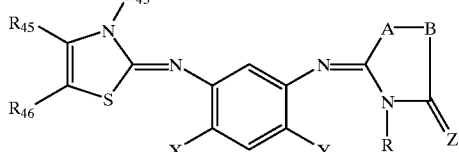

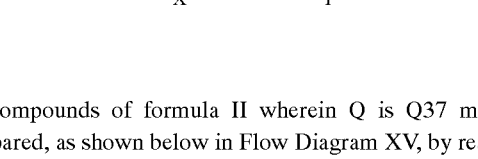

Compounds of formula II wherein Q is Q37 may be prepared, as shown below in Flow Diagram XV, by reacting a urea or thiourea of formula XXXVIII with an acid chloride of formula XXXIX.

FLOW DIAGRAM XV

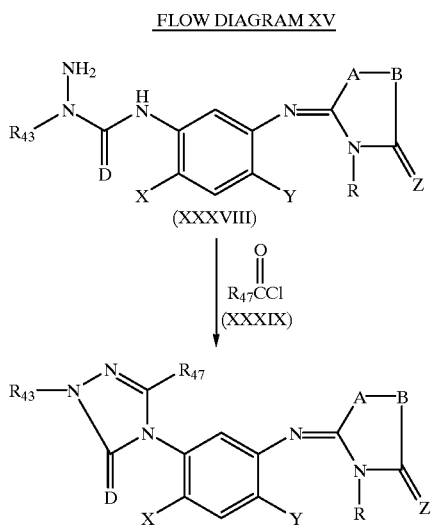

Formula I compounds wherein Q is Q38 may be prepared by reacting an amine of formula II with a chloride compound of formula XL to form an intermediate compound of formula XLI, and reacting the intermediate compound with hydrogen sulfide, hydrogen chloride and sodium periodate. The reaction scheme is shown in Flow Diagram XVI.

FLOW DIAGRAM XVI

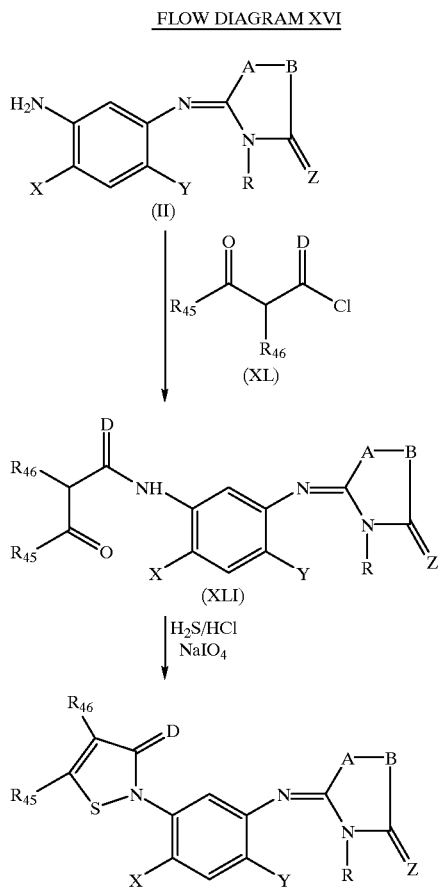

Compounds of formula I wherein Q is Q39 may be prepared by diazotizing an amine of formula II using conventional methods to form an intermediate compound, reducing the intermediate compound with sodium sulfite to form a hydrazine of formula XLII, sequentially reacting the hydrazine with an acid chloride of formula XLIII and phosphorous pentasulfide to form a substituted hydrazine of formula XLIV, and reacting the formula XLIV compound with phosgene or thiophosgene. The reaction scheme is shown in Flow Diagram XVII.

FLOW DIAGRAM XVII

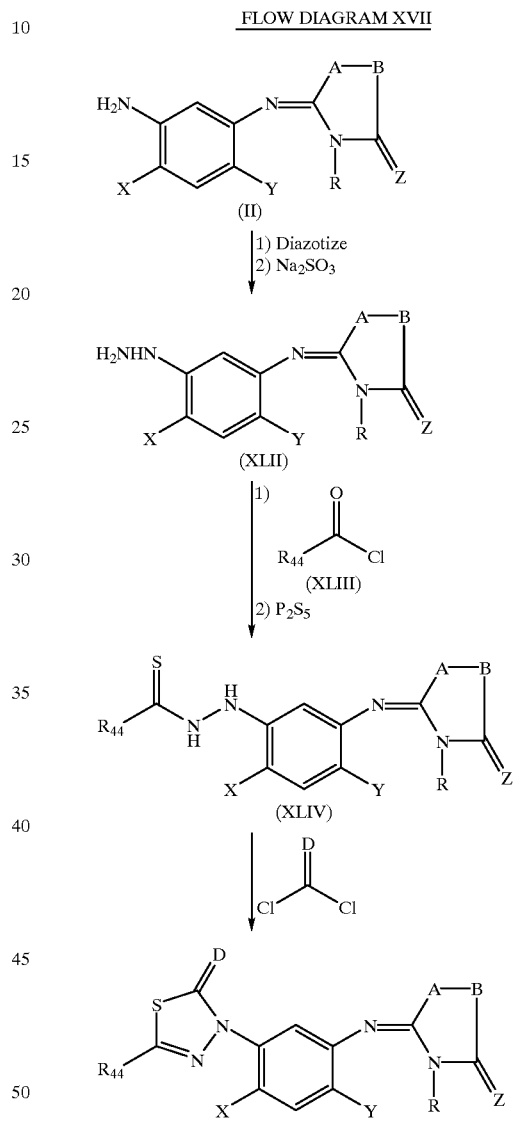

Certain formula II compounds wherein A is S, Z is O, and B is $CR_{37}R_{38}$ may be prepared by reacting an aniline of formula XLV with nitric acid and sulfuric acid to form a 3-nitroaniline of formula XLVI, reacting the 3-nitroaniline with thiophosgene to form an isothiocyanate of formula XLVII, reacting the isothiocyanate with an amine of formula XLVIII to form a thiourea of formula XLIX, reacting the thiourea with an a-halo ester of formula L optionally in the presence of a base to form an intermediate compound of formula LI, and reducing the formula LI compound using conventional procedures. The reaction scheme is shown below in Flow Diagram XVIII.

FLOW DIAGRAM XVIII

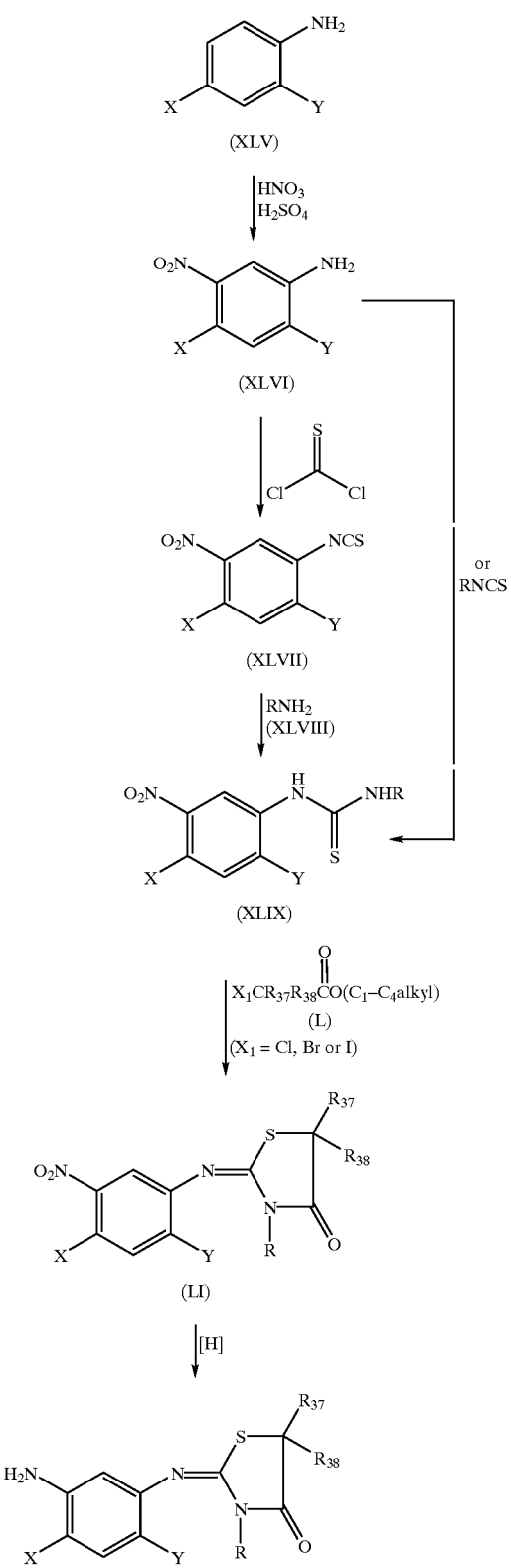

Certain formula II compounds wherein A is S, Z is O, B is —C(=T)—, and T is O may be prepared, as shown in Flow Diagram XIX, by reacting a thiourea of formula XLIX with oxalyl chloride to form an intermediate compound of formula LII, and reducing the formula LII compound using conventional procedures.

FLOW DIAGRAM XIX

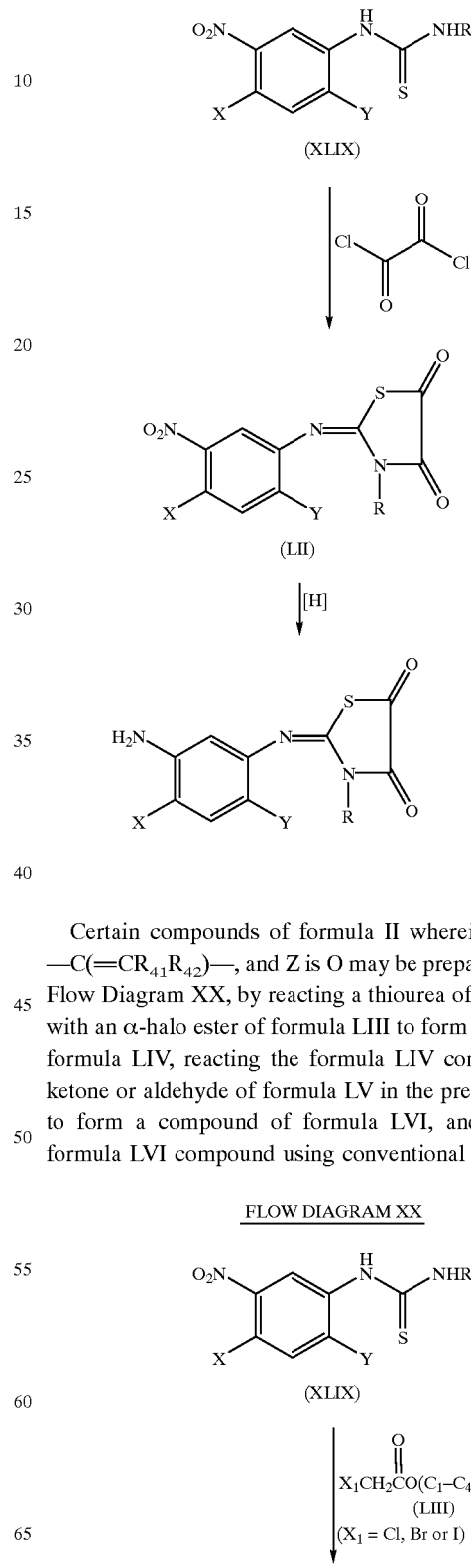

Certain compounds of formula II wherein A is S, B is —C(=CR$_{41}$R$_{42}$)—, and Z is O may be prepared, as show in Flow Diagram XX, by reacting a thiourea of formula XLIX with an α-halo ester of formula LIII to form a compound of formula LIV, reacting the formula LIV compound with a ketone or aldehyde of formula LV in the presence of a base to form a compound of formula LVI, and reducing the formula LVI compound using conventional procedures.

FLOW DIAGRAM XX

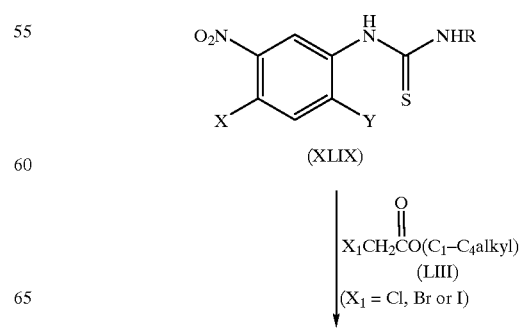

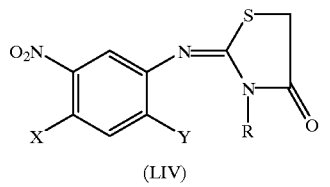

(LIV)

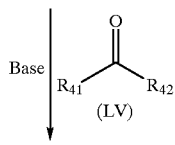

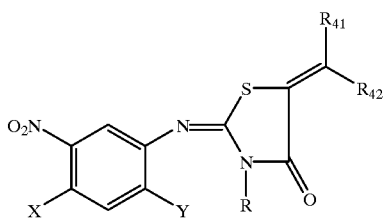

(LVI)

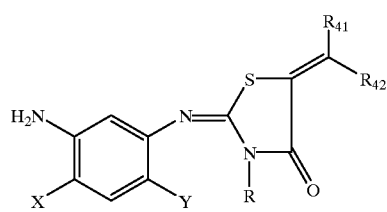

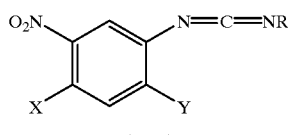

(LVII)

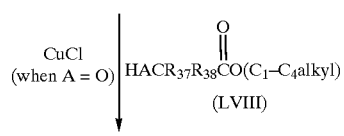

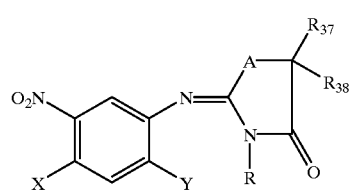

(LIX)

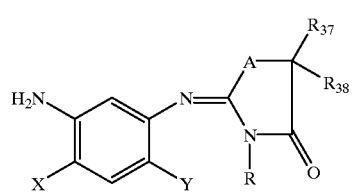

Certain formula II compounds wherein A is O, S or $NR_{34}$, B is $CR_{37}R_{38}$ and Z is O may be prepared by reacting a thiourea of formula XLIX with triethylamine, methanesulfonyl chloride and 4-dimethylaminopyridine to form a compound of formula LVII, cyclizing the formula LVII compound with an ester compound of formula LVIII in the presence of copper(I)chloride when A is O to form a compound of formula LIX, and reducing the formula LIX compound using conventional procedures. The reaction scheme is shown below in Flow Diagram XXI.

Formula II compounds wherein B is $-C(=CR_{42}R_{43})-$ and Z is O may be prepared, as shown in Flow Diagram XXII, by reacting a formula LIX compound wherein $R_{37}$ and $R_{38}$ are hydrogen with a ketone or aldehyde of formula LV in the presence of a base to form an intermediate compound of formula LX, and reducing the intermediate compound using conventional procedures.

FLOW DIAGRAM XXI

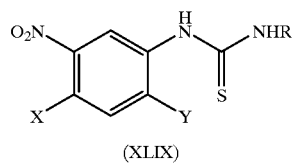

(XLIX)

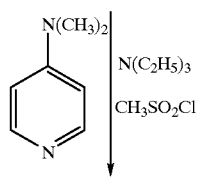

FLOW DIAGRAM XXII

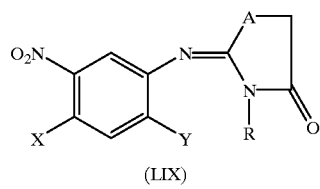

(LIX)

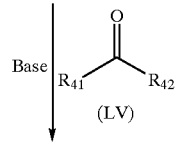

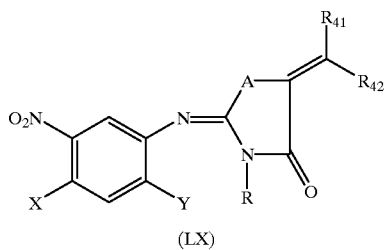

(LX)

↓[H]

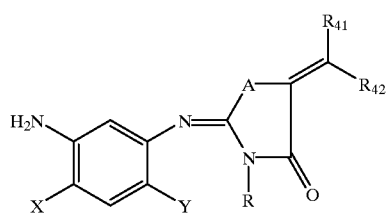

Alternatively, compounds of formula XLIX may be prepared as shown below in Flow Diagram XXIII.

FLOW DIAGRAM XXIII

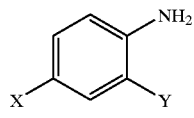

↓ 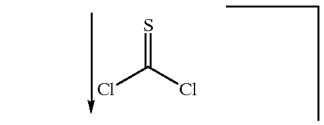

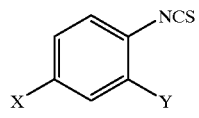

↓ RNH₂

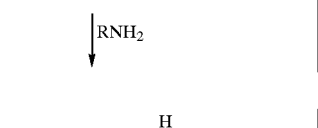

↓ HNO₃

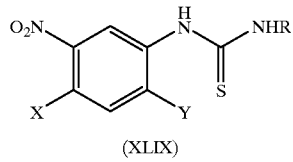

(XLIX)

Intermediate compounds of formula LIX may also be prepared as shown below in Flow Diagram XXIV.

FLOW DIAGRAM XXIV

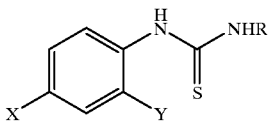

↓ N(CH₃)₂ / CH₃SO₂Cl / N(C₂H₅)₃ (pyridine)

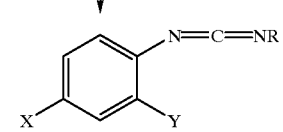

↓ HACR₃₇R₃₈CO(C₁—C₄alkyl)
(LVIII)

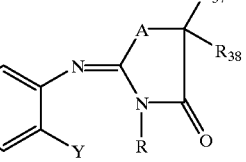

↓ HNO₃

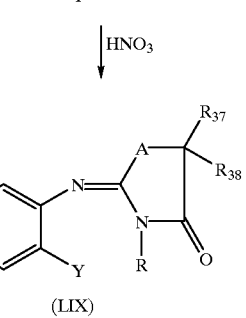

(LIX)

Formula I compounds wherein Q is Q24, A is S, and B is CR₃₇R₃₈ may also be prepared as shown below in Flow Diagram XXV.

FLOW DIAGRAM XXV
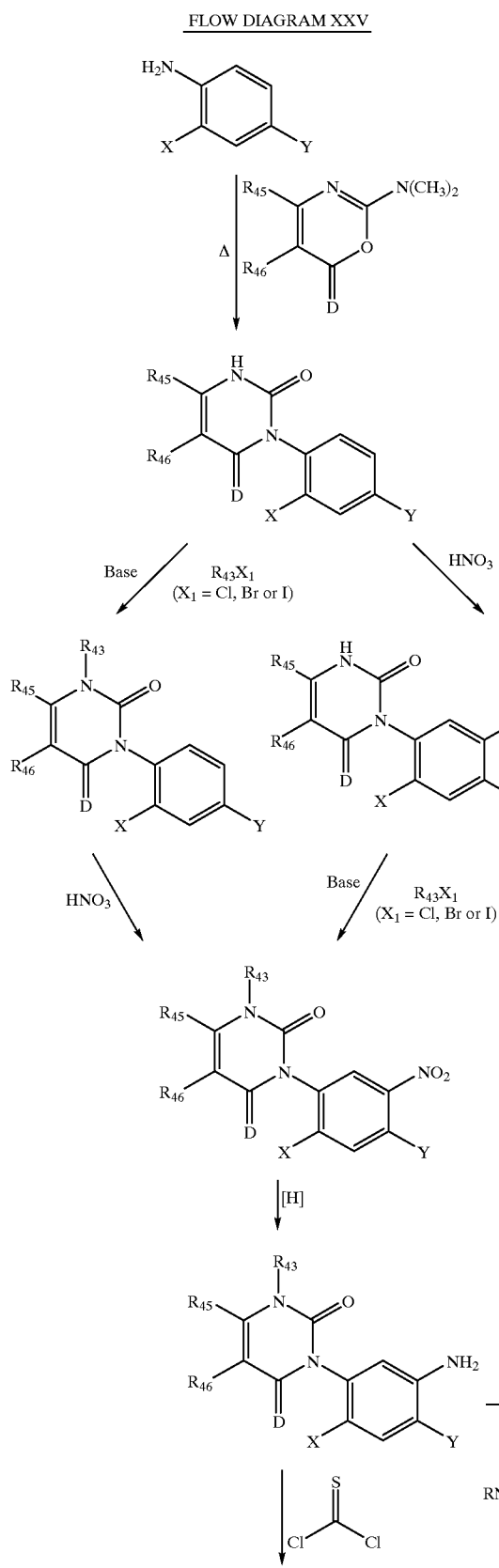
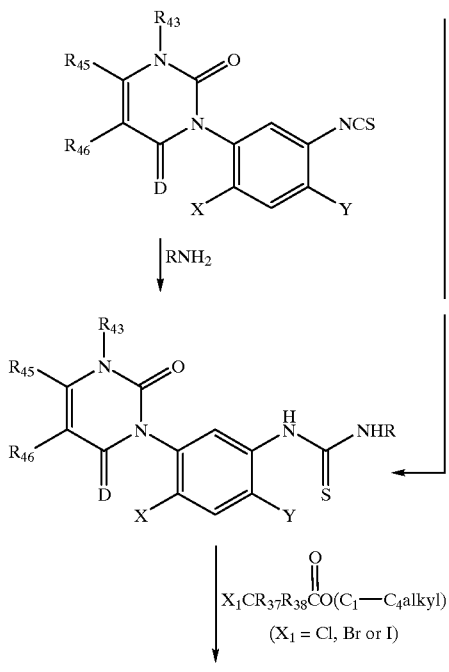
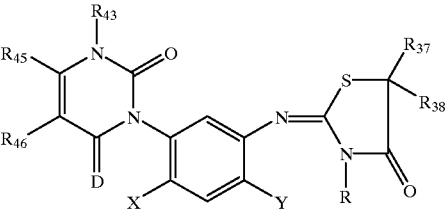
Alternatively, one of the intermediates used in the reaction scheme described in Flow Diagram XXV may be prepared as shown below in Flow Diagram XXVI.
FLOW DIAGRAM XXVI
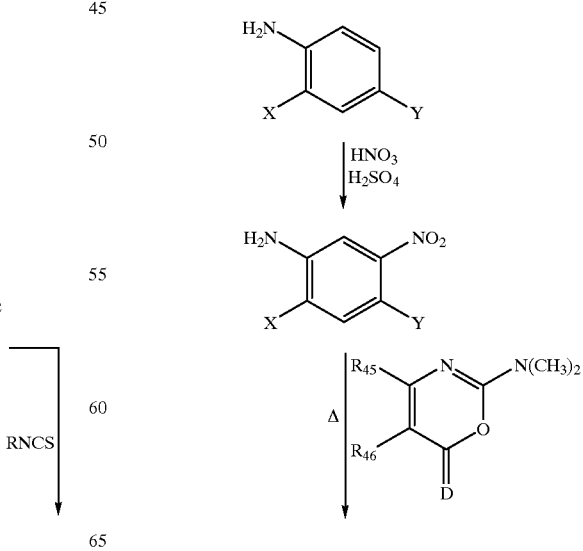

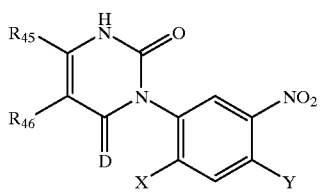

Formula I compounds wherein A is S, B is $CR_{37}R_{38}$, Z is O, and Q is Q1–Q32, Q34 and Q36–Q39 may also be prepared by substituting an aniline of formula LXI or a 3-nitroaniline of formula LXII for the formula II amines used hereinabove to obtain compounds of formula LXIII, and converting the formula LXIII compounds to the desired formula I compounds as shown below in Flow Diagram XXVII.

FLOW DIAGRAM XXVII

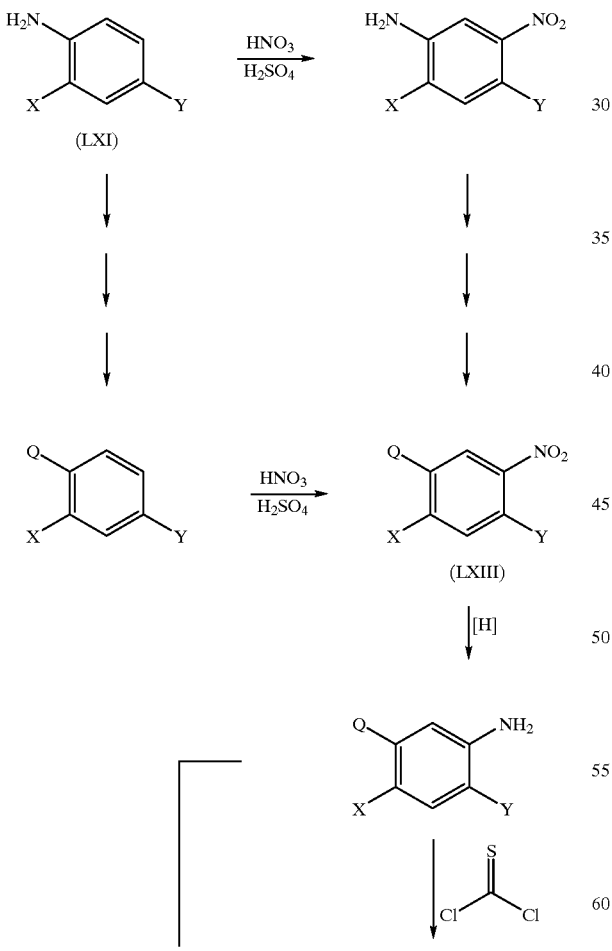

Alternatively, certain formula I compounds wherein Q is Q1–Q32, Q34 and Q36–Q39, B is $CR_{37}R_{38}$, and Z is O may be prepared, as shown below in Flow Diagram XXVIII, by reacting a thiourea of formula LXIV with methanesulfonyl chloride, triethylamine and 4-dimethylaminopyridine to form an intermediate compound of formula LXV, and reacting the intermediate compound with an ester of formula LVIII and copper(I)chloride when A is O.

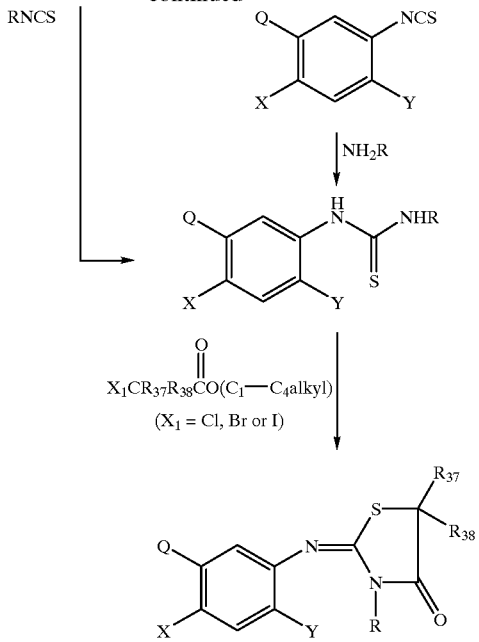

FLOW DIAGRAM XXVIII

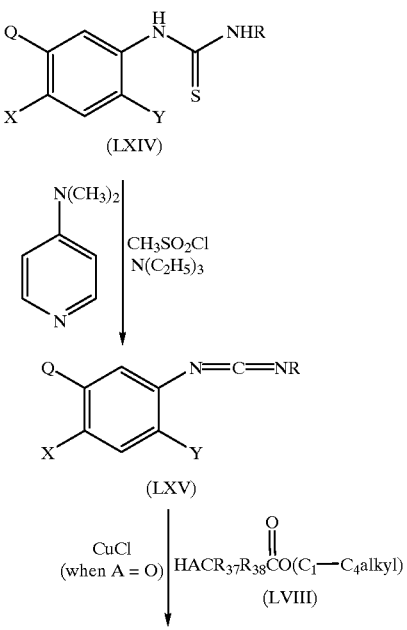

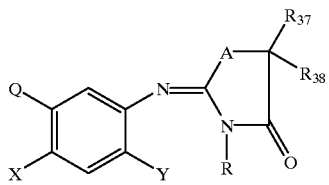

Compounds of formula I wherein A is S, B is —C(=T)—, and T and Z are O may be prepared, as shown in Flow Diagram XXIX, by reacting a thiourea of formula LXIV with oxalyl chloride.

FLOW DIAGRAM XXIX

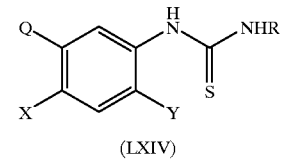

(LXIV)

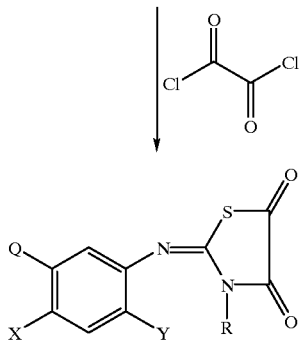

Formula I compounds wherein A is S, B is —C(=CR$_{41}$R$_{42}$)—, and Z is O may be prepared as shown below in Flow Diagram XXX.

FLOW DIAGRAM XXX

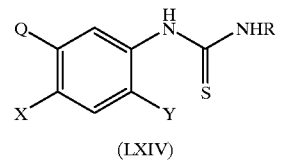

(LXIV)

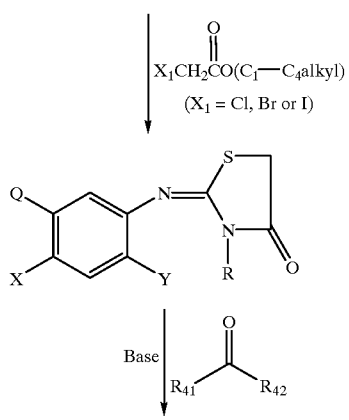

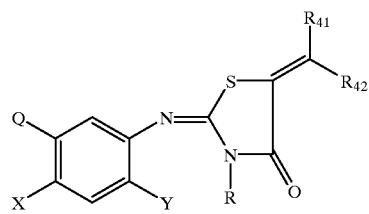

Compounds of formula I wherein R is NR$_{18}$R$_{19}$, A is S, B is CR$_{37}$R$_{38}$, and Z is O may be prepared, as shown in Flow Diagram XXXI, by reacting an isothiocyanate of formula LXVI with a hydrazine of formula LXVII to form a thiourea of formula LXVIII and reacting the thiourea with an α-halo ester of formula L optionally in the presence of a base.

FLOW DIAGRAM XXXI

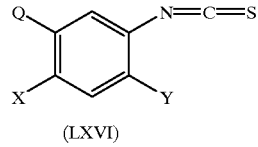

(LXVI)

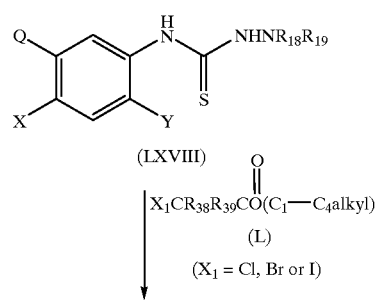

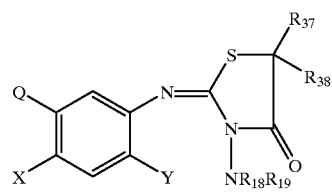

Alternatively, formula I compounds wherein R is NR$_{18}$R$_{19}$ may be prepared as shown below in Flow Diagram XXXII.

FLOW DIAGRAM XXXII

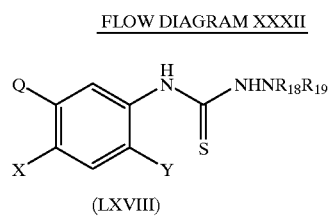

(LXVIII)

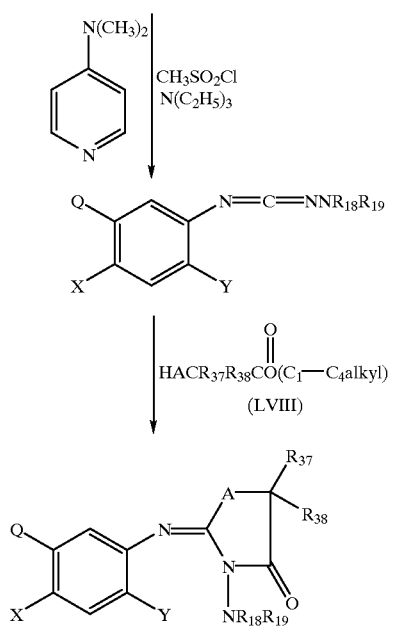

Formula I compounds wherein R is OR$_{17}$ may be prepared, as shown in Flow Diagram XXXIII, by reacting an isocyanate of formula LXVI with an amine of formula LXIX to form a thiourea of formula LXX, and reacting the thiourea with an α-halo ester of formula L.

FLOW DIAGRAM XXXIII

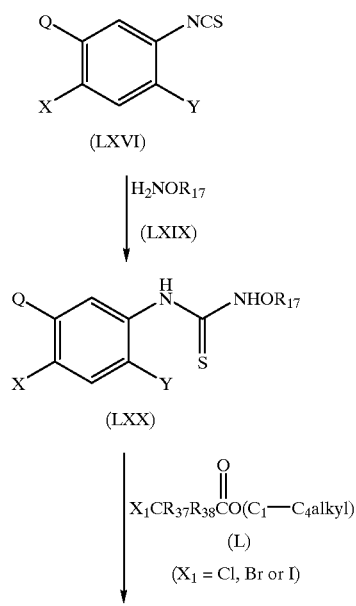

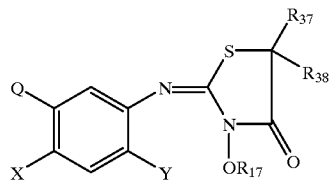

Formula I compounds wherein Q is Q24 and R$_{46}$ is hydrogen may be prepared as shown below in Flow Diagram XXXIV.

FLOW DIAGRAM XXXIV

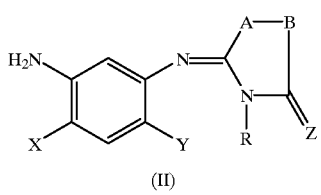

(II)

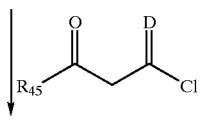

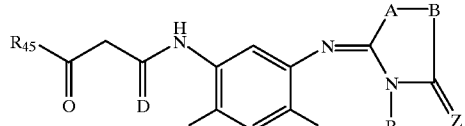

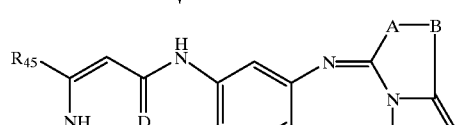

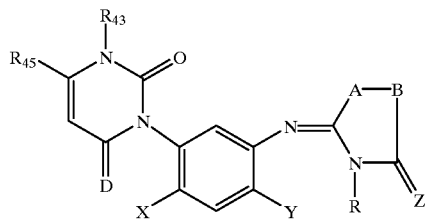

Other methods for the preparation of formula I compounds will become apparent from the examples set forth below. In addition, certain compounds of formula I may be converted into other compounds of formula I by using conventional procedures known to those skilled in the art.

The present invention also relates to intermediate compounds having the structural formula LXXI (LXXI)

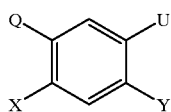

wherein

U is —N=C=NR, —N=C=S or

Q is Q5, Q7, Q24 or Q29 as described hereinabove; and
R, X and Y are as described hereinabove.
Preferred formula LXXI compounds are those wherein
U is —N=C=NR, —N=C=S or

Q is

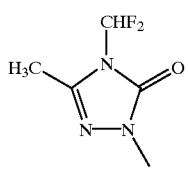 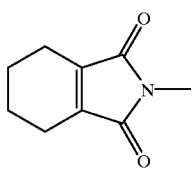

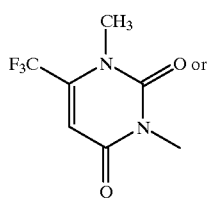 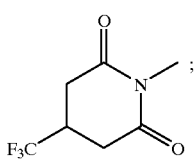

X is hydrogen, fluorine or chlorine;
Y is fluorine, chlorine, nitro or cyano; and
R is hydrogen,
  $C_1$–$C_6$alkyl optionally substituted with one to three halogen atoms, one or two C(O)OR$_3$ groups, one cyano group, one OR$_7$ group, one SR$_8$ group, one P(O)(OR$_6$)$_2$ group, or
  a $C_3$–$C_6$alkenyl, $C_3$–$C_6$alkynyl, phenyl, benzyl or furfural group, wherein each group is optionally substituted with one to three halogen atoms, one $C_1$–$C_3$alkoxy group or one C(O)OR$_3$ group;
$R_3$ is hydrogen, $C_1$–$C_6$alkyl or $C_1$–$C_6$haloalkyl;
$R_6$ is hydrogen or $C_1$–$C_3$alkyl;
$R_7$ is hydrogen, $C_1$–$C_3$alkyl or $C_3$–$C_6$alkoxycarbonylalkyl; and
$R_8$ is hydrogen, $C_1$–$C_3$alkyl or $C_3$–$C_6$alkoxycarbonyl.

In order to facilitate a further understanding of the invention, following examples are presented to illustrate more specific details thereof. This invention is not to be limited thereby except as defined in the claims.

EXAMPLE 1

Preparation of 4-chloro-2-fluoro-5-nitroaniline

Preparation of 4-Chloro-2-fluoro-5-nitroaniline

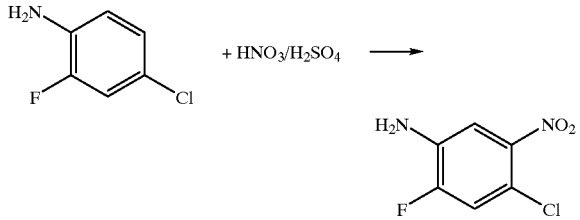

A solution of 4-chloro-2-fluoroaniline (10.0 g, 69 mmol) in concentrated sulfuric acid is cooled to −20° C., treated dropwise with 90% nitric acid (5.0 mL, 107 mmol) over ten minutes, stirred at −15° C. for 90 minutes, and poured onto ice. The resultant aqueous mixture is extracted with diethyl ether, neutralized with 50% sodium hydroxide solution, and extracted again with diethyl ether. The organic extracts are combined, washed sequentially with dilute sodium hydroxide solution and brine, dried over anhydrous magnesium sulfate, and concentrated in vacuo to give the title product as a brown solid (11.3 g, 86% yield, mp 82–83.5° C.) which is identified by $^1$H, $^{19}$F and $^{13}$C NMR spectral analyses.

Using essentially the same procedure, but substituting 2,4-dichloroaniline for 4-chloro-2-fluoroaniline, 2,4-dichloro-5-nitroaniline is obtained. EXAMPLE 2

Preparation of 3-(4-chloro-2-fluoro-5-nitrophenyl)-6-(trifluoromethyl)-2,4(1H,3H)-pyrimidinedione

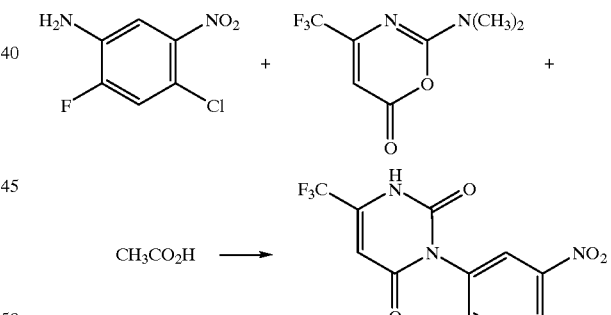

A solution of 4-chloro-2-fluoro-5-nitroaniline (5.0 g, 26.3 mmol) and 2-dimethylamino-4-(trifluoromethyl)-6H-1,3-oxazin-6-one (5.73 g, 27.6 mmnol) in acetic acid is refluxed for 4 hours and poured onto ice. The resultant aqueous mixture is filtered to obtain a solid. The solid is washed with water and air-dried to give the title product as a beige solid (7.5 g, 81% yield, mp 230–232° C.) which is identified by $^1$H, $^{13}$C and $^{19}$F NMR spectral analyses.

Using essentially the same procedure, but substituting 2,4-dichloro-5-nitroaniline for 4-chloro-2-fluoro-5-nitroaniline, 3-(2,4-dichloro-5-nitrophenyl)-6-(trifluoromethyl)-2,4 (1H,3H) -pyrimidinedione, mp 188.5–190° C., is obtained.

EXAMPLE 3

Preparation of 3-(4-chloro-2-fluoro-5-nitrophenyl)-1-methyl-6-(trifluoromethyl)-2,4(1H,3H)-pyrimidinedione

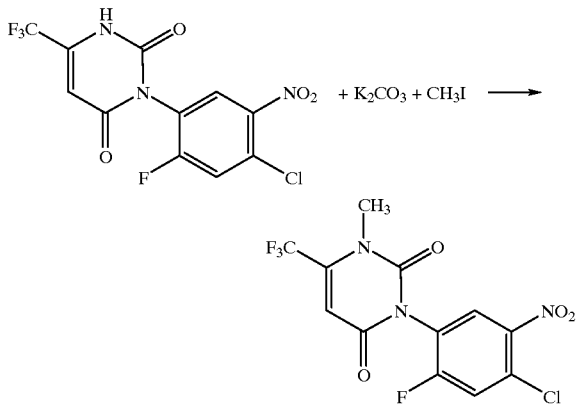

A solution of 3-(4-chloro-2-fluoro-5-nitrophenyl)-6-trifluoromethyl)-2,4(1H,3H)-pyrimidinedione (5.66 g, 16 mmol) in N,N-dimethylformamide is treated sequentially with potassium carbonate (2.43 g, 17.6 mmol) and iodomethane (1.1 mL, 17.6 mmol), stirred overnight at room temperature, and poured into water. After acidifying the resultant aqueous mixture to pH 5, the solids are collected, washed with water and dried to obtain a dark, brown solid. The solid is dissolved in methylene chloride and the resultant solution is washed sequentially with water and brine, passed through a silica gel plug, and concentrated in vacuo to give the title product as a light, brown solid (4.7 g, 80% yield, mp 124–126.5° C.) which is identified by $^1$H and $^{13}$C NMR spectral analyses.

Using essentially the same procedure, but substituting 3-(2,4-dichloro-5-nitrophenyl)-6-(trifluoromethyl)-2,4(1H,3H)-pyrimidinedione for 3-(4-chloro-2-fluoro-5-nitrophenyl)-6-(trifluoromethyl)-2,4(1H,3H)-pyrimidinedione, 3-(2,4-dichloro-5-nitrophenyl)-1-methyl-6-(trifluoromethyl)-2,4(1H,3H)-pyrimidinedione, mp 127–128.5° C., is obtained.

EXAMPLE 4

Preparation of 3-(5-amino-4-chloro-2-fluorophenyl)-1-methyl-6-(trifluoromethyl)-2,4(1H,3H)-Pyrimidinedione

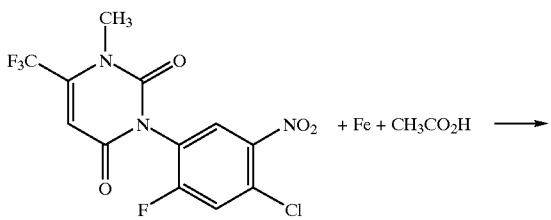

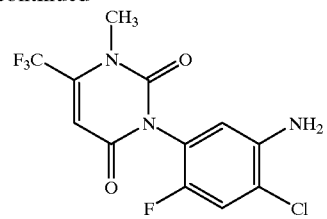

A solution of 3-(4-chloro-2-fluoro-5-nitrophenyl)-1-methyl-6-(trifluoromethyl)-2,4(1H,3H)-pyrimidinedione (3.00 g, 8.16 mmol) in acetic acid is heated to 50–60° C., treated portionwise with iron powder (2.28 g, 40.8 mmol) over 10 minutes, stirred at 50–60° C. for 90 minutes, cooled to room temperature, and diluted with water. The resultant aqueous mixture is filtered to remove solids and extracted with diethyl ether. The organic extracts are combined, washed sequentially with 1 M sodium hydroxide solution and brine, dried over anhydrous magnesium sulfate, and concentrated in vacuo to give the title product as a brown solid (2.37 g, 86% yield, mp 132–135° C.) which is identified by $^1$H and $^{13}$C NMR spectral analyses.

Using essentially the same procedure, but substituting 3-(2,4-dichloro-5-nitrophenyl)-1-methyl-6-(trifluoromethyl)-2,4(1H,3H)-pyrimidinedione for 3-(4-chloro-2-fluoro-5-nitrophenyl)-1-methyl-6-(trifluoromethyl)-2,4(1H,3H)-pyrimidinedione, 3-(5-amino-2,4-dichlorophenyl)-1-methyl-6-(trifluoromethyl)-2,4(1H,3H)-pyrimidinedione, mp 163–165° C., is obtained.

EXAMPLE 5

Preparation of N-(4-chloro-2-fluorophenyl)-1-cyclohexene-1,2-dicarboximide

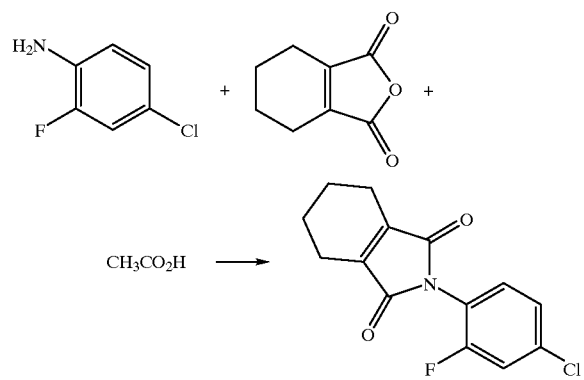

A solution of 4-chloro-2-fluoroaniline (19.0 g, 130.6 mmol) and 3,4,5,6-tetrahydrophthalic anhydride (19.85 g, 130.6 mmol) in acetic acid is refluxed for 2 hours, treated with additional 4-chloro-2-fluoroaniline (3.0 g), refluxed for 90 minutes, stirred at room temperature overnight and poured into water. The resultant aqueous mixture is extracted with ethyl acetate. The organic extract is washed sequentially with water, saturated sodium hydrogen carbonate solution and brine, dried over anhydrous magnesium sulfate, and concentrated in vacuo to obtain a purple oil. Flash column chromatography of the oil using silica gel and 15 to 20% ethyl acetate in hexanes solutions gives the title product as an off-white solid (25.3 g, 69% yield, mp 81–82° C.) which is identified by $^1$H, $^{13}$C and $^{19}$F NMR spectral analyses.

EXAMPLE 6

Preparation of N-(4-chloro-2-fluoro-5-nitrophenyl)-1-cyclohexene-1,2-dicarboximide

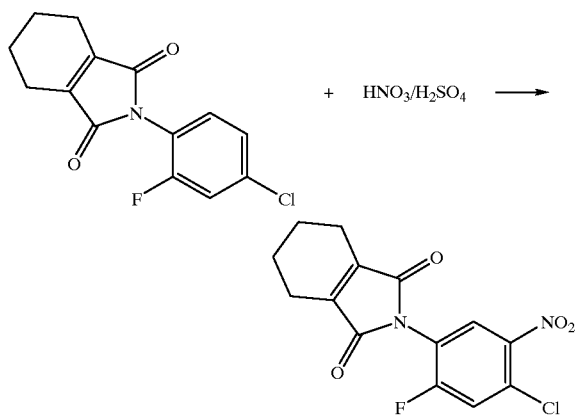

A mixture of N-(4-chloro-2-fluorophenyl)-1-cyclohexene-1,2-dicarboximide (24.4 g, 86.7 mmol) in sulfuric acid is cooled to −3° C., treated dropwise with 70% nitric acid (6.7 mL, 104.0 mmol) while maintaining the temperature from 0° to 2° C., warmed to and stirred at room temperature for 90 minutes, and poured onto ice. The resultant aqueous mixture is filtered to obtain a solid. The solid is washed with water and air-dried overnight to give the title product as a white powder (28.68 g, mp 152–155° C.) which is identified by $^1$H, 13C and $^{19}$F NMR spectral analyses.

EXAMPLE 7

Preparation of N-(5-amino-4-chloro-2-fluorophenyl)-1-cyclohexene-1,2-dicarboximide

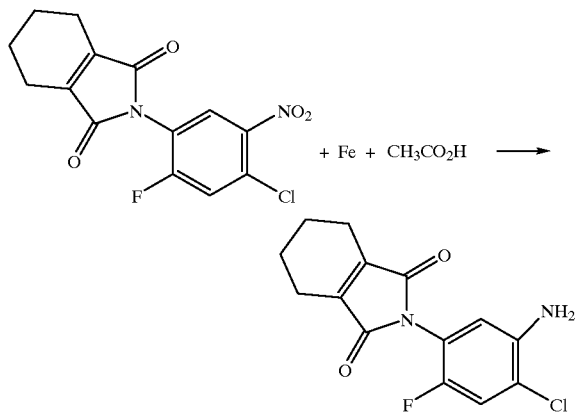

A mixture of N-(4-chloro-2-fluoro-5-nitrophenyl)-1-cyclohexene-1,2-dicarboximide (10.6 g, 32.7 mmol) in acetic acid is heated to 65° C., treated portionwise with iron powder (7.30 g, 130.7 mmol) over 40 minutes, stirred for 10 minutes, and filtered through diatomaceous earth. The resultant filtrate is washed with ethyl acetate, concentrated in vacuo, diluted with ethyl acetate and saturated sodium hydrogen carbonate solution, and filtered through a filter pad. The phases are separated and the organic phase is washed sequentially with saturated sodium hydrogen carbonate solution and brine, dried over anhydrous magnesium sulfate, and concentrated in vacuo to give the title product as a yellow solid (8.94 g, 94% yield, mp 164–165° C.).

EXAMPLE 8

Preparation of N-{{2-chloro-5-[3,6-dihydro-3-methyl-2,6-dioxo-4-(trifluoromethyl)-1(2H)-pyrimidinyl]-4-fluorophenyl}(thiocarbamoyl)}glycine, ethyl ester

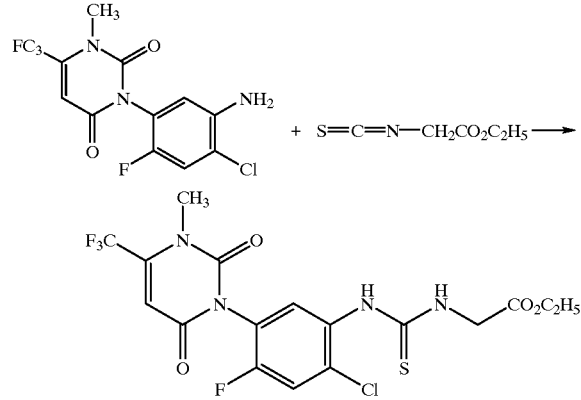

A solution of 3-(5-amino-4-chloro-2-fluorophenyl)-1-methyl-6-(trifluoromethyl)-2,4(1H,3H)-pyrimidinedione (3.0 g, 8.89 mmol) in a tetrahydrofuran/ethanol solution (1:1) is treated with ethyl isothiocyanatoacetate (1.93 g, 13.34 mmol), refluxed for 9 hours, stirred at room temperature overnight, and concentrated in vacuo to obtain an orange-brown gum. Flash column chromatography of the gum using silica gel and 25% to 30% ethyl acetate in hexanes solutions gives the title product as a white foam (2.24 g, 52% yield, mp 95–103° C.) which is identified by $^1$H, $^{13}$C and $^{19}$F NMR spectral analyses.

Using essentially the same procedure, the following compounds are obtained:

| Q | X | R | mp ° C. |
|---|---|---|---|
| ![CF3-pyrimidinedione] | F | CH$_3$ | 110–116 |

-continued

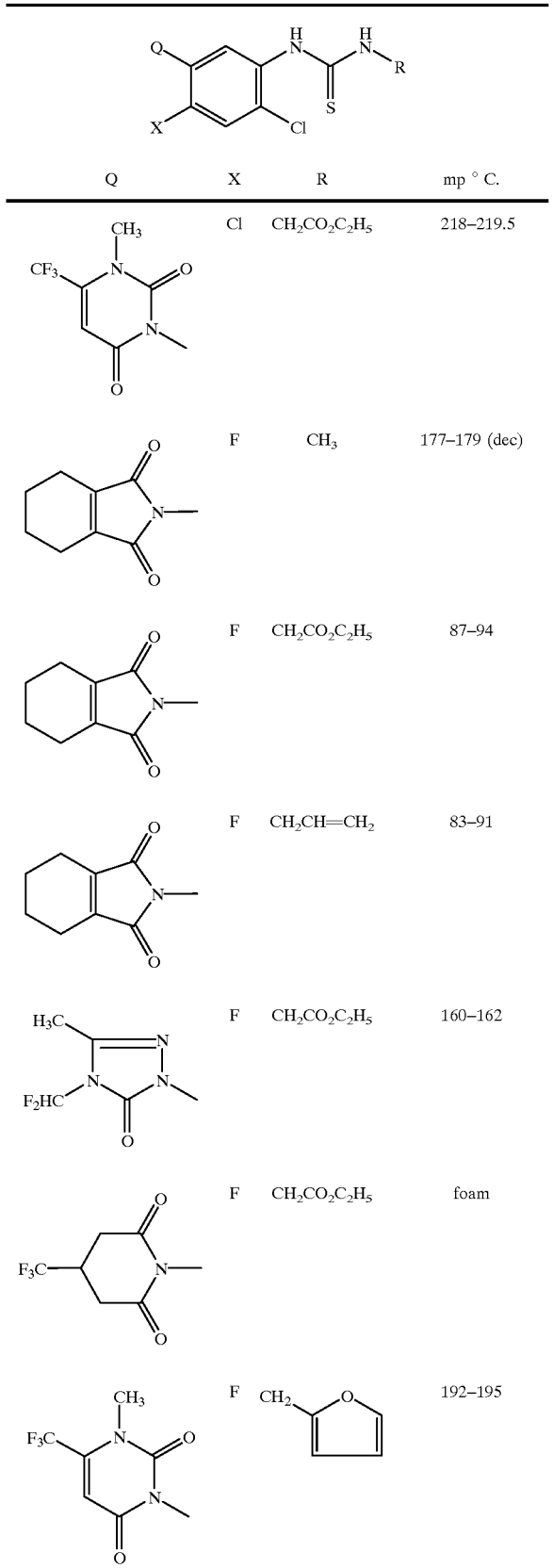

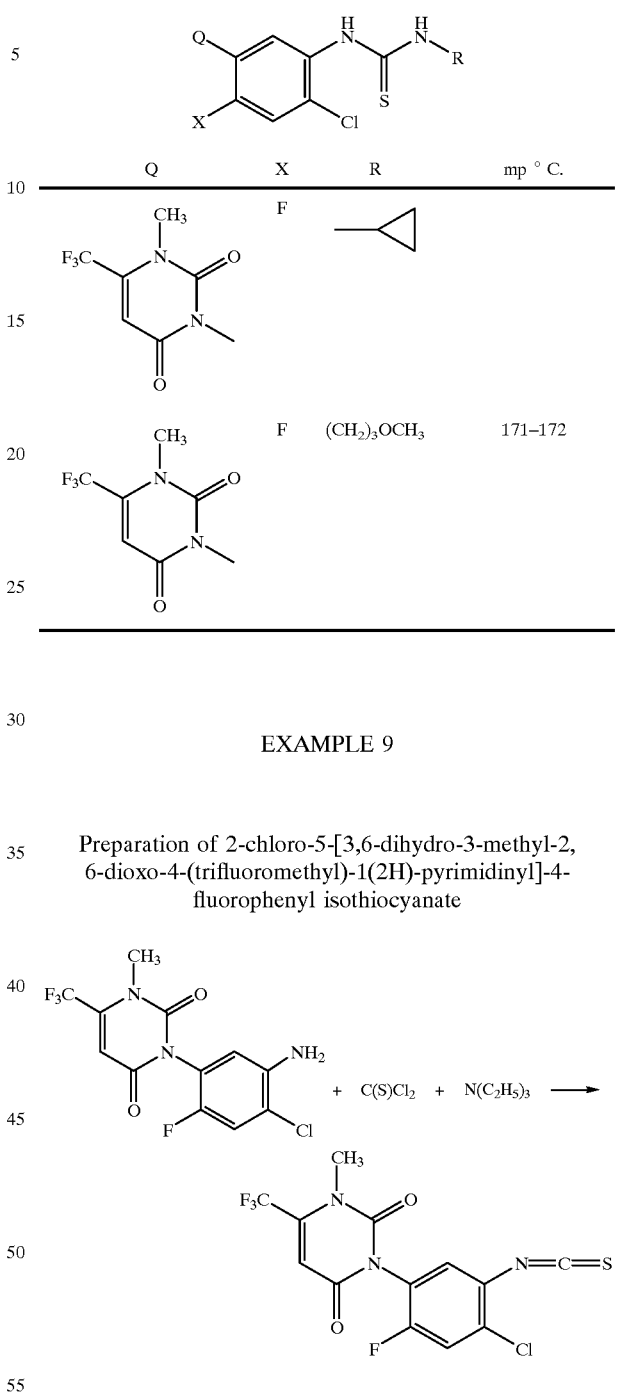

EXAMPLE 9

Preparation of 2-chloro-5-[3,6-dihydro-3-methyl-2,6-dioxo-4-(trifluoromethyl)-1(2H)-pyrimidinyl]-4-fluorophenyl isothiocyanate A mixture of 3-(5-amino-4-chloro-2-fluorophenyl)-1-methyl-6-(trifluoromethyl)-2,4 (1H,3H)-pyrimidinedione (1.0 g, 2.96 mmol) in toluene is cooled to 0° C., treated sequentially with triethylamine (0.91 mL, 6.52 mmol) and thiophosgene (0.25 mL, 3.26 mmol), warmed to and stirred at room temperature for 5 hours, and filtered to remove solids. The resultant filtrate is concentrated in vacuo to give the title product as an orange solid (1.1 g, 98% yield) which is identified by $^1$H NMR spectral analysis.

EXAMPLE 10

Preparation of N-{{2-chloro-5-[3,6-dihydro-3-methyl-2,6-dioxo-4-(trifluoromethyl)-1(2H)-pyrimidinyl]-4-fluoropheny}-(thiocarbamoyl)}-β-alanine, methyl ester

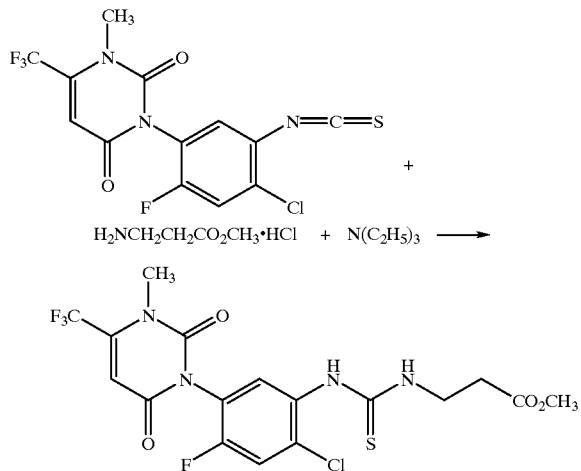

A solution of 2-chloro-5-[3,6-dihydro-3-methyl-2,6-dioxo-4-(trifluoromethyl)-1(2H)-pyrimidinyl]-4-fluorophenyl isothiocyanate (6.0 g, 15.8 mmol) and β-alanine, methyl ester, hydrochloride salt (2.65 g, 19.0 mmol) in acetone is cooled to 0° C., treated dropwise with a solution of triethylamine (1.92 g, 19.0 mmol) in methylene chloride, stirred overnight at room temperature, and poured into water. The resultant aqueous mixture is extracted with ethyl acetate. The organic extracts are combined, washed sequentially with 5% hydrochloric acid and brine, dried over anhydrous magnesium sulfate, and concentrated in vacuo to obtain a brown foam. Flash column chromatography of the foam using silica gel and a (9:1) methylene chloride/diethyl ether solution gives the title product as an off-white foam (5.68 g, 74.4% yield, mp 110° C.) which is identified by $^1$H NMR spectral analysis.

Using essentially the same procedure, but substituting the appropriate amine for β-alanine, methyl ester, hydrochloride salt, the following compounds are obtained:

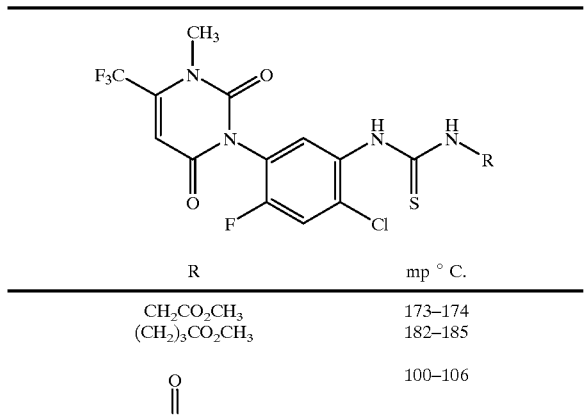

| R | mp ° C. |
|---|---|
| CH$_2$CO$_2$CH$_3$ | 173–174 |
| (CH$_2$)$_3$CO$_2$CH$_3$ | 182–185 |
| CH$_2$P(O)(OC$_2$H$_5$)$_2$ | 100–106 |

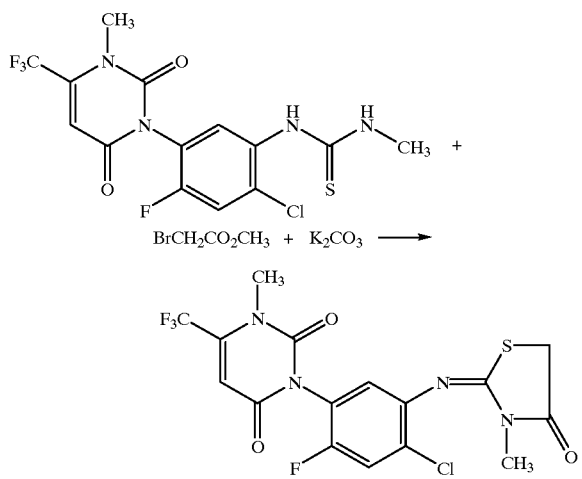

| R | mp ° C. |
|---|---|
| CH$_2$CO$_2$C(CH$_3$)$_3$ | 205–206 |
| CH$_2$C≡CH$_2$ | 196–199 |
| (CH$_2$)$_2$OCH$_3$ | 153–155 |
| C$_2$H$_5$ | 207–208 |
| CH(CH$_3$)C≡CH | 163–165 |
| (CH$_2$)$_2$SCH$_3$ | glass |
| (CH$_2$)$_2$SCH$_2$CO$_2$CH$_3$ | glass |
| CH$_2$CF$_3$ | glass |
| CH(CH$_3$)$_2$ | 235–238 |
| cyclopentyl | 223–225 |
| cyclobutyl | 225–228 |
| (CH$_2$)$_2$CH$_3$ | 214–215 |
| (CH$_2$)$_2$F | 159–160 |

EXAMPLE 11

Preparation of 3-{4-chloro-2-fluoro-5-[3-methyl-4-oxo-2-thiazolidinylidene)amino]phenyl}-1-methyl-6-(trifluoromethyl)-2,4(1H,3H)-pyrimidinedione A solution of 1-{2-chloro-5-[3,6-dihydro-3-methyl-2,6-dioxo-4-(trifluoromethyl)-1(2H)-pyrimidinyl]-4-fluorophenyl}-3-methyl-2-thiourea (0.92 g, 2.24 mmol) in N,N-dimethylformamide is treated sequentially with potassium carbonate (0.34 g, 2.47 mmol) and methyl bromoacetate (3.2 mL, 3.36 mmol), stirred at room temperature for 5.5 hours, and poured into water. The resultant aqueous mixture is extracted with diethyl ether and ethyl acetate. The organic extracts are combined, washed sequentially with water and brine, dried over anhydrous magnesium sulfate, and concentrated in vacuo to obtain a yellow oil. Flash column chromatography of the oil using silica gel and a (1:2) ethyl acetate/hexanes solution gives the title product as a palm, yellow solid (0.6 g, 59% yield, mp 96–105° C.) which is identified by $^1$H, $^{13}$C and $^{19}$F NMR spectral analyses.

Using essentially the same procedure, or alternatively heating the reaction mixture in the absence of base, the following compounds are obtained:

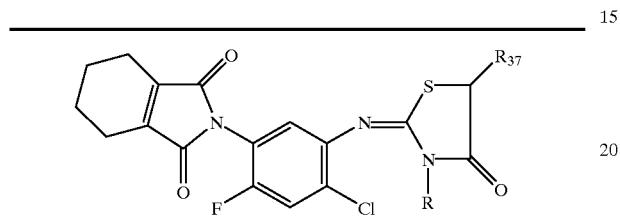

| R | $R_{37}$ | mp ° C. |
|---|---|---|
| $CH_3$ | H | 83–103 |
| $CH_2CH=CH_2$ | H | 163–165 |
| $C_6H_5$ | H | 175–180 |
| $CH_3$ | $CH_3$ | 91–97 |
| $CH_3$ | F | 80–95 |
| $CH_3$ | $C_2H_5$ | 80–88 |
| $CH_2CO_2C_2H_5$ | H | 92–100 |

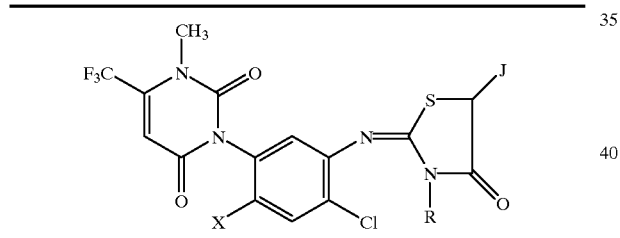

| X | R | J | mp ° C. |
|---|---|---|---|
| F | 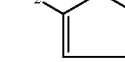 CH$_2$-furan | H | 125–126 |
| F |  cyclopropyl | H | 99–101 |
| F | $(CH_2)_2OCH_3$ | H | glass |
| F | $C_2H_5$ | H | glass |
| F | $CH(CH_3)C\equiv CH$ | H | 118–121 |
| F | $(CH_2)_3OCH_3$ | H | glass |
| F | $CH_2CO_2C_2H_5$ | Br | 82–84 |
| F | $CH_2CO_2C_2H_5$ | $CH_2OCH_3$ | 158–159 |
| F | $CH_2CO_2C_2H_5$ | $SCH_3$ | 67–70 |
| F | $CH_2CO_2C_2H_5$ | Cl | 55–57 |
| F | $CH_2CO_2C_2H_5$ | $CO_2C_2H_5$ | 60–62 |
| F | $CH_2CO_2C_2H_5$ | $CO_2CH_3$ | 46–48 |
| F | $CH_2CO_2C_2H_5$ | $=CH_2$ | 207–208 |
| F | $(CH_2)_2SCH_3$ | H | glass |
| F | $(CH_2)_2SCH_2CO_2CH_3$ | H | glass |
| F | $CH_2CO_2C_2H_5$ | $OCH_3$ | 84–86 |
| F | $CH_2CF_3$ | H | 135–138 |
| F | $CH(CH_3)_2$ | H | 108–109 |

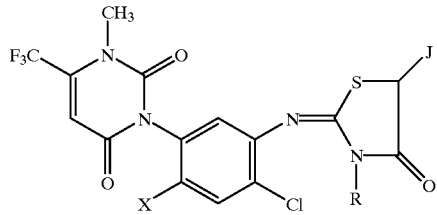

| X | R | J | mp ° C. |
|---|---|---|---|
| F | 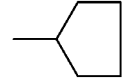 cyclopentylmethyl | H | 150–152 |
| F | $CH_2CO_2C_2H_5$ | $CO_2CH(CH_3)_2$ | 75–77 |
| F | 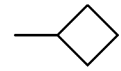 cyclobutyl | H | glass |
| F | $(CH_2)_2CH_3$ | H | glass |
| F | $(CH_2)_3OCH_3$ | H | glass |
| F | $(CH_2)_2F$ | H | 156–158 |
| F | $CH_2CO_2C_2H_5$ | H | 85–95 |
| F | $CH_3$ | $CH_3$ | 93–99 |
| F | $CH_3$ | $C_2H_5$ | 78–84 |
| F | $CH_2CO_2C_2H_5$ | F | glass |
| F | $CH_2CO_2C_2H_5$ | $CH_3$ | glass |
| F | $CH_2CO_2C_2H_5$ | $C_2H_5$ | glass |
| F | $CH_2CO_2C_2H_5$ | spirocyclopropyl | glass |
| F | $CH_2CO_2CH_3$ | H | glass |
| F | $N(CH_3)_2$ | H | 192–193 |
| F | $CH_2C_6H_5$ | H | oil |
| F | $CH_2CH=CH_2$ | H | 64–68 |
| F | $CH_2CH_2CO_2CH_3$ | H | oil |
| F | $(CH_2)_3CO_2CH_3$ | H | 65–70 |
| Cl | $CH_2CO_2C_2H_5$ | H | 90–105 |
| F | $CH_2P(O)(OC_2H_5)_2$ | H | foam |
| F | $CH_2CO_2C(CH_3)_3$ | H | 114–115 |

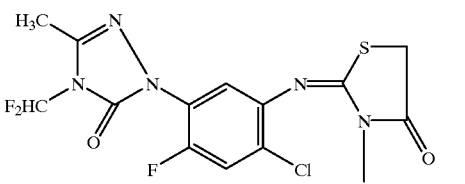

mp 60–70° C.

and

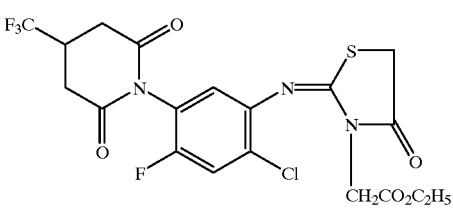

EXAMPLE 12

Preparation of 2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester

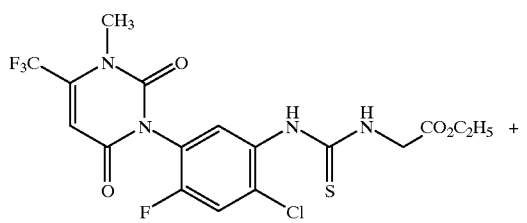
+
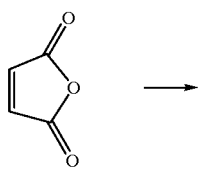
→
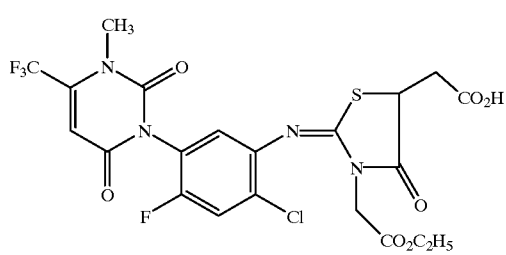

A solution of N-{{2-chloro-5-[3,6-dihydro-3-methyl-2,6-dioxo-4-(trifluoromethyl)-1(2H)-pyrimidinyl]-4-fluorophenyl}(thiocarbamoyl)}glycine, ethyl ester (2.94 g, 6.2 mmol) and maleic anhydride (0–67 g, 6.8 mmol) in N,N-dimethylformamide is stirred at 80° C. for 2 days, treated with additional maleic anhydride (0.67 g), stirred overnight at 84° C., and poured into an ice-water mixture. The resultant aqueous mixture is filtered to obtain a solid. Column chromatography of the solid using silica gel and a diethyl ether/methylene chloride/hexanes acetic acid solution (33:33:33:1) gives the title product as a pale, yellow glass (1.14 g) which is identified by $^{1}$H, $^{13}$C and $^{19}$F NMR spectral analyses.

Using essentially the same procedure, the following compounds are obtained:

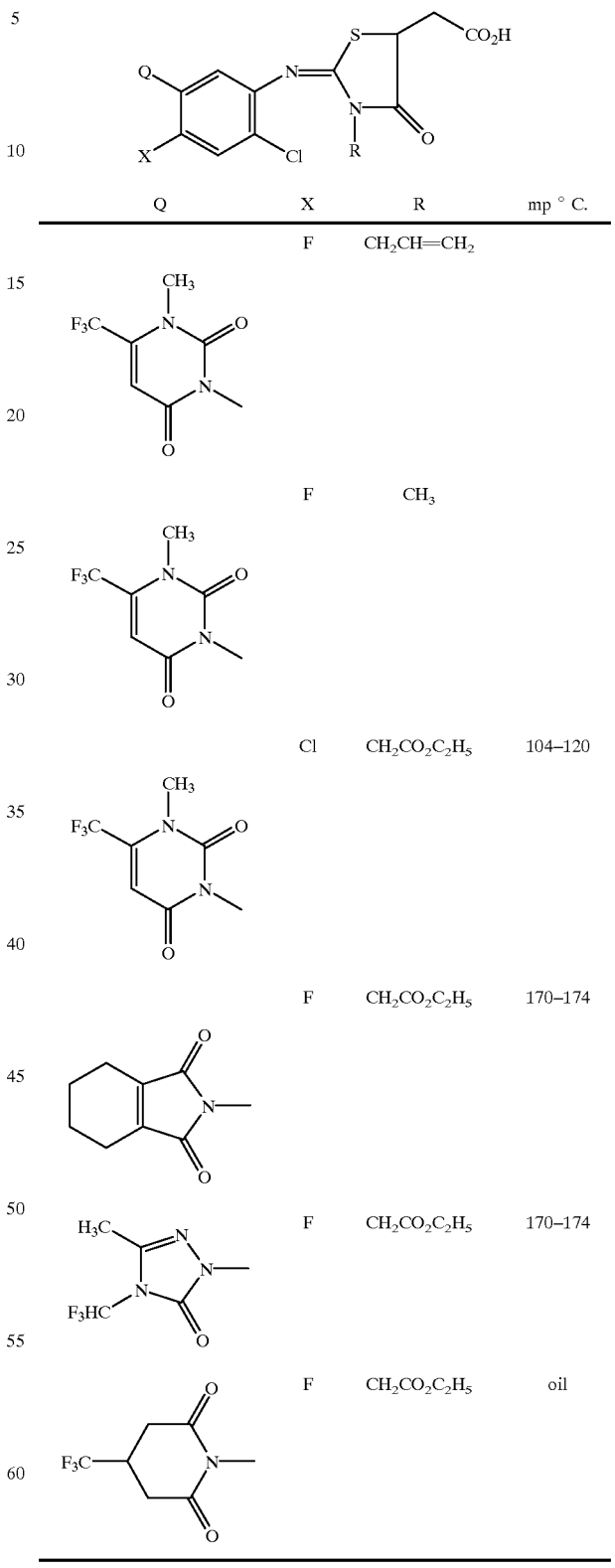

| Q | X | R | mp ° C. |
|---|---|---|---|
| | F | CH$_2$CH=CH$_2$ | |
| | F | CH$_3$ | |
| | Cl | CH$_2$CO$_2$C$_2$H$_5$ | 104–120 |
| | F | CH$_2$CO$_2$C$_2$H$_5$ | 170–174 |
| | F | CH$_2$CO$_2$C$_2$H$_5$ | 170–174 |
| | F | CH$_2$CO$_2$C$_2$H$_5$ | oil |

EXAMPLE 13

Preparation of 3-(Carboxymethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-delta5, alphathiazolidineacetic acid, diethyl ester

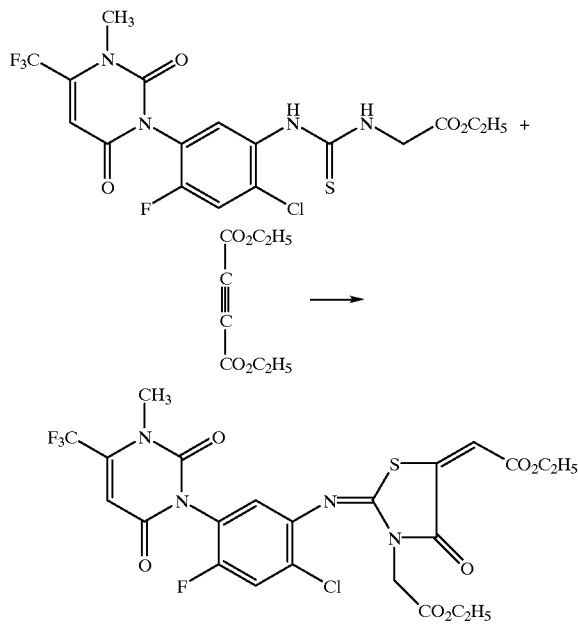

A solution of N-{{2-chloro-5-[3,6-dihydro-3-methyl-2,6-dioxo-4-(trifluoromethyl)-1(2H)-pyrimidinyl]-4-fluorophenyl}(thiocarbamoyl)}glycine, ethyl ester (3.0 g, 6.2 mmol) and diethyl acetylenedicarboxylate (1.06 g, 6.2 mmol) in methanol is refluxed for 3 hours, cooled, and concentrated in vacuo to obtain a glass. Column chromatography of the glass using silica gel and a 3% ethyl acetate in methylene chloride solution gives the title product as a yellow glass (2.49 g) which is identified by $^1$H, $^{13}$C and $^{19}$F NMR spectral analyses.

EXAMPLE 14

Preparation of N-{{{2-chloro-5-[3,6-dihydro-3-methyl-2,6-dioxo-4-(trifluoromethyl)-1(2H)-pyrimidinyl]-4-fluorophenyl}imino}methylene}glycine, ethyl ester

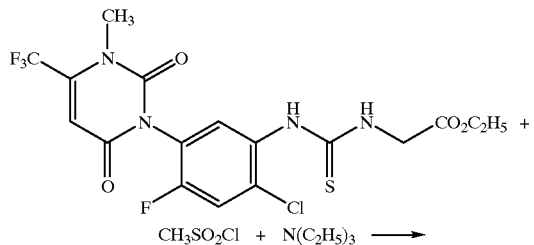

-continued

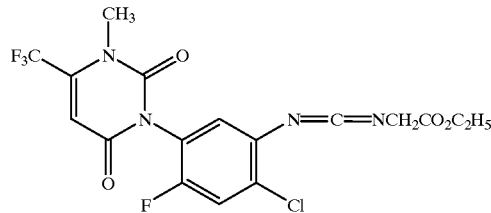

A solution of N-{{2-chloro-5-[3,6-dihydro-3-methyl-2,6-dioxo-4-(trifluoromethyl)-1(2H)-pyrimidinyl]-4-fluorophenyl}(thiocarbamoyl)}glycine, ethyl ester (5.0 g, 10.4 mmol) in methylene chloride is treated sequentially with triethylamine (4.3 mL, 31.1 mmol), 4-dimethylaminopyridine (0.05 g) and methanesulfonyl chloride (1.6 mL, 20.7 mmol) stirred at room temperature for 10 minutes, and partially concentrated in vacuo to obtain a heterogeneous mixture. The heterogeneous mixture is placed onto silica gel and eluted with methylene chloride. The resultant solution is concentrated in vacuo to give the title product as an amber syrup (4.68 g) which is identified by $^1$H and $^{13}$C NMR spectral analyses.

EXAMPLE 15

Preparation of Ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate

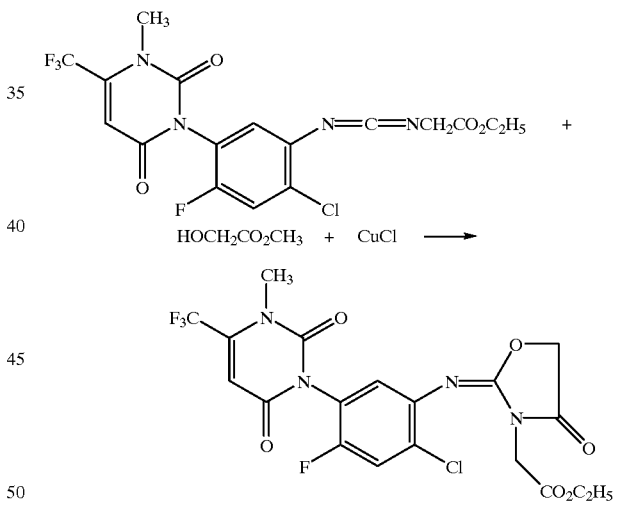

A solution of N-{{{2-chloro-5-[3,6-dihydro-3-methyl-2,6-dioxo-4-(trifluoromethyl)-1(2H)-pyrimidinyl]-4-fluorophenyl}imino}methylene}glycine, ethyl ester (0.63 g, 1.41 mmol) in methylene chloride is treated with methyl glycolate (0.14 g), stirred for 90 minutes, treated with copper(I) chloride (0.05 g), stirred at room temperature for 16 hours, refluxed for 5 hours, and filtered to remove solids. The resultant filtrate is concentrated in vacuo to obtain an amber gum. Flash column chromatography of the gum using silica gel and 20% to 25% ethyl acetate in hexanes solutions gives the title product as an off-white foam (0.37 g, mp 67–87° C.) which is identified by $^1$H and $^{13}$C NMR spectral analyses.

Using essentially the same procedure, the following compounds are obtained:

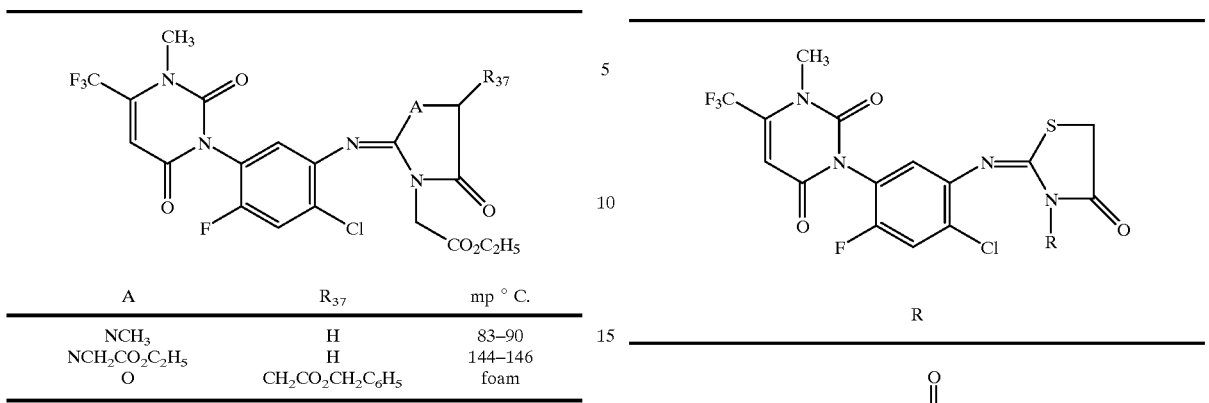

| A | R<sub>37</sub> | mp °C. |
|---|---|---|
| NCH$_3$ | H | 83–90 |
| NCH$_2$CO$_2$C$_2$H$_5$ | H | 144–146 |
| O | CH$_2$CO$_2$CH$_2$C$_6$H$_5$ | foam |

EXAMPLE 16

Preparation of Methyl α-benzyl-2-{{2-chloro-5-[3, 6-dihydro-3-methyl-2,6-dioxo-4-(trifluoromethyl)-1 (2H)-primidinyl]-4-fluorophenyl}imino}-4-oxo-3-thiazolidineacetate, L-

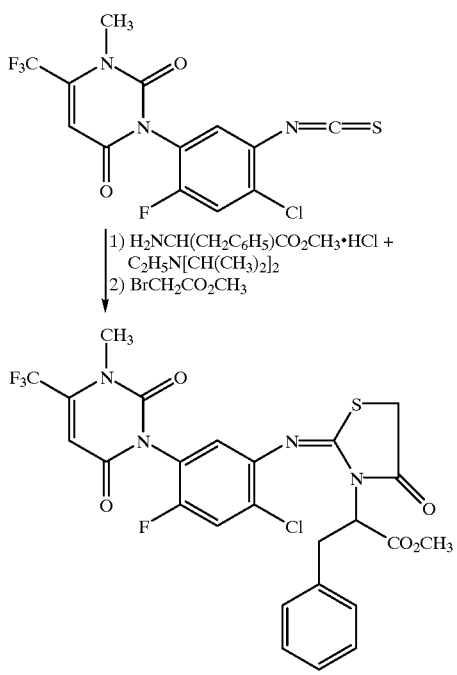

A solution of 2-chloro-5-[3,6-dihydro-3-methyl-2,6-dioxo-4-(trifluoromethyl)-1(2H)-pyrimidinyl]-4-fluorophenyl isothiocyanate (0.38 g, 1.0 mmol) and N,N-diisopropylethylamine (1.0 mL) in tetrahydrofuran is treated with L-phenylalanine, methyl ester, hydrochloride (0.18 g, 1.0 mmol), shaken at 40° C. for 1 hour, treated with methyl bromoacetate (0.46 g, 3.0 mmol), shaken at 40° C. for 16 hours, and concentrated in vacuo to obtain a residue. Column chromatography of the residue using silica gel and 0% to 10% diethyl ether in methylene chloride solutions gives the title product (0.37 g) which is identified by $^1$H and $^{13}$C NMR spectral analyses.

Using essentially the same procedure, the following compounds are obtained:

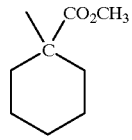

R

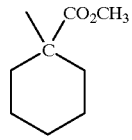

CH(CH$_2$C$_6$H$_5$)CO$_2$CH$_3$
CH(CH$_3$)CO$_2$C(CH$_3$)$_3$
CH(CH$_3$)CO$_2$C$_2$H$_5$
CH(CH$_2$C$_6$H$_4$-p-Cl)CO$_2$CH$_3$
CH(CH$_2$C$_6$H$_4$-p-NO$_2$)CO$_2$CH$_3$
CH(C$_6$H$_4$-p-Cl)CO$_2$C$_2$H$_5$
CH(CH$_2$C$_6$H$_5$)CO$_2$C$_2$H$_5$

CH$_2$C$_6$H$_4$-o-CH$_3$
CH$_2$C$_6$H$_4$-m-CH$_3$
CH$_2$C$_6$H$_4$-m-Cl
CH$_2$C$_6$H$_4$-m-OCH$_3$
CH$_2$C$_6$H$_4$-o-Cl
CH$_2$C$_6$H$_4$-m-CF$_3$
CH$_2$C$_6$H$_4$-p-CF$_3$
CH$_2$C$_6$H$_4$-p-Cl
CH$_2$C$_6$H$_4$-p-Br
CH$_2$C$_6$H$_4$-p-F
CH$_2$C$_6$H$_4$-p-SO$_2$NH$_2$
CH$_2$C$_6$H$_4$-p-N(CH$_3$)$_2$
CH$_2$C$_6$H$_3$-3,4-di-Cl
CH$_2$C$_6$H$_3$-3,5-di-Cl
CH$_2$C$_6$H$_3$-3,4-di-OCH$_3$
CH$_2$C$_6$H$_3$-2,4-di-OCH$_3$
CH$_2$C$_6$H$_3$-3,5-di-CH$_3$
CH$_2$C$_6$H$_3$-3,4-di-CH$_3$
CH$_2$C$_6$H$_3$-3-Cl-4-CH$_3$
CH$_2$C$_6$H$_2$-3,4,5-tri-OCH$_3$
CH$_2$-2-pyridyl
CH$_2$-3-pyridyl
CH$_2$-4-pyridyl

EXAMPLE 17

Preparation of 2-{{2-chloro-5-[3,6-dihydro-3-methyl-2,6-dioxo-4-(trifluoromethyl)-1(2H)-pyrimidinyl]-4-fluorophenyl}imino}-α-methyl-4-oxo-3-thiazolidineacetic acid, L-

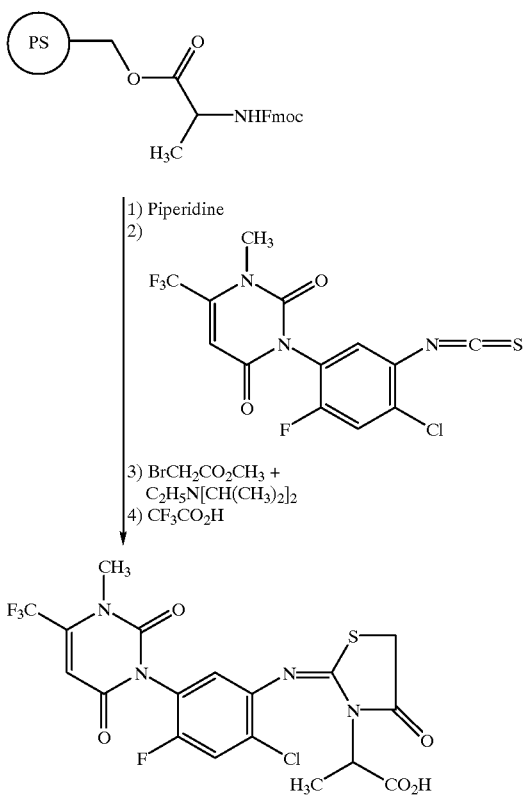

An alanine substituted resin (1.0 mmol) which is N-protected with Fmoc and supported on polystyrene (commercially available as Fmoc-gly-Wang resin from Midwest Bio-tech Inc., Fishers, Ind.) is treated with a 20% piperdine in N,N-dimethylformamide solution to remove the Fmoc protecting group. The solvents are removed and the resin is washed with N,N-dimethylformamide, methanol and methylene chloride, treated with a solution of 2-chloro-5-[3,6-dihydro-3-methyl-2,6-dioxo-4-(trifluoromethyl)-1(2H)-pyrimidinyl]-4-fluorophenyl isothiocyanate (0.57 g, 1.5 mmol) in methylene chloride, and stirred at room temperature for 6 hours. The solvents are removed and the resin is washed with N,N-dimethylformamide, methanol and methylene chloride, diluted with N,N-dimethylformamide, treated with methyl bromoacetate (0.46 g, 3 mmol) and N,N-diisopropylethylamine (1 ml), and stirred overnight at room temperature. The solvents are removed and the resultant resin is washed sequentially with N,N-dimethylformamide, methanol and methylene chloride, air-dried, and cleaved with trifluoroacetic acid. Column chromatography of the resultant reaction mixture using silica gel and a 15% methanol in methylene chloride solution gives the title product (0.55 g) which is identified by $^1$H and $^{13}$C NMR spectral analyses.

Using essentially the same procedure, the following compounds are obtained:

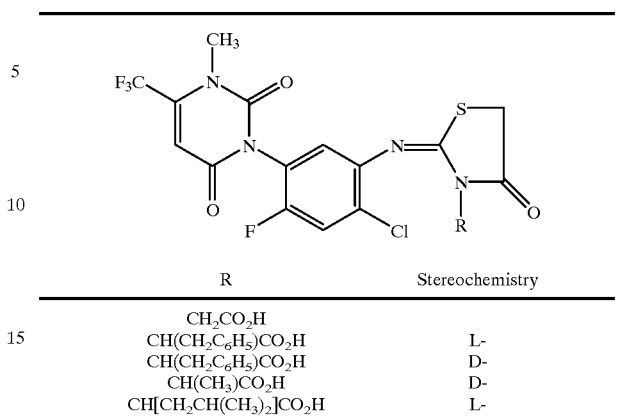

| R | Stereochemistry |
|---|---|
| CH$_2$CO$_2$H | |
| CH(CH$_2$C$_6$H$_5$)CO$_2$H | L- |
| CH(CH$_2$C$_6$H$_5$)CO$_2$H | D- |
| CH(CH$_3$)CO$_2$H | D- |
| CH[CH$_2$CH(CH$_3$)$_2$]CO$_2$H | L- |

EXAMPLE 18

Preparation of 2-[{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid

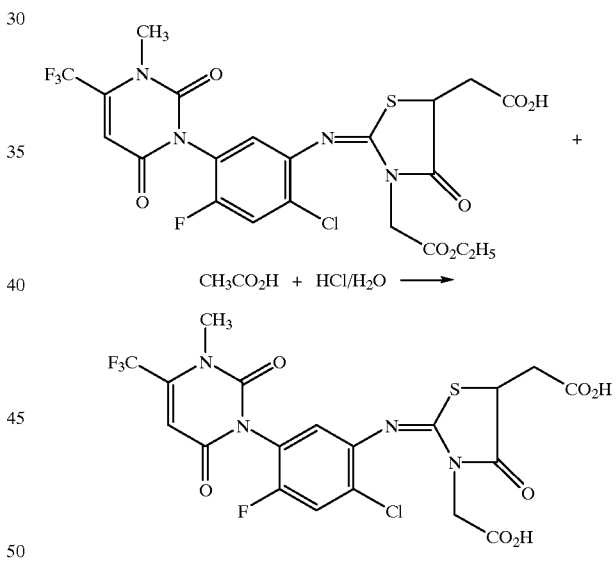

A solution of 2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester (0.5 g, 0.9 mmol) in 10% hydrochloric acid (1.4 mL) and acetic acid (5.6 mL) is stirred at 55° C. for 5 days, and concentrated in vacuo to obtain a yellow glass. Column chromatography of the glass using silica gel and a 5% methanol in methylene chloride solution gives the title product as a white solid which is identified by $^1$H NMR spectral analysis.

Using essentially the same procedure, the following compounds are obtained:

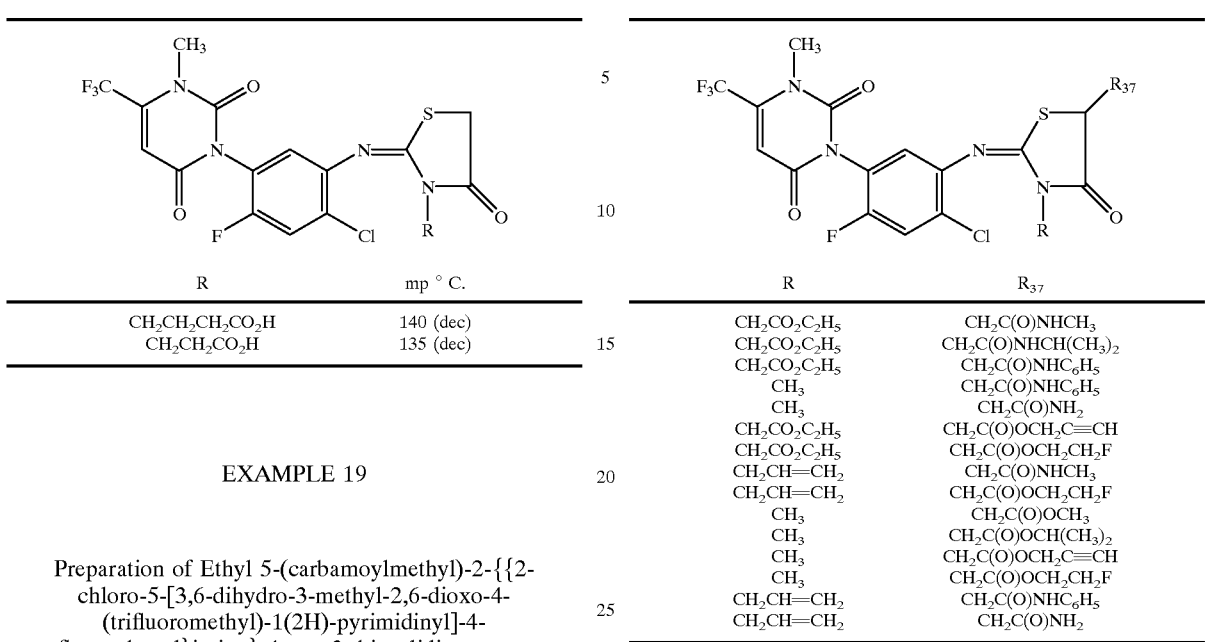

| R | mp °C. |
|---|---|
| CH$_2$CH$_2$CH$_2$CO$_2$H | 140 (dec) |
| CH$_2$CH$_2$CO$_2$H | 135 (dec) |

EXAMPLE 19

Preparation of Ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate A solution of 2-{{2-chloro-5-[3,6-dihydro-3-methyl-2,6-dioxo-4-(trifluoromethyl)-1(2H)-pyrimidinyl]-4-fluorophenyl)-4-oxo-3,5-thiazolidinediacetic acid, 3-ethyl ester (0.5 g, 0.9 mmol) in methylene chloride is treated with oxalyl chloride (0.5 mL), stirred at room temperature for 2 hours, concentrated in vacuo, treated with a 0.5 M ammonia solution in dioxane (2 mL), stirred overnight at room temperature, and concentrated in vacuo to obtain a residue. Chromatography of the residue gives the title product which is identified by $^1$H NMR spectral analysis.

Using essentially the same procedure, the following compounds are obtained:

| R | R$_{37}$ |
|---|---|
| CH$_2$CO$_2$C$_2$H$_5$ | CH$_2$C(O)NHCH$_3$ |
| CH$_2$CO$_2$C$_2$H$_5$ | CH$_2$C(O)NHCH(CH$_3$)$_2$ |
| CH$_2$CO$_2$C$_2$H$_5$ | CH$_2$C(O)NHC$_6$H$_5$ |
| CH$_3$ | CH$_2$C(O)NHC$_6$H$_5$ |
| CH$_3$ | CH$_2$C(O)NH$_2$ |
| CH$_2$CO$_2$C$_2$H$_5$ | CH$_2$C(O)OCH$_2$C≡CH |
| CH$_2$CO$_2$C$_2$H$_5$ | CH$_2$C(O)OCH$_2$CH$_2$F |
| CH$_2$CH=CH$_2$ | CH$_2$C(O)NHCH$_3$ |
| CH$_2$CH=CH$_2$ | CH$_2$C(O)OCH$_2$CH$_2$F |
| CH$_3$ | CH$_2$C(O)OCH$_3$ |
| CH$_3$ | CH$_2$C(O)OCH(CH$_3$)$_2$ |
| CH$_3$ | CH$_2$C(O)OCH$_2$C≡CH |
| CH$_3$ | CH$_2$C(O)OCH$_2$CH$_2$F |
| CH$_2$CH=CH$_2$ | CH$_2$C(O)NHC$_6$H$_5$ |
| CH$_2$CH=CH$_2$ | CH$_2$C(O)NH$_2$ |

EXAMPLE 20

Preparation of Ethyl 2-{{2-chloro-5-[3,6-dihydro-3-methyl-2,6-dioxo-4-(trifluoromethyl)-1(2H)-pryrimidinyl]-4-fluorophenyl}imino}-5-[(methylsulfonyl)carbamoyl]-methyl}-4-oxo-3-thiazolidineacetate

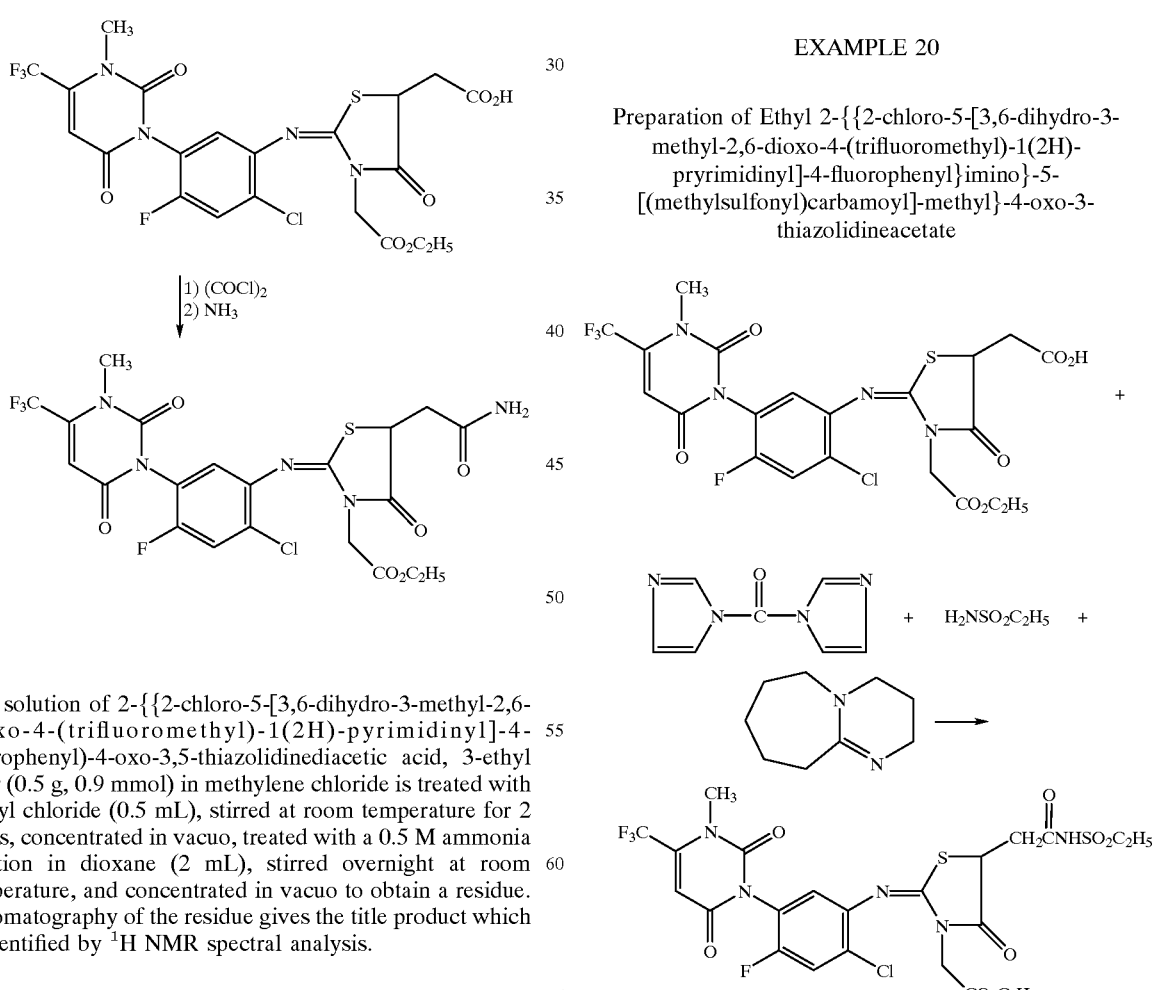

A solution of 2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester (0.5 g, 0.9 mmol) and 1,1'-carbonyldiimidazole (0.23 g, 1.3 mmol) in tetrahydrofuran is refluxed for 2 hours, cooled to room temperature, treated portionwise with a solution of ethanesulfonamide (0.22 g, 1.1 mmol) and 1,8-diazabicyclo[5.4.0]undec-7-ene (0.21 g, 1.3 mmol) in tetrahydrofuran, stirred overnight at room temperature, and poured into dilute hydrochloric acid. The resultant aqueous mixture is extracted with methylene chloride. The organic extracts are combined, washed with water, dried over anhydrous sodium sulfate, and concentrated in vacuo to obtain a tan liquid. Column chromatography of the liquid using silica gel and a 7.5% methanol in methylene chloride solution gives the title product which is identified by $^1$H NMR spectral analyses.

Using essentially the same procedure, the following compounds are obtained:

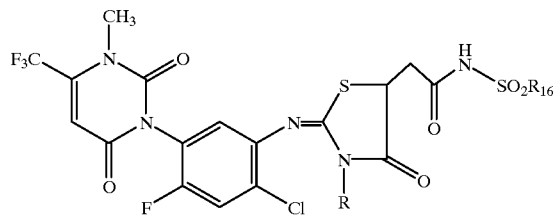

| R | $R_{16}$ |
|---|---|
| $CH_2CH=CH_2$ | $CH_3$ |
| $CH_3$ | $CH_3$ |
| $CH_2CO_2C_2H_5$ | $C_6H_5$ |
| $CH_2CH=CH_2$ | $C_6H_5$ |
| $CH_3$ | $C_6H_5$ |
| $CH_2CO_2C_2H_5$ | $C_2H_5$ |
| $CH_2CH=CH_2$ | $C_2H_5$ |
| $CH_3$ | $C_2H_5$ |
| $CH_2CO_2C_2H_5$ | $CH(CH_3)_2$ |
| $CH_2CH=CH_2$ | $CH(CH_3)_2$ |
| $CH_3$ | $CH(CH_3)_2$ | and

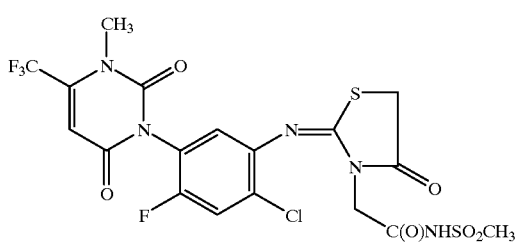

EXAMPLE 21

Preparation of 2-{{2-chloro-5-[3,6-dihydro-3-methyl-2,6-dioxo-1(2H)-pyrimidinyl]-4-fluorophenyl}imino}-4-oxo-3,5-thiazolidinediacetic acid, 3-ethyl ester, 5-ester with ethyl lactate

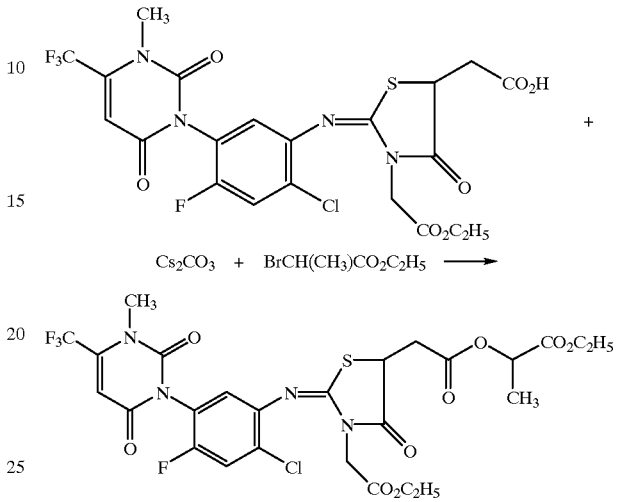

A mixture of 2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester (0.5 g, 0–9 mmol) and cesium carbonate (0.28 g, 0.9 mmol) in N,N-dimethylformamide is heated to 40° C., treated with ethyl 2-bromopropionate (0.16 g, 0.9 mmol), stirred at 40° C. for 45 minutes, concentrated in vacuo, and diluted with methylene chloride. The resultant organic solution is washed with water, dried over anhydrous sodium sulfate, and concentrated in vacuo to obtain a brown oil. Column chromatography of the oil using silica gel and a methylene chloride/diethyl ether/hexanes/acetic acid solution (33:33:33:1) gives the title product as a clear, yellow oil which is identified by $^1$H NMR spectral analyses.

Using essentially the same procedure, the following compounds are obtained:

| R | $R_{37}$ | mp ° C. |
|---|---|---|
| $CH_2CH=CH_2$ | $CH_2CO_2CH(CH_3)CO_2C_2H_5$ | |
| $CH_2CO_2CH_2CH=CH_2$ | H | glass |
| $CH_2CO_2CH_2CO_2CH_3$ | H | glass |
| $CH_2CO_2CH_2CN$ | H | glass |
| $CH_2CO_2CH(CH_3)_2$ | H | glass |
| $CH_2CO_2CH_2C\equiv CH$ | H | glass |
| $CH_2CO_2CH_2$—△ | H | glass |

-continued

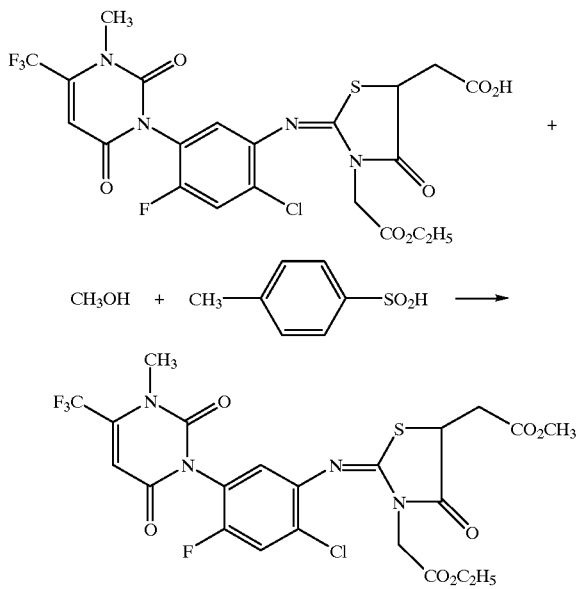

| R | R37 | mp ° C. |
|---|---|---|
| CH2CO2(CH2)2OCH3 | H | glass |
| CH2CO2(CH2)3CH3 | H | glass |
| CH2CO2CH(CH3)CO2CH3 | H | 198–200 |
| CH2CO2-cyclopentyl | H | glass |
| CH2CO2CH2CH(CH3)2 | H | glass |
| CH2CO2CH2-cyclohexyl | H | glass |

EXAMPLE 22

Preparation of 2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl methyl ester

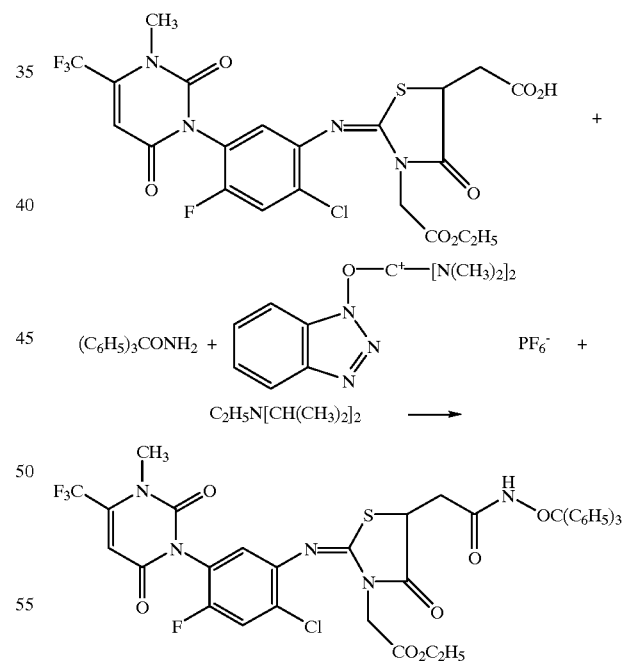

A mixture of 2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester (0.5 g, 0.9 mmol), methanol (1 mL) and a catalytic amount of p-toluenesulfonic acid in methylene chloride is stirred overnight at 40° C., and concentrated in vacuo to obtain a residue. Column chromatography of the residue using silica gel and a methylene chloride/diethyl ether/hexanes/acetic acid solution (33:33:33:1) gives the title product which is identified by $^1$H NMR spectral analyses.

Using essentially the same procedure, the following compounds are obtained:

| R3 | R |
|---|---|
| CH(CH3)2 | CH2CO2C2H5 |
| CH3 | CH2CH=CH2 |
| CH2CH=CH2 | CH2CH=CH2 |
| CH(CH3)2 | CH2CH=CH2 |
| CH2C≡CH | CH2CH=CH2 |

EXAMPLE 23

Preparation of Ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-5-{[(trityloxy)carbamoyl]-methyl}-3-thiazolidineacetate A mixture of 2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester (0.1 g, 0.17 mmol), O-trityihydroxylamine (0.047 g, 0.17 mmol) and (1H-benzotriazol-1-yloxy)bis-(dimethylamino)methylium hexafluorophosphate (0.065 g, 0.17 mmol) is treated with a solution of N,N-diisopropylethylamine (0.04 mL, 0.17 mmol) in N,N- dimethylformamide, stirred at room temperature overnight, and concentrated in vacuo to obtain a residue. Column chromatography of the residue using silica gel and a 5% methanol in methylene chloride solution gives the title product which is identified by ¹H NMR spectral analysis.

Using essentially the same procedure, but substituting methoxylamine hydrochloride for O-tritylhydroxylamine, the following compounds are obtained:

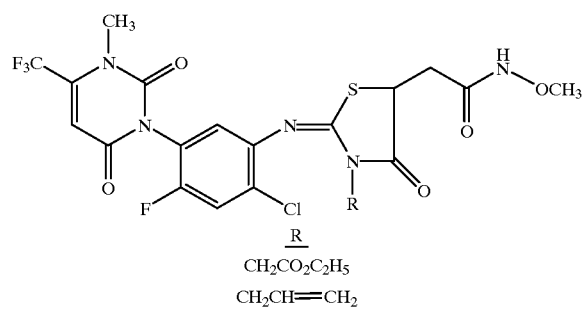

R
CH₂CO₂C₂H₅
CH₂CH=CH₂

EXAMPLE 24

Preparation of Ethyl 2-{{2-chloro-5-[3,6-dihydro-3-methyl-2,6-dioxo-4-(trifluoromethyl)-1(2H)-pyrimidinyl]-4-fluorophenyl}imino}-5-[(hydroxycarbamoyl)methyl]-4-oxo-3-thiazolidineacetate

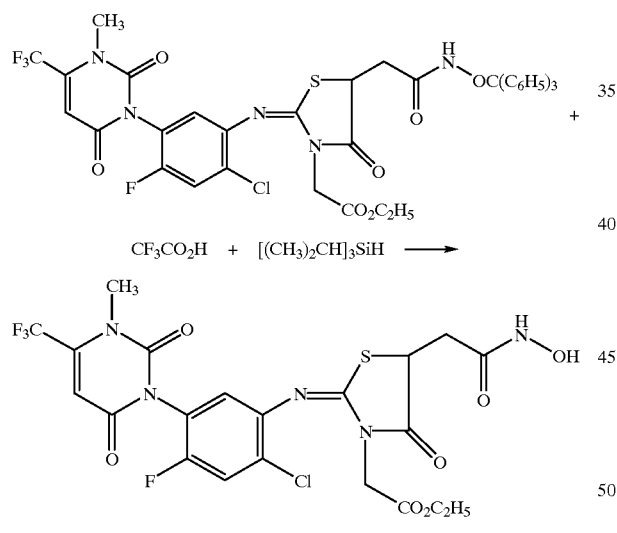

A solution of ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-5-{[(trityloxy)carbamoyl]methyl}-3-thiazolidineacetate (entire sample from Example 23) and triisopropylsilane (1 mL) in trifluoroacetic acid (19 mL) is stirred at room temperature for 4 hours, cooled with an ice-water bath, and filtered. The resultant filtrate is concentrated in vacuo and chased three times with toluene to obtain a solid. Column chromatography of the solid using silica gel and a 7.5% methanol in methylene chloride solution gives the title product as a yellow solid which is identified by ¹H NMR spectral analysis.

Using essentially the same procedure, the following compounds are obtained:

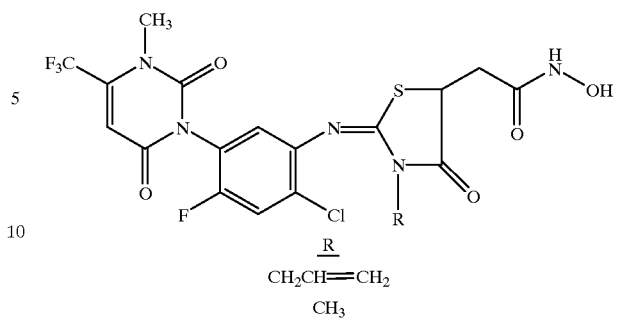

R
CH₂CH=CH₂
CH₃

EXAMPLE 25

Preparation of 2'-Chloro-4'-fluoro-5'-nitroacetanilide

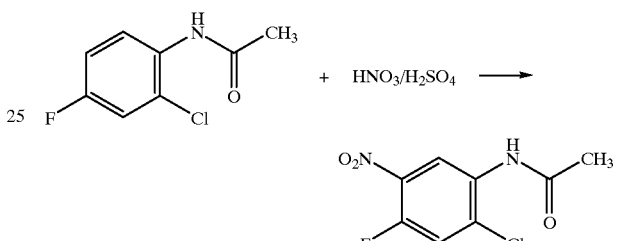

A solution of 2'-chloro-4'-fluoroacetanilide (85.5 g, 456 mmol) in concentrated sulfuric acid is cooled to 0° C., treated slowly with 70% nitric acid (32 mL, 502 mmol) while maintaining the temperature from 5–8° C., stirred at room temperature overnight and poured into water. The resultant aqueous mixture is filtered to obtain a solid which is recrystallized from ethanol to give the title product as pale, yellow plates (27.0 g, mp 158–160° C.).

EXAMPLE 26

Preparation of 5'-Amino-2'-chloro-4'-fluoroacetanilide

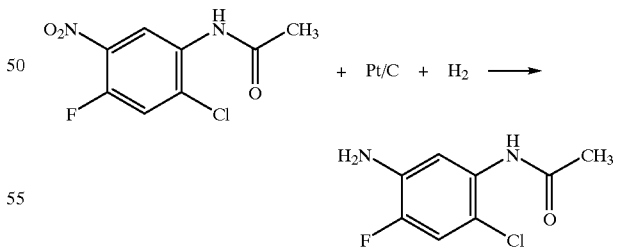

A mixture of 2'-chloro-4'-fluoro-5'-nitroacetanilide (26.1 g, 112 mmol) and 5% platinum on carbon (7.8 g, 30 wt %) in a tetrahydrofuran/ethyl acetate/ethanol solution (1:1:1) is hydrogenated at 50 psi for 22 hours and filtered. The resultant filtrate is concentrated in vacuo to obtain a solid which is recrystallized from an ethanol/water solution to give the title product as off-white plates (14.5 g, mp 176–178° C.).

EXAMPLE 27

Preparation of 2'-Chloro-5'-[3,6-dihydro-2,6-dioxo-4-(trifluoromethyl)-1(2H)-pyrimidinyl]-4'-fluoroacetanilide

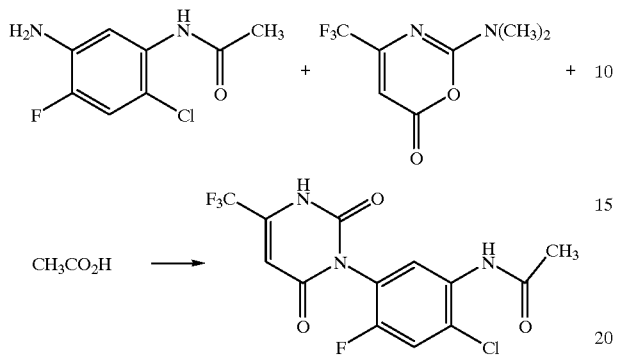

A mixture of 5'-amino-2'-chloro-4'-fluoroacetanilide (1.0 g, 4.9 mmol) and 2-dimethylamino-4-(trifluoromethyl)-6H-1,3-oxazin-6-one (1.0 g, 4.9 mmol) in acetic acid is refluxed for 90 minutes and diluted with water. The resultant aqueous mixture is filtered to obtain the title product as an off-white solid (1.4 g, mp 264–266° C.) which is identified by $^1$H, $^{13}$C and $^9$F NMR spectral analyses.

EXAMPLE 28

Preparation of 2'-Chloro-5'-[3,6-dihydro-3-methyl-2,6-dioxo-4-(trifluoromethyl)-1(2H)-pyrimidinyl]-4'-fluoroacetanilide

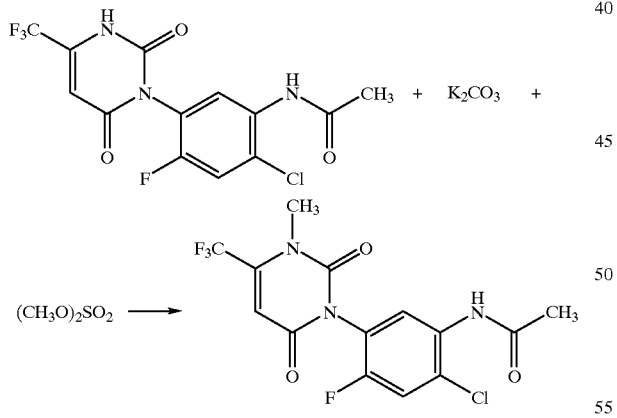

A mixture of 2'-chloro-5'-[3,6-dihydro-2,6-dioxo-4-(trifluoromethyl)-1(2H)-pyrimidinyl]-4'-fluoroacetanilide (0.85 g, 2.3 mmol), potassium carbonate (0.32 g, 2.3 mmol) and dimethylsulfate (0.22 mL, 2.3 mmol) in tetrahydrofuran is refluxed for 90 minutes, cooled to room temperature, and diluted with water and chloroform. The resultant mixture is concentrated in vacuo to obtain an aqueous suspension which is filtered to give the title product as an off-white solid (0.75 g, mp 257–258.5° C.).

EXAMPLE 29

Preparation of 3-(5-Amino-4-chloro-2-fluorophenyl)-1-methyl-6-(trifluoromethyl)-2,4(1H,3H)-pyrimidinedione

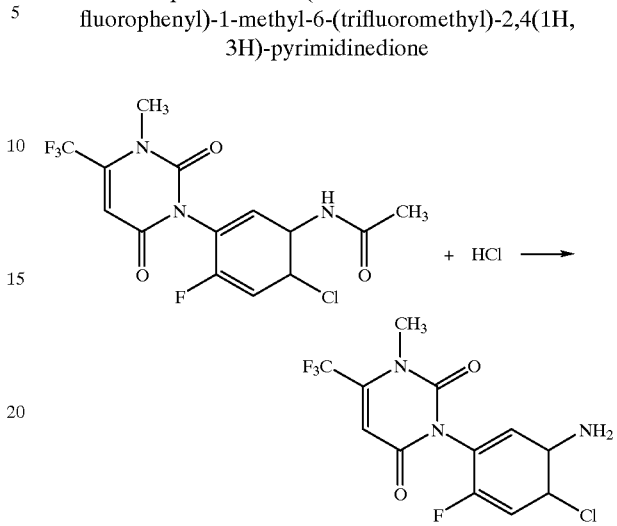

A mixture of 2'-chloro-5'-[3,6-dihydro-3-methyl-2,6-dioxo-4-(trifluoromethyl)-1(2H)-pyrimidinyl]-4'-fluoroacetanilide (24.42 g, 64.3 mmol) in ethanol is treated with 2N hydrochloric acid (200 ml), diluted with tetrahydrofuran, refluxed overnight, cooled to room temperature, partially concentrated in vacuo to remove ethanol and tetrahydrofuran, neutralized with 3N sodium hydroxide solution, and extracted with ethyl acetate. The organic extracts are combined, washed sequentially with saturated sodium hydrogen carbonate solution and brine, dried over anhydrous magnesium sulfate, and concentrated in vacuo to give the title product as a light, brown solid (20.3 g, mp 132–135° C.).

EXAMPLE 30

Preparation of Ethyl 2-{{2-chloro-5-[3,6-dihydro-3-methyl-2,6-dioxo-4-(trifluoromethyl)-1(2H)-primidinyl]-4-fluorophenyl}imino}-5-isopropylidene-4-oxo-3-thiazolidineacetate

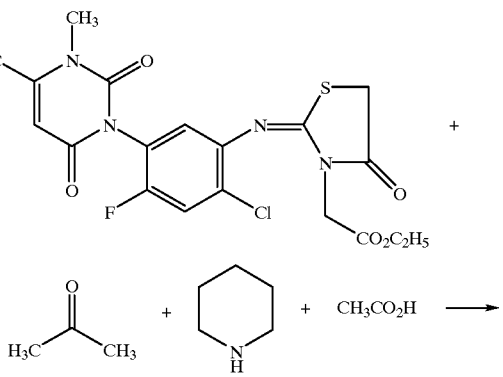

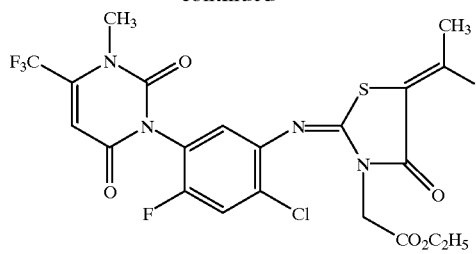

A mixture of ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate (2.0 g, 3.83 mmol), acetone (0.562 mL, 7.65 mmol), piperidine (0.20 mL, 2.02 mmol) and acetic acid (20 μL) in ethanol is refluxed for 90 minutes, treated with additional acetone (0.562 mL), refluxed for 3.5 hours, stirred at room temperature overnight, concentrated in vacuo, and chased with ethyl acetate to obtain a residue. Column chromatography of the residue using silica gel and an ethyl acetate/hexanes solution (1:3) gives the title product as a white solid (1.5 g, mp 67–80° C.).

Using essentially the same procedure, the following compounds are obtained:

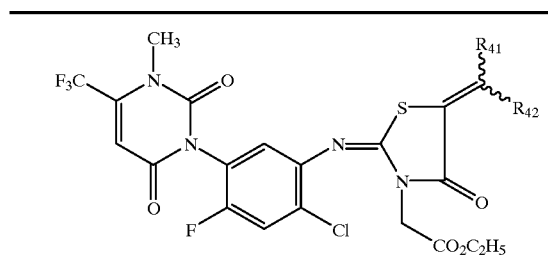

| $R_{41}$ | $R_{42}$ | mp ° C. |
|---|---|---|
| —CH$_2$CH$_2$CH$_2$CH$_2$— | | 84–92 |
| 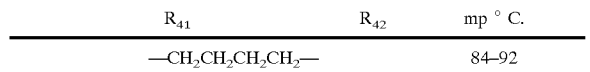 | H | 189–191 |
|  | H | 207–210 |
|  | H | |
|  | H | |

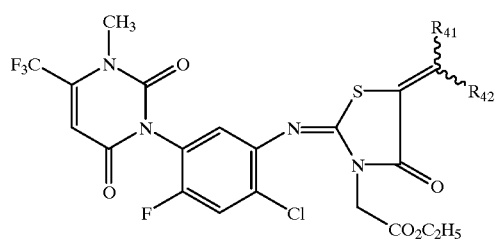

| $R_{41}$ | $R_{42}$ | mp ° C. |
|---|---|---|
|  | H | |
|  | H | |
|  | H | |

EXAMPLE 31

Preparation of 2-{{2-chloro-5-[3,6-dihydro-3-methyl-2,6-dioxo-4-(trifluoromethyl)-1(2H)-pyrimidinyl]-4-fluorophenyl}imino}-5-(o-hydroxybenzyl)-4-oxo-3-thiazolidineacetic acid, ethyl ester, ester with ethyl glycolate

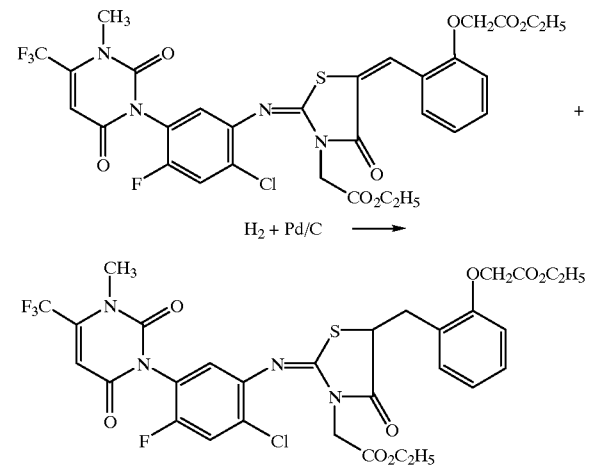

A mixture of 5-[o-(carboxymethoxy)benzylidene]-2-{{2-chloro-5-[3,6-dihydro-3-methyl-2,6-dioxo-4-

(trifluoromethyl)-1(2H)-pyrimidinyl]-4-fluorophenyl}imino}-4-oxo-3-thiazolidineacetic acid, diethyl ester (2.1 g, 2.95 mmol) and 10% palladium on carbon (2.0 g) in ethyl acetate is hydrogenated at 50 psi for 72 hours at room temperature, and filtered to remove solids. The resultant filtrate is concentrated in vacuo to give a residue. Column chromatography of the residue using silica gel and an ethyl acetate/hexanes solution (1:2) gives the title product as a white solid (0.79 g, mp 47–60° C.) which is identified by $^1$H NMR spectral analysis.

Using essentially the same procedure, the following compounds are obtained:

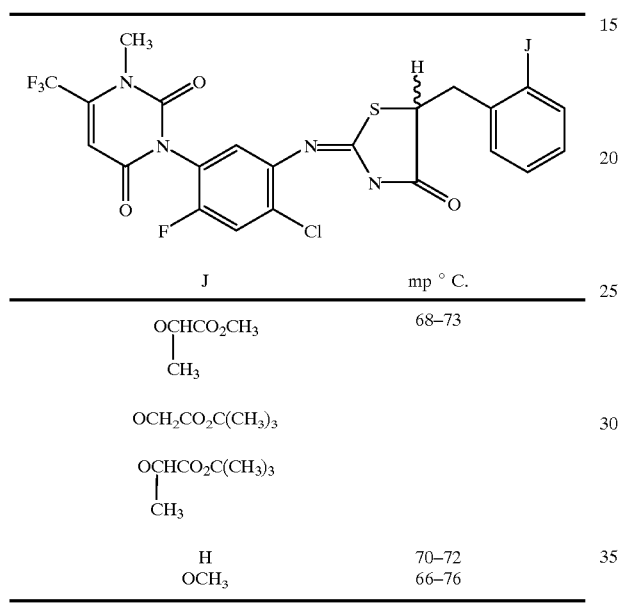

| J | mp ° C. |
|---|---|
| OCHCO$_2$CH$_3$<br>\|<br>CH$_3$ | 68–73 |
| OCH$_2$CO$_2$C(CH$_3$)$_3$ | |
| OCHCO$_2$C(CH$_3$)$_3$<br>\|<br>CH$_3$ | |
| H | 70–72 |
| OCH$_3$ | 66–76 |

EXAMPLE 32

Preparation of 5-[o-(Carboxymethoxy)benzyl]-2-{{2-chloro-5-[3,6-dihydro-3-methyl-2,6-dioxo-4-(trifluoromethyl)-1(2H)-pryrimidinyl]-4-fluorophenyl}imino}-4-oxo-3-thiazolidineacetic acid, 3-ethyl ester

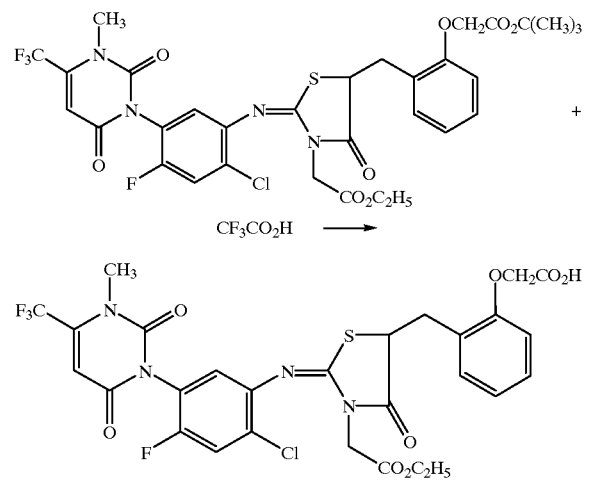

A solution of 5-[o-(carboxymethoxy)benzyl]-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, 5-tert-butyl ethyl ester (2.2 g, 2.96 mmol) in methylene chloride is treated with trifluoroacetic acid (5.5 mL, 71.4 mmol), stirred at room temperature for 7.5 hours, concentrated in vacuo, and chased with toluene and hexanes to obtain a residue. The residue is dissolved in diethyl ether, diluted with hexanes, held overnight at 0° C., and filtered to give the title product as a white solid (2.0 g, mp 93–98° C.).

Using essentially the same procedure, the following compound is obtained:

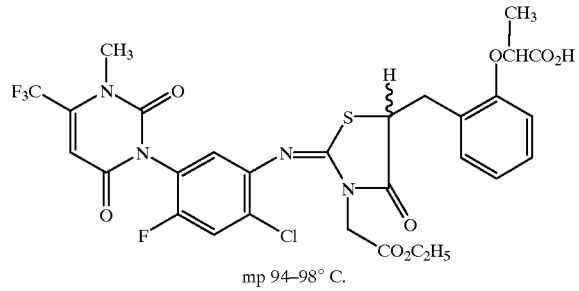

mp 94–98° C.

EXAMPLE 33

Preparation of 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, ethyl ester, 1-oxide

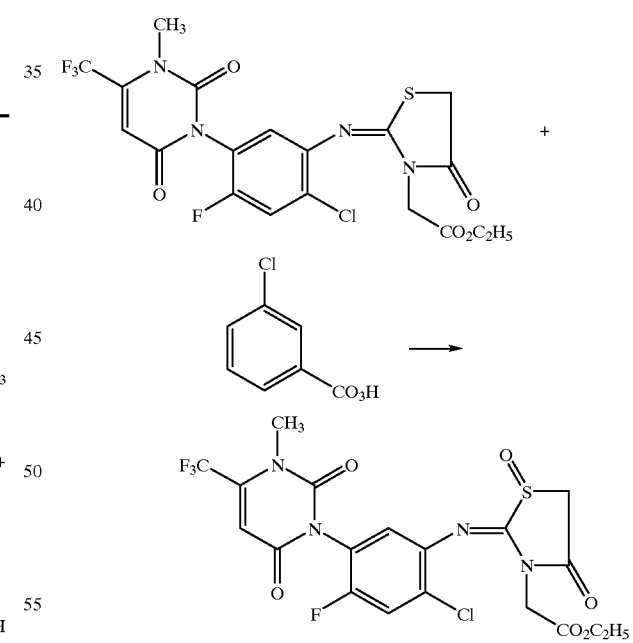

A solution of ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate (3.00 g, 5.74 mmol) in methylene chloride is treated with 3-chloroperoxybenzoic acid (1.23 g, 57%–86% real), stirred at room temperature for 3 hours, and poured into saturated sodium hydrogen carbonate solution. After separating the phases, the organic phase is washed with saturated sodium hydrogen carbonate solution, dried over anhydrous magnesium sulfate, and concentrated in vacuo to obtain a residue. Column chromatography of the residue using silica gel and an ethyl acetate/hexanes solution (2:3) gives the title product as a yellow solid (1.0 g, mp 105–115° C.) which is identified by $^1$H and $^{13}$C NMR spectral analyses.

Following essentially the same procedure, but using at least 2 equivalents of 3-chloroperoxybenzoic acid, 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, ethyl ester, 1,1-dioxide is obtained as a white solid (mp 75–88° C.).

EXAMPLE 34

Preparation of Ethyl 2-{{2-chloro-5-[3,6-dihydro-3-methyl-2,6-dioxo-4-(trifluoromethyl)-1(2H)-primidinyl]-4-fluorophenyl}imino}-5-(hydroxyethyl)-4-oxo-3-thiazolidineacetate

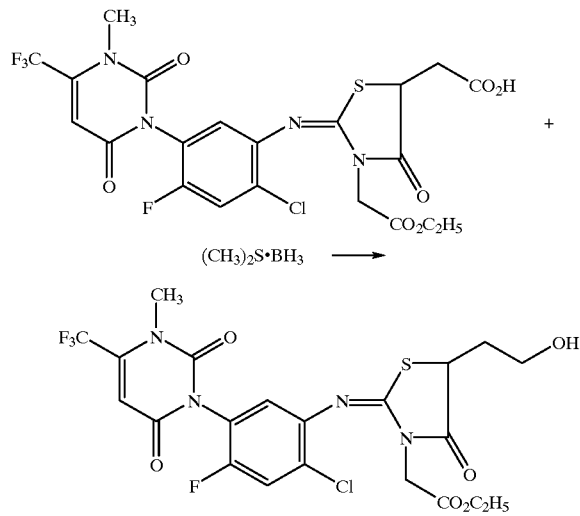

A mixture of 2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester (2.0 g, 3.44 mmol) and borane-methyl sulfide complex (0.36 g, 3.8 mmol) in tetrahydrofuran is stirred at 40–45° C. for 2 days with additional borane-methyl sulfide complex (2×0.36 g) being added at equal intervals. The reaction mixture is then cooled to room temperature, treated with methanol (5 mL), stirred overnight at room temperature, and concentrated in vacuo to obtain a glass. Column chromatography of the glass using silica gel and 2% to 10% ethyl acetate in methylene chloride solutions gives the title product (0.46 g, mp 137–139° C.).

EXAMPLE 35

Preparation of 2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 3-ethyl ester

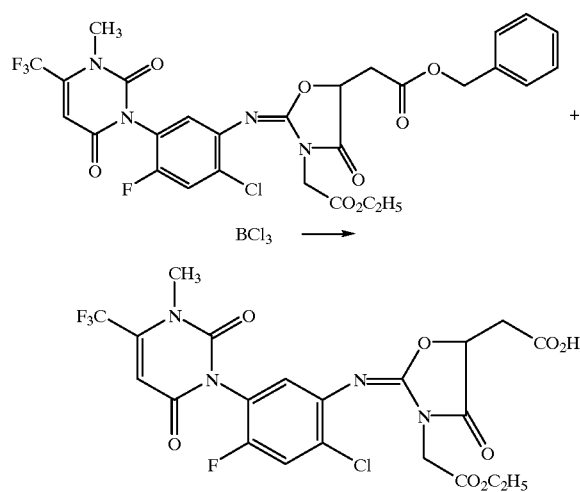

A solution of 2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 5-benzyl ethyl ester (0.65 g, 1.0 mmol) in methylene chloride is cooled to 0° C., treated with boron trichloride (1 mL of a 1M solution in methylene chloride), stirred at 0° C. for 30 minutes, treated with additional boron trichloride (1 mL of a 1M solution in methylene chloride), stirred at room temperature for 90 minutes, and poured into an ice-water mixture. The resultant aqueous mixture is extracted with methylene chloride. The organic extracts are combined, washed with brine, dried over anhydrous magnesium sulfate, and concentrated in vacuo to give the title product (0.2 g) which is identified by $^1$H and $^{13}$C NMR spectral analyses.

EXAMPLE 36

Preparation of 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid

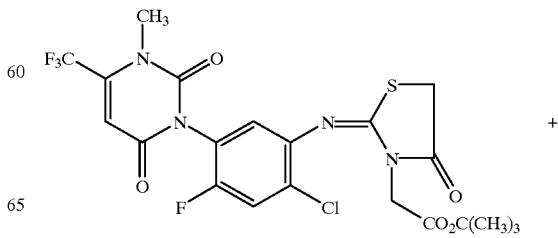

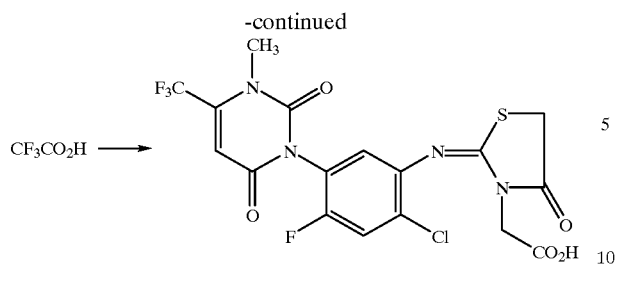

A solution of tert-butyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate (41.93 g, 76.1 mmol) in trifluoroacetic acid is stirred at room temperature for 3 hours, stirred at 35° C. for 1 hour, and concentrated in vacuc to obtain a yellow liquid. A solution of the yellow liquid in diethyl ether is cooled and filtered to obtain a solid. The solid is washed with diethyl ether and air-dried to give the title product as a white solid (31.6 g) which is identified by $^1$H and $^{13}$C NMR spectral analyses.

EXAMPLE 37

Postemergence Herbicidal Evaluation of Test Compounds

The postemergence herbicidal activity of the compounds of the present invention is demonstrated by the following tests wherein a variety of dicotyledonous and monocotyledonous plants are treated with test compounds. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.0156 kg to 0.500 kg per hectare of active compound when applied to the plants through a spray nozzle operating at 40 psi for a predetermined time. After spraying, the plants are placed on greenhouse benches and are cared for in accordance with conventional greenhouse procedures. From four to five weeks after treatment, the seedling plants are examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this postemergence herbicidal evaluation are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
|---|---|---|
| 9 | Complete kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |

A ▓ blank space ▓ indicates that no evaluation was conducted.

PLANT SPECIES EMPLOYED IN HERBICIDAL EVALUATIONS

| Header Abbr. | Common Name | Scientific Name |
|---|---|---|
| ABUTH | Velvetleaf | *Abutilon theophrasti*, Medic. |
| AMBEL | Ragweed, Common | *Ambrosia artemisifolia*, L. |
| CASOB | Sicklepod | *Cassia obtusifolia*, L. |
| CHEAL | Lambsquarters, Common | *Chenopodium album*, L. |
| GALAP | Galium | *Galium aparine* |
| IPOHE | Morningglory, Ivyleaf | *Ipomoea hederacea*, (L.) Jacq. |
| IPOSS | Morningglory Spp. | *Ipomoea* Spp. |
| ECHCG | Barnyardgrass | *Echinochloa crus-galli*, (L.) Beau |
| SETVI | Foxtail, Green | *Setaria viridis*, (L.) Beau |
| GLXMAW | Soybean, Williams | *Glycine max*, (L.) Merr. cv Williams |
| GLXMA | Soybean | *Glycine max*, (L.) Merr. |
| ORYSAT | Rice, Tebonnet | *Oryza sativa*, (L.) Tebonnet |
| TRZAWR | Wheat, Winter, cv Riband | *Triticum aestivum*, cv Riband |
| ZEAMX | Corn, Field | *Zea mays*, L. |

COMPOUNDS EVALUATED AS HERBICIDAL AGENTS

| Compound Number | |
|---|---|
| 1 | N-{4-chloro-2-fluoro-5-[(3-methyl-4-oxo-2-thiazolidinylidene)amino]phenyl}-1-cyclohexene-1,2-dicarboximide |
| 2 | N-{5-[(3-allyl-4-oxo-2-thiazolidinylidene)amino]-4-chloro-2-fluorophenyl}-1-cyclohexene-1,2-dicarboximide |
| 3 | N-{4-chloro-2-fluoro-5-[(4-oxo-3-phenyl-2-thiazolidinylidene)amino]phenyl}-1-cyclohexene-1,2-dicarboximide |
| 4 | N-{4-chloro-2-fluoro-5-(3,5-dimethyl-4-oxo-2-thiazolidinylidene)amino]phenyl}-1-cyclohexene-1,2-dicarboximide |
| 5 | N-{4-chloro-2-fluoro-5-[(5-fluoro-3-methyl-4-oxo-2-thiazolidinylidene)amino]phenyl}-1-cyclohexene-1,2-dicarboximide |
| 6 | N-{4-chloro-5-[(5-ethyl-3-methyl-4-oxo-2-thiazolidinylidene)amino]-2-fluorophenyl}-1-cyclohexene-1,2-dicarboximide |
| 7 | 3-{4-Chloro-2-fluoro-5-[3-methyl-4-oxo-2-thiazolidinylidene)amino]phenyl}-1-methyl-6-(trifluoromethyl)-2,4(1H,3H)-pyrimidinedione |

COMPOUNDS EVALUATED AS HERBICIDAL AGENTS

| Compound Number | |
|---|---|
| 8 | Ethyl 2-{{2-chloro-5-[3,6-dihydro-3-methyl-2,6-dioxo-4-(trifluoromethyl)-1(2H)pyrimidinyl]-4-fluorophenyl}imino}-4-oxo-3-thiazolidineacetate |
| 9 | 3-{4-Chloro-5-[(3,5-dimethyl-4-oxo-2-thiazolidinylidene)amino]-2-fluorophenyl}-1-methyl-6-trifluoromethyl)-2,4(1H,3H)-pyrimidinedione |
| 10 | 3-{4-Chloro-5-[(5-ethyl-3-methyl-4-oxo-2-thiazolidinylidene)amino]-2-fluorophenyl}-1-methyl-6-trifluoromethyl-2,4(1H,3H)-pyrimidinedione |
| 11 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-fluoro-4-oxo-3-thiazolidineacetate |
| 12 | Ethyl 2-{{2-chloro-5-[3,6-dihydro-3-methyl-2,6-dioxo-4-(trifluoromethyl)-1(2H)-pyrimidinyl]-4-fluorophenyl}imino-5-methyl-4-oxo-3-thiazolidineacetate |
| 13 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-ethyl-4-oxo-3-thiazolidineacetate |
| 14 | 3-(Carboxymethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-delta5,alpha-thiazolidineacetic acid, diethyl ester |
| 15 | Ethyl 5-{{2-chloro-5-[3,6-dihydro-3-methyl-2,6-dioxo-4-(trifluoromethyl)-1(2H)-pyrimidinyl]-4-fluorophenyl}imino}-7-oxo-4-thia-6-azaspiro[2.4]-heptane-6-acetate |
| 16 | 2-{{2-Chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester |
| 17 | Methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 18 | Ethyl 2-{{2-chloro-5-[3,6-dihydro-3-methyl-2,6-dioxo-4-(trifluoromethyl)-(2H)-pyrimidinyl]-4-fluorophenyl}imino}-5-cyclopentylidene-4-oxo-3-thiazolidineacetate |
| 19 | Ethyl 5-benzylidene-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 20 | Ethyl 2-{(2-chloro-5-[3,6-dihydro-3-methyl-2,6-dioxo-4-(trifluoromethyl)-1(2H)-pyrimidinyl]-4-fluorophenyl}imino}-5-isopropylidene-4-oxo-3-thiazolidineacetate |
| 21 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-(p-fluorobenzylidene)-4-oxo-3-thiazolidineacetate |
| 22 | Ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-oxazolidineacetate |
| 23 | 3-{4-Chloro-5-{[3-(dimethylamino)-4-oxo-2-thiazolidinylidine]amino}-2-fluorophenyl}-1-methyl-6-(trifluoromethyl)-2,4(1H,3H)-pyrimidinedione |
| 24 | Ethyl 5-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 25 | Ethyl 2-{{2-chloro-5-[3,6-dihydro-3-methyl-2,6-dioxo-4-(trifluoromethyl)-1(2H)-pyrimidinyl]-4-fluorophenyl}imino}-3-methyl-5-oxo-1-imidazolidineacetate |
| 26 | 3-{5-[(3-Benzyl-4-oxo-2-thiazolidinylidene)amino]-4-chloro-2-fluorophenyl}-1-methyl-6-(trifluoromethyl)-2,4(1H,3H)-pyrimidinedione |
| 27 | 3-{5-[(3-Allyl-4-oxo-2-thiazolidinylidene)amino]-4-chloro-2-fluorophenyl}-1-methyl-6-(trifluoromethyl)-2,4(1H,3H)-pyrimidinedione |
| 28 | Methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinepropionate |
| 29 | Methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinebutyrate |
| 30 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3-thiazolidinepropionic acid |
| 31 | 2-{{2-Chloro-5-[3,6-dihydro-3-methyl-2,6-dioxo-4-(trifluoromethyl)-(2H)-pyrimidinyl]-4-fluorophenyl}imino}-4-oxo-3-thiazolidinepropionic acid |
| 32 | Ethyl 2-{{2,4-dichloro-5-[3,6-dihydro-3-methyl-2,6-dioxo-4-(trifluoromethyl)-1(2H)-pyrimidinyl]-phenyl}imino}-4-oxo-3-thiazolidinepropionate |
| 33 | 2-{{2,4-Dichloro-5-[3,6-dihydro-3-methyl-2,6-dioxo-4-(trifluoromethyl)-1(2H)-pyrimidinyl]phenyl}imino}-4-oxo-3,5-thiazolidinediacetic acid, 3-ethyl ester |
| 34 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-1,3-imidazolidinediacetic acid, diethyl ester |
| 35 | Diethyl ({{2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinyl}methyl}phosphonate |
| 36 | Ethyl 2-{{2-chloro-5-[4-(difluoromethyl-4,5-dihydro-3-methyl-5-oxo-1H-1,2,4-triazol-1-yl]-4-fluorophenyl}imino}-3-thiazolidineacetate |
| 37 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-(o-methoxybenzyl)-4-oxo-3-thiazolidineacetate |
| 38 | 2-{{2-Chloro-5-[3,6-dihydro-3-methyl-2,6-dioxo-4-(trifluoromethyl)-1(2H)-pyrimidinyl]-4-fluorophenyl}imino}-N-(methylsulfonyl)-4-oxo-3-thiazolidineacetamide |
| 39 | 3-{4-Chloro-2-fluoro-5-[(4-oxo-2-thiazolidinylidene)amino]phenyl}-1-methyl-6-(trifluoromethyl)-2,4(1H,3H)-pyrimidinedione |
| 40 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 5-benzyl ethyl ester |
| 41 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 3-ethyl ester |
| 42 | 2-{{2-Chloro-5-[3,6-dihydro-3-methyl-2,6-dioxo-4-(trifluoromethyl)-1(2H)-pyrimidinyl]-4-fluorophenyl}imino}-5-(o-hydroxybenzyl)-4-oxo-3-thiazolidineacetic acid, ethyl ester, ester with ethyl glycolate |
| 43 | tert-Butyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 44 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetanilide |
| 45 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, ethyl ester, 1-oxide |
| 46 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, ethyl ester, 1,1-dioxide |
| 47 | Ethyl 2-{[2-chloro-5-(1-cyclohexene-1,2-dicarboximido)-4-fluorophenyl]imino}-4-oxo-3-thiazolidineacetate |
| 48 | 2-{[2-Chloro-5-(1-cyclohexene-1,2-dicarboximido)-4-fluorophenyl]imino}-4-oxo-3,5-thiazolidinediacetic acid |

COMPOUNDS EVALUATED AS HERBICIDAL AGENTS

| Compound Number | |
|---|---|
| 49 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-(hydroxyethyl)-4-oxo-3-thiazolidineacetate |
| 50 | 2-{{2-Chloro-5-[3,6-dihydro-3-methyl-2,6-dioxo-4-(trifluoromethyl)-1(2H)-pyrimidinyl]-4-fluorophenyl}imino}-5-(o-hydroxybenzyl)-4-oxo-3-thiazolidineacetic acid, ethyl ester, ester with methyl lactate |
| 51 | 2-{{2-Chloro-5-[3,6-dihydro-3-methyl-2,6-dioxo-4-(trifluoromethyl)-1(2H)-pyrimidinyl]-4-fluorophenyl}imino}-α-methyl-4-oxo-3-thiazolidineacetic acid, L- |
| 52 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid |
| 53 | α-Benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, L- |
| 54 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl methyl ester |
| 55 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl isopropyl ester |
| 56 | Ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 57 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-[(methylcarbamoyl)methyl]-4-oxo-3-thiazolidineacetate |
| 58 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-thiazolidenediacetic acid, 3-ethyl (2-propynyl) ester, (2:1) mixture with di-2-propynyl ester |
| 59 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl (2-propynyl) ester |
| 60 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl isopropyl ester |
| 61 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid |
| 62 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetic acid |
| 63 | 2-{{2-Chloro-5-[3,6-dihydro-3-methyl-2,6-dioxo-4-(trifluoromethyl)-1(2H)-pyrimidinyl]-4-fluorophenyl}imino}-3-methyl-4-oxo-5-thiazolidineacetic acid |
| 64 | Methyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate |
| 65 | Allyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate |
| 66 | Isopropyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate |
| 67 | 2-Propynyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate |
| 68 | Ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-5-[(phenylcarbamoyl)methyl]-3-thiazolidineacetate |
| 69 | α-Benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, D- |
| 70 | 2-{{2-Chloro-5-[3,6-dihydro-3-methyl-2,6-dioxo-4-(trifluoromethyl)-1(2H)-pyrimidinyl]-4-fluorophenyl}imino}-α-methyl-4-oxo-3-thiazolidineacetic acid, D- |
| 71 | α-Isobutyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, L- |
| 72 | Methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L- |
| 73 | 3-{4-Chloro-2-fluoro-5-{[4-oxo-3-(tetrahydro-2-oxo-3-furyl)-2-thiazolidinylidene]amino}phenyl-1-methyl-6-(trifluoromethyl)-2,4(1H,3H)-pyrimidinedione |
| 74 | Methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, D- |
| 75 | tert-Butyl 2-{{2-chloro-5-[3,6-dihydro-3-methyl-2,6-dioxo-4-(trifluoromethyl)-1(2H)-pyrimidinyl]-4-fluorophenyl}imino}-α-methyl-4-oxo-3-thiazolidineacetate, L- |
| 76 | Ethyl 2-{{2-chloro-5-[3,6-dihydro-3-methyl-2,6-dioxo-4-(trifluoromethyl)-1(2H)-pyrimidinyl]-4-fluorophenyl}imino}-α-methyl-4-oxo-3-thiazolidineacetate, L- |
| 77 | Methyl α-(p-chlorobenzyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, DL- |
| 78 | Methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-α-(p-nitrobenzyl)-3-thiazolidineacetate, L- |
| 79 | Ethyl α-(p-chlorophenyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, DL- |
| 80 | Ethyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L- |
| 81 | Methyl 1-{2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinyl}-cyclohexanecarboxylate |
| 82 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl 2-fluoroethyl ester |
| 83 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-[(methoxycarbamoyl)methyl]-4-oxo-3-thiazolidineacetate |
| 84 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-N-methyl-4-oxo-5-thiazolidineacetamide |
| 85 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-N-methoxy-4-oxo-5-thiazolidineacetamide |

COMPOUNDS EVALUATED AS HERBICIDAL AGENTS

| Compound Number | |
|---|---|
| 86 | 2-Fluoroethyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate |
| 87 | 2-{{2-Chloro-5-[3,6-dihydro-3-methyl-2,6-dioxo-1(2H)-pyrimidinyl]-4-fluorophenyl}imino}-4-oxo-3,5-thiazolidinediacetic acid, 3-ethyl ester, 5-ester with ethyl lactate |
| 88 | Methyl 2-{{2-chloro-5-[3,6-dihydro-3-methyl-2,6-dioxo-4-(trifluoromethyl)-1(2H)-pyrimidinyl]-4-fluorophenyl}imino}-3-methyl-4-oxo-5-thiazolidineacetate |
| 89 | Isopropyl 2-{{2-chloro-5-[3,6-dihydro-3-methyl-2,6-dioxo-4-(trifluoromethyl)-1(2H)-pyrimidinyl]-4-fluorophenyl}imino}-3-methyl-4-oxo-5-thiazolidineacetate |
| 90 | 2-Propynyl 2-{{2-chloro-5-[3,6-dihydro-3-methyl-2,6-dioxo-4-(trifluoromethyl)-1(2H)-pyrimidinyl]-4-fluorophenyl}imino}-3-methyl-4-oxo-5-thiazolidineacetate |
| 91 | 2-{{2-Chloro-5-[3,6-dihydro-3-methyl-2,6-dioxo-4-(trifluoromethyl)-1(2H)-pyrimidinyl]-4-fluorophenyl}imino}-3-methyl-4-oxo-5-thiazolidineacetanilide |
| 92 | 2-{{2-Chloro-5-[3,6-dihydro-3-methyl-2,6-dioxo-4-(trifluoromethyl)-1(2H)-pyrimidinyl]-4-fluorophenyl}imino}-3-methyl-4-oxo-5-thiazolidineacetamide |
| 93 | 2-Fluoroethyl 2-{{2-chloro-5-[3,6-dihydro-3-methyl-2,6-dioxo-4-(trifluoromethyl)-1(2H)-pyrimidinyl]-4-fluorophenyl}imino}-3-methyl-4-oxo-5-thiazolidineacetate |
| 94 | 3-Allyl-2-{{2-chloro-5-[3,6-dihydro-3-methyl-2,6-dioxo-1(2H)-pyrimidinyl]-4-fluorophenyl}imino}-4-oxo-5-thiazolidineacetic acid, ester with ethyl lactate, (R,S)- |
| 95 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-{[(methylsulfonyl)carbamoyl]methyl}-4-oxo-3-thiazolidineacetate |
| 96 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-N-(methylsulfonyl)-4-oxo-5-thiazolidineacetamide |
| 97 | 2-{{2-Chloro-5-[3,6-dihydro-3-methyl-2,6-dioxo-4-(trifluoromethyl)-1(2H)-pyrimidinyl]-4-fluorophenyl}imino}-3-methyl-N-(methylsulfonyl)-4-oxo-5-thiazolidineacetamide |
| 98 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-[(hydroxycarbamoyl)methyl]-4-oxo-3-thiazolidineacetate |
| 99 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetamide |
| 100 | Ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-5-{[(phenylsulfonyl)carbamoyl]methyl}-3-thiazolidineacetate |
| 101 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-N-(phenylsulfonyl)-5-thiazolidineacetamide |
| 102 | 2-{{2-Chloro-5-[3,6-dihydro-3-methyl-2,6-dioxo-4-(trifluoromethyl)-1(2H)-pyrimidinyl]-4-fluorophenyl}imino}-3-methyl-4-oxo-N-(phenylsulfonyl)-5-thiazolidineacetamide |
| 103 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-{[(ethylsulfonyl)carbamoyl]methyl}-4-oxo-3-thiazolidineacetate |
| 104 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-N-(ethylsulfonyl)-4-oxo-5-thiazolidineacetamide |
| 105 | 2-{{2-Chloro-5-[3,6-dihydro-3-methyl-2,6-dioxo-4-(trifluoromethyl)-1(2H)-pyrimidinyl]-4-fluorophenyl}imino}-N-(ethylsulfonyl)-3-methyl-4-oxo-5-thiazolidineacetamide |
| 106 | Allyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 107 | 2-Methoxyethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 108 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, ester with methyl glycolate |
| 109 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, ester with glycolonitrile |
| 110 | Isopropyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 111 | Butyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 112 | 2-{{2-Chloro-5-[4-(difluoromethyl)-4,5-dihydro-3-methyl-5-oxo-1H-1,2,4-triazol-1-yl]-4-fluorophenyl}imino}-4-oxo-3,5-thiazolidinediacetic acid, 3-ethyl ester |
| 113 | 5-[o-(Carboxymethoxy)benzyl]-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, 3-ethyl ester |
| 114 | 5-[o-(1-Carboxyethoxy)benzyl]-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, 3-ethyl ester |
| 115 | 2-Propynyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 116 | 2-{{2-Chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, ester with methyl lactate |
| 117 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-{[(isopropylsulfonyl)carbamoyl]methyl}-4-oxo-3-thiazolidineacetate |
| 118 | 3-Allyl-2-{{2-chloro-5-[3,6-dihydro-3-methyl-2,6-dioxo-4-(trifluoromethyl)-1(2H)-pyrimidinyl]-4-fluorophenyl}imino}-N-(isopropylsulfonyl)-4-oxo-5-thiazolidineacetamide |
| 119 | 2-{{2-Chloro-5-[3,6-dihydro-3-methyl-2,6-dioxo-4-(trifluoromethyl)-1(2H)-pyrimidinyl]-4-fluorophenyl}imino}-N-(isopropylsulfonyl)-3-methyl-4-oxo-5-thiazolidineacetamide |
| 120 | Cyclopentyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 121 | Isobutyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 122 | 3-{4-Chloro-2-fluoro-5-[(3-furfuryl-4-oxo-2-thiazolidinylidene)amino]phenyl}-1-methyl-6-(trifluoromethyl)-2,4(1H,3H)-pyrimidinedione |
| 123 | Cyclohexylmethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |

COMPOUNDS EVALUATED AS HERBICIDAL AGENTS

| Compound Number | |
|---|---|
| 124 | Cyclopropylmethyl 2-{{2-chloro-5-[3,6-dihydro-3-methyl-2,6-dioxo-4-(trifluoromethyl)-1(2H)-pyrimidinyl]-4-fluorophenyl}imino)-4-oxo-3-thiazolidineacetate |
| 125 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-(methylthio)-4-oxo-3-thiazolidineacetate |
| 126 | Ethyl 5-chloro-2-{{2-chloro-5-[3,6-dihydro-3-methyl-2,6-dioxo-4-(trifluoromethyl)-1(2H)-pyrimidinyl]-4-fluorophenyl}imino{-4-oxo-3-thiazolidineacetate |
| 127 | 5-Carboxy-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, diethyl ester |
| 128 | 5-Carboxy-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, 3-ethyl methyl ester |
| 129 | 3-{4-Chloro-2-fluoro-5-{[3-(o-methylbenzyl)-4-oxo-2-thiazolidinylidene]amino}phenyl}-1-methyl-6-(trifluoromethyl)-2,4(1H,3H)-pyrimidinedione |
| 130 | 3-{4-Chloro-2-fluoro-5-{[3-(m-methylbenzyl)-4-oxo-2-thiazolidinylidene]amino}phenyl}-1-methyl-6-(trifluoromethyl)-2,4(1H,3H)-pyrimidinedione |
| 131 | 3-{4-Chloro-2-fluoro-5-{[4-oxo-3-(2-pyridylmethyl)-2-thiazolidinylidene]amino}phenyl}-1-methyl-6-(trifluoromethyl)-2,4(1H,3H)-pyrimidinedione |
| 132 | 3-{4-Chloro-2-fluoro-5-{[4-oxo-3-(3-pyridylmethyl)-2-thiazolidinylidene]amino}phenyl}-1-methyl-6-(trifluoromethyl)-2,4(1H,3H)-pyrimidinedione |
| 133 | 3-{4-Chloro-2-fluoro-5-{[4-oxo-3-(4-pyridylmethyl)-2-thiazolidinylidene]amino}phenyl}-1-methyl-6-(trifluoromethyl)-2,4(1H,3H)-pyrimidinedione |
| 134 | 3-{4-Chloro-5-{[3-(3,4-dimethoxybenzyl)-4-oxo-2-thiazolidinylidene]amino}-2-fluorophenyl}-1-methyl-6-(trifluoromethyl)-2,4(1H,3H)-pyrimidinedione |
| 135 | Alpha-{2-{{2-chloro-5-[3,6-dihydro-3-methyl-2,6-dioxo-4-(trifluoromethyl)-1(2H)-pyrimidinyl]-4-fluorophenyl}imino)-4-oxo-3-thiazolidinyl}-p-toluenesulfonamide |
| 136 | 3-{4-Chloro-5-{[3-(m-chlorobenzyl)-4-oxo-2-thiazolidinylidene]amino}-2-fluorophenyl}-1-methyl-6-(trifluoromethyl)-2,4(1H,3H)-pyrimidinedione |
| 137 | 3-{4-Chloro-2-fluoro-5-{[3-(m-methoxybenzyl)-4-oxo-2-thiazolidinylidene]amino}phenyl}-1-methyl-6-(trifluoromethyl)-2,4(1H,3H)-pyrimidinedione |
| 138 | 3-{4-Chloro-5-{{3-[p-(dimethylamino)benzyl]-4-oxo-2-thiazolidinylidene}amino}-2-fluorophenyl}-1-methyl-6-(trifluoromethyl)-2,4(1H,3H)-pyrimidinedione |
| 139 | 3-{4-Chloro-5-{[3-(2,4-dimethoxybenzyl)-4-oxo-2-thiazolidinylidene]amino}-2-fluorophenyl}-1-methyl-6-(trifluoromethyl)-2,4(1H,3H)-pyrimidinedione |
| 140 | 3-{4-Chloro-2-fluoro-5-{{3-(3,4,5-trimethoxybenzyl)-4-oxo-2-thiazolidinylidene]amino}phenyl}-1-methyl-6-(trifluoromethyl)-2,4(1H,3H)-pyrimidinedione |
| 141 | 3-{4-Chloro-2-fluoro-5-{{3-[p-(trifluoromethyl)benzyl]-4-oxo-2-thiazolidinylidene}-amino}phenyl}-1-methyl-6-(trifluoromethyl)-2,4(1H,3H)-pyrimidinedione |
| 142 | 3-{4-Chloro-2-fluoro-5-{{3-[m-(trifluoromethyl)benzyl]-4-oxo-2-thiazolidinylidene}-amino}phenyl}-1-methyl-6-(trifluoromethyl)-2,4(1H,3H)-pyrimidinedione |
| 143 | 3-{4-Chloro-5-{[3-(o-chlorobenzyl)-4-oxo-2-thiazolidinylidene]amino}-2-fluorophenyl}-1-methyl-6-(trifluoromethyl)-2,4(1H,3H)-pyrimidinedione |
| 144 | 3-{4-Chloro-5-{[3-(3,4-dichlorobenzyl)-4-oxo-2-thiazolidinylidene]amino}-2-fluorophenyl}-1-methyl-6-(trifluoromethyl)-2,4(1H,3H)-pyrimidinedione |
| 145 | 3-{4-Chloro-5-{[3-(p-chlorobenzyl)-4-oxo-2-thiazolidinylidene]amino}-2-fluorophenyl}-1-methyl-6-(trifluoromethyl)-2,4(1H,3H)-pyrimidinedione |
| 146 | 3-{4-Chloro-5-{[3-(3,5-dimethylbenzyl)-4-oxo-2-thiazolidinylidene]amino}-2-fluorophenyl}-1-methyl-6-(trifluoromethyl)-2,4(1H,3H)-pyrimidinedione |
| 147 | 3-{4-Chloro-5-{[3-(3,4-dimethylbenzyl)-4-oxo-2-thiazolidinylidene]amino}-2-fluorophenyl}-1-methyl-6-(trifluoromethyl)-2,4(1H,3H)-pyrimidinedione |
| 148 | 3-{5-{[3-(p-Bromobenzyl)-4-oxo-2-thiazolidinylidene]amino}-4-chloro-2-fluorophenyl}-1-methyl-6-(trifluoromethyl)-2,4(1H,3H)-pyrimidinedione |
| 149 | 3-{4-Chloro-5-{[3-(3-chloro-4-methylbenzyl)-4-oxo-2-thiazolidinylidene]amino}-2-fluorophenyl}-1-methyl-6-(trifluoromethyl)-2,4(1H,3H)-pyrimidinedione |
| 150 | 3-{4-Chloro-5-{[3-(3,5-dichlorobenzyl)-4-oxo-2-thiazolidinylidene]amino}-2-fluorophenyl}-1-methyl-6-(trifluoromethyl)-2,4(1H,3H)-pyrimidinedione |
| 151 | 3-{4-Chloro-2-fluoro-5-{[3-(p-fluorobenzyl)-4-oxo-2-thiazolidinylidene]amino}phenyl}-1-methyl-6-(trifluoromethyl)-2,4(1H,3H)-pyrimidinedione |
| 152 | 3-{4-Chloro-5-[(3-cyclopropyl-4-oxo-2-thiazolidinylidene)amino]-2-fluorophenyl}-1-methyl-6-(trifluoromethyl)-2,4(1H,3H)-pyrimidinedione |
| 153 | Ethyl 5-bromo-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate |
| 154 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-methylene-4 oxo-3-thiazolidineacetate |
| 155 | 3-{4-Chloro-2-fluoro-5-{[3-(2-methoxyethyl)-4-oxo-2-thiazolidinylidene]amino}phenyl}-1-methyl-6-(trifluoromethyl)-2,4(1H,3H)-pyrimidinedione |
| 156 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-(methoxymethyl)-4-oxo-3-thiazolidineacetate |
| 157 | 3-{4-Chloro-2-fluoro-5-{{3-[2-(methylthio)ethyl]-4-oxo-2-thiazolidinylidene}amino}phenyl}-1-methyl-6-(trifluoromethyl)-2,4(1H,3H)-pyrimidinedione |
| 158 | Methyl {{2-{2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinyl}ethyl}-thio}acetate |
| 159 | 3-{4-Chloro-5-[(3-ethyl-4-oxo-2-thiazolidinylidene)amino]-2-fluorophenyl}-1-methyl-6-(trifluoromethyl)-2,4(1H,3H)-pyrimidinedione |
| 160 | Ethyl 2-{{2-chloro-5-[3,6-dihydro-3-methyl-2,6-dioxo-4-(trifluoromethyl)-1(2H)-pyrimidinyl]-4-fluorophenyl}imino}-5-methoxy-4-oxo-3-thiazolidineacetate |
| 161 | 3-Allyl-2-{{2-chloro-5-[3,6-dihydro-3-methyl-2,6-dioxo-4-(trifluoromethyl)-1(2H)-pyrimidinyl]-4-fluorophenyl}imino)-4-oxo-5-thiazolidineacetohydroxamic acid |
| 162 | 2-{{2-Chloro-5-[3,6-dihydro-3-methyl-2,6-dioxo-4-(trifluoromethyl)-1(2H)-pyrimidinyl]-4-fluorophenyl}imino}-3-methyl-4-oxo-5-thiazolidineacetohydroxamic acid |
| 163 | 3-{4-Chloro-2-fluoro-5-{[4-oxo-3-(2,2,2-trifluoroethyl)-2-thiazolidinylidene]amino}phenyl}-1-methyl-6-(trifluoromethyl)-2,4(1H,3H)-pyrimidinedione |
| 164 | 3-{4-Chloro-2-fluoro-5-[(3-isopropyl-4-oxo-2-thiazolidinylidene)amino]phenyl}-1-methyl-6-(trifluoromethyl)-2,4(1H,3H)-pyrimidinedione |
| 165 | 3-{4-Chloro-2-fluoro-5-{[3-(1-methyl-2-propynyl)-4-oxo-2-thiazolidinylidene]amino}phenyl}-1-methyl-6-(trifluoromethyl)-2,4(1H,3H)-pyrimidinedione |

| Compound Number | COMPOUNDS EVALUATED AS HERBICIDAL AGENTS |
|---|---|
| 166 | 3-{4-Chloro-5-[(3-cyclopentyl-4-oxo-2-thiazolidinylidene)amino]-2-fluorophenyl}-1-methyl-6-(trifluoromethyl)-2,4(1H,3H)-pyrimidinedione |
| 167 | 5-Carboxy-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, 5-tert-butyl ethyl ester |
| 168 | 3-{4-Chloro-5-[(3-cyclobutyl-4-oxo-2-thiazolidinylidene)amino]-2-fluorophenyl}-1-methyl-6-(trifluoromethyl)-2,4(1H,3H)-pyrimidinedione |
| 169 | Ethyl 2-{{2-chloro-5-[2,6-dioxo-4-(trifluoromethyl)piperidino]-4-fluorophenyl}imino}-4-oxo-3-thiazolidineacetate |
| 170 | 2-{{2-Chloro-5-[2,6-dioxo-4-(trifluoromethyl)piperidino]-4-fluorophenyl}imino}-4-oxo-3,5-thiazolidinediacetic acid, 3-ethyl ester |
| 171 | 3-{4-Chloro-2-fluoro-5-[(4-oxo-3-propyl-2-thiazolidinylidene)amino]phenyl}-1-methyl-6-(trifluoromethyl)-2,4(1H,3H)-pyrimidinedione |
| 172 | 3-{4-Chloro-2-fluoro-5-{[3-(3-methoxypropyl)-4-oxo-2-thiazolidinylidene]amino}phenyl}-1-methyl-6-(trifluoromethyl)-2,4(1H,3H)-pyrimidinedione |
| 173 | 3-{4-Chloro-2-fluoro-5-{[3-(2-fluoroethyl)-4-oxo-2-thiazolidinylidene]amino}phenyl}-1-methyl-6-(trifluoromethyl)-2,4(1H,3H)-pyrimidinedione |

TABLE I

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 1 | 0.5000 | 9.0 | 8.0 | 7.0 | 9.0 | 9.0 | | 9.0 | 7.0 | 9.0 | 6.0 | | 5.5 | 6.0 | 6.5 |
|  | 0.2500 | 9.0 | 7.0 | 6.0 | 9.0 | 9.0 | | 9.0 | 5.0 | 7.0 | 5.5 | | 5.5 | 5.5 | 5.5 |
|  | 0.1250 | 9.0 | 5.0 | 4.0 | 9.0 | 8.0 | | 9.0 | 2.0 | 7.0 | 5.0 | | 3.5 | 5.0 | 5.0 |
|  | 0.0625 | 8.0 | 3.0 | 4.0 | 7.0 | 6.0 | | 9.0 | 2.0 | 4.0 | 4.5 | | 3.0 | 4.0 | 4.0 |
|  | 0.0313 | 8.0 | 3.0 | 2.0 | 7.0 | 6.0 | | 9.0 | 0.0 | 3.0 | 4.5 | | 1.5 | 3.5 | 3.5 |
|  | 0.0157 | 5.0 | 2.0 | 0.0 | 6.0 | 4.0 | | 6.0 | 0.0 | 1.0 | 4.0 | | 1.0 | 2.5 | 2.5 |
| 2 | 0.5000 | 9.0 | 9.0 | 7.0 | 9.0 | 4.0 | | 9.0 | 0.0 | 0.0 | 4.0 | | 3.0 | 3.0 | 4.0 |
|  | 0.2500 | 9.0 | 6.0 | 4.0 | 7.0 | 4.0 | | 6.0 | 0.0 | 0.0 | 3.0 | | 3.5 | 2.5 | 3.5 |
|  | 0.1250 | 9.0 | 2.0 | 2.0 | 9.0 | 4.0 | | 6.0 | 0.0 | 0.0 | 3.0 | | 3.5 | 2.5 | 3.5 |
|  | 0.0625 | 4.0 | 6.0 | 2.0 | 8.0 | 4.0 | | 4.0 | 0.0 | 0.0 | 3.5 | | 3.0 | 3.0 | 3.0 |
|  | 0.0313 | 4.0 | 2.0 | 4.0 | 6.0 | 8.0 | | 4.0 | 0.0 | 0.0 | 3.5 | | 3.0 | 2.5 | 3.0 |
|  | 0.0157 | 0.0 | 4.0 | 0.0 | 7.0 | 4.0 | | 4.0 | 0.0 | 0.0 | 3.5 | | 3.0 | 1.5 | 3.0 |
| 3 | 0.5000 | 9.0 | 9.0 | 6.0 | 9.0 | 9.0 | | 9.0 | 0.0 | 0.0 | 4.5 | | 3.5 | 4.0 | 3.5 |
|  | 0.2500 | 6.0 | 6.0 | 6.0 | 9.0 | 6.0 | | 8.0 | 0.0 | 0.0 | 4.0 | | 2.0 | 3.0 | 3.5 |
|  | 0.1250 | 9.0 | 6.0 | 0.0 | 9.0 | 4.0 | | 9.0 | 0.0 | 2.0 | 4.0 | | 3.0 | 2.5 | 3.0 |
|  | 0.0625 | 6.0 | 6.0 | 0.0 | 6.0 | 4.0 | | 4.0 | 0.0 | 0.0 | 3.0 | | 3.0 | 3.0 | 3.0 |
|  | 0.0313 | 6.0 | 0.0 | 0.0 | 6.0 | 2.0 | | 4.0 | 0.0 | 0.0 | 3.5 | | 2.5 | 2.5 | 3.0 |
|  | 0.0157 | 6.0 | 2.0 | 0.0 | 7.0 | 9.0 | | 2.0 | 0.0 | 0.0 | 2.5 | | 2.0 | 2.5 | 3.0 |
| 4 | 0.5000 | 9.0 | 6.0 | 2.0 | 4.0 | 6.0 | | 4.0 | 2.0 | 8.0 | | 4.5 | 3.0 | 4.5 | 4.0 |
|  | 0.2500 | 9.0 | 6.0 | 0.0 | 4.0 | 2.0 | | 1.0 | 4.0 | 2.0 | | 4.5 | 1.5 | 4.5 | 4.0 |
|  | 0.1250 | 4.0 | 2.0 | 0.0 | 8.0 | 2.0 | | 0.0 | 0.0 | 0.0 | | 4.5 | 2.5 | 4.0 | 3.5 |
|  | 0.0625 | 2.0 | 0.0 | 0.0 | 6.0 | 0.0 | | 0.0 | 0.0 | 0.0 | | 2.5 | 1.0 | 3.5 | 3.0 |
|  | 0.0313 | 9.0 | 9.0 | 9.0 | 9.0 | 9.0 | | 9.0 | 2.0 | 4.0 | | 4.5 | 2.5 | 4.5 | 3.5 |
| 5 | 0.5000 | 9.0 | 0.0 | 0.0 | 8.0 | 9.0 | | 9.0 | 4.0 | 8.0 | | 4.0 | 2.5 | 5.0 | 4.0 |
|  | 0.2500 | 9.0 | 0.0 | 0.0 | 6.0 | 9.0 | | 4.0 | 3.0 | 4.0 | | 4.0 | 2.5 | 4.5 | 3.5 |
|  | 0.1250 | 2.0 | 0.0 | 0.0 | 2.0 | 8.0 | | 2.0 | 0.0 | 2.0 | | 3.0 | 2.5 | 3.5 | 4.0 |
|  | 0.0625 | 1.0 | 0.0 | 0.0 | 2.0 | 2.0 | | 1.0 | 0.0 | 0.0 | | 3.0 | 1.5 | 3.0 | 3.5 |
|  | 0.0313 | 9.0 | 0.0 | 0.0 | 2.0 | 0.0 | | 0.0 | 0.0 | 0.0 | | 3.0 | 1.5 | 3.0 | 3.5 |
| 6 | 0.5000 | 9.0 | 4.0 | 6.0 | 9.0 | 9.0 | | 9.0 | 2.0 | 2.0 | | 4.0 | 2.5 | 3.5 | 4.0 |
|  | 0.2500 | 9.0 | 4.0 | 2.0 | 7.0 | 7.0 | | 4.0 | 1.0 | 2.0 | | 4.0 | 2.5 | 3.5 | 3.5 |
|  | 0.1250 | 9.0 | 4.0 | 0.0 | 2.0 | 2.0 | | 2.0 | 0.0 | 2.0 | | 3.5 | 2.5 | 3.0 | 3.5 |
|  | 0.0625 | 8.0 | 2.0 | 6.0 | 2.0 | 0.0 | | 0.0 | 2.0 | 0.0 | | 3.0 | 2.5 | 3.0 | 3.5 |
|  | 0.0313 | 8.0 | 2.0 | 2.0 | 0.0 | 0.0 | | 0.0 | 1.0 | 0.0 | | 3.0 | 2.5 | 2.5 | 3.5 |
|  | 0.0157 | 7.0 | 2.0 | 0.0 | 0.0 | 0.0 | | 0.0 | 0.0 | 0.0 | | 3.0 | 2.5 | 2.5 | 3.0 |
| 7 | 0.1250 | 9.0 | 9.0 | 7.0 | 9.0 | 9.0 | 9.0 | 9.0 | 4.0 | 9.0 | 7.5 | | 6.5 | 6.0 | 7.0 |
|  | 0.0625 | 9.0 | 7.0 | 5.0 | 6.0 | 5.0 | 9.0 | 9.0 | 3.0 | 9.0 | 7.5 | | 4.5 | 5.0 | 7.0 |
|  | 0.0313 | 9.0 | 5.0 | 5.0 | 5.0 | 4.0 | 9.0 | 7.0 | 0.0 | 4.0 | 6.5 | | 4.0 | 3.0 | 6.0 |
|  | 0.0157 | 9.0 | 5.0 | 4.0 | 0.0 | 3.0 | 9.0 | 6.0 | 2.0 | 5.0 | 5.0 | | 4.5 | 4.5 | 5.0 |
| 8 | 0.1250 | 9.0 | 8.6 | 3.0 | 9.0 | 6.8 | 9.0 | | 8.2 | 9.0 | 8.4 | | 5.3 | 6.4 | 7.6 |
|  | 0.0625 | 9.0 | 8.3 | 3.0 | 8.4 | 6.3 | 9.0 | | 5.3 | 7.6 | 7.9 | | 4.1 | 6.4 | 7.4 |
|  | 0.0313 | 9.0 | 7.8 | 1.8 | 7.5 | 4.5 | 9.0 | | 2.1 | 5.3 | 7.6 | | 2.7 | 5.1 | 7.3 |
|  | 0.0157 | 9.0 | 9.0 | 4.0 | 5.0 | 3.0 | 7.0 | | 3.0 | | 7.5 | | 2.0 | 3.5 | 7.5 |
| 9 | 0.1250 | 9.0 | 7.0 | 4.5 | 9.0 | 7.5 | | | 4.5 | 9.0 | 7.3 | | 3.5 | 5.0 | 7.0 |
|  | 0.0625 | 9.0 | 7.5 | 2.0 | 6.0 | 4.5 | | | 2.0 | 6.5 | 6.8 | | 3.0 | 4.3 | 5.5 |
|  | 0.0313 | 9.0 | 3.5 | 1.0 | 6.0 | 2.5 | | | 0.0 | 2.0 | 5.8 | | 2.3 | 3.5 | 5.0 |
|  | 0.0156 | 9.0 | 2.0 | 0.0 | 6.5 | 1.5 | | | 0.0 | 1.0 | 4.5 | | 2.0 | 3.3 | 4.8 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 10 | 0.1250 | 9.0 | 4.5 | 3.0 | 9.0 | 4.5 | 8.0 | | 1.0 | 3.0 | 5.8 | | 3.0 | 3.5 | 5.3 |
| | 0.0625 | 7.0 | 2.0 | 0.5 | 9.0 | 3.5 | 9.0 | | 0.0 | 1.0 | 5.3 | | 2.5 | 3.3 | 5.3 |
| | 0.0313 | 6.5 | 1.0 | 0.0 | 7.0 | 2.0 | 7.0 | | 0.0 | 0.0 | 4.5 | | 2.5 | 3.3 | 5.3 |
| | 0.0156 | 9.0 | 0.5 | 0.0 | 7.0 | 1.0 | 3.0 | | 0.0 | 0.0 | 4.0 | | 1.8 | 2.5 | 4.3 |
| 11 | 0.1250 | 9.0 | 9.0 | 3.0 | 9.0 | 6.0 | 9.0 | | 7.0 | 9.0 | 9.0 | | 3.0 | 6.0 | 7.5 |
| | 0.0625 | 9.0 | 9.0 | 0.0 | 9.0 | 6.0 | 9.0 | | 6.0 | 6.0 | 9.0 | | 3.0 | 5.5 | 7.5 |
| | 0.0313 | 9.0 | 9.0 | 0.0 | 9.0 | 5.0 | 9.0 | | 0.0 | 0.0 | 7.5 | | 2.0 | 4.5 | 7.5 |
| | 0.0156 | 9.0 | 1.0 | 0.0 | 7.0 | 3.0 | 9.0 | | 0.0 | 0.0 | 5.0 | | 2.0 | 4.5 | 6.5 |
| 12 | 0.1250 | 9.0 | 9.0 | 7.0 | 9.0 | 8.0 | 9.0 | | 9.0 | 9.0 | 8.0 | | 5.0 | 7.5 | 8.0 |
| | 0.0625 | 9.0 | 7.0 | 7.0 | 9.0 | 7.0 | 9.0 | | 4.0 | 9.0 | 8.5 | | 3.0 | 7.5 | 7.5 |
| | 0.0313 | 9.0 | 9.0 | 3.0 | 9.0 | 5.0 | 9.0 | | 1.0 | 4.0 | 7.0 | | 3.0 | 7.0 | 7.0 |
| | 0.0156 | 9.0 | 7.0 | 0.0 | 9.0 | 3.0 | 9.0 | | 0.0 | 0.0 | 5.0 | | 2.5 | 5.5 | 6.5 |
| 13 | 0.1250 | 9.0 | 9.0 | 0.0 | 9.0 | 5.0 | 9.0 | | 7.0 | 9.0 | 7.5 | | 3.0 | 6.0 | 8.0 |
| | 0.0625 | 9.0 | 9.0 | 3.0 | 9.0 | 5.0 | 9.0 | | 3.0 | 4.0 | 5.5 | | 2.5 | 6.0 | 7.5 |
| | 0.0313 | 9.0 | 9.0 | 0.0 | 9.0 | 5.0 | 9.0 | | 2.0 | 4.0 | 5.5 | | 2.5 | 4.5 | 7.0 |
| | 0.0156 | 9.0 | 7.0 | 0.0 | 8.0 | 3.0 | 9.0 | | 2.0 | 0.0 | 5.0 | | 1.5 | 4.5 | 7.0 |
| 14 | 0.1250 | 9.0 | 9.0 | 9.0 | 9.0 | 6.0 | 9.0 | | 9.0 | 9.0 | 8.5 | | 8.5 | 9.0 | 7.5 |
| | 0.0625 | 9.0 | 9.0 | 2.0 | 9.0 | 5.0 | 9.0 | | 9.0 | 9.0 | 9.0 | | 6.0 | 7.5 | 7.5 |
| | 0.0313 | 9.0 | 9.0 | 2.0 | 9.0 | 4.0 | 9.0 | | 9.0 | 8.0 | 8.0 | | 5.5 | 6.0 | 7.0 |
| | 0.0156 | 9.0 | 9.0 | 0.0 | 9.0 | 2.0 | 9.0 | | 7.0 | 7.0 | 6.0 | | 3.5 | 5.5 | 7.0 |
| 15 | 0.1250 | 9.0 | 9.0 | 4.0 | 9.0 | 6.0 | 9.0 | | 9.0 | 9.0 | 5.5 | | 6.5 | 7.0 | 7.5 |
| | 0.0625 | 9.0 | 4.0 | 0.0 | 4.0 | 3.0 | 9.0 | | 3.0 | 2.0 | 4.5 | | 6.5 | 6.5 | 7.0 |
| | 0.0313 | 9.0 | 0.0 | 0.0 | 3.0 | 0.0 | 9.0 | | 0.0 | 0.0 | 4.0 | | 5.0 | 6.0 | 6.0 |
| | 0.0156 | 9.0 | 0.0 | 0.0 | 3.0 | 0.0 | 6.0 | | 0.0 | 0.0 | 3.5 | | 4.5 | 5.0 | 5.0 |
| 16 | 0.2500 | 9.0 | 9.0 | 9.0 | 9.0 | 8.4 | 9.0 | | 9.0 | 9.0 | 9.0 | | 7.5 | 8.5 | 9.0 |
| | 0.1250 | 9.0 | 9.0 | 8.0 | 9.0 | 6.8 | 9.0 | | 9.0 | 9.0 | 8.9 | | 7.3 | 7.9 | 8.7 |
| | 0.0625 | 9.0 | 8.0 | 6.2 | 8.2 | 5.3 | 9.0 | | 9.0 | 9.0 | 8.6 | | 5.7 | 7.5 | 8.4 |
| | 0.0313 | 9.0 | 9.0 | 9.0 | 9.0 | 5.0 | 9.0 | | 8.8 | 7.8 | 9.0 | | 4.2 | 6.5 | 8.1 |
| | 0.0157 | 9.0 | 9.0 | 5.5 | 8.0 | 6.0 | 9.0 | | 3.0 | 9.0 | 7.5 | | 3.0 | 7.5 | 8.0 |
| 17 | 0.1250 | 9.0 | 6.0 | 1.0 | 4.0 | 5.5 | 9.0 | | 8.0 | 5.5 | 5.8 | | 5.0 | 7.3 | 7.8 |
| | 0.0625 | 9.0 | 6.0 | 1.0 | 3.0 | 3.5 | 8.5 | | 2.5 | 4.0 | 5.5 | | 3.5 | 5.5 | 7.8 |
| | 0.0313 | 9.0 | 3.0 | 0.0 | 2.5 | 1.5 | 7.0 | | 0.0 | 2.5 | 4.3 | | 3.0 | 4.5 | 7.3 |
| | 0.0156 | 9.0 | 7.0 | 0.0 | 9.0 | 6.0 | 9.0 | | 2.0 | 6.0 | 3.5 | | 1.8 | 3.3 | 7.0 |
| 18 | 0.0630 | 9.0 | 9.0 | 1.0 | 9.0 | 5.0 | 6.0 | | 1.0 | 0.0 | 3.5 | | 1.5 | 3.0 | 4.0 |
| | 0.0315 | 9.0 | 4.0 | 0.0 | 6.0 | 2.0 | 2.0 | | 1.0 | 0.0 | 3.5 | | 1.5 | 3.0 | 4.5 |
| 19 | 0.0630 | 9.0 | 7.0 | 1.0 | 9.0 | 3.0 | 5.0 | | 2.0 | 2.0 | 4.5 | | 2.0 | 2.5 | 4.0 |
| | 0.0315 | 9.0 | 3.0 | 0.0 | 7.0 | 3.0 | 2.0 | | 1.0 | 2.0 | 4.5 | | 2.5 | 4.5 | 5.0 |
| 20 | 0.0630 | 9.0 | 6.0 | 2.0 | 3.0 | 2.0 | 9.0 | | 2.0 | 1.0 | 3.0 | | 1.5 | 3.0 | 4.0 |
| | 0.0315 | 9.0 | 5.0 | 0.0 | 7.0 | 6.0 | 3.0 | | 1.0 | 4.0 | 5.5 | | 3.0 | 4.0 | 5.5 |
| | 0.0158 | 9.0 | 4.0 | 0.0 | 4.0 | 2.0 | 9.0 | | 2.0 | 1.0 | 4.0 | | 2.0 | 4.0 | 5.0 |
| 21 | 0.0630 | 9.0 | 6.0 | 0.0 | 7.0 | 4.0 | 9.0 | | 1.0 | 2.0 | 3.5 | | 2.5 | 3.5 | 4.5 |
| | 0.0315 | 7.0 | 4.0 | 0.0 | 5.0 | 2.0 | 2.0 | | 2.0 | 2.0 | 2.5 | | 2.5 | 3.5 | 4.0 |
| | 0.0158 | 4.0 | 4.0 | 0.0 | 2.0 | 2.0 | 1.0 | | 1.0 | 0.0 | 2.0 | | 2.0 | 2.5 | 4.0 |
| 22 | 0.0630 | 9.0 | 7.0 | 1.0 | 3.0 | 3.0 | 9.0 | | 1.0 | 7.0 | 5.5 | | 4.5 | 5.0 | 7.5 |
| | 0.0315 | 9.0 | 6.0 | 2.0 | 6.0 | 4.0 | 9.0 | | 2.0 | 5.0 | 6.5 | | 3.0 | 3.5 | 7.5 |
| | 0.0158 | 9.0 | 6.0 | 1.0 | 4.0 | 4.0 | 9.0 | | 2.0 | 3.0 | 5.5 | | 2.5 | 4.0 | 7.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 23 | 0.0630 | 5.0 | 7.0 | 3.0 | 9.0 | 9.0 | 9.0 | | 2.0 | 4.0 | 5.0 | | 4.5 | 5.0 | 5.0 |
| | 0.0315 | 4.0 | 4.0 | 1.0 | 7.0 | 7.0 | 9.0 | | 2.0 | 4.0 | 3.5 | | 2.5 | 4.0 | 3.5 |
| | 0.0158 | 3.0 | 2.0 | 0.0 | 2.0 | 3.0 | 4.0 | | 0.0 | 2.0 | 3.0 | | 2.0 | 2.5 | 3.0 |
| 24 | 0.0630 | 9.0 | 9.0 | 0.0 | 9.0 | 6.0 | | | 0.0 | 0.0 | 5.5 | | 3.0 | 3.5 | 5.5 |
| | 0.0315 | 9.0 | 3.0 | 0.0 | 4.0 | 4.0 | 9.0 | | 0.0 | 0.0 | 5.0 | | 3.0 | 3.5 | 4.5 |
| | 0.0158 | 9.0 | 2.0 | 0.0 | 2.0 | 1.0 | 2.0 | | 0.0 | 0.0 | 4.0 | | 2.5 | 3.5 | 4.0 |
| 25 | 0.0625 | 9.0 | 9.0 | 0.0 | 9.0 | 7.0 | 9.0 | | 0.0 | 0.0 | 5.0 | | 2.0 | 3.0 | 7.0 |
| | 0.0313 | 9.0 | 4.0 | 0.0 | 5.0 | 5.0 | 9.0 | | 0.0 | 0.0 | 7.5 | | 2.0 | 3.0 | 5.5 |
| | 0.0156 | 9.0 | 3.0 | 0.0 | 2.0 | 2.0 | 9.0 | | 0.0 | 0.0 | 7.0 | | 0.5 | 2.0 | 3.5 |
| 26 | 0.0625 | 9.0 | 9.0 | 0.0 | 9.0 | 5.0 | 9.0 | | 0.0 | 0.0 | 6.0 | | 1.5 | 3.5 | 5.5 |
| | 0.0313 | 9.0 | 8.0 | 0.0 | 9.0 | 5.0 | 9.0 | | 0.0 | 0.0 | 5.5 | | 1.0 | 2.5 | 5.5 |
| | 0.0156 | 9.0 | 9.0 | 0.0 | 9.0 | 3.0 | 9.0 | | 1.0 | 0.0 | 5.5 | | 0.5 | 1.5 | 4.5 |
| 27 | 0.0630 | 9.0 | 7.0 | 1.0 | 9.0 | 4.0 | 9.0 | | 2.0 | 4.0 | 7.5 | | 4.5 | 4.5 | 3.5 |
| | 0.0315 | 9.0 | 5.0 | 1.0 | 6.0 | 4.0 | 9.0 | | 2.0 | 2.0 | 6.5 | | 2.5 | 4.0 | 6.5 |
| | 0.0158 | 9.0 | 4.0 | 1.0 | 2.0 | 1.0 | 9.0 | | 0.0 | 0.0 | 6.0 | | 2.0 | 3.0 | 5.5 |
| 28 | 0.0630 | 9.0 | 9.0 | 4.0 | 4.0 | 8.0 | 9.0 | | 9.0 | 9.0 | 8.5 | | 6.0 | 6.5 | 5.0 |
| | 0.0315 | 9.0 | 4.0 | 1.0 | 4.0 | 7.0 | 9.0 | | 5.0 | 9.0 | 8.0 | | 3.5 | 5.0 | 9.0 |
| | 0.0158 | 9.0 | 4.0 | 0.0 | 2.0 | 3.0 | 9.0 | | 0.0 | 0.0 | 6.5 | | 2.5 | 5.5 | 7.5 |
| | 0.0630 | 9.0 | 9.0 | 0.0 | 5.0 | 7.0 | 9.0 | | 4.0 | 4.0 | 8.0 | | 3.5 | 5.0 | 7.5 |
| 29 | 0.0315 | 7.0 | 4.0 | 0.0 | 1.0 | 1.0 | 3.0 | | 1.0 | 1.0 | 7.5 | | 3.0 | 5.0 | 7.5 |
| | 0.0158 | 9.0 | 1.0 | 0.0 | 3.0 | 1.0 | 0.0 | | 0.0 | 0.0 | 6.5 | | 1.0 | 4.5 | 5.5 |
| 30 | 0.0630 | 9.0 | 1.0 | 0.0 | 0.0 | 0.0 | 0.0 | | 0.0 | 0.0 | 6.5 | | 3.5 | 5.5 | 5.5 |
| | 0.0315 | 9.0 | 0.0 | 0.0 | 0.0 | 0.0 | 0.0 | | 0.0 | 0.0 | 6.5 | | 2.5 | 4.5 | 6.0 |
| | 0.0158 | 3.0 | 0.0 | 0.0 | 0.0 | 0.0 | 0.0 | | 0.0 | 0.0 | 6.5 | | 2.0 | 4.0 | 4.5 |
| 31 | 0.0630 | 9.0 | 7.0 | 0.0 | 7.0 | 3.0 | 9.0 | | 5.0 | 7.0 | 7.0 | | 5.5 | 6.5 | 3.0 |
| | 0.0315 | 9.0 | 2.0 | 0.0 | 2.0 | 1.0 | 0.0 | | 0.0 | 0.0 | 6.5 | | 4.0 | 5.5 | 8.0 |
| | 0.0158 | 9.0 | 0.0 | 0.0 | 0.0 | 0.0 | 0.0 | | 0.0 | 0.0 | 6.5 | | 3.5 | 5.0 | 7.5 |
| 32 | 0.1250 | 9.0 | 9.0 | 3.0 | 6.0 | 2.0 | 9.0 | | 2.0 | 7.0 | 6.0 | | 3.5 | 4.0 | 7.0 |
| | 0.0625 | 9.0 | 3.0 | 0.0 | 2.0 | 0.0 | 9.0 | | 0.0 | 0.0 | 6.0 | | 3.0 | 4.0 | 7.0 |
| | 0.0313 | 5.0 | 0.0 | 0.0 | 0.0 | 0.0 | 9.0 | | 0.0 | 0.0 | 5.5 | | 2.0 | 3.5 | 6.0 |
| 33 | 0.0630 | 9.0 | 3.0 | 5.0 | 3.0 | 0.0 | 9.0 | | 9.0 | 8.0 | 3.5 | | 1.0 | 2.0 | 4.0 |
| | 0.0315 | 9.0 | 9.0 | 1.0 | 9.0 | 5.0 | 9.0 | | 9.0 | 7.0 | 8.5 | | 2.0 | 6.0 | 8.5 |
| | 0.0158 | 9.0 | 9.0 | 0.0 | 9.0 | 4.0 | 9.0 | | 2.0 | 4.0 | 8.5 | | 2.0 | 5.5 | 8.0 |
| 34 | 0.0630 | 9.0 | 9.0 | 0.0 | 9.0 | 3.0 | 9.0 | | 1.0 | 0.0 | 7.0 | | 0.5 | 3.5 | 7.5 |
| | 0.0315 | 9.0 | 9.0 | 0.0 | 9.0 | 6.0 | 9.0 | | 0.0 | 4.0 | 7.0 | | 3.5 | 5.0 | 7.0 |
| | 0.0158 | 9.0 | 9.0 | 0.0 | 7.0 | 4.0 | 9.0 | | 0.0 | 0.0 | 7.0 | | 2.0 | 4.0 | 6.5 |
| 35 | 0.0630 | 9.0 | 9.0 | 0.0 | 9.0 | 5.0 | 9.0 | | 1.0 | 4.0 | 7.0 | | 1.0 | 4.0 | 5.5 |
| | 0.0315 | 9.0 | 9.0 | 3.0 | 9.0 | 5.0 | 9.0 | | 0.0 | 2.0 | 9.0 | | 3.5 | 3.5 | 4.5 |
| | 0.0158 | 9.0 | 9.0 | 0.0 | 9.0 | 4.0 | 9.0 | | 1.0 | 0.0 | 7.5 | | 3.0 | 3.0 | 3.5 |
| 36 | 0.0630 | 9.0 | 3.0 | 3.0 | 7.0 | 4.0 | 9.0 | | 0.0 | 0.0 | 8.0 | | 2.0 | 2.5 | 3.5 |
| | 0.0315 | 9.0 | 0.0 | 0.0 | 4.0 | 4.0 | 9.0 | | 9.0 | 9.0 | 5.5 | | 6.0 | 3.5 | 7.5 |
| | 0.0158 | 9.0 | 3.0 | 0.0 | 3.0 | 1.0 | 9.0 | | 2.0 | 3.0 | 5.0 | | 1.0 | 2.5 | 6.0 |
| 37 | 0.0630 | 9.0 | 2.0 | 0.0 | 2.0 | 1.0 | 9.0 | | 0.0 | 0.0 | 5.0 | | 0.5 | 1.5 | 4.5 |
| | 0.0315 | 9.0 | 9.0 | 0.0 | 3.0 | 4.0 | 9.0 | | 0.0 | 0.0 | 5.0 | | 1.5 | 2.0 | 4.0 |
| | 0.0158 | 9.0 | 9.0 | 0.0 | 3.0 | 3.0 | 9.0 | | 0.0 | 0.0 | 4.5 | | 1.0 | 2.0 | 4.0 |
| 38 | 0.2500 | 9.0 | 3.0 | 3.0 | 3.0 | 8.0 | 9.0 | | 9.0 | 9.0 | 8.5 | | 7.5 | 8.0 | 3.5 |
| | 0.1250 | 9.0 | 9.0 | 3.0 | 6.0 | 3.0 | 9.0 | | 5.0 | 9.0 | 8.5 | | 6.0 | 8.0 | 7.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 39 | 0.0625 | 9.0 | 5.0 | 2.0 | 4.0 | 3.0 | 9.0 |  | 2.0 | 5.0 | 8.0 |  | 2.5 | 6.5 | 7.5 |
|  | 0.0313 | 9.0 | 5.0 | 1.0 | 3.0 | 1.0 | 9.0 |  | 2.0 | 3.0 | 6.5 |  | 0.5 | 5.5 | 7.5 |
|  | 0.0156 | 9.0 | 3.0 | 0.0 | 1.0 | 0.0 | 9.0 |  | 0.0 | 0.0 | 6.5 |  | 0.5 | 5.0 | 7.5 |
|  | 0.0630 | 9.0 | 7.0 | 0.0 | 1.0 | 0.0 | 7.0 |  | 0.0 | 0.0 | 5.0 |  | 2.0 | 2.5 | 3.0 |
|  | 0.0315 | 9.0 | 3.0 | 0.0 | 1.0 | 0.0 | 7.0 |  | 0.0 | 0.0 | 5.0 |  | 1.5 | 1.5 | 3.0 |
|  | 0.0158 | 0.0 | 3.0 | 0.0 | 1.0 | 0.0 | 2.0 |  | 0.0 | 0.0 | 4.5 |  | 1.5 | 2.0 | 3.0 |
| 40 | 0.0630 | 9.0 | 9.0 | 5.0 | 9.0 | 4.0 | 9.0 |  | 9.0 | 9.0 | 8.0 |  | 3.0 | 4.5 | 8.5 |
|  | 0.0315 | 9.0 | 9.0 | 2.0 | 7.0 | 2.0 | 9.0 |  | 7.0 | 7.0 | 9.0 |  | 3.0 | 4.0 | 7.5 |
|  | 0.0158 | 9.0 | 9.0 | 0.0 | 2.0 | 1.0 | 9.0 |  | 1.0 | 1.0 | 7.0 |  | 2.5 | 4.0 | 7.0 |
| 41 | 0.0630 | 9.0 | 9.0 | 5.0 | 9.0 | 5.0 | 9.0 |  | 9.0 | 9.0 | 9.0 |  | 3.5 | 5.0 | 7.5 |
|  | 0.0315 | 9.0 | 9.0 | 1.0 | 7.0 | 2.0 | 9.0 |  | 7.0 | 3.0 | 8.0 |  | 3.5 | 4.0 | 8.0 |
|  | 0.0158 | 9.0 | 9.0 | 1.0 | 3.0 | 1.0 | 9.0 |  | 2.0 | 1.0 | 8.0 |  | 2.5 | 4.0 | 7.0 |
| 42 | 0.0630 | 9.0 | 9.0 | 7.0 | 6.0 | 3.0 | 9.0 |  | 4.0 | 1.0 | 6.5 |  | 3.0 | 3.5 | 4.5 |
|  | 0.0315 | 9.0 | 9.0 | 3.0 | 9.0 | 3.0 | 9.0 |  | 2.0 | 1.0 | 6.0 |  | 2.5 | 3.5 | 4.5 |
|  | 0.0158 | 9.0 | 9.0 | 4.0 | 3.0 | 1.0 | 9.0 |  | 1.0 | 0.0 | 5.5 |  | 2.5 | 3.5 | 4.5 |
| 43 | 0.0630 | 9.0 | 9.0 | 9.0 | 9.0 | 4.0 | 9.0 |  | 0.0 | 8.0 | 7.0 |  | 3.0 | 4.0 | 5.5 |
|  | 0.0315 | 9.0 | 9.0 | 9.0 | 9.0 | 0.0 | 9.0 |  | 0.0 | 3.0 | 7.0 |  | 2.0 | 3.5 | 5.0 |
|  | 0.0158 | 9.0 | 9.0 | 2.0 | 5.0 | 1.0 | 9.0 |  | 0.0 | 0.0 | 7.5 |  | 1.0 | 3.0 | 4.5 |
| 44 | 0.1250 | 9.0 | 9.0 | 2.0 | 9.0 | 1.0 | 9.0 |  | 1.0 | 2.0 | 6.0 |  | 4.0 | 4.0 | 5.0 |
|  | 0.0625 | 9.0 | 7.0 | 2.0 | 5.0 | 1.0 | 9.0 |  | 2.0 | 2.0 | 5.5 |  | 4.0 | 4.0 | 5.0 |
|  | 0.0313 | 9.0 | 4.0 | 0.0 | 4.0 | 1.0 | 9.0 |  | 1.0 | 0.0 | 5.0 |  | 3.0 | 3.0 | 5.0 |
|  | 0.0156 | 9.0 | 9.0 | 0.0 | 1.0 | 0.0 | 9.0 |  | 0.0 | 2.0 | 4.5 |  | 2.0 | 4.5 | 5.5 |
| 45 | 0.0625 | 9.0 | 9.0 | 0.0 | 9.0 | 0.0 | 9.0 |  | 0.0 | 0.0 | 7.0 |  | 1.5 | 4.0 | 5.0 |
|  | 0.0313 | 9.0 | 4.0 | 0.0 | 5.0 | 0.0 | 9.0 |  | 0.0 | 2.0 | 6.5 |  | 1.5 | 4.0 | 4.5 |
|  | 0.0156 | 9.0 | 9.0 | 0.0 | 0.0 | 0.0 | 9.0 |  | 0.0 | 0.0 | 5.5 |  | 1.0 | 3.0 | 5.0 |
| 46 | 0.0625 | 9.0 | 5.0 | 0.0 | 0.0 | 0.0 | 9.0 |  | 0.0 | 0.0 | 5.0 |  | 3.0 | 2.0 | 4.5 |
|  | 0.0313 | 4.0 | 0.0 | 2.0 | 0.0 | 3.0 | 3.0 |  | 0.0 | 0.0 | 7.5 |  | 1.5 | 4.5 | 7.5 |
| 47 | 0.0625 | 9.0 | 9.0 | 2.0 | 4.0 | 3.0 | 9.0 |  | 0.0 | 0.0 | 7.0 |  | 3.5 | 3.5 | 7.0 |
|  | 0.0313 | 9.0 | 3.0 | 0.0 | 3.0 | 0.0 | 9.0 |  | 0.0 | 0.0 | 5.5 |  | 2.5 | 2.5 | 5.0 |
|  | 0.0156 | 9.0 | 9.0 | 0.0 | 4.0 | 0.0 | 9.0 |  | 2.0 | 2.0 | 7.5 |  | 2.0 | 5.0 | 6.5 |
| 48 | 0.0625 | 9.0 | 5.0 | 3.0 | 4.0 | 0.0 | 9.0 |  | 2.0 | 0.0 | 6.0 |  | 0.5 | 5.0 | 5.5 |
|  | 0.0313 | 9.0 | 3.0 | 2.0 | 3.0 | 0.0 | 9.0 |  | 0.0 | 2.0 | 5.5 |  | 0.5 | 5.0 | 5.5 |
|  | 0.0156 | 9.0 | 9.0 | 0.0 | 9.0 | 4.0 | 9.0 |  | 0.0 | 7.0 | 8.0 |  | 3.0 | 4.5 | 6.0 |
| 49 | 0.0625 | 9.0 | 9.0 | 3.0 | 9.0 | 4.0 | 9.0 |  | 0.0 | 4.0 | 7.5 |  | 2.5 | 4.5 | 5.5 |
|  | 0.0313 | 9.0 | 9.0 | 2.0 | 5.0 | 2.0 | 9.0 |  | 2.0 | 3.0 | 5.5 |  | 1.0 | 4.0 | 5.0 |
|  | 0.0156 | 9.0 | 9.0 | 2.0 | 3.0 | 4.0 | 9.0 |  | 0.0 | 2.0 | 5.5 |  | 2.0 | 4.5 | 5.5 |
| 50 | 0.0625 | 9.0 | 9.0 | 1.0 | 0.0 | 2.0 | 9.0 |  | 0.0 | 0.0 | 5.5 |  | 1.0 | 3.5 | 5.0 |
|  | 0.0313 | 6.0 | 6.0 | 0.0 | 0.0 | 0.0 | 4.0 |  | 0.0 | 0.0 | 8.0 |  | 4.0 | 3.0 | 5.0 |
|  | 0.0630 | 9.0 | 9.0 | 7.0 | 9.0 | 9.0 | 9.0 |  | 9.0 | 9.0 | 8.0 |  | 3.5 | 7.0 | 7.5 |
| 51 | 0.0315 | 9.0 | 6.0 | 2.0 | 9.0 | 4.0 | 9.0 |  | 5.0 | 7.0 | 6.0 |  | 2.0 | 5.5 | 7.0 |
|  | 0.0158 | 9.0 | 5.0 | 2.0 | 6.0 | 5.0 | 9.0 |  | 4.0 | 7.0 | 6.0 |  | 2.0 | 4.0 | 4.5 |
|  | 0.0630 | 9.0 | 6.0 | 2.0 | 4.0 | 4.0 | 9.0 |  | 4.0 | 3.0 | 6.0 |  | 1.0 | 3.0 | 7.0 |
| 52 | 0.0315 | 9.0 | 3.0 | 1.0 | 4.0 | 1.0 | 9.0 |  | 1.0 | 1.0 | 5.0 |  | 1.0 | 2.5 | 7.5 |
|  | 0.0158 | 1.0 | 1.0 | 1.0 | 4.0 | 1.0 | 4.0 |  | 1.0 | 1.0 | 5.0 |  | 3.5 | 4.0 | 5.0 |
|  | 0.0630 | 9.0 | 9.0 | 9.0 | 9.0 | 9.0 | 9.0 |  | 9.0 | 9.0 | 9.0 |  | 2.5 | 4.0 | 8.0 |
| 53 | 0.0315 | 9.0 | 9.0 | 7.0 | 9.0 | 7.0 | 9.0 |  | 3.0 | 6.0 | 9.0 |  | 2.0 | 3.0 | 7.5 |
|  | 0.0158 | 9.0 | 9.0 | 4.0 | 7.0 | 3.0 | 9.0 |  | 2.0 | 6.0 | 9.0 |  | 2.0 | 2.5 | 5.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 54 | 0.0630 | 9.0 | 9.0 | 9.0 | 9.0 | 9.0 | 9.0 | | 9.0 | 9.0 | 9.0 | | 6.5 | 9.0 | 9.0 |
| | 0.0315 | 9.0 | 9.0 | 6.0 | 9.0 | 9.0 | 9.0 | | 9.0 | 9.0 | 9.0 | | 3.0 | 7.0 | 8.0 |
| | 0.0158 | 9.0 | 9.0 | 5.0 | 9.0 | 6.0 | 9.0 | | 9.0 | 9.0 | 9.0 | | 3.0 | 5.0 | 7.5 |
| 55 | 0.2500 | 9.0 | 9.0 | 9.0 | 9.0 | 9.0 | 9.0 | | 9.0 | 9.0 | 8.3 | | 6.5 | 7.5 | 9.0 |
| | 0.1250 | 9.0 | 9.0 | 8.0 | 9.0 | 9.0 | 9.0 | | 9.0 | 9.0 | 8.0 | | 5.5 | 7.5 | 8.8 |
| | 0.0625 | 9.0 | 9.0 | 9.0 | 9.0 | 7.0 | 9.0 | | 9.0 | 9.0 | 8.0 | | 4.2 | 7.5 | 8.7 |
| | 0.0313 | 9.0 | 9.0 | 7.7 | 9.0 | 3.3 | 9.0 | | 9.0 | 9.0 | 8.2 | | 3.5 | 6.8 | 8.3 |
| | 0.0158 | 8.0 | 9.0 | 1.0 | 9.0 | 6.0 | 9.0 | | 3.0 | 9.0 | 8.0 | | 2.5 | 5.5 | 7.5 |
| 56 | 0.0630 | 9.0 | 9.0 | 9.0 | 9.0 | 9.0 | 9.0 | | 3.0 | 9.0 | 8.0 | | 2.5 | 5.0 | 6.5 |
| | 0.0315 | 9.0 | 9.0 | 4.0 | 9.0 | 6.0 | 9.0 | | 2.0 | 7.0 | 7.5 | | 2.0 | 4.5 | 5.5 |
| | 0.0158 | 9.0 | 9.0 | 4.0 | 9.0 | 3.0 | 9.0 | | 2.0 | 6.0 | 7.0 | | 1.5 | 4.0 | 5.5 |
| 57 | 0.0630 | 9.0 | 9.0 | 6.0 | 9.0 | 5.0 | 9.0 | | 1.0 | 5.0 | 9.0 | | 3.0 | 4.0 | 5.0 |
| | 0.0315 | 9.0 | 9.0 | 2.0 | 9.0 | 6.0 | 9.0 | | 1.0 | 4.0 | 6.5 | | 2.5 | 4.0 | 5.0 |
| | 0.0158 | 9.0 | 9.0 | 3.0 | 9.0 | 4.0 | 9.0 | | 1.0 | 2.0 | 6.5 | | 1.5 | 3.0 | 4.5 |
| 58 | 0.0630 | 9.0 | 9.0 | 2.0 | 9.0 | 3.0 | 9.0 | | 9.0 | 9.0 | 8.5 | | 6.0 | 7.5 | 8.0 |
| | 0.0315 | 9.0 | 9.0 | 0.0 | 9.0 | 1.0 | 9.0 | | 7.0 | 9.0 | 7.0 | | 5.5 | 5.0 | 7.0 |
| | 0.0158 | 9.0 | 9.0 | 9.0 | 9.0 | 6.0 | 9.0 | | 7.0 | 9.0 | 7.0 | | 5.5 | 5.0 | 7.0 |
| 59 | 0.0630 | 9.0 | 9.0 | 9.0 | 9.0 | 6.0 | 9.0 | | 9.0 | 9.0 | 9.0 | | 5.5 | 8.0 | 8.5 |
| | 0.0315 | 9.0 | 9.0 | 3.0 | 9.0 | 6.0 | 9.0 | | 9.0 | 9.0 | 8.0 | | 6.0 | 8.0 | 8.0 |
| | 0.0158 | 9.0 | 9.0 | 3.0 | 4.0 | 5.0 | 9.0 | | 0.0 | 5.0 | 7.0 | | 4.5 | 4.5 | 7.5 |
| 60 | 0.0630 | 9.0 | 9.0 | 3.0 | 4.0 | 2.0 | 9.0 | | 0.0 | 4.0 | 6.5 | | 5.0 | 4.5 | 5.5 |
| | 0.0315 | 9.0 | 7.0 | 0.0 | 0.0 | 0.0 | 9.0 | | 0.0 | 0.0 | 6.5 | | 3.0 | 5.0 | 5.0 |
| | 0.0158 | 9.0 | 0.0 | 0.0 | 0.0 | 0.0 | 9.0 | | 0.0 | 2.0 | 4.0 | | 3.0 | 4.5 | 5.0 |
| 61 | 0.0630 | 0.0 | 0.0 | 0.0 | 0.0 | 0.0 | 1.0 | | 0.0 | 0.0 | 3.0 | | 1.5 | 1.5 | 3.0 |
| | 0.0315 | 0.0 | 0.0 | 0.0 | 0.0 | 0.0 | 2.0 | | 0.0 | 0.0 | 2.0 | | 0.5 | 0.5 | 2.0 |
| | 0.0158 | 0.0 | 0.0 | 0.0 | 0.0 | 0.0 | 1.0 | | 0.0 | 0.0 | 2.0 | | 0.5 | 0.5 | 2.0 |
| 62 | 0.0630 | 9.0 | 9.0 | 6.0 | 9.0 | 5.0 | 9.0 | | 7.0 | 8.0 | 8.5 | | 7.0 | 7.0 | 8.0 |
| | 0.0315 | 9.0 | 7.0 | 2.0 | 9.0 | 5.0 | 9.0 | | 6.0 | 9.0 | 7.5 | | 5.0 | 5.5 | 8.0 |
| | 0.0158 | 9.0 | 9.0 | 1.0 | 9.0 | 1.0 | 9.0 | | 4.0 | 9.0 | 7.5 | | 4.5 | 5.0 | 7.5 |
| 63 | 0.0630 | 9.0 | 9.0 | 5.0 | 7.0 | 7.0 | 9.0 | | 6.0 | 9.0 | 8.5 | | 6.0 | 6.0 | 7.5 |
| | 0.0315 | 6.0 | 6.0 | 3.0 | 9.0 | 6.0 | 9.0 | | 2.0 | 9.0 | 6.5 | | 5.0 | 5.5 | 7.5 |
| | 0.0158 | 9.0 | 6.0 | 0.0 | 9.0 | 1.0 | 9.0 | | 2.0 | 9.0 | 7.5 | | 5.0 | 7.0 | 7.0 |
| 64 | 0.0630 | 9.0 | 9.0 | 3.0 | 9.0 | 7.0 | 9.0 | | 7.0 | 9.0 | 7.5 | | 6.0 | 6.0 | 8.0 |
| | 0.0315 | 9.0 | 9.0 | 2.0 | 9.0 | 7.0 | 9.0 | | 5.0 | 6.0 | 7.5 | | 6.0 | 6.0 | 7.0 |
| | 0.0158 | 9.0 | 9.0 | 3.0 | 9.0 | 5.0 | 9.0 | | 3.0 | 6.0 | 7.0 | | 6.0 | 6.0 | 7.0 |
| 65 | 0.0630 | 9.0 | 9.0 | 2.0 | 9.0 | 9.0 | 9.0 | | 7.0 | 7.0 | 7.0 | | 6.0 | 7.0 | 8.0 |
| | 0.0315 | 9.0 | 7.0 | 3.0 | 9.0 | 5.0 | 9.0 | | 7.0 | 6.0 | 7.5 | | 6.0 | 6.0 | 7.5 |
| | 0.0158 | 9.0 | 9.0 | 0.0 | 9.0 | 2.0 | 9.0 | | 3.0 | 7.0 | 8.0 | | 6.0 | 7.0 | 8.0 |
| 66 | 0.1250 | 9.0 | 9.0 | 6.0 | 9.0 | 5.0 | 9.0 | | 9.0 | 9.0 | 9.0 | | 4.0 | 4.0 | 9.0 |
| | 0.0625 | 9.0 | 9.0 | 3.0 | 9.0 | 4.0 | 9.0 | | 9.0 | 8.0 | 8.5 | | 5.5 | 7.5 | 9.0 |
| | 0.0313 | 9.0 | 6.0 | 0.0 | 5.0 | 3.0 | 9.0 | | 9.0 | 8.0 | 8.5 | | 5.0 | 8.0 | 8.5 |
| | 0.0158 | 6.0 | 6.0 | 3.0 | 6.0 | 2.0 | 9.0 | | 2.0 | 2.0 | 6.5 | | 3.5 | 7.0 | 7.0 |
| 67 | 0.0630 | 9.0 | 9.0 | 3.0 | 9.0 | 5.0 | 9.0 | | 7.0 | 9.0 | 7.5 | | 5.0 | 5.5 | 8.0 |
| | 0.0315 | 9.0 | 7.0 | 2.0 | 9.0 | 6.0 | 9.0 | | 6.0 | 9.0 | 7.5 | | 4.5 | 6.5 | 8.0 |
| | 0.0158 | 5.0 | 6.0 | 0.0 | 4.0 | 2.0 | 9.0 | | 3.0 | 9.0 | 8.5 | | 4.0 | 6.0 | 8.0 |
| 68 | 0.0630 | 7.0 | 9.0 | 7.0 | 7.0 | 4.0 | 9.0 | | 5.0 | 6.0 | 7.0 | | 4.0 | 5.0 | 7.5 |
| | 0.0315 | 9.0 | 7.0 | 4.0 | 7.0 | 3.0 | 9.0 | | 2.0 | 6.0 | 5.5 | | 3.5 | 4.0 | 5.5 |
| | 0.0158 | 7.0 | 9.0 | 1.0 | 4.0 | 2.0 | 9.0 | | 2.0 | 2.0 | 6.0 | | 3.0 | 3.0 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 69 | 0.0630 | 9.0 | 9.0 | 2.0 | 9.0 | 5.0 | 9.0 | | 4.0 | 1.0 | 6.0 | | 4.5 | 4.5 | 5.5 |
| | 0.0315 | 9.0 | 9.0 | 2.0 | 9.0 | 1.0 | 9.0 | | 1.0 | 1.0 | 6.0 | | 3.0 | 3.0 | 4.5 |
| | 0.0158 | 9.0 | 9.0 | 1.0 | 7.0 | 0.0 | 9.0 | | 2.0 | 3.0 | 5.5 | | 2.5 | 3.0 | 4.5 |
| 70 | 0.0630 | 9.0 | 7.0 | 3.0 | | 3.0 | 9.0 | | 9.0 | 9.0 | 7.0 | | 5.0 | 5.5 | 7.0 |
| | 0.0315 | 6.0 | 6.0 | 0.0 | | 0.0 | 9.0 | | 2.0 | 2.0 | 5.5 | | 3.5 | 4.0 | 5.5 |
| | 0.0158 | 1.0 | 6.0 | 0.0 | 9.0 | 0.0 | 9.0 | | 0.0 | 1.0 | 4.5 | | 2.5 | 2.5 | 4.0 |
| 71 | 0.0630 | 9.0 | 9.0 | 4.0 | 4.0 | 7.0 | 9.0 | | 4.0 | 9.0 | 4.5 | | 4.5 | 4.5 | 7.0 |
| | 0.0315 | 9.0 | 6.0 | 3.0 | | 6.0 | 9.0 | | 4.0 | 7.0 | 7.5 | | 3.5 | 3.5 | 5.0 |
| | 0.0158 | 9.0 | 9.0 | 2.0 | 7.0 | 4.0 | 9.0 | | 4.0 | 4.0 | 7.5 | | 3.5 | 2.5 | 5.0 |
| 72 | 0.0630 | 9.0 | 6.0 | 7.0 | 6.0 | 9.0 | 9.0 | | 3.0 | 2.0 | 6.5 | | 4.5 | 4.5 | 6.5 |
| | 0.0315 | 9.0 | 9.0 | 6.0 | | 7.0 | 9.0 | | 3.0 | 4.0 | 7.0 | | 3.0 | 4.0 | 4.5 |
| | 0.0158 | 9.0 | 5.0 | 8.0 | 9.0 | 6.0 | 9.0 | | 1.0 | 2.0 | 5.5 | | 3.5 | 3.5 | 4.0 |
| 73 | 0.0630 | 9.0 | 9.0 | 7.0 | 7.0 | 6.0 | 9.0 | | 3.0 | 4.0 | 5.5 | | 4.0 | 4.0 | 5.0 |
| | 0.0315 | 9.0 | 9.0 | 7.0 | 9.0 | 7.0 | 9.0 | | 2.0 | 2.0 | 7.5 | | 3.0 | 3.5 | 4.5 |
| | 0.0158 | 9.0 | 9.0 | 1.0 | 4.0 | 3.0 | 9.0 | | 2.0 | 1.0 | 5.5 | | 2.5 | 3.5 | 5.0 |
| 74 | 0.0630 | 9.0 | 9.0 | 9.0 | | 9.0 | 9.0 | | 1.0 | 2.0 | 6.0 | | 5.5 | 6.0 | 5.5 |
| | 0.0315 | 9.0 | 9.0 | 4.0 | 9.0 | 4.0 | 9.0 | | 1.0 | 1.0 | 6.5 | | 4.5 | 4.5 | 5.0 |
| | 0.0158 | 9.0 | 9.0 | 3.0 | 9.0 | 1.0 | 9.0 | | 1.0 | 1.0 | 5.0 | | 3.5 | 3.5 | 5.0 |
| 75 | 0.0630 | 9.0 | 9.0 | 3.0 | 7.0 | 5.0 | 9.0 | | 1.0 | 3.0 | 5.5 | | 2.5 | 2.5 | 4.5 |
| | 0.0315 | 9.0 | 5.0 | 1.0 | 7.0 | 2.0 | 7.0 | | 1.0 | 5.0 | 5.0 | | 2.5 | 2.5 | 5.0 |
| | 0.0158 | 9.0 | 7.0 | 5.0 | 7.0 | 1.0 | 9.0 | | 1.0 | 9.0 | 4.5 | | 2.0 | 2.5 | 4.0 |
| 76 | 0.0630 | 9.0 | 9.0 | 4.0 | 7.0 | 7.0 | 9.0 | | 2.0 | 2.0 | 4.0 | | 5.0 | 5.5 | 7.0 |
| | 0.0315 | 9.0 | 9.0 | 1.0 | 7.0 | 6.0 | 9.0 | | 1.0 | 7.0 | 6.0 | | 4.0 | 5.0 | 6.0 |
| | 0.0158 | 9.0 | 9.0 | 1.0 | 3.0 | 1.0 | 9.0 | | 1.0 | 2.0 | 5.5 | | 3.0 | 3.5 | 4.5 |
| 77 | 0.0630 | 9.0 | 9.0 | 1.0 | 7.0 | 7.0 | 9.0 | | 1.0 | 1.0 | 4.0 | | 3.0 | 3.0 | 4.5 |
| | 0.0315 | 9.0 | 9.0 | 1.0 | 9.0 | 1.0 | 9.0 | | 1.0 | 7.0 | 5.0 | | 2.0 | 2.5 | 3.5 |
| | 0.0158 | 9.0 | 9.0 | 1.0 | 9.0 | 1.0 | 9.0 | | 1.0 | 6.0 | 3.5 | | 2.0 | 3.0 | 4.0 |
| 78 | 0.0630 | 9.0 | 9.0 | 3.0 | 6.0 | 2.0 | 9.0 | | 1.0 | 1.0 | 5.5 | | 2.0 | 3.0 | 5.0 |
| | 0.0315 | 9.0 | 9.0 | 1.0 | 9.0 | 1.0 | 9.0 | | 1.0 | 1.0 | 4.5 | | 4.0 | 3.5 | 5.0 |
| | 0.0158 | 7.0 | 7.0 | 2.0 | 9.0 | 1.0 | 9.0 | | 1.0 | 1.0 | 4.0 | | 3.5 | 3.0 | 4.5 |
| 79 | 0.0630 | 9.0 | 9.0 | 1.0 | 7.0 | 1.0 | 9.0 | | 1.0 | 1.0 | 5.0 | | 4.0 | 5.0 | 5.0 |
| | 0.0315 | 9.0 | 7.0 | 1.0 | 7.0 | 2.0 | 9.0 | | 3.0 | 1.0 | 5.0 | | 2.5 | 2.5 | 4.5 |
| | 0.0158 | 9.0 | 9.0 | 1.0 | 1.0 | 1.0 | 9.0 | | 2.0 | 4.0 | 4.5 | | 3.0 | 3.0 | 5.0 |
| 80 | 0.0630 | 9.0 | 9.0 | 9.0 | 9.0 | 5.0 | 9.0 | | 3.0 | 4.0 | 6.5 | | 4.0 | 4.0 | 5.5 |
| | 0.0315 | 9.0 | 9.0 | 5.0 | 9.0 | 1.0 | 9.0 | | 2.0 | 2.0 | 5.5 | | 3.5 | 3.5 | 5.0 |
| | 0.0158 | 9.0 | 9.0 | 1.0 | 9.0 | 4.0 | 9.0 | | 1.0 | 1.0 | 4.5 | | 3.5 | 3.5 | 5.0 |
| 81 | 0.0630 | 9.0 | 6.0 | 5.0 | | 4.0 | 9.0 | | 6.0 | 9.0 | 6.5 | | 5.5 | 6.0 | 7.0 |
| | 0.0315 | 7.0 | 7.0 | 2.0 | 3.0 | 5.0 | 9.0 | | 2.0 | 1.0 | 6.5 | | 4.5 | 5.0 | 7.0 |
| | 0.0158 | 9.0 | 9.0 | 1.0 | 4.0 | 1.0 | 9.0 | | 1.0 | 1.0 | 5.5 | | 4.5 | 4.5 | 6.5 |
| 82 | 0.0630 | 9.0 | 9.0 | 9.0 | 9.0 | 9.0 | 9.0 | | 9.0 | 9.0 | 9.0 | | 8.5 | 8.5 | 9.0 |
| | 0.0315 | 9.0 | 9.0 | 9.0 | 7.0 | 9.0 | 9.0 | | 9.0 | 8.0 | 9.0 | | 3.0 | 7.5 | 8.5 |
| | 0.0158 | 9.0 | 9.0 | 9.0 | 9.0 | 4.0 | 9.0 | | 9.0 | 8.0 | 8.5 | | 3.0 | 7.5 | 7.5 |
| 83 | 0.1250 | 9.0 | 9.0 | 9.0 | 9.0 | 5.0 | 9.0 | | 4.0 | 2.0 | 8.0 | | 3.0 | 6.5 | 7.5 |
| | 0.0625 | 9.0 | 9.0 | 7.0 | 9.0 | 3.0 | 9.0 | | 2.0 | 0.0 | 6.5 | | 3.0 | 4.5 | 7.5 |
| | 0.0313 | 9.0 | 9.0 | 0.0 | 7.0 | 0.0 | 9.0 | | 0.0 | 0.0 | 4.5 | | 2.5 | 4.0 | 4.5 |
| 84 | 0.0156 | 9.0 | 9.0 | 3.0 | 5.0 | 0.0 | 9.0 | | 0.0 | 2.0 | 8.5 | | 1.5 | 3.5 | 5.0 |
| | 0.1250 | 9.0 | 9.0 | 0.0 | 9.0 | 7.0 | 9.0 | | 0.0 | 2.0 | 8.5 | | 3.0 | 5.0 | 4.5 |
| | 0.0625 | 9.0 | 9.0 | 0.0 | 9.0 | 4.0 | 9.0 | | 0.0 | 0.0 | 4.5 | | 1.5 | 4.5 | 4.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0313 | 9.0 | 9.0 | 0.0 | 7.0 | 2.0 | 9.0 | | 0.0 | 0.0 | 4.5 | | 1.0 | 3.5 | 4.0 |
| | 0.0156 | 9.0 | 4.0 | 0.0 | 6.0 | 1.0 | 9.0 | | 0.0 | 0.0 | 4.0 | | 0.5 | 3.0 | 4.0 |
| 85 | 0.1250 | 9.0 | 9.0 | 2.0 | 9.0 | 5.0 | 9.0 | | 9.0 | 9.0 | 7.5 | | 2.5 | 5.0 | 8.5 |
| | 0.0625 | 9.0 | 9.0 | 0.0 | 4.0 | 3.0 | 9.0 | | 0.0 | 0.0 | 6.0 | | 1.5 | 4.5 | 7.5 |
| | 0.0313 | 9.0 | 9.0 | 0.0 | 4.0 | 1.0 | 9.0 | | 0.0 | 0.0 | 6.0 | | 1.0 | 3.5 | 6.5 |
| | 0.0156 | 9.0 | 9.0 | 0.0 | 2.0 | 0.0 | 9.0 | | 0.0 | 0.0 | 4.5 | | 1.0 | 3.0 | 4.0 |
| 86 | 0.1250 | 9.0 | 9.0 | 9.0 | 9.0 | 9.0 | 9.0 | | 9.0 | 9.0 | 9.0 | | 8.5 | 8.5 | 9.0 |
| | 0.0625 | 9.0 | 9.0 | 7.0 | 9.0 | 5.0 | 9.0 | | 9.0 | 9.0 | 9.0 | | 7.5 | 7.5 | 8.5 |
| | 0.0313 | 9.0 | 9.0 | 2.0 | 9.0 | 2.0 | 9.0 | | 3.0 | 8.0 | 8.5 | | 7.5 | 7.0 | 8.0 |
| | 0.0156 | 9.0 | 9.0 | 1.0 | 9.0 | 3.0 | 9.0 | | 9.0 | 7.0 | 9.0 | | 3.0 | 6.0 | 7.5 |
| 87 | 0.2500 | 9.0 | 9.0 | 9.0 | 4.0 | 1.0 | 9.0 | | 9.0 | 7.0 | 8.0 | | 4.0 | 6.0 | 8.0 |
| | 0.1250 | 9.0 | 7.0 | 2.0 | 3.0 | 0.0 | 9.0 | | 9.0 | 2.0 | 7.5 | | 1.5 | 4.5 | 7.5 |
| | 0.0625 | 9.0 | 4.0 | 0.0 | 0.0 | 0.0 | 9.0 | | 2.0 | 0.0 | 5.5 | | 1.0 | 4.5 | 5.5 |
| | 0.0313 | 4.0 | 4.0 | 0.0 | 0.0 | 0.0 | 9.0 | | 0.0 | 0.0 | 5.5 | | 0.5 | 3.0 | 4.5 |
| | 0.0156 | 2.0 | 0.0 | 0.0 | 0.0 | 0.0 | 9.0 | | 0.0 | 0.0 | 4.5 | | 0.0 | 2.5 | 4.0 |
| 88 | 0.0630 | 9.0 | 9.0 | 3.0 | 9.0 | 4.0 | 9.0 | | 7.0 | 9.0 | 9.0 | | 6.0 | 7.5 | 9.0 |
| | 0.0315 | 9.0 | 9.0 | 3.0 | 9.0 | 4.0 | 9.0 | | 7.0 | 9.0 | 8.5 | | 5.5 | 7.0 | 8.5 |
| | 0.0158 | 9.0 | 9.0 | 9.0 | 9.0 | 4.0 | 9.0 | | 1.0 | 9.0 | 8.5 | | 2.0 | 5.5 | 7.5 |
| 89 | 0.1250 | 9.0 | 9.0 | 9.0 | 9.0 | 9.0 | 9.0 | | 9.0 | 9.0 | 9.0 | | 8.0 | 7.0 | 9.0 |
| | 0.0825 | 9.0 | 9.0 | 6.0 | 9.0 | 5.0 | 9.0 | | 9.0 | 9.0 | 9.0 | | 6.5 | 7.0 | 8.5 |
| | 0.0313 | 9.0 | 4.0 | 0.0 | 4.0 | 4.0 | 9.0 | | 9.0 | 7.0 | 9.0 | | 4.0 | 5.5 | 7.5 |
| | 0.0158 | 9.0 | 9.0 | 1.0 | 9.0 | 3.0 | 9.0 | | 2.0 | 9.0 | 7.5 | | 1.0 | 7.5 | 7.5 |
| 90 | 0.0630 | 9.0 | 9.0 | 9.0 | 9.0 | 7.0 | 9.0 | | 9.0 | 9.0 | 9.0 | | 6.5 | 7.0 | 9.0 |
| | 0.0315 | 9.0 | 9.0 | 4.0 | 4.0 | 7.0 | 9.0 | | 5.0 | 9.0 | 9.0 | | 6.5 | 5.5 | 8.5 |
| | 0.0158 | 9.0 | 9.0 | 3.0 | 9.0 | 5.0 | 9.0 | | 3.0 | 7.0 | 9.0 | | 4.0 | 7.0 | 8.0 |
| 91 | 0.0630 | 9.0 | 4.0 | 2.0 | 4.0 | 0.0 | 9.0 | | 0.0 | 0.0 | 5.5 | | 2.0 | 3.0 | 5.0 |
| | 0.0315 | 9.0 | 0.0 | 0.0 | 3.0 | 0.0 | 9.0 | | 0.0 | 0.0 | 4.5 | | 1.0 | 2.5 | 4.0 |
| | 0.0158 | 7.0 | 0.0 | 0.0 | 0.0 | 0.0 | 9.0 | | 0.0 | 0.0 | 4.5 | | 1.0 | 2.5 | 4.0 |
| 92 | 0.0630 | 9.0 | 9.0 | 9.0 | 9.0 | 4.0 | 9.0 | | 1.0 | 9.0 | 9.0 | | 3.5 | 6.5 | 8.0 |
| | 0.0315 | 9.0 | 9.0 | 5.0 | 9.0 | 3.0 | 9.0 | | 1.0 | 9.0 | 9.0 | | 2.0 | 6.0 | 7.5 |
| 93 | 0.0630 | 9.0 | 9.0 | 3.0 | 2.0 | 0.0 | 9.0 | | 0.0 | 0.0 | 7.5 | | 1.5 | 5.0 | 6.0 |
| | 0.0315 | 9.0 | 9.0 | 2.0 | 9.0 | 6.0 | 9.0 | | 7.0 | 9.0 | 9.0 | | 6.0 | 7.5 | 8.0 |
| | 0.0158 | 9.0 | 9.0 | 1.0 | 4.0 | 5.0 | 9.0 | | 2.0 | 9.0 | 9.0 | | 4.0 | 6.0 | 7.5 |
| 94 | 0.0630 | 9.0 | 9.0 | 9.0 | 4.0 | 0.0 | 9.0 | | 9.0 | 9.0 | 8.5 | | 1.0 | 5.0 | 7.5 |
| | 0.0315 | 9.0 | 9.0 | 3.0 | 4.0 | 4.0 | 9.0 | | 7.0 | 7.0 | 9.0 | | 5.0 | 8.0 | 9.0 |
| | 0.0158 | 9.0 | 7.0 | 9.0 | 9.0 | 3.0 | 9.0 | | 1.0 | 9.0 | 9.0 | | 4.5 | 9.0 | 8.5 |
| 95 | 0.1250 | 9.0 | 9.0 | 3.0 | 6.0 | 3.0 | 9.0 | | 2.0 | 3.0 | 7.0 | | 2.0 | 6.0 | 5.5 |
| | 0.0625 | 9.0 | 6.0 | 0.0 | 7.0 | 0.0 | 9.0 | | 1.0 | 2.0 | 6.5 | | 2.5 | 3.5 | 5.5 |
| | 0.0313 | 9.0 | 6.0 | 0.0 | 4.0 | 1.0 | 6.0 | | 1.0 | 0.0 | 4.5 | | 1.5 | 3.0 | 4.0 |
| | 0.0156 | 5.0 | 1.0 | 0.0 | 1.0 | 0.0 | 9.0 | | 0.0 | 4.0 | 3.0 | | 2.0 | 3.0 | 4.5 |
| 96 | 0.1250 | 9.0 | 7.0 | 0.0 | | 1.0 | 9.0 | | 2.0 | 7.0 | 4.0 | | 1.5 | 2.5 | 5.0 |
| | 0.0625 | 9.0 | 4.0 | 0.0 | 2.0 | 0.0 | 9.0 | | 0.0 | 1.0 | 4.5 | | 2.0 | 2.5 | 4.5 |
| | 0.0313 | 7.0 | 3.0 | 0.0 | 2.0 | 0.0 | 6.0 | | 0.0 | 0.0 | 4.0 | | 2.0 | 2.0 | 4.5 |
| | 0.0156 | 1.0 | 0.0 | 1.0 | 7.0 | 1.0 | 9.0 | | 2.0 | 0.0 | 6.5 | | 3.0 | 4.0 | 5.0 |
| 97 | 0.1250 | 9.0 | 4.0 | 0.0 | 4.0 | 0.0 | 9.0 | | 6.0 | 9.0 | 5.5 | | 2.5 | 2.5 | 4.5 |
| | 0.0625 | 7.0 | 4.0 | 1.0 | 7.0 | 1.0 | 9.0 | | 3.0 | 9.0 | 5.5 | | 3.0 | 4.0 | 5.0 |
| | 0.0313 | 4.0 | 1.0 | 0.0 | 1.0 | 0.0 | 9.0 | | 1.0 | 6.0 | 4.0 | | 0.5 | 1.5 | 4.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 98 | 0.0156 | 4.0 | 0.0 | 0.0 | 0.0 | 0.0 | 7.0 | | 1.0 | 1.0 | 4.5 | | 0.5 | 1.0 | 3.5 |
| | 0.1250 | 9.0 | 9.0 | 1.0 | 9.0 | 1.0 | 9.0 | | 1.0 | 2.0 | 5.5 | | 2.0 | 3.0 | 5.0 |
| | 0.0625 | 9.0 | 4.0 | 0.0 | 3.0 | 0.0 | 9.0 | | 1.0 | 1.0 | 5.5 | | 2.5 | 3.0 | 4.0 |
| | 0.0313 | 7.0 | 3.0 | 0.0 | 1.0 | 0.0 | 3.0 | | 0.0 | 0.0 | 4.5 | | 2.5 | 2.5 | 4.0 |
| | 0.0156 | 2.0 | 3.0 | 0.0 | 0.0 | 0.0 | 3.0 | | 0.0 | 1.0 | 4.5 | | 1.5 | 2.5 | 3.0 |
| 99 | 0.1250 | 9.0 | 9.0 | 9.0 | 9.0 | 9.0 | 9.0 | | 6.0 | 8.0 | 8.0 | | 6.5 | 6.5 | 8.0 |
| | 0.0625 | 9.0 | 9.0 | 8.0 | 9.0 | 7.0 | 9.0 | | 7.0 | 9.0 | 8.0 | | 5.5 | 5.5 | 7.5 |
| | 0.0313 | 9.0 | 9.0 | 4.0 | 7.0 | 6.0 | 9.0 | | 4.0 | 7.0 | 7.5 | | 4.5 | 4.5 | 6.0 |
| | 0.0156 | 9.0 | 7.0 | 9.0 | 7.0 | 3.0 | 9.0 | | 4.0 | 6.0 | 6.5 | | 4.0 | 4.0 | 5.0 |
| 100 | 0.1250 | 9.0 | 9.0 | 6.0 | 9.0 | 3.0 | 9.0 | | 7.0 | 7.0 | 7.0 | | 3.5 | 3.5 | 5.0 |
| | 0.0625 | 9.0 | 9.0 | 7.0 | 7.0 | 3.0 | 9.0 | | 4.0 | 6.0 | 6.0 | | 3.5 | 4.0 | 5.0 |
| | 0.0313 | 9.0 | 9.0 | 2.0 | 7.0 | 2.0 | 9.0 | | 3.0 | 9.0 | 5.5 | | 3.5 | 3.0 | 5.0 |
| | 0.0156 | 9.0 | 9.0 | 0.0 | 5.0 | 1.0 | 5.0 | | 1.0 | 2.0 | 6.5 | | 3.0 | 5.0 | 4.5 |
| 101 | 0.1250 | 9.0 | 9.0 | 3.0 | 7.0 | 2.0 | 9.0 | | 5.0 | 5.0 | 6.5 | | 4.0 | 4.0 | 5.0 |
| | 0.0625 | 9.0 | 9.0 | 1.0 | 4.0 | 1.0 | 9.0 | | 3.0 | 5.0 | 6.0 | | 4.0 | 3.5 | 4.5 |
| | 0.0313 | 7.0 | 7.0 | 0.0 | 4.0 | 0.0 | 5.0 | | 2.0 | 1.0 | 5.5 | | 3.0 | 3.0 | 4.5 |
| | 0.0156 | 3.0 | 9.0 | 0.0 | 3.0 | 0.0 | 9.0 | | 1.0 | 2.0 | 5.5 | | 2.5 | 3.5 | 6.5 |
| 102 | 0.1250 | 9.0 | 9.0 | 3.0 | 6.0 | 4.0 | 9.0 | | 6.0 | 4.0 | 6.5 | | 3.0 | 4.5 | 5.5 |
| | 0.0625 | 9.0 | 7.0 | 1.0 | 4.0 | 1.0 | 9.0 | | 2.0 | 2.0 | 7.5 | | 3.0 | 3.0 | 5.5 |
| | 0.0313 | 9.0 | 9.0 | 1.0 | 3.0 | 1.0 | 9.0 | | 1.0 | 1.0 | 6.0 | | 3.0 | 4.5 | 5.0 |
| | 0.0156 | 7.0 | 7.0 | 0.0 | 5.0 | 1.0 | 9.0 | | 0.0 | 0.0 | 5.0 | | 2.5 | 3.0 | 4.5 |
| 103 | 0.1250 | 9.0 | 9.0 | 3.0 | 3.0 | 7.0 | 9.0 | | 9.0 | 9.0 | 9.0 | | 3.5 | 7.5 | 8.5 |
| | 0.0625 | 9.0 | 9.0 | 3.0 | 5.0 | 5.0 | 9.0 | | 9.0 | 9.0 | 9.0 | | 2.5 | 7.5 | 8.5 |
| | 0.0313 | 9.0 | 9.0 | 3.0 | 3.0 | 3.0 | 9.0 | | 9.0 | 5.0 | 7.0 | | 2.0 | 6.0 | 7.5 |
| | 0.0156 | 9.0 | 9.0 | 0.0 | 3.0 | 0.0 | 9.0 | | 3.0 | 4.0 | 8.0 | | 1.5 | 3.5 | 5.5 |
| 104 | 0.1250 | 9.0 | 9.0 | 1.0 | 5.0 | 2.0 | 9.0 | | 0.0 | 3.0 | 8.5 | | 2.0 | 4.0 | 8.0 |
| | 0.0625 | 9.0 | 9.0 | 0.0 | 4.0 | 1.0 | 9.0 | | 0.0 | 0.0 | 7.0 | | 1.0 | 3.0 | 6.0 |
| | 0.0313 | 7.0 | 7.0 | 0.0 | 2.0 | 0.0 | 9.0 | | 0.0 | 0.0 | 5.5 | | 0.5 | 4.0 | 6.0 |
| | 0.0156 | 9.0 | 3.0 | 0.0 | 0.0 | 2.0 | 9.0 | | 3.0 | 5.0 | 4.5 | | 0.0 | 3.0 | 4.5 |
| 105 | 0.1250 | 4.0 | 9.0 | 0.0 | 2.0 | 1.0 | 9.0 | | 0.0 | 2.0 | 7.5 | | 2.0 | 3.5 | 7.0 |
| | 0.0625 | 9.0 | 3.0 | 3.0 | 2.0 | 1.0 | 9.0 | | 3.0 | 0.0 | 6.5 | | 0.0 | 3.0 | 6.0 |
| | 0.0313 | 4.0 | 0.0 | 0.0 | 0.0 | 0.0 | 5.0 | | 0.0 | 0.0 | 4.5 | | 0.0 | 3.0 | 5.0 |
| | 0.0156 | 4.0 | 0.0 | 0.0 | 0.0 | 0.0 | 9.0 | | 0.0 | 0.0 | 3.0 | | 0.0 | 3.5 | 3.5 |
| 106 | 0.0630 | 9.0 | 7.0 | 3.0 | 7.0 | 1.0 | 9.0 | | 7.0 | 9.0 | 6.0 | | 4.0 | 4.5 | 7.0 |
| | 0.0315 | 9.0 | 9.0 | 1.0 | 7.0 | 1.0 | 9.0 | | 2.0 | 3.0 | 5.5 | | 2.5 | 3.0 | 6.5 |
| | 0.0158 | 9.0 | 2.0 | 1.0 | 1.0 | 1.0 | 9.0 | | 2.0 | 4.0 | 4.5 | | 2.0 | 2.5 | 5.0 |
| 107 | 0.0630 | 9.0 | 9.0 | 0.0 | 0.0 | 1.0 | 9.0 | | 3.0 | 9.0 | 5.5 | | 4.5 | 5.0 | 7.0 |
| | 0.0315 | 7.0 | 9.0 | 0.0 | 0.0 | 0.0 | 7.0 | | 1.0 | 9.0 | 5.0 | | 2.0 | 3.0 | 6.0 |
| | 0.0158 | 9.0 | 2.0 | 0.0 | 2.0 | 0.0 | 9.0 | | 1.0 | 1.0 | 4.5 | | 2.0 | 2.0 | 4.0 |
| 108 | 0.0630 | 9.0 | 9.0 | 9.0 | 9.0 | 3.0 | 9.0 | | 4.0 | 7.0 | 6.0 | | 3.5 | 4.5 | 6.5 |
| | 0.0315 | 9.0 | 5.0 | 1.0 | 7.0 | 1.0 | 9.0 | | 4.0 | 6.0 | 5.5 | | 3.0 | 3.5 | 6.0 |
| | 0.0158 | 9.0 | 5.0 | 1.0 | 4.0 | 0.0 | 9.0 | | 3.0 | 4.0 | 5.0 | | 3.0 | 3.0 | 5.0 |
| 109 | 0.0630 | 9.0 | 9.0 | 9.0 | 9.0 | 5.0 | 9.0 | | 3.0 | 9.0 | 8.0 | | 5.0 | 4.5 | 7.0 |
| | 0.0315 | 9.0 | 9.0 | 7.0 | 9.0 | 3.0 | 9.0 | | 3.0 | 7.0 | 8.0 | | 4.5 | 4.0 | 6.5 |
| | 0.0158 | 9.0 | 4.0 | 1.0 | 9.0 | 1.0 | 9.0 | | 0.0 | 6.0 | 7.0 | | 3.0 | 3.0 | 6.5 |
| 110 | 0.0630 | 9.0 | 9.0 | 1.0 | 9.0 | 4.0 | 9.0 | | 4.0 | 9.0 | 6.5 | | 3.5 | 4.0 | 7.0 |
| | 0.0315 | 9.0 | 4.0 | 1.0 | 9.0 | 3.0 | 9.0 | | 5.0 | 9.0 | 6.5 | | 3.5 | 3.5 | 6.5 |
| | 0.0158 | 9.0 | 5.0 | 1.0 | 9.0 | 1.0 | 9.0 | | 1.0 | 1.0 | 5.0 | | 2.5 | 2.5 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 111 | 0.0630 | 9.0 | 9.0 | 1.0 | 7.0 | 1.0 | 9.0 | | 9.0 | 9.0 | 6.0 | | 4.5 | 5.5 | 7.0 |
|  | 0.0315 | 9.0 | 6.0 | 1.0 | 6.0 | 0.0 | 9.0 | | 4.0 | 9.0 | 6.0 | | 4.5 | 4.5 | 6.5 |
|  | 0.0158 | 7.0 | 4.0 | 0.0 | 2.0 | 0.0 | 4.0 | | 3.0 | 1.0 | 6.0 | | 2.5 | 2.5 | 6.5 |
| 112 | 0.0630 | 9.0 | 9.0 | 2.0 | 9.0 | 2.0 | 9.0 | | 4.0 | 6.0 | 6.0 | | 2.5 | 3.0 | 5.0 |
|  | 0.0315 | 9.0 | 9.0 | 1.0 | 9.0 | 0.0 | 9.0 | | 4.0 | 9.0 | 5.0 | | 2.0 | 2.0 | 4.5 |
|  | 0.0158 | 9.0 | 5.0 | 1.0 | 4.0 | 0.0 | 9.0 | | 2.0 | 3.0 | 5.5 | | 2.0 | 2.0 | 4.5 |
| 113 | 0.0630 | 9.0 | 9.0 | 4.0 | 7.0 | 2.0 | 9.0 | | 1.0 | 3.0 | 5.5 | | 2.0 | 3.0 | 4.5 |
|  | 0.0315 | 9.0 | 5.0 | 0.0 | 4.0 | 0.0 | 9.0 | | 1.0 | | 5.5 | | 2.0 | 2.0 | 4.5 |
|  | 0.0158 | 9.0 | 7.0 | 1.0 | 5.0 | 3.0 | 7.0 | | 0.0 | 3.0 | 4.5 | | 2.0 | 2.0 | 4.0 |
| 114 | 0.0630 | 9.0 | 9.0 | 1.0 | 6.0 | 1.0 | 9.0 | | 4.0 | 9.0 | 6.5 | | 3.0 | 4.0 | 7.0 |
|  | 0.0315 | 9.0 | 4.0 | 1.0 | 7.0 | 2.0 | 9.0 | | 1.0 | 3.0 | 5.5 | | 2.0 | 3.0 | 7.0 |
|  | 0.0158 | 9.0 | 7.0 | 1.0 | 4.0 | 2.0 | 9.0 | | 0.0 | 4.0 | 6.0 | | 1.5 | 2.0 | 6.5 |
| 115 | 0.0630 | 9.0 | 6.0 | 1.0 | 4.0 | 1.0 | 9.0 | | 2.0 | 9.0 | 5.0 | | 2.5 | 3.0 | 7.0 |
|  | 0.0315 | 9.0 | 1.0 | 0.0 | 1.0 | 0.0 | 9.0 | | 3.0 | 4.0 | 5.0 | | 2.0 | 2.5 | 6.5 |
|  | 0.0158 | 3.0 | 1.0 | 1.0 | 0.0 | 0.0 | 9.0 | | 0.0 | 0.0 | 5.0 | | 1.5 | 1.5 | 5.0 |
| 116 | 0.0630 | 9.0 | 7.0 | 1.0 | 9.0 | 1.0 | 9.0 | | 2.0 | 3.0 | 5.5 | | 2.0 | 2.5 | 4.5 |
|  | 0.0315 | 9.0 | 9.0 | 1.0 | 5.0 | 1.0 | 9.0 | | 1.0 | 3.0 | 5.0 | | 2.0 | 2.5 | 5.0 |
|  | 0.0158 | 9.0 | 9.0 | 1.0 | 4.0 | 0.0 | 9.0 | | 3.0 | 1.0 | 5.5 | | 1.5 | 1.5 | 5.0 |
| 117 | 0.0630 | 9.0 | 7.0 | 1.0 | 9.0 | 1.0 | 9.0 | | 1.0 | 2.0 | 6.0 | | 3.0 | 3.5 | 5.0 |
|  | 0.0315 | 9.0 | 5.0 | 1.0 | 4.0 | 1.0 | 9.0 | | 2.0 | 2.0 | 5.0 | | 2.0 | 3.5 | 4.5 |
| 118 | 0.0630 | 9.0 | 4.0 | 0.0 | 5.0 | 1.0 | 9.0 | | 1.0 | 4.0 | 6.0 | | 2.0 | 3.0 | 4.5 |
|  | 0.0315 | 9.0 | 2.0 | 0.0 | 0.0 | 0.0 | 9.0 | | 1.0 | 0.0 | 5.0 | | 2.0 | 2.0 | 4.0 |
|  | 0.0158 | 4.0 | 0.0 | 0.0 | 0.0 | 0.0 | 7.0 | | 1.0 | 0.0 | 4.5 | | 2.0 | 2.0 | 3.5 |
| 119 | 0.0625 | 9.0 | 9.0 | 7.0 | 9.0 | 3.0 | 9.0 | | 1.0 | 9.0 | 8.5 | | 3.0 | 3.5 | 6.0 |
|  | 0.0313 | 9.0 | 9.0 | 5.0 | 9.0 | 1.0 | 9.0 | | 1.0 | 9.0 | 8.5 | | 2.0 | 3.5 | 5.5 |
|  | 0.0158 | 9.0 | 9.0 | 3.0 | 9.0 | 1.0 | 9.0 | | 0.0 | 3.0 | 7.0 | | 1.5 | 2.5 | 4.5 |
| 120 | 0.0625 | 9.0 | 9.0 | 8.0 | 9.0 | 3.0 | 9.0 | | 5.0 | 9.0 | 9.0 | | 2.5 | 5.0 | 8.0 |
|  | 0.0313 | 9.0 | 9.0 | 5.0 | 9.0 | 3.0 | 9.0 | | 2.0 | 9.0 | 9.0 | | 2.5 | 4.5 | 7.0 |
|  | 0.0156 | 9.0 | 9.0 | 3.0 | 9.0 | 2.0 | 9.0 | | 1.0 | 4.0 | 7.5 | | 2.0 | 3.5 | 6.0 |
| 121 | 0.0625 | 9.0 | 9.0 | 7.0 | 9.0 | 3.0 | 9.0 | | 0.0 | 9.0 | 8.0 | | 3.0 | 5.0 | 6.0 |
|  | 0.0313 | 9.0 | 9.0 | 1.0 | 7.0 | 0.0 | 9.0 | | 0.0 | 8.0 | 8.0 | | 2.5 | 4.0 | 5.0 |
|  | 0.0156 | 9.0 | 9.0 | 0.0 | 4.0 | 0.0 | 9.0 | | 0.0 | 8.0 | 6.0 | | 2.0 | 3.0 | 5.0 |
| 122 | 0.1250 | 9.0 | 9.0 | 4.0 | 9.0 | 6.0 | 9.0 | | 5.0 | 9.0 | 6.5 | | 2.5 | 5.0 | 7.0 |
|  | 0.0625 | 9.0 | 9.0 | 3.0 | 9.0 | 4.0 | 9.0 | | 4.0 | 9.0 | 6.5 | | 5.0 | 4.5 | 7.0 |
|  | 0.0313 | 9.0 | 9.0 | 3.0 | 9.0 | 2.0 | 9.0 | | 3.0 | 7.0 | 5.5 | | 3.5 | 3.5 | 7.0 |
|  | 0.0156 | 9.0 | 7.0 | 1.0 | 6.0 | 2.0 | 9.0 | | 2.0 | 6.0 | 5.5 | | 3.5 | 3.0 | 4.5 |
| 123 | 0.1250 | 9.0 | 9.0 | 8.0 | 9.0 | 7.0 | 9.0 | | 9.0 | 9.0 | 9.0 | | 5.5 | 6.5 | 7.5 |
|  | 0.0625 | 9.0 | 9.0 | 9.0 | 9.0 | 6.0 | 9.0 | | 7.0 | 9.0 | 8.0 | | 5.5 | 6.0 | 7.5 |
|  | 0.0313 | 9.0 | 9.0 | 3.0 | 9.0 | 4.0 | 9.0 | | 5.0 | 9.0 | 6.5 | | 4.0 | 4.5 | 7.0 |
|  | 0.0156 | 9.0 | 9.0 | 3.0 | 9.0 | 2.0 | 9.0 | | 5.0 | 9.0 | 6.5 | | 4.0 | 4.0 | 6.5 |
| 124 | 0.0625 | 9.0 | 9.0 | 3.0 | 9.0 | 6.0 | 9.0 | | 3.0 | 5.0 | 7.0 | | 3.0 | 5.0 | 8.0 |
|  | 0.0313 | 9.0 | 9.0 | 2.0 | 9.0 | 1.0 | 9.0 | | 3.0 | 3.0 | 7.3 | | 3.0 | 4.3 | 7.3 |
|  | 0.0156 | 7.0 | 9.0 | 2.0 | 9.0 | 0.0 | 9.0 | | 3.0 | 3.0 | 6.7 | | 3.3 | 3.7 | 6.3 |
| 125 | 0.0625 | 9.0 | 8.0 | 2.0 | 9.0 | 5.0 | 9.0 | | 3.0 | 5.0 | 8.7 | | 3.7 | 5.0 | 8.0 |
|  | 0.0313 | 9.0 | 8.0 | 2.0 | 9.0 | 2.0 | 9.0 | | 2.0 | 5.0 | 8.0 | | 4.0 | 5.0 | 7.3 |
|  | 0.0156 | 9.0 | 3.0 | 1.0 | 3.0 | 1.0 | 9.0 | | 1.0 | 2.0 | 7.3 | | 3.3 | 4.3 | 6.7 |
| 126 | 0.1250 | 9.0 | 9.0 | 4.0 | 9.0 | 3.0 | 9.0 | | 0.0 | 9.0 | 7.0 | | 1.0 | 3.5 | 6.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 127 | 0.0625 | 9.0 | 9.0 | 2.0 | 4.0 | 0.0 | 9.0 | | 0.0 | 3.0 | 6.0 | | 0.5 | 3.0 | 4.5 |
| | 0.0313 | 9.0 | 9.0 | 0.0 | 4.0 | 0.0 | 9.0 | | 0.0 | 3.0 | 5.5 | | 0.5 | 2.5 | 4.0 |
| | 0.0156 | 5.0 | 5.0 | 0.0 | 4.0 | 0.0 | 9.0 | | 0.0 | 0.0 | 5.0 | | 0.0 | 2.0 | 4.0 |
| | 0.1250 | 9.0 | 9.0 | 1.0 | 9.0 | 3.0 | 9.0 | | 3.0 | 9.0 | 9.0 | | 2.5 | 6.0 | 8.0 |
| | 0.0625 | 9.0 | 9.0 | 1.0 | 9.0 | 2.0 | 9.0 | | 1.0 | 7.0 | 7.5 | | 0.5 | 3.5 | 7.0 |
| | 0.0313 | 9.0 | 9.0 | 0.0 | 4.0 | 0.0 | 9.0 | | 0.0 | 1.0 | 5.5 | | 0.5 | 2.5 | 4.5 |
| | 00156 | 9.0 | 9.0 | 0.0 | 4.0 | 0.0 | 9.0 | | 0.0 | 0.0 | 5.0 | | 0.5 | 2.5 | 4.5 |
| 128 | 0.0625 | 9.0 | 9.0 | 7.0 | 9.0 | 3.0 | 9.0 | | 1.0 | 4.0 | 6.0 | | 2.5 | 3.5 | 6.0 |
| | 0.0313 | 9.0 | 9.0 | 1.0 | 9.0 | 1.0 | 9.0 | | 2.0 | 1.0 | 4.5 | | 2.0 | 3.0 | 4.0 |
| | 0.0156 | 6.0 | 7.0 | 1.0 | 4.0 | 1.0 | 9.0 | | 1.0 | 1.0 | 4.5 | | 1.5 | 2.0 | 3.5 |
| 129 | 0.0625 | 9.0 | 9.0 | 4.0 | 9.0 | 4.0 | 9.0 | | 3.0 | 5.0 | 6.0 | | 3.0 | 3.5 | 4.5 |
| | 0.0313 | 9.0 | 9.0 | 4.0 | 5.0 | 4.0 | 9.0 | | 2.0 | 3.0 | 5.0 | | 3.5 | 3.5 | 4.5 |
| | 0.0156 | 9.0 | 9.0 | 5.0 | 9.0 | 5.0 | 9.0 | | 1.0 | 2.0 | 5.0 | | 3.5 | 4.0 | 4.0 |
| 130 | 0.0625 | 9.0 | 9.0 | 5.0 | 9.0 | 3.0 | 9.0 | | 3.0 | 7.0 | 8.0 | | 3.0 | 3.5 | 5.0 |
| | 0.0313 | 9.0 | 9.0 | 4.0 | 9.0 | 2.0 | 9.0 | | 2.0 | 6.0 | 7.0 | | 3.0 | 3.0 | 4.5 |
| | 0.0156 | 9.0 | 9.0 | 2.0 | 7.0 | 2.0 | 9.0 | | 2.0 | 4.0 | 5.5 | | 3.0 | 3.5 | 4.5 |
| 131 | 0.0625 | 9.0 | 9.0 | 3.0 | 9.0 | 3.0 | 9.0 | | 2.0 | 5.0 | 5.5 | | 3.0 | 3.0 | 4.0 |
| | 0.0313 | 9.0 | 9.0 | 1.0 | 5.0 | 3.0 | 9.0 | | 2.0 | 4.0 | 5.0 | | 2.5 | 3.0 | 4.5 |
| | 0.0156 | 7.0 | 7.0 | 1.0 | 3.0 | 1.0 | 7.0 | | 2.0 | 3.0 | 4.5 | | 2.0 | 3.0 | 4.0 |
| 132 | 0.0625 | 9.0 | 9.0 | 6.0 | 9.0 | 3.0 | 9.0 | | 2.0 | 3.0 | 6.0 | | 3.5 | 4.0 | 4.5 |
| | 0.0313 | 9.0 | 5.0 | 1.0 | 4.0 | 2.0 | 9.0 | | 1.0 | 4.0 | 5.0 | | 3.0 | 3.5 | 4.0 |
| | 0.0156 | 9.0 | 9.0 | 1.0 | 9.0 | 3.0 | 6.0 | | 1.0 | 2.0 | 5.0 | | 2.0 | 3.0 | 3.5 |
| 133 | 0.0625 | 9.0 | 9.0 | 3.0 | 9.0 | 2.0 | 9.0 | | 1.0 | 1.0 | 5.0 | | 3.0 | 3.5 | 4.0 |
| | 0.0313 | 9.0 | 6.0 | 1.0 | 6.0 | 2.0 | 9.0 | | 1.0 | 2.0 | 5.0 | | 2.5 | 3.0 | 4.0 |
| | 0.0156 | 9.0 | 9.0 | 0.0 | 4.0 | 0.0 | 9.0 | | 1.0 | 1.0 | 5.0 | | 2.5 | 4.0 | 4.0 |
| 134 | 0.0625 | 9.0 | 7.0 | 0.0 | 9.0 | 2.0 | 9.0 | | 2.0 | 0.0 | 5.0 | | 2.0 | 3.5 | 4.5 |
| | 0.0313 | 7.0 | 4.0 | 0.0 | 3.0 | 1.0 | 3.0 | | 0.0 | 0.0 | 4.0 | | 1.5 | 2.5 | 4.5 |
| | 0.0156 | 5.0 | 3.0 | 0.0 | 1.0 | 0.0 | 9.0 | | 2.0 | 6.0 | 3.5 | | 1.0 | 3.0 | 3.5 |
| 135 | 0.0625 | 9.0 | 9.0 | 4.0 | 9.0 | 4.0 | 9.0 | | 2.0 | 6.0 | 5.0 | | 2.5 | 3.0 | 4.0 |
| | 0.0313 | 9.0 | 9.0 | 3.0 | 7.0 | 3.0 | 9.0 | | 2.0 | 4.0 | 5.0 | | 2.0 | 2.5 | 4.0 |
| | 0.0156 | 4.0 | 4.0 | 2.0 | 4.0 | 1.0 | 9.0 | | 1.0 | 2.0 | 5.0 | | 2.0 | 3.0 | 3.5 |
| 136 | 0.0625 | 9.0 | 9.0 | 7.0 | 9.0 | 3.0 | 9.0 | | 3.0 | 6.0 | 5.5 | | 2.5 | 3.0 | 4.0 |
| | 0.0313 | 9.0 | 9.0 | 4.0 | 9.0 | 2.0 | 9.0 | | 3.0 | 6.0 | 5.5 | | 3.0 | 3.0 | 4.0 |
| | 0.0156 | 9.0 | 9.0 | 1.0 | 9.0 | 1.0 | 9.0 | | 3.0 | 4.0 | 4.5 | | 2.5 | 2.5 | 4.0 |
| 137 | 0.0625 | 9.0 | 9.0 | 4.0 | 9.0 | 3.0 | 9.0 | | 1.0 | 3.0 | 5.5 | | 3.5 | 4.5 | 5.0 |
| | 0.0313 | 9.0 | 9.0 | 1.0 | 6.0 | 1.0 | 9.0 | | 2.0 | 1.0 | 5.5 | | 3.0 | 3.0 | 4.0 |
| | 0.0156 | 9.0 | 9.0 | 0.0 | 9.0 | 1.0 | 9.0 | | 1.0 | 2.0 | 6.0 | | 3.0 | 3.5 | 4.0 |
| 138 | 0.0625 | 9.0 | 9.0 | 6.0 | 9.0 | 2.0 | 9.0 | | 2.0 | 4.0 | 6.5 | | 3.0 | 3.0 | 4.0 |
| | 0.0313 | 9.0 | 9.0 | 1.0 | 9.0 | 2.0 | 9.0 | | 1.0 | 3.0 | 5.0 | | 2.5 | 2.5 | 4.0 |
| | 0.0156 | 9.0 | 9.0 | 0.0 | 9.0 | 1.0 | 5.0 | | 1.0 | 1.0 | 5.0 | | 1.5 | 3.5 | 5.0 |
| 139 | 0.0625 | 9.0 | 7.0 | 5.0 | 9.0 | 4.0 | 9.0 | | 3.0 | 5.0 | 7.0 | | 3.5 | 3.5 | 4.5 |
| | 0.0313 | 9.0 | 9.0 | 4.0 | 9.0 | 3.0 | 9.0 | | 2.0 | 2.0 | 6.5 | | 3.0 | 2.5 | 4.0 |
| | 0.0156 | 9.0 | 9.0 | 0.0 | 9.0 | 1.0 | 9.0 | | 3.0 | 0.0 | 5.5 | | 2.0 | 3.0 | 4.0 |
| 140 | 0.0625 | 9.0 | 4.0 | 0.0 | 9.0 | 2.0 | 5.0 | | 0.0 | 0.0 | 5.5 | | 1.5 | 2.5 | 5.0 |
| | 0.0313 | 4.0 | 2.0 | 0.0 | 3.0 | 0.0 | 9.0 | | 0.0 | 0.0 | 4.5 | | 0.5 | 4.0 | 4.0 |
| | 0.0156 | 4.0 | 2.0 | 0.0 | 3.0 | 0.0 | 9.0 | | 0.0 | 0.0 | 3.5 | | 0.5 | 3.5 | 4.0 |
| 141 | 0.0625 | 8.0 | 9.0 | 0.0 | 9.0 | 2.0 | 9.0 | | 0.0 | 0.0 | 4.5 | | 2.0 | 4.5 | 5.0 |
| | 0.0313 | 7.0 | 7.0 | 0.0 | 5.0 | 2.0 | 9.0 | | 0.0 | 0.0 | 4.0 | | 1.5 | 3.5 | 4.5 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 142 | 0.0156 | 7.0 | 7.0 | 0.0 | 3.0 | 0.0 | 9.0 | | 0.0 | 0.0 | 4.0 | | 0.5 | 3.0 | 4.0 |
| | 0.0625 | 9.0 | 9.0 | 3.0 | 9.0 | 1.0 | 9.0 | | 2.0 | 3.0 | 5.5 | | 2.0 | 2.5 | 4.5 |
| | 0.0313 | 9.0 | 9.0 | 1.0 | 9.0 | 1.0 | 7.0 | | 1.0 | 1.0 | 5.0 | | 1.5 | 2.5 | 4.0 |
| 143 | 0.0156 | 3.0 | 9.0 | 0.0 | 4.0 | 0.0 | 7.0 | | 1.0 | 2.0 | 5.0 | | 2.0 | 2.5 | 4.0 |
| | 0.0625 | 9.0 | 9.0 | 3.0 | 6.0 | 3.0 | 9.0 | | 1.0 | 3.0 | 5.0 | | 2.0 | 3.5 | 4.0 |
| | 0.0313 | 9.0 | 9.0 | 1.0 | 6.0 | 1.0 | 9.0 | | 2.0 | 1.0 | 4.5 | | 1.5 | 2.0 | 4.0 |
| | 0.0156 | 9.0 | 9.0 | 0.0 | 2.0 | 0.0 | 9.0 | | 1.0 | 2.0 | 4.0 | | 1.5 | 1.5 | 4.5 |
| 144 | 0.0625 | 9.0 | 9.0 | 7.0 | 9.0 | 4.0 | 9.0 | | 4.0 | 6.0 | 6.5 | | 3.0 | 4.0 | 4.0 |
| | 0.0313 | 9.0 | 7.0 | 5.0 | 9.0 | 3.0 | 9.0 | | 3.0 | 3.0 | 5.5 | | 2.5 | 3.5 | 4.0 |
| | 0.0156 | 9.0 | 9.0 | 3.0 | 7.0 | 3.0 | 9.0 | | 2.0 | 3.0 | 5.0 | | 2.5 | 3.5 | 4.0 |
| 145 | 0.0625 | 9.0 | 9.0 | 5.0 | 9.0 | 7.0 | 9.0 | | 3.0 | 5.0 | 5.0 | | 3.5 | 4.0 | 5.0 |
| | 0.0313 | 9.0 | 9.0 | 2.0 | 5.0 | 4.0 | 9.0 | | 3.0 | 3.0 | 5.0 | | 2.5 | 3.0 | 4.0 |
| | 0.0156 | 9.0 | 9.0 | 1.0 | 9.0 | 1.0 | 9.0 | | 2.0 | 1.0 | 4.5 | | 2.5 | 3.5 | 4.5 |
| 146 | 0.0625 | 9.0 | 9.0 | 4.0 | 9.0 | 4.0 | 9.0 | | 2.0 | 3.0 | 6.0 | | 4.0 | 4.5 | 4.5 |
| | 0.0313 | 9.0 | 9.0 | 2.0 | 6.0 | 4.0 | 9.0 | | 2.0 | 2.0 | 6.0 | | 3.5 | 3.5 | 4.0 |
| | 0.0156 | 9.0 | 9.0 | 1.0 | 5.0 | 2.0 | 9.0 | | 1.0 | 1.0 | 5.0 | | 2.5 | 2.5 | 4.5 |
| 147 | 0.0625 | 9.0 | 9.0 | 2.0 | 9.0 | 3.0 | 9.0 | | 2.0 | 2.0 | 6.0 | | 3.0 | 4.0 | 4.0 |
| | 0.0313 | 9.0 | 9.0 | 1.0 | 6.0 | 1.0 | 9.0 | | 2.0 | 1.0 | 5.5 | | 2.5 | 3.5 | 4.5 |
| | 0.0156 | 9.0 | 6.0 | 1.0 | 5.0 | 0.0 | 9.0 | | 1.0 | 1.0 | 5.5 | | 1.5 | 2.5 | 4.0 |
| 148 | 0.0625 | 9.0 | 9.0 | 3.0 | 7.0 | 2.0 | 9.0 | | 3.0 | 4.0 | 6.5 | | 3.0 | 4.0 | 5.0 |
| | 0.0313 | 9.0 | 7.0 | 3.0 | 9.0 | 2.0 | 9.0 | | 3.0 | 2.0 | 5.0 | | 2.0 | 2.5 | 4.0 |
| | 0.0156 | 9.0 | 9.0 | 0.0 | 4.0 | 2.0 | 9.0 | | 0.0 | 0.0 | 4.5 | | 1.0 | 3.5 | 4.5 |
| 149 | 0.0625 | 8.0 | 9.0 | 3.0 | 3.0 | 0.0 | 9.0 | | 0.0 | 0.0 | 4.5 | | 1.0 | 3.5 | 4.5 |
| | 0.0313 | 4.0 | 4.0 | 0.0 | 3.0 | 0.0 | 9.0 | | 0.0 | 0.0 | 4.0 | | 0.5 | 3.0 | 4.0 |
| | 0.0156 | 9.0 | 9.0 | 3.0 | 9.0 | 4.0 | 9.0 | | 2.0 | 5.0 | 6.0 | | 3.0 | 3.5 | 4.0 |
| 150 | 0.0625 | 9.0 | 9.0 | 3.0 | 9.0 | 2.0 | 9.0 | | 1.0 | 1.0 | 5.5 | | 2.5 | 3.5 | 4.0 |
| | 0.0313 | 9.0 | 7.0 | 1.0 | 9.0 | 1.0 | 9.0 | | 2.0 | 1.0 | 5.0 | | 2.0 | 3.5 | 4.0 |
| | 0.0156 | 9.0 | 9.0 | 4.0 | 9.0 | 6.0 | 9.0 | | 4.0 | 9.0 | 5.5 | | 3.5 | 4.0 | 5.0 |
| 151 | 0.0625 | 9.0 | 9.0 | 4.0 | 7.0 | 4.0 | 9.0 | | 3.0 | 5.0 | 4.5 | | 2.5 | 2.5 | 4.5 |
| | 0.0313 | 9.0 | 7.0 | 2.0 | 9.0 | 4.0 | 9.0 | | 3.0 | 3.0 | 4.0 | | 2.0 | 4.0 | 4.0 |
| | 0.0156 | 9.0 | 9.0 | 3.0 | 9.0 | 2.0 | 9.0 | | 2.0 | 3.0 | 6.0 | | 3.0 | 3.5 | 6.5 |
| 152 | 0.0625 | 4.0 | 4.0 | 0.0 | 4.0 | 0.0 | 9.0 | | 2.0 | 0.0 | 4.5 | | 2.0 | 3.5 | 5.0 |
| | 0.0313 | 6.0 | 2.0 | 1.0 | 0.0 | 0.0 | 7.0 | | 1.0 | 0.0 | 4.0 | | 1.5 | 3.0 | 4.0 |
| | 0.0156 | 5.0 | 1.0 | 0.0 | 1.0 | 0.0 | 6.0 | | 0.0 | 0.0 | 4.0 | | 1.5 | 3.0 | 4.5 |
| 153 | 0.0625 | 1.0 | 1.0 | 0.0 | 1.0 | 0.0 | 4.0 | | 0.0 | 5.0 | 4.0 | | 1.5 | 2.0 | 3.5 |
| | 0.0313 | 1.0 | 0.0 | 0.0 | 0.0 | 0.0 | 2.0 | | 0.0 | 0.0 | 3.5 | | 1.5 | 2.0 | 3.0 |
| 154 | 0.0625 | 9.0 | 9.0 | 1.0 | 9.0 | 4.0 | 9.0 | | 2.0 | 5.0 | 7.5 | | 2.0 | 4.0 | 5.0 |
| | 0.0313 | 9.0 | 3.0 | 0.0 | 9.0 | 3.0 | 9.0 | | 1.0 | 1.0 | 6.0 | | 1.5 | 3.5 | 4.0 |
| | 0.0156 | 9.0 | 9.0 | 0.0 | 9.0 | 3.0 | 9.0 | | 0.0 | 0.0 | 5.5 | | 0.5 | 3.5 | 4.0 |
| 155 | 0.0625 | 9.0 | 9.0 | 0.0 | 0.0 | 0.0 | 6.0 | | 0.0 | 0.0 | 5.0 | | 0.0 | 3.0 | 4.0 |
| | 0.0313 | 3.0 | 3.0 | 0.0 | 0.0 | 0.0 | 4.0 | | 0.0 | 0.0 | 4.0 | | 0.0 | 1.0 | 4.0 |
| 156 | 0.0625 | 9.0 | 9.0 | 0.0 | 9.0 | 0.0 | 9.0 | | 0.0 | 0.0 | 5.5 | | 2.0 | 4.0 | 4.5 |
| | 0.0313 | 9.0 | 7.0 | 1.0 | 9.0 | 3.0 | 9.0 | | 2.0 | 5.0 | 4.0 | | 0.5 | 3.5 | 4.5 |
| | 0.0156 | 9.0 | 5.0 | 3.0 | 9.0 | 2.0 | 6.0 | | 2.0 | 7.0 | 5.5 | | 3.0 | 4.0 | 7.0 |
| 157 | 0.0625 | 9.0 | 5.0 | 3.0 | 9.0 | 2.0 | 6.0 | | 2.0 | 7.0 | 7.5 | | 3.0 | 4.0 | 7.0 |
| | 0.0313 | 9.0 | 2.0 | 0.0 | 4.0 | 0.0 | 7.0 | | 1.0 | 1.0 | 5.0 | | 2.5 | 3.5 | 7.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 158 | 0.0156 | 7.0 | 2.0 | 0.0 | 2.0 | 0.0 | 3.0 | | 0.0 | 0.0 | 4.5 | | 2.0 | 2.5 | 7.0 |
| | 0.0625 | 9.0 | 9.0 | 9.0 | 9.0 | 3.0 | 9.0 | | 3.0 | 9.0 | 7.0 | | 3.5 | 3.5 | 5.5 |
| | 0.0313 | 9.0 | 7.0 | 4.0 | 7.0 | 2.0 | 9.0 | | 2.0 | 3.0 | 5.0 | | 2.5 | 4.0 | 4.5 |
| 159 | 0.0156 | 9.0 | 6.0 | 4.0 | 6.0 | 0.0 | 9.0 | | 2.0 | 2.0 | 5.0 | | 2.0 | 3.5 | 4.0 |
| | 0.0625 | 9.0 | 7.0 | 7.0 | 5.0 | 4.0 | 9.0 | | 3.0 | 7.0 | 7.0 | | 2.0 | 3.5 | 7.0 |
| | 0.0313 | 9.0 | 7.0 | 1.0 | 4.0 | 1.0 | 9.0 | | 3.0 | 2.0 | 5.5 | | 2.0 | 3.5 | 6.5 |
| | 0.0156 | 9.0 | 4.0 | 0.0 | 3.0 | 0.0 | 9.0 | | 2.0 | 1.0 | 5.0 | | 1.5 | 2.5 | 5.0 |
| 160 | 0.1250 | 9.0 | 9.0 | 4.0 | 9.0 | 4.0 | 9.0 | | 7.0 | 9.0 | 7.0 | | 4.5 | 6.0 | 7.5 |
| | 0.0625 | 9.0 | 9.0 | 1.0 | 9.0 | 2.0 | 9.0 | | 4.0 | 9.0 | 7.0 | | 4.5 | 5.0 | 7.0 |
| | 0.0313 | 9.0 | 7.0 | 0.0 | 6.0 | 0.0 | 9.0 | | 5.0 | 6.0 | 6.0 | | 3.5 | 4.0 | 7.0 |
| | 0.0156 | 9.0 | 7.0 | 0.0 | 2.0 | 0.0 | 9.0 | | 3.0 | 0.0 | 5.0 | | 2.0 | 3.0 | 6.5 |
| 161 | 0.1250 | 9.0 | 9.0 | 3.0 | 9.0 | 4.0 | 9.0 | | 4.0 | 7.0 | 8.5 | | 3.5 | 4.5 | 7.5 |
| | 0.0625 | 7.0 | 9.0 | 1.0 | 7.0 | 2.0 | 9.0 | | 4.0 | 7.0 | 7.0 | | 3.5 | 4.0 | 7.0 |
| | 0.0313 | 5.0 | 4.0 | 1.0 | 5.0 | 1.0 | 3.0 | | 0.0 | 1.0 | 6.5 | | 3.0 | 3.5 | 6.5 |
| | 0.0156 | 0.0 | 1.0 | 0.0 | 1.0 | 0.0 | 1.0 | | 0.0 | 0.0 | 5.0 | | 2.5 | 2.5 | 4.5 |
| 162 | 0.0625 | 9.0 | 9.0 | 2.0 | 9.0 | 6.0 | 9.0 | | 0.0 | 4.0 | 8.5 | | 1.5 | 3.5 | 5.5 |
| | 0.0313 | 9.0 | 9.0 | 0.0 | 9.0 | 3.0 | 9.0 | | 0.0 | 3.0 | 6.5 | | 1.5 | 3.5 | 5.0 |
| | 0.0156 | 9.0 | 9.0 | 0.0 | 9.0 | 0.0 | 9.0 | | 0.0 | 0.0 | 6.0 | | 0.5 | 3.5 | 4.5 |
| 163 | 0.0625 | 9.0 | 9.0 | 3.0 | 9.0 | 5.0 | 9.0 | | 1.0 | 3.0 | 8.0 | | 2.0 | 4.5 | 5.5 |
| | 0.0313 | 9.0 | 9.0 | 0.0 | 9.0 | 3.0 | 9.0 | | 0.0 | 0.0 | 7.0 | | 1.5 | 4.0 | 5.5 |
| | 0.0156 | 9.0 | 9.0 | 0.0 | 9.0 | 0.0 | 9.0 | | 0.0 | 0.0 | 6.0 | | 1.0 | 3.5 | 5.0 |
| 164 | 0.1250 | 9.0 | 9.0 | 6.0 | 9.0 | 6.0 | 9.0 | | 3.0 | 6.0 | 7.5 | | 5.0 | 5.5 | 6.5 |
| | 0.0625 | 9.0 | 9.0 | 5.0 | 9.0 | 7.0 | 9.0 | | 3.0 | 9.0 | 7.0 | | 5.0 | 5.5 | 5.5 |
| | 0.0313 | 9.0 | 9.0 | 2.0 | 9.0 | 4.0 | 9.0 | | 3.0 | 7.0 | 6.0 | | 4.0 | 4.5 | 5.0 |
| | 0.0156 | 9.0 | 7.0 | 2.0 | 9.0 | 3.0 | 9.0 | | 2.0 | 4.0 | 6.0 | | 2.5 | 4.0 | 5.0 |
| 165 | 0.1250 | 9.0 | 9.0 | 3.0 | 9.0 | 5.0 | 9.0 | | 5.0 | 7.0 | 6.0 | | 4.0 | 5.0 | 5.5 |
| | 0.0625 | 9.0 | 7.0 | 3.0 | 7.0 | 4.0 | 9.0 | | 3.0 | 9.0 | 7.0 | | 3.0 | 4.0 | 5.0 |
| | 0.0313 | 9.0 | 6.0 | 2.0 | 6.0 | 1.0 | 9.0 | | 4.0 | 6.0 | 6.5 | | 1.5 | 3.0 | 5.0 |
| | 0.0156 | 9.0 | 2.0 | 0.0 | 5.0 | 0.0 | 9.0 | | 2.0 | 2.0 | 5.0 | | 2.0 | 3.0 | 4.0 |
| 166 | 0.1250 | 9.0 | 7.0 | 1.0 | 7.0 | 2.0 | 7.0 | | 2.0 | 1.0 | 5.0 | | 2.0 | 3.0 | 4.5 |
| | 0.0625 | 3.0 | 6.0 | 0.0 | 4.0 | 0.0 | 2.0 | | 1.0 | 0.0 | 4.0 | | 1.5 | 2.5 | 3.5 |
| | 0.0313 | 1.0 | 3.0 | 0.0 | 1.0 | 0.0 | 2.0 | | 0.0 | 0.0 | 3.5 | | 0.5 | 1.5 | 3.0 |
| | 0.0156 | 2.0 | 0.0 | 0.0 | 0.0 | 0.0 | 0.0 | | 0.0 | 0.0 | 4.0 | | 1.0 | 1.5 | 3.0 |
| 167 | 0.1250 | 9.0 | 7.0 | 4.0 | 9.0 | 4.0 | 9.0 | | 3.0 | 9.0 | 6.5 | | 4.0 | 4.5 | 5.5 |
| | 0.0625 | 9.0 | 9.0 | 1.0 | 9.0 | 4.0 | 9.0 | | 3.0 | 9.0 | 6.5 | | 3.5 | 4.0 | 5.5 |
| | 0.0313 | 9.0 | 7.0 | 2.0 | 7.0 | 3.0 | 9.0 | | 3.0 | 4.0 | 6.0 | | 3.5 | 4.0 | 5.5 |
| | 0.0156 | 9.0 | 4.0 | 1.0 | 4.0 | 2.0 | 9.0 | | 3.0 | 2.0 | 5.0 | | 3.0 | 4.0 | 4.5 |
| 168 | 0.0625 | 9.0 | 9.0 | 2.0 | 9.0 | 3.0 | 9.0 | | 4.0 | 3.0 | 7.0 | | 2.5 | 4.0 | 7.0 |
| | 0.0313 | 9.0 | 9.0 | 0.0 | 3.0 | 1.0 | 9.0 | | 0.0 | 0.0 | 6.5 | | 1.5 | 3.5 | 4.5 |
| | 0.0156 | 9.0 | 3.0 | 3.0 | 2.0 | 0.0 | 5.0 | | 0.0 | 0.0 | 5.5 | | 1.0 | 3.5 | 4.5 |
| 169 | 0.0625 | 9.0 | 9.0 | 1.0 | 4.0 | 0.0 | 9.0 | | 7.0 | 9.0 | 7.5 | | 2.0 | 7.0 | 8.5 |
| | 0.0313 | 9.0 | 9.0 | 0.0 | 3.0 | 0.0 | 9.0 | | 4.0 | 5.0 | 6.5 | | 1.0 | 6.0 | 7.5 |
| | 0.0156 | 9.0 | 9.0 | 0.0 | 0.0 | 0.0 | 9.0 | | 2.0 | 0.0 | 5.0 | | 0.5 | 4.5 | 6.0 |
| 170 | 0.0625 | 9.0 | 9.0 | 1.0 | 9.0 | 4.0 | 9.0 | | 1.0 | 9.0 | 7.5 | | 2.5 | 5.0 | 6.0 |
| | 0.0313 | 9.0 | 9.0 | 0.0 | 9.0 | 3.0 | 9.0 | | 1.0 | 9.0 | 7.5 | | 2.0 | 4.0 | 6.0 |
| | 0.0156 | 9.0 | 9.0 | 0.0 | 4.0 | 0.0 | 9.0 | | 1.0 | 6.0 | 7.5 | | 2.0 | 3.5 | 5.0 |

TABLE I-continued

Postemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 171 | 0.0625 | 9.0 | 9.0 | 4.0 | 9.0 | 7.0 | 9.0 | | 3.0 | 9.0 | 7.0 | | 5.0 | 6.0 | 7.0 |
| | 0.0313 | 9.0 | 9.0 | 3.0 | 9.0 | 6.0 | 9.0 | | 4.0 | 7.0 | 6.5 | | 4.0 | 5.0 | 6.5 |
| | 0.0156 | 9.0 | 6.0 | 2.0 | 7.0 | 3.0 | 9.0 | | 4.0 | 7.0 | 5.5 | | 3.5 | 4.0 | 5.0 |
| 172 | 0.0625 | 9.0 | 9.0 | 2.0 | 9.0 | 7.0 | 9.0 | | 3.0 | 2.0 | 7.0 | | 4.0 | 4.0 | 5.0 |
| | 0.0313 | 9.0 | 9.0 | 2.0 | 9.0 | 4.0 | 9.0 | | 3.0 | 3.0 | 6.5 | | 3.5 | 4.5 | 5.0 |
| | 0.0456 | 9.0 | 6.0 | 1.0 | 6.0 | 3.0 | 9.0 | | 2.0 | 2.0 | 6.0 | | 3.5 | 4.0 | 5.0 |

EXAMPLE 38

Preemergence Herbicidal Evaluation of Test Compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.0156 to 0.500 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system provided in Example 37.

The data obtained are reported in Table II below. The compounds evaluated are reported by compound number given in Example 37.

TABLE II

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 1 | 0.5000 | 9.0 | 6.7 | 6.7 | 9.0 | 8.0 |  | 8.0 | 7.7 | 8.0 | 3.0 |  | 6.0 | 6.0 | 2.0 |
|   | 0.2500 | 9.0 | 5.0 | 6.0 | 9.0 | 9.0 |  | 6.0 | 5.0 | 9.0 | 4.0 |  | 3.0 | 6.0 | 0.0 |
|   | 0.1250 | 9.0 | 5.0 | 2.0 | 9.0 | 9.0 |  | 7.0 | 6.0 | 8.0 | 2.0 |  | 2.0 | 3.0 | 0.0 |
|   | 0.0625 | 9.0 | 2.0 | 3.0 | 9.0 | 7.0 |  | 6.0 | 5.0 | 9.0 | 2.0 |  | 0.0 | 4.0 | 0.0 |
|   | 0.0313 | 5.0 | 0.0 | 0.0 | 9.0 | 9.0 |  | 1.0 | 2.0 | 5.0 | 0.0 |  | 0.0 | 2.0 | 0.0 |
| 2 | 0.5000 | 4.0 | 0.0 | 2.0 | 9.0 |  |  | 0.0 | 8.0 | 9.0 | 1.0 |  | 3.0 | 0.0 | 0.0 |
|   | 0.2500 |  | 0.0 |  | 9.0 |  |  | 0.0 | 0.0 | 6.0 | 0.0 |  | 2.0 | 0.0 | 0.0 |
|   | 0.1250 |  | 0.0 |  |  |  |  | 0.0 | 4.0 | 6.0 | 0.0 |  | 2.0 | 0.0 | 0.0 |
|   | 0.0625 | 0.0 | 0.0 | 2.0 |  |  |  | 0.0 | 0.0 | 0.0 | 0.0 |  | 2.0 | 0.0 | 0.0 |
|   | 0.0313 | 0.0 | 0.0 | 2.0 | 7.0 |  |  | 0.0 | 0.0 | 0.0 | 0.0 |  | 2.0 | 0.0 | 0.0 |
| 3 | 0.5000 | 6.0 | 7.0 | 2.0 | 9.0 |  |  | 4.0 | 6.0 | 9.0 | 2.0 |  | 1.0 | 2.0 | 4.0 |
|   | 0.2500 | 0.0 | 2.0 | 0.0 | 9.0 |  |  | 2.0 | 4.0 | 4.0 | 0.0 |  | 0.0 | 2.0 | 2.0 |
|   | 0.1250 | 2.0 | 2.0 | 0.0 | 9.0 |  |  | 0.0 | 2.0 | 4.0 | 0.0 |  | 0.0 | 0.0 | 1.0 |
|   | 0.0625 | 2.0 | 0.0 | 0.0 | 9.0 |  |  | 0.0 | 0.0 | 4.0 | 0.0 |  | 0.0 | 0.0 | 0.0 |
|   | 0.0313 |  | 0.0 | 0.0 | 6.0 | 4.0 |  | 0.0 | 0.0 | 0.0 | 0.0 |  | 0.0 | 0.0 | 0.0 |
| 4 | 0.5000 | 8.0 | 4.0 | 7.0 | 9.0 |  |  | 9.0 | 6.0 | 9.0 |  | 4.0 | 4.0 | 3.0 | 4.0 |
|   | 0.2500 | 2.0 | 1.0 | 2.0 | 2.0 |  |  | 2.0 | 2.0 | 4.0 |  | 2.0 | 2.0 | 3.0 | 2.0 |
|   | 0.1250 | 0.0 | 0.0 | 0.0 | 0.0 |  |  | 0.0 | 0.0 | 2.0 |  | 0.0 | 0.0 | 2.0 | 2.0 |
| 5 | 0.5000 | 0.0 | 0.0 | 0.0 | 9.0 |  |  | 0.0 | 7.0 | 9.0 |  | 2.0 | 2.0 | 2.0 | 2.0 |
|   | 0.2500 | 0.0 | 0.0 | 0.0 | 9.0 |  |  | 0.0 | 6.0 | 6.0 |  | 2.0 | 2.0 | 1.0 | 2.0 |
|   | 0.1250 | 0.0 | 0.0 | 0.0 | 5.0 |  |  | 0.0 | 2.0 | 2.0 |  | 1.0 | 0.0 | 0.0 | 1.0 |
|   | 0.0625 | 0.0 | 0.0 | 0.0 | 4.0 |  |  | 0.0 | 0.0 | 0.0 |  | 1.0 | 0.0 | 0.0 | 0.0 |
| 6 | 0.5000 | 0.0 | 0.0 | 0.0 | 9.0 |  |  | 0.0 | 2.0 |  |  | 0.0 | 0.0 | 0.0 | 0.0 |
|   | 0.2500 | 0.0 | 0.0 | 0.0 | 4.0 |  |  | 0.0 | 0.0 | 2.0 |  | 0.0 | 0.0 | 0.0 | 0.0 |
|   | 0.1250 | 0.0 | 0.0 | 0.0 | 2.0 |  |  | 0.0 | 0.0 | 0.0 |  | 0.0 | 0.0 | 0.0 | 0.0 |
| 7 | 0.2500 | 9.0 | 9.0 | 9.0 | 9.0 | 9.0 | 9.0 | 9.0 | 9.0 | 9.0 | 8.5 |  | 9.0 | 8.5 | 9.0 |
|   | 0.1250 | 9.0 | 9.0 | 8.0 | 9.0 | 9.0 | 9.0 | 9.0 | 9.0 | 9.0 | 8.0 |  | 8.5 | 8.5 | 8.5 |
|   | 0.0625 | 9.0 | 9.0 | 9.0 | 9.0 | 9.0 | 4.0 | 9.0 | 9.0 | 9.0 | 7.5 |  | 8.0 | 7.5 | 8.5 |
|   | 0.0313 | 9.0 | 8.5 | 9.0 | 9.0 | 7.5 | 4.0 | 9.0 | 9.0 | 9.0 | 6.5 |  | 7.5 | 6.5 | 8.0 |
|   | 0.0157 | 9.0 | 5.0 | 9.0 | 9.0 | 4.0 |  | 9.0 | 5.0 | 9.0 | 5.0 |  | 5.0 | 5.0 | 7.0 |
| 8 | 0.5000 | 9.0 | 9.0 | 3.8 | 9.0 | 9.0 | 9.0 |  | 9.0 | 9.0 | 8.8 |  | 8.5 | 7.8 | 8.3 |
|   | 0.2500 | 9.0 | 8.9 | 3.3 | 9.0 | 9.0 | 8.6 |  | 8.9 | 9.0 | 7.9 |  | 7.1 | 7.2 | 7.9 |
|   | 0.1250 | 9.0 | 8.5 | 1.7 | 9.0 | 7.5 | 8.6 |  | 7.4 | 9.0 | 5.9 |  | 5.4 | 5.5 | 7.4 |
|   | 0.0625 | 8.7 | 5.7 | 1.2 | 9.0 | 5.5 | 6.4 |  | 4.4 | 8.2 | 3.2 |  | 2.8 | 2.8 | 6.4 |
|   | 0.0313 | 8.4 | 4.5 | 0.1 | 9.0 | 1.3 | 4.4 |  | 2.2 | 6.1 | 1.1 |  | 0.8 | 0.8 | 4.9 |
|   | 0.0156 | 7.3 | 1.6 | 0.0 | 9.0 | 0.0 | 1.1 |  | 0.4 | 2.8 | 0.2 |  | 0.6 | 0.2 | 2.2 |
| 9 | 0.2500 | 9.0 | 9.0 | 8.0 | 9.0 | 9.0 | 9.0 |  | 9.0 | 9.0 | 9.0 |  | 9.0 | 9.0 | 8.7 |
|   | 0.1250 | 9.0 | 9.0 | 5.3 | 9.0 | 9.0 | 9.0 |  | 9.0 | 9.0 | 8.7 |  | 9.0 | 9.0 | 8.7 |
|   | 0.0625 | 9.0 | 7.3 | 3.0 | 9.0 | 9.0 | 7.0 |  | 8.7 | 9.0 | 6.3 |  | 7.5 | 7.5 | 8.3 |
|   | 0.0313 | 9.0 | 6.3 | 1.0 | 9.0 | 4.5 | 7.7 |  | 8.3 | 9.0 | 6.0 |  | 8.5 | 7.0 | 7.0 |
|   | 0.0156 | 9.0 | 3.0 | 1.0 | 9.0 | 1.0 | 5.0 |  | 5.7 | 8.3 | 4.0 |  | 5.5 | 4.0 | 6.7 |
| 10 | 0.2500 | 9.0 | 6.3 | 3.3 | 9.0 | 9.0 | 9.0 |  | 9.0 | 9.0 | 7.0 |  | 7.5 | 7.5 | 8.0 |
|   | 0.1250 | 9.0 | 4.7 | 1.3 | 9.0 | 9.0 | 8.3 |  | 9.0 | 9.0 | 6.7 |  | 6.5 | 6.5 | 7.3 |
|   | 0.0625 | 9.0 | 3.3 | 0.7 | 9.0 | 4.5 | 5.3 |  | 7.0 | 9.0 | 3.7 |  | 4.5 | 5.5 | 7.0 |
|   | 0.0313 | 8.0 | 0.3 | 0.7 | 9.0 | 2.0 | 3.0 |  | 4.0 | 5.7 | 2.3 |  | 3.0 | 3.5 | 6.7 |
|   | 0.0156 | 5.5 | 0.3 | 0.0 | 9.0 | 0.5 | 2.0 |  | 2.0 | 2.3 | 2.0 |  | 1.0 | 1.0 | 4.7 |
| 11 | 0.2500 | 9.0 | 9.0 | 5.5 | 9.0 | 9.0 | 9.0 |  | 7.0 | 9.0 | 8.0 |  | 4.0 | 5.0 | 5.5 |
|   | 0.1250 | 9.0 | 6.5 | 0.0 | 9.0 | 0.0 | 9.0 |  | 3.5 | 7.5 | 6.0 |  | 2.0 | 2.0 | 4.5 |
|   | 0.0625 | 8.5 | 5.5 | 0.0 | 9.0 | 0.0 | 8.0 |  | 0.0 | 7.0 | 3.5 |  | 0.0 | 0.0 | 3.5 |
|   | 0.0313 | 8.5 | 1.0 | 0.0 | 9.0 | 0.0 | 8.0 |  | 0.0 | 1.0 | 1.5 |  | 0.0 | 0.0 | 0.5 |
|   | 0.0156 | 7.5 | 0.0 | 0.0 | 7.5 | 0.0 | 2.0 |  | 0.0 | 0.0 | 1.5 |  | 0.0 | 0.0 | 0.0 |
| 12 | 0.2500 | 9.0 | 9.0 | 6.0 | 9.0 | 9.0 | 9.0 |  | 9.0 | 9.0 | 9.0 |  | 7.0 | 8.0 | 8.5 |
|   | 0.1250 | 9.0 | 9.0 | 4.5 | 9.0 | 9.0 | 9.0 |  | 9.0 | 9.0 | 6.5 |  | 7.0 | 8.0 | 6.5 |
|   | 0.0625 | 9.0 | 9.0 | 4.5 | 9.0 | 9.0 | 9.0 |  | 6.0 | 9.0 | 3.5 |  | 4.0 | 5.0 | 5.5 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0313 | 9.0 | 4.5 | 0.0 | 9.0 | 0.0 | 9.0 | | 5.0 | 9.0 | 2.0 | | 1.0 | 1.0 | 5.0 |
| | 0.0156 | 7.5 | 0.0 | 0.0 | 9.0 | 0.0 | 4.5 | | 2.0 | 8.5 | 1.5 | | 0.0 | 0.0 | 4.0 |
| 13 | 0.2500 | 9.0 | 9.0 | 3.0 | 9.0 | 0.0 | 9.0 | | 8.0 | 9.0 | 4.0 | | 4.0 | 6.0 | 7.0 |
| | 0.1250 | 9.0 | 9.0 | 1.0 | 9.0 | 0.0 | 8.0 | | 7.0 | 9.0 | 2.0 | | 3.0 | 4.0 | 5.0 |
| | 0.0625 | 9.0 | 6.0 | 0.0 | 9.0 | 0.0 | 9.0 | | 1.0 | 9.0 | 1.0 | | 0.0 | 1.0 | 4.0 |
| | 0.0313 | 9.0 | 2.0 | 0.0 | 9.0 | 0.0 | 3.5 | | 0.0 | 4.5 | 0.0 | | 0.0 | 1.0 | 2.0 |
| | 0.0156 | 6.0 | 0.0 | 0.0 | 9.0 | 0.0 | 2.5 | | 0.0 | 2.5 | 0.0 | | 0.0 | | 0.0 |
| 14 | 0.5000 | 9.0 | 9.0 | 5.0 | 9.0 | | 9.0 | | 6.0 | 9.0 | 6.0 | | 3.0 | | 3.0 |
| | 0.2500 | 9.0 | 9.0 | 2.0 | 9.0 | 9.0 | 9.0 | | 3.0 | 9.0 | 3.0 | | 1.0 | 0.0 | 2.0 |
| | 0.1250 | 9.0 | 6.5 | 1.5 | 9.0 | 9.0 | 7.5 | | 1.0 | 6.5 | 2.0 | | 0.5 | 0.0 | 1.5 |
| | 0.0625 | 2.0 | 1.0 | 1.0 | 9.0 | 0.0 | 1.5 | | 0.0 | 0.5 | 0.0 | | 0.0 | 0.0 | 0.0 |
| | 0.0313 | 1.0 | 0.0 | 0.0 | 9.0 | 0.0 | 0.0 | | 0.0 | 0.5 | 0.0 | | 0.0 | 0.0 | 0.0 |
| 15 | 0.2500 | 9.0 | 9.0 | 6.5 | 9.0 | 9.0 | 9.0 | | 4.5 | 9.0 | 5.5 | | 1.5 | 5.0 | 5.0 |
| | 0.1250 | 9.0 | 3.0 | 2.0 | 9.0 | 9.0 | 7.0 | | 2.0 | 4.0 | 2.5 | | 1.0 | 5.0 | 3.0 |
| | 0.0625 | 9.0 | 1.5 | 0.5 | 9.0 | 9.0 | 1.5 | | 1.0 | 0.5 | 1.0 | | 0.5 | 0.0 | 2.5 |
| | 0.0313 | 3.0 | 1.0 | 0.5 | 9.0 | 0.0 | 1.5 | | 0.5 | 0.5 | 0.5 | | 0.0 | 0.0 | 1.0 |
| | 0.0156 | 1.5 | 0.5 | 0.0 | 6.5 | 0.0 | 1.0 | | 0.0 | 0.5 | 0.5 | | 0.0 | 0.0 | 1.0 |
| 16 | 0.5000 | 9.0 | 9.0 | 9.0 | 9.0 | 9.0 | 9.0 | | 7.1 | 8.9 | 9.0 | 7.0 | 6.4 | 5.8 | 6.0 |
| | 0.2500 | 9.0 | 8.9 | 8.3 | 9.0 | 8.2 | 9.0 | | 4.4 | 8.5 | 7.7 | 3.5 | 4.3 | 2.6 | 3.7 |
| | 0.1250 | 8.9 | 8.5 | 5.3 | 9.0 | 6.4 | 8.7 | | 1.8 | 7.5 | 4.5 | 2.0 | 2.2 | 0.8 | 1.8 |
| | 0.0625 | 8.8 | 7.8 | 2.7 | 8.8 | 4.8 | 7.6 | | 0.6 | 3.7 | 1.5 | 2.0 | 1.0 | 0.5 | 1.4 |
| | 0.0313 | 8.1 | 4.5 | 0.6 | 8.4 | 2.0 | 3.5 | | 0.3 | 1.0 | 0.7 | 0.0 | 0.3 | 0.5 | 0.6 |
| | 0.0156 | 5.6 | 2.3 | 0.3 | 5.7 | 1.2 | 0.9 | | 0.0 | 0.2 | 0.5 | 0.0 | 0.1 | 0.1 | 0.1 |
| 17 | 0.5000 | 9.0 | 9.0 | 7.0 | 9.0 | 9.0 | 9.0 | | 9.0 | 9.0 | 6.5 | | 6.5 | 7.0 | 5.5 |
| | 0.2500 | 9.0 | 6.7 | 3.7 | 9.0 | 9.0 | 9.0 | | 4.3 | 9.0 | 3.3 | | 3.3 | 7.0 | 3.3 |
| | 0.1250 | 9.0 | 4.3 | 0.0 | 9.0 | 1.0 | 5.7 | | 0.7 | 6.7 | 0.3 | | 1.0 | 2.0 | 1.0 |
| | 0.0625 | 9.0 | 1.7 | 0.7 | 9.0 | 0.0 | 4.0 | | 1.0 | 2.3 | 0.3 | | 1.0 | 0.0 | 1.0 |
| | 0.0313 | 4.0 | 0.7 | 0.7 | 6.0 | 0.0 | 0.7 | | 0.7 | 1.3 | 0.0 | | 0.0 | 0.0 | 0.3 |
| | 0.0156 | 0.0 | 0.0 | 0.0 | 4.5 | 0.0 | 0.5 | | 0.5 | 0.5 | 0.0 | | 0.0 | 0.0 | 0.0 |
| 18 | 0.2500 | 9.0 | 4.0 | 0.0 | 9.0 | 9.0 | 1.0 | | 0.0 | 2.0 | 3.0 | | 0.0 | 0.0 | 0.0 |
| | 0.1250 | 2.0 | 1.0 | 0.0 | 8.0 | 0.0 | 0.0 | | 0.0 | 0.0 | 0.0 | | 0.0 | 0.0 | 0.0 |
| 19 | 0.2500 | 9.0 | 1.0 | 0.0 | 9.0 | 0.0 | 0.0 | | 0.0 | 0.0 | 0.0 | | 0.0 | 0.0 | 0.0 |
| | 0.1250 | 9.0 | 0.0 | 0.0 | 9.0 | 0.0 | 0.0 | | 0.0 | 0.0 | 0.0 | | 0.0 | 0.0 | 0.0 |
| 20 | 0.2500 | 9.0 | 3.0 | 9.0 | 9.0 | 0.0 | 2.0 | | 0.0 | 7.0 | 4.0 | | 0.0 | 0.0 | 0.0 |
| | 0.1250 | 9.0 | 0.0 | 0.0 | 9.0 | 0.0 | 0.0 | | 0.0 | 0.0 | 0.0 | | 0.0 | 0.0 | 0.0 |
| | 0.0625 | 0.0 | 0.0 | 0.0 | 9.0 | 0.0 | 0.0 | | 0.0 | 0.0 | 0.0 | | 0.0 | 0.0 | 0.0 |
| 21 | 0.2500 | 2.0 | 0.0 | 0.0 | 9.0 | 0.0 | 0.0 | | 0.0 | 0.0 | 0.0 | | 0.0 | 0.0 | 0.0 |
| 22 | 0.2500 | 9.0 | 9.0 | 9.0 | 9.0 | 9.0 | 9.0 | | 9.0 | 9.0 | 9.0 | | 8.0 | 7.0 | 9.0 |
| | 0.1250 | 9.0 | 9.0 | 3.0 | 9.0 | 0.0 | 9.0 | | 3.0 | 9.0 | 7.0 | | 5.0 | 5.0 | 8.0 |
| | 0.0625 | 9.0 | 7.0 | 0.0 | 9.0 | 0.0 | 9.0 | | 0.0 | 9.0 | 3.0 | | 0.0 | 1.0 | 7.0 |
| | 0.0313 | 9.0 | 5.0 | 0.0 | 9.0 | 0.0 | 2.0 | | 0.0 | 7.0 | 0.0 | | 0.0 | 0.0 | 5.0 |
| | 0.0156 | 9.0 | 0.0 | 0.0 | 9.0 | 0.0 | 0.0 | | 0.0 | 0.0 | 0.0 | | 0.0 | 0.0 | 2.0 |
| 23 | 0.2500 | 9.0 | 7.0 | 5.0 | 9.0 | 2.0 | 9.0 | | 6.0 | 6.0 | 7.0 | | 7.0 | 7.0 | 7.0 |
| | 0.1250 | 9.0 | 6.0 | 2.0 | 9.0 | 0.0 | 5.0 | | 4.0 | 5.0 | 6.0 | | 1.0 | 5.0 | 5.0 |
| | 0.0625 | 9.0 | 3.0 | 1.0 | 7.0 | 1.0 | 1.0 | | 2.0 | 5.0 | 2.0 | | 1.0 | 1.0 | 2.0 |
| | 0.0313 | 1.0 | 0.0 | 0.0 | 1.0 | 1.0 | 0.0 | | 1.0 | 1.0 | 0.0 | | 0.0 | 0.0 | 1.0 |
| | 0.0156 | 0.0 | 0.0 | 0.0 | 0.0 | 0.0 | 0.0 | | 0.0 | 1.0 | 0.0 | | 0.0 | 0.0 | 0.0 |
| 24 | 0.2500 | 9.0 | 2.0 | 0.0 | 9.0 | 4.0 | 0.0 | | 0.0 | 1.0 | 0.0 | | 0.0 | 0.0 | 1.0 |
| | 0.1250 | 9.0 | 0.0 | 0.0 | 9.0 | 0.0 | 0.0 | | 0.0 | 0.0 | 0.0 | | 0.0 | 0.0 | 0.0 |
| | 0.0625 | 4.0 | 0.0 | 0.0 | 9.0 | 0.0 | 0.0 | | 0.0 | 0.0 | 0.0 | | 0.0 | 0.0 | 0.0 |
| 25 | 0.2500 | 9.0 | 9.0 | 3.0 | 9.0 | 0.0 | 5.0 | | 7.0 | 9.0 | 6.0 | | 5.0 | 6.0 | 9.0 |
| | 0.1250 | 9.0 | 9.0 | 2.0 | 9.0 | 0.0 | 2.0 | | 0.0 | 9.0 | 3.0 | | 2.0 | 3.0 | 8.0 |
| | 0.0625 | 9.0 | 9.0 | 0.0 | 9.0 | 0.0 | 0.0 | | 0.0 | 7.0 | 2.0 | | 0.0 | 2.0 | 6.0 |
| | 0.0313 | 9.0 | 2.0 | 0.0 | 9.0 | 0.0 | 0.0 | | 0.0 | 0.0 | 0.0 | | 0.0 | 1.0 | 0.0 |
| | 0.0156 | 9.0 | 0.0 | 0.0 | 7.0 | 0.0 | 0.0 | | 0.0 | 0.0 | 0.0 | | 0.0 | 0.0 | 0.0 |
| 26 | 0.2500 | 9.0 | 5.0 | 0.0 | 9.0 | 9.0 | 3.0 | | 2.0 | 9.0 | 1.0 | | 0.0 | 1.0 | 5.0 |
| | 0.1250 | 6.0 | 5.0 | 0.0 | 9.0 | 9.0 | 2.0 | | 1.0 | 5.0 | 0.0 | | 0.0 | 0.0 | 4.0 |
| | 0.0625 | 0.0 | 0.0 | 0.0 | 9.0 | 0.0 | 0.0 | | 0.0 | 0.0 | 0.0 | | 0.0 | 0.0 | 2.0 |
| | 0.0313 | 0.0 | 0.0 | 0.0 | 9.0 | 0.0 | 0.0 | | 0.0 | 0.0 | 0.0 | | 0.0 | 0.0 | 0.0 |
| | 0.0156 | 0.0 | 0.0 | 0.0 | 3.0 | 0.0 | 0.0 | | 0.0 | 0.0 | 0.0 | | 0.0 | 0.0 | 0.0 |
| 27 | 0.2500 | 9.0 | 7.0 | 0.0 | 9.0 | 9.0 | 9.0 | | 9.0 | 9.0 | 7.0 | | 8.0 | 9.0 | 9.0 |
| | 0.1250 | 9.0 | 9.0 | 0.0 | 9.0 | 9.0 | 9.0 | | 9.0 | 9.0 | 9.0 | | 3.0 | 7.0 | 9.0 |
| | 0.0625 | 9.0 | 2.0 | 0.0 | 9.0 | 9.0 | 8.0 | | 9.0 | 9.0 | 9.0 | | 3.0 | 3.0 | 8.0 |
| | 0.0313 | 9.0 | 2.0 | 0.0 | 9.0 | 9.0 | 0.0 | | 8.0 | 9.0 | 0.0 | | 0.0 | | 7.0 |
| | 0.0156 | 7.0 | 0.0 | 0.0 | 0.0 | 0.0 | 0.0 | | 0.0 | 0.0 | 0.0 | | 0.0 | 0.0 | 0.0 |
| 28 | 0.2500 | 9.0 | 7.0 | 0.0 | 9.0 | 9.0 | 9.0 | | 9.0 | 9.0 | 9.0 | | 8.0 | 8.0 | 8.0 |
| | 0.1250 | 3.0 | 0.0 | 0.0 | 9.0 | 0.0 | 2.0 | | 9.0 | 9.0 | 5.0 | | 2.0 | | 9.0 |
| | 0.0625 | | 0.0 | 0.0 | 0.0 | 0.0 | 0.0 | | 0.0 | 7.0 | 3.0 | | 0.0 | 0.0 | 5.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 29 | 0.2500 | 9.0 | 0.0 | 0.0 | 0.0 | 0.0 | 4.0 | | 0.0 | 9.0 | 2.0 | 3.0 | 4.0 | 6.0 |
| | 0.1250 | 9.0 | 0.0 | 0.0 | 0.0 | 0.0 | 0.0 | | 0.0 | 0.0 | 0.0 | 0.0 | 0.0 | 0.0 |
| | 0.0625 | 9.0 | 0.0 | 0.0 | 0.0 | 0.0 | 0.0 | | 0.0 | 0.0 | 0.0 | 0.0 | 0.0 | 0.0 |
| 30 | 0.2500 | 9.0 | 6.0 | 1.0 | 9.0 | 9.0 | 2.0 | | 0.0 | 9.0 | 4.0 | 4.0 | 6.0 | 6.0 |
| | 0.1250 | 9.0 | 5.0 | 1.0 | 9.0 | 1.0 | 1.0 | | 0.0 | 7.0 | 1.0 | 1.0 | 2.0 | 3.0 |
| | 0.0625 | 9.0 | 1.0 | 0.0 | 0.0 | 0.0 | 0.0 | | 0.0 | 0.0 | 3.0 | 1.0 | 1.0 | 3.0 |
| | 0.0313 | 9.0 | 0.0 | 0.0 | 0.0 | 0.0 | 0.0 | | 0.0 | 0.0 | 2.0 | 1.0 | 0.0 | 1.0 |
| 31 | 0.2500 | 9.0 | 9.0 | 1.0 | 9.0 | 6.0 | 9.0 | | 9.0 | 9.0 | 6.0 | 6.0 | 7.0 | 9.0 |
| | 0.1250 | 9.0 | 4.0 | 2.0 | 9.0 | | 5.0 | | 9.0 | 9.0 | 5.0 | 2.0 | 3.0 | 7.0 |
| | 0.0625 | 0.0 | 0.0 | 0.0 | 0.0 | 0.0 | 0.0 | | 0.0 | 1.0 | 3.0 | 0.0 | 0.0 | 3.0 |
| 32 | 0.5000 | 9.0 | 9.0 | 0.0 | 9.0 | 7.0 | 1.0 | | 1.0 | 9.0 | 3.0 | 4.0 | 3.0 | 6.0 |
| | 0.2500 | 9.0 | 5.5 | 0.0 | 9.0 | 3.5 | 0.0 | | 0.0 | 9.0 | 1.0 | 1.5 | 1.0 | 4.5 |
| | 0.1250 | 9.0 | 0.5 | 0.0 | 9.0 | 0.5 | 0.5 | | 0.5 | 3.5 | 0.5 | 0.0 | 0.0 | 0.5 |
| | 0.0625 | 1.5 | 0.5 | 0.0 | 9.0 | 0.0 | 0.5 | | 0.0 | 0.5 | 0.5 | 0.0 | 0.0 | 0.0 |
| | 0.0313 | 2.5 | 0.5 | 0.0 | 4.5 | 0.0 | 0.0 | | 0.0 | 0.0 | 0.5 | 0.0 | 0.0 | 0.0 |
| | 0.0156 | 0.0 | 0.0 | 0.5 | 4.5 | 0.0 | 0.0 | | 0.0 | 0.0 | 0.0 | 0.0 | 0.0 | 0.0 |
| 33 | 0.2500 | 9.0 | 9.0 | 9.0 | 9.0 | | 9.0 | | 0.0 | 9.0 | 0.0 | 0.0 | 0.0 | 0.0 |
| | 0.1250 | 9.0 | 9.0 | 4.0 | 9.0 | | 0.0 | | 0.0 | 3.0 | 0.0 | 0.0 | 0.0 | 0.0 |
| | 0.0625 | 9.0 | 9.0 | 0.0 | 7.0 | 0.0 | 0.0 | | 0.0 | 3.0 | 0.0 | 0.0 | 0.0 | 0.0 |
| | 0.0313 | 0.0 | 0.0 | 0.0 | | 0.0 | 0.0 | | 0.0 | 0.0 | 0.0 | 0.0 | 0.0 | 0.0 |
| | 0.0156 | 0.0 | 0.0 | 0.0 | 4.0 | 0.0 | 0.0 | | 0.0 | 0.0 | 0.0 | 0.0 | 0.0 | 0.0 |
| 34 | 0.2500 | 9.0 | 7.0 | 0.0 | 9.0 | 9.0 | 9.0 | | 5.0 | 9.0 | 0.0 | 5.0 | 5.0 | 9.0 |
| | 0.1250 | 9.0 | 4.0 | 0.0 | 9.0 | 7.0 | 3.0 | | 2.0 | 9.0 | 0.0 | 2.0 | 1.0 | 7.0 |
| | 0.0625 | 9.0 | 4.0 | 0.0 | 9.0 | 7.0 | 3.0 | | 0.0 | 9.0 | 0.0 | 0.0 | 0.0 | 3.0 |
| | 0.0313 | 9.0 | 0.0 | 0.0 | 9.0 | 0.0 | 0.0 | | 0.0 | 3.0 | 0.0 | 0.0 | 0.0 | 0.0 |
| 35 | 0.2500 | 9.0 | 9.0 | 3.0 | 9.0 | 9.0 | 9.0 | | 0.0 | 9.0 | 2.0 | 0.0 | 3.0 | 0.0 |
| | 0.1250 | 9.0 | 3.0 | 0.0 | 9.0 | 0.0 | 3.0 | | 0.0 | 0.0 | 0.0 | 0.0 | 1.0 | 0.0 |
| | 0.0625 | 9.0 | 0.0 | 0.0 | 9.0 | 0.0 | 0.0 | | 0.0 | 0.0 | 0.0 | 0.0 | 0.0 | 0.0 |
| 36 | 0.2500 | 9.0 | 9.0 | 0.0 | 9.0 | 9.0 | 0.0 | | 6.0 | 9.0 | 0.0 | 4.0 | 0.0 | 6.0 |
| | 0.1250 | 9.0 | 0.0 | | 9.0 | 9.0 | 0.0 | | 2.0 | 9.0 | 0.0 | 0.0 | 1.0 | 3.0 |
| | 0.0625 | 9.0 | 0.0 | 0.0 | 0.0 | 9.0 | 0.0 | | 0.0 | 0.0 | 0.0 | 0.0 | 0.0 | 0.0 |
| 37 | 0.2500 | 3.0 | 0.0 | 0.0 | 9.0 | 9.0 | 0.0 | | 0.0 | 0.0 | 0.0 | 0.0 | 0.0 | 0.0 |
| | 0.1250 | 0.0 | 0.0 | 0.0 | 9.0 | 0.0 | 0.0 | | 0.0 | 0.0 | 0.0 | 0.0 | 0.0 | 0.0 |
| 38 | 0.2500 | 9.0 | 5.0 | 3.0 | 9.0 | 9.0 | 9.0 | | 1.0 | 9.0 | 6.0 | 2.0 | 7.0 | 4.0 |
| | 0.1250 | 9.0 | 0.0 | 0.0 | 9.0 | 8.0 | 5.0 | | 0.0 | 7.0 | 2.0 | 0.0 | 2.0 | 0.0 |
| | 0.0625 | 9.0 | 0.0 | 0.0 | 9.0 | 5.0 | 4.0 | | 0.0 | 3.0 | 2.0 | 0.0 | 0.0 | 0.0 |
| | 0.0313 | 9.0 | 0.0 | 0.0 | 9.0 | 0.0 | 0.0 | | 0.0 | 0.0 | 0.0 | 0.0 | 0.0 | 0.0 |
| 39 | 0.2500 | 9.0 | 7.0 | 1.0 | 9.0 | 9.0 | 9.0 | | 0.0 | 2.0 | 7.0 | 2.0 | 2.0 | 5.0 |
| | 0.1250 | 9.0 | 6.0 | 2.0 | 7.0 | 6.0 | 1.0 | | 0.0 | 0.0 | 5.0 | 1.0 | 1.0 | 2.0 |
| | 0.0625 | 1.0 | 0.0 | 0.0 | 7.0 | 0.0 | 1.0 | | 0.0 | 0.0 | 0.0 | 0.0 | 0.0 | 0.0 |
| | 0.0313 | 0.0 | 0.0 | 0.0 | 0.0 | 0.0 | 0.0 | | 0.0 | 0.0 | 0.0 | 0.0 | 0.0 | 0.0 |
| | 0.0156 | 0.0 | 0.0 | | 1.0 | 0.0 | 0.0 | | 0.0 | 0.0 | 0.0 | 0.0 | 0.0 | 0.0 |
| 40 | 0.2500 | 9.0 | 6.0 | 1.0 | 9.0 | 0.0 | 9.0 | | 1.0 | 6.0 | 3.0 | 1.0 | 1.0 | 1.0 |
| | 0.1250 | 9.0 | 6.0 | 0.0 | 9.0 | 0.0 | 9.0 | | 1.0 | 6.0 | 1.0 | 0.0 | 0.0 | 0.0 |
| | 0.0625 | 6.0 | 2.0 | 0.0 | 9.0 | 0.0 | 0.0 | | 0.0 | 0.0 | 0.0 | 0.0 | 0.0 | 0.0 |
| | 0.0313 | 0.0 | 0.0 | 0.0 | 9.0 | 0.0 | 0.0 | | 0.0 | 0.0 | 0.0 | 0.0 | 0.0 | 0.0 |
| 41 | 0.2500 | 9.0 | 8.0 | 9.0 | 9.0 | 0.0 | 9.0 | | 2.0 | 9.0 | 6.0 | 0.0 | 0.0 | 2.0 |
| | 0.1250 | 9.0 | 9.0 | 9.0 | 9.0 | 0.0 | 9.0 | | 0.0 | 1.0 | 2.0 | 0.0 | 0.0 | 0.0 |
| | 0.0625 | 9.0 | 2.0 | 0.0 | 9.0 | 0.0 | 7.0 | | 0.0 | 1.0 | 3.0 | 0.0 | 0.0 | 1.0 |
| | 0.0313 | 9.0 | 1.0 | 0.0 | 4.0 | | 0.0 | | 0.0 | 0.0 | 1.0 | 0.0 | 0.0 | 0.0 |
| | 0.0156 | 7.0 | 0.0 | 0.0 | 0.0 | 0.0 | 0.0 | | 0.0 | 0.0 | 0.0 | 0.0 | 0.0 | 0.0 |
| 42 | 0.2500 | 9.0 | 6.0 | 0.0 | 9.0 | 0.0 | 0.0 | | 0.0 | 0.0 | 1.0 | 0.0 | 0.0 | 1.0 |
| | 0.1250 | 9.0 | 0.0 | 0.0 | 3.0 | 0.0 | 0.0 | | 0.0 | 0.0 | 1.0 | 0.0 | 0.0 | 0.0 |
| | 0.0625 | 1.0 | 0.0 | 1.0 | 1.0 | 0.0 | 0.0 | | 0.0 | 1.0 | 0.0 | 0.0 | 0.0 | 1.0 |
| | 0.0313 | 1.0 | 0.0 | 0.0 | 0.0 | 0.0 | 0.0 | | 0.0 | 0.0 | 0.0 | 0.0 | 0.0 | 0.0 |
| 43 | 0.2500 | 9.0 | 4.0 | 9.0 | 9.0 | 9.0 | 9.0 | | 5.0 | 9.0 | 2.0 | 0.0 | 4.0 | 6.0 |
| | 0.1250 | 9.0 | 3.0 | 8.0 | 9.0 | 9.0 | 2.0 | | 0.0 | 5.0 | 0.0 | 0.0 | 1.0 | 3.0 |
| | 0.0625 | 9.0 | 0.0 | 0.0 | 9.0 | 0.0 | 0.0 | | 0.0 | 0.0 | 0.0 | 0.0 | 0.0 | 0.0 |
| | 0.0313 | 9.0 | 0.0 | 0.0 | 9.0 | 0.0 | 0.0 | | 0.0 | 0.0 | 0.0 | 0.0 | 0.0 | 0.0 |
| | 0.0156 | 9.0 | 0.0 | 0.0 | 9.0 | 0.0 | 0.0 | | 0.0 | 0.0 | 0.0 | 0.0 | 0.0 | 0.0 |
| 44 | 0.5000 | 9.0 | 4.0 | 1.0 | 9.0 | 9.0 | 0.0 | | 0.0 | 0.0 | 0.0 | 0.0 | 0.0 | 0.0 |
| | 0.2500 | 9.0 | 2.0 | 0.0 | 9.0 | 9.0 | 0.0 | | 0.0 | 0.0 | 0.0 | 0.0 | 0.0 | 0.0 |
| | 0.1250 | 9.0 | 0.0 | 1.0 | 9.0 | 9.0 | 1.0 | | 0.0 | 0.0 | 0.0 | 0.0 | 0.0 | 1.0 |
| | 0.0625 | 0.0 | 0.0 | 0.0 | 4.0 | 1.0 | 0.0 | | 0.0 | 0.0 | 0.0 | 0.0 | 0.0 | 0.0 |
| | 0.0313 | 0.0 | 0.0 | 0.0 | 5.0 | 1.0 | 0.0 | | 0.0 | 0.0 | 0.0 | 0.0 | 0.0 | 0.0 |
| | 0.0156 | 0.0 | 0.0 | 0.0 | 3.0 | 1.0 | 0.0 | | 0.0 | 0.0 | 0.0 | 0.0 | 0.0 | 0.0 |
| 45 | 0.2500 | 9.0 | 2.0 | 0.0 | 9.0 | 7.0 | 1.0 | | 0.0 | 0.0 | 3.0 | 0.0 | 5.0 | 4.0 |
| | 0.1250 | 9.0 | 0.0 | 0.0 | 9.0 | 0.0 | 0.0 | | 0.0 | 0.0 | 0.0 | 0.0 | 2.0 | 2.0 |
| | 0.0625 | 9.0 | 0.0 | 0.0 | 9.0 | 0.0 | 0.0 | | 0.0 | 0.0 | 0.0 | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0313 | 9.0 | 0.0 | 0.0 | 9.0 | 0.0 | 0.0 | | 0.0 | 0.0 | 0.0 | 0.0 | 0.0 | 0.0 | 0.0 |
| | 0.0156 | 0.0 | 0.0 | 0.0 | 9.0 | 0.0 | 0.0 | | 0.0 | 0.0 | 0.0 | 0.0 | 0.0 | 0.0 | 0.0 |
| 46 | 0.2500 | 9.0 | 1.0 | 0.0 | 9.0 | 0.0 | 1.0 | | 0.0 | 0.0 | 0.0 | 0.0 | 0.0 | 0.0 | 1.0 |
| | 0.1250 | 9.0 | 1.0 | 0.0 | 9.0 | 0.0 | 0.0 | | 0.0 | 0.0 | 0.0 | 0.0 | 0.0 | 0.0 | 0.0 |
| 47 | 0.2500 | 9.0 | 0.0 | 0.0 | 9.0 | 9.0 | 9.0 | | 0.0 | 4.0 | 0.0 | 0.0 | 0.0 | 0.0 | 2.0 |
| | 0.1250 | 9.0 | 0.0 | 0.0 | 9.0 | 0.0 | 0.0 | | 0.0 | 0.0 | 0.0 | 0.0 | 0.0 | 0.0 | 0.0 |
| | 0.0625 | 9.0 | 0.0 | 0.0 | 9.0 | 0.0 | 0.0 | | 0.0 | 0.0 | 0.0 | 0.0 | 0.0 | 0.0 | 0.0 |
| | 0.0313 | 4.0 | 0.0 | 0.0 | 9.0 | 0.0 | 0.0 | | 0.0 | 0.0 | 0.0 | 0.0 | 0.0 | 0.0 | 0.0 |
| | 0.0156 | 4.0 | 0.0 | 0.0 | 9.0 | 0.0 | 0.0 | | 0.0 | 0.0 | 0.0 | 0.0 | 0.0 | 0.0 | 0.0 |
| 48 | 0.2500 | 9.0 | 4.0 | 3.0 | 9.0 | 0.0 | 0.0 | | 0.0 | 0.0 | 2.0 | 3.0 | 2.0 | 2.0 | |
| | 0.1250 | 9.0 | 0.0 | 0.0 | 9.0 | 0.0 | | | 0.0 | 0.0 | 0.0 | 0.0 | 0.0 | 0.0 | |
| | 0.0625 | 4.0 | 0.0 | 0.0 | 9.0 | 0.0 | 0.0 | | 0.0 | 0.0 | 0.0 | 0.0 | 0.0 | 0.0 | |
| | 0.0313 | 0.0 | 0.0 | 0.0 | 9.0 | 0.0 | 0.0 | | 0.0 | 0.0 | 0.0 | 0.0 | 0.0 | 0.0 | |
| | 0.0156 | 0.0 | 0.0 | 0.0 | 9.0 | 0.0 | 0.0 | | 0.0 | 0.0 | 0.0 | 0.0 | 0.0 | 0.0 | |
| 49 | 0.2500 | 9.0 | 9.0 | 9.0 | 9.0 | 9.0 | 9.0 | | 3.0 | 5.0 | 2.0 | 5.0 | 2.0 | 3.0 | |
| | 0.1250 | 9.0 | 9.0 | 3.0 | 9.0 | 7.0 | 9.0 | | 0.0 | | 2.0 | 5.0 | 0.0 | 3.0 | |
| | 0.0625 | 9.0 | 9.0 | | 9.0 | 7.0 | 2.0 | | 0.0 | 5.0 | 2.0 | 0.0 | 0.0 | 0.0 | |
| | 0.0313 | 9.0 | 0.0 | 3.0 | 9.0 | 0.0 | 0.0 | | 0.0 | 4.0 | 0.0 | 0.0 | 0.0 | 0.0 | |
| | 0.0156 | 9.0 | 0.0 | 0.0 | 9.0 | 0.0 | 0.0 | | 0.0 | 0.0 | 0.0 | 0.0 | 0.0 | 0.0 | |
| 50 | 0.2500 | 9.0 | 0.0 | 9.0 | 9.0 | 0.0 | 0.0 | | 0.0 | 0.0 | 0.0 | 0.0 | 0.0 | 0.0 | |
| | 0.1250 | 9.0 | 0.0 | 9.0 | 9.0 | 0.0 | 0.0 | | 0.0 | 0.0 | 0.0 | 0.0 | 0.0 | 0.0 | |
| | 0.0625 | 9.0 | 0.0 | 0.0 | 0.0 | 0.0 | 0.0 | | 0.0 | 0.0 | 0.0 | 0.0 | 0.0 | 0.0 | |
| 51 | 0.2500 | 9.0 | 9.0 | 1.0 | 9.0 | 9.0 | 9.0 | | 1.0 | 9.0 | 7.0 | 7.0 | 6.0 | 6.0 | |
| | 0.1250 | 7.0 | 9.0 | 1.0 | 9.0 | 7.0 | 9.0 | | 1.0 | 6.0 | 1.0 | 1.0 | 2.0 | 2.0 | |
| | 0.0625 | 9.0 | 4.0 | 0.0 | 9.0 | 5.0 | 9.0 | | 1.0 | 3.0 | 1.0 | 1.0 | 0.0 | 1.0 | |
| | 0.0313 | 9.0 | 0.0 | 0.0 | 9.0 | 0.0 | 9.0 | | 0.0 | 0.0 | 0.0 | 1.0 | 0.0 | 1.0 | |
| | 0.0156 | 9.0 | 0.0 | 0.0 | 3.0 | 0.0 | 2.0 | | 0.0 | 1.0 | 0.0 | 0.0 | 0.0 | 1.0 | |
| 52 | 0.2500 | 9.0 | 3.0 | 1.0 | 9.0 | 7.0 | 9.0 | | 1.0 | 9.0 | 2.0 | 4.0 | 5.0 | 3.0 | |
| | 0.1250 | 9.0 | 2.0 | 1.0 | 9.0 | 0.0 | 2.0 | | 0.0 | 1.0 | 1.0 | 0.0 | 2.0 | 1.0 | |
| | 0.0625 | 9.0 | 0.0 | 0.0 | 6.0 | 0.0 | 1.0 | | 0.0 | 0.0 | 1.0 | 0.0 | 0.0 | 0.0 | |
| | 0.0313 | 9.0 | 0.0 | 0.0 | 0.0 | 0.0 | 0.0 | | 0.0 | 0.0 | 0.0 | 0.0 | 0.0 | 0.0 | |
| 53 | 0.2500 | 9.0 | 9.0 | 1.0 | 9.0 | 7.0 | 9.0 | | 9.0 | 9.0 | 4.0 | 7.0 | 7.0 | 6.0 | |
| | 0.1250 | 9.0 | 9.0 | 1.0 | 9.0 | 0.0 | 9.0 | | 7.0 | 7.0 | 2.0 | 5.0 | 2.0 | 5.0 | |
| | 0.0625 | 9.0 | 9.0 | 0.0 | 9.0 | 0.0 | 9.0 | | 4.0 | 4.0 | 0.0 | 1.0 | 1.0 | 1.0 | |
| | 0.0313 | 7.0 | 0.0 | 0.0 | 9.0 | 0.0 | 0.0 | | 1.0 | 1.0 | 0.0 | 0.0 | 0.0 | 1.0 | |
| 54 | 0.5000 | 9.0 | 9.0 | 9.0 | 9.0 | | 9.0 | | 9.0 | 9.0 | 9.0 | 6.0 | | 3.0 | |
| | 0.2500 | 9.0 | 9.0 | 6.0 | 9.0 | 9.0 | 9.0 | | 5.0 | 9.0 | 7.5 | 4.5 | 3.0 | 4.0 | |
| | 0.1250 | 9.0 | 9.0 | 4.5 | 9.0 | 9.0 | 7.5 | | 2.0 | 7.0 | 3.0 | 2.0 | 1.0 | 2.0 | |
| | 0.0625 | 9.0 | 8.0 | 0.0 | 9.0 | 0.0 | 9.0 | | 0.0 | 3.5 | 1.5 | 1.0 | 0.0 | 1.0 | |
| | 0.0313 | 7.5 | 0.5 | 0.0 | 9.0 | 0.0 | 6.0 | | 0.0 | 2.0 | 0.5 | 0.0 | 0.0 | 1.0 | |
| | 0.0156 | 4.5 | 0.0 | 0.0 | 4.5 | 0.0 | 1.5 | | 0.0 | 1.0 | 0.0 | 0.0 | 0.0 | 0.0 | |
| 55 | 0.5000 | 9.0 | 9.0 | 6.0 | 9.0 | 9.0 | 9.0 | | 9.0 | 9.0 | 9.0 | 7.5 | 4.0 | 6.0 | |
| | 0.2500 | 9.0 | 9.0 | 5.0 | 9.0 | 4.0 | 9.0 | | 7.5 | 9.0 | 3.8 | 5.0 | 0.3 | 2.5 | |
| | 0.1250 | 9.0 | 8.0 | 3.0 | 9.0 | 3.0 | 9.0 | | 2.3 | 9.0 | 2.5 | 2.8 | 0.0 | 1.3 | |
| | 0.0625 | 9.0 | 5.0 | 0.0 | 9.0 | 1.7 | 7.8 | | 0.3 | 5.0 | 1.3 | 1.0 | 0.0 | 0.8 | |
| | 0.0313 | 7.8 | 1.0 | 0.0 | 8.5 | 0.0 | 2.8 | | 0.0 | 1.8 | 0.3 | 0.3 | 0.0 | 0.3 | |
| | 0.0156 | 4.0 | 0.0 | 0.0 | 6.3 | 0.0 | 1.0 | | 0.0 | 0.3 | 0.3 | 0.0 | 0.0 | 0.0 | |
| 56 | 0.5000 | 9.0 | 9.0 | 6.0 | 9.0 | | 9.0 | | 2.0 | 9.0 | 9.0 | 6.0 | | 5.0 | |
| | 0.2500 | 9.0 | 8.0 | 6.5 | 9.0 | 7.0 | 9.0 | | 1.5 | 7.0 | 5.5 | 2.0 | 2.0 | 3.0 | |
| | 0.1250 | 9.0 | 8.0 | 1.5 | 9.0 | 7.0 | 6.5 | | 1.0 | 3.0 | 1.5 | 0.5 | 1.0 | 1.0 | |
| | 0.0625 | 9.0 | 6.0 | 0.5 | 9.0 | 0.0 | 6.0 | | 0.5 | 2.5 | 0.5 | 0.0 | 0.0 | 0.5 | |
| | 0.0313 | 7.5 | 0.5 | 0.0 | 7.0 | 0.0 | 1.5 | | 0.0 | 1.0 | 0.0 | 0.0 | 1.0 | 0.5 | |
| 57 | 0.5000 | 9.0 | 9.0 | 4.0 | 9.0 | | 9.0 | | 6.0 | 9.0 | 8.0 | 4.0 | | 9.0 | |
| | 0.2500 | 9.0 | 9.0 | 6.5 | 9.0 | 9.0 | 9.0 | | 2.5 | 9.0 | 4.5 | 3.0 | 3.0 | 5.5 | |
| | 0.1250 | 9.0 | 8.0 | 2.0 | 9.0 | 7.0 | 9.0 | | 2.5 | 6.5 | 3.0 | 2.0 | 2.0 | 3.5 | |
| | 0.0625 | 9.0 | 3.5 | 0.0 | 9.0 | 0.0 | 4.5 | | 0.5 | 2.5 | 2.0 | 0.0 | 0.0 | 1.0 | |
| | 0.0313 | 6.5 | 1.0 | 0.0 | 9.0 | 0.0 | 0.0 | | 0.0 | 0.5 | 0.0 | 0.0 | 0.0 | 0.0 | |
| | 0.0156 | 2.0 | 2.0 | 0.0 | 1.0 | 0.0 | 0.0 | | 0.0 | 0.0 | 0.0 | 0.0 | 0.0 | 0.0 | |
| 58 | 0.2500 | 9.0 | 7.0 | 6.0 | 9.0 | 7.0 | 9.0 | | 2.0 | 9.0 | 3.0 | 2.0 | 2.0 | 3.0 | |
| | 0.1250 | 9.0 | 7.0 | 1.0 | 7.0 | 1.0 | 7.0 | | 1.0 | 6.0 | 1.0 | 0.0 | 0.0 | 1.0 | |
| | 0.0625 | 9.0 | 6.0 | 0.0 | 4.0 | | 2.0 | | 0.0 | 2.0 | 1.0 | 0.0 | 0.0 | 1.0 | |
| | 0.0313 | 9.0 | 0.0 | 0.0 | | 0.0 | 0.0 | | 0.0 | 0.0 | 1.0 | 0.0 | 0.0 | 0.0 | |
| | 0.0156 | 0.0 | 1.0 | 0.0 | 0.0 | 0.0 | 0.0 | | 0.0 | 0.0 | 0.0 | 0.0 | 0.0 | 0.0 | |
| 59 | 0.5000 | 9.0 | 9.0 | 9.0 | 9.0 | | 9.0 | | 9.0 | 9.0 | 9.0 | 7.0 | | 6.0 | |
| | 0.2500 | 9.0 | 9.0 | 7.5 | 9.0 | 9.0 | 9.0 | | 6.0 | 9.0 | 7.0 | 3.5 | 2.0 | 3.5 | |
| | 0.1250 | 9.0 | 9.0 | 7.0 | 9.0 | 7.0 | 9.0 | | 2.0 | 8.0 | 4.0 | 2.5 | 2.0 | 3.0 | |
| | 0.0625 | 8.5 | 6.5 | 2.0 | 9.0 | 6.0 | 8.5 | | 0.5 | 1.5 | 1.0 | 0.5 | 0.0 | 1.5 | |
| | 0.0313 | 6.0 | 3.5 | 0.0 | 9.0 | 0.0 | 4.0 | | 0.0 | 0.0 | 0.5 | 0.0 | 0.0 | 0.5 | |
| | 0.0156 | 2.0 | 2.0 | 0.0 | 9.0 | 0.0 | 1.0 | | 0.0 | 0.0 | 1.0 | 0.0 | 0.0 | 1.0 | |
| 60 | 0.5000 | 9.0 | 9.0 | 4.0 | 9.0 | | 9.0 | | 2.0 | 8.0 | 6.0 | 7.0 | | 8.0 | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.2500 | 9.0 | 7.0 | 5.5 | 9.0 | 0.0 | 5.0 | | 0.5 | 4.5 | 3.5 | | 2.0 | 1.0 | 3.0 |
| | 0.1250 | 9.0 | 7.0 | 1.0 | 9.0 | 0.0 | 2.0 | | 0.0 | 4.5 | 3.0 | | 0.5 | 1.0 | 1.5 |
| | 0.0625 | 7.0 | 2.0 | 0.0 | 9.0 | 0.0 | 0.0 | | 0.0 | 0.5 | 1.5 | | 0.0 | 0.0 | 0.5 |
| | 0.0313 | 9.0 | 0.0 | 0.0 | 8.0 | 0.0 | 0.0 | | 0.0 | 0.5 | 0.5 | | 0.0 | 0.0 | 0.0 |
| | 0.0156 | 2.0 | 0.0 | 0.0 | 9.0 | 0.0 | 0.0 | | 0.0 | 0.0 | 1.0 | | 0.0 | 0.0 | 0.0 |
| 61 | 0.2500 | 1.0 | 0.0 | 1.0 | 9.0 | 0.0 | 0.0 | | 0.0 | 1.0 | 1.0 | | 1.0 | 1.0 | 1.0 |
| | 0.1250 | 0.0 | 0.0 | 0.0 | 7.0 | 0.0 | 0.0 | | 0.0 | 0.0 | 0.0 | | 0.0 | 0.0 | 0.0 |
| 62 | 0.2500 | 9.0 | 7.0 | 1.0 | 9.0 | 9.0 | 9.0 | | 7.0 | 9.0 | 7.0 | | 6.0 | 2.0 | 7.0 |
| | 0.1250 | 9.0 | 9.0 | 1.0 | 9.0 | 6.0 | 7.0 | | 3.0 | 9.0 | 2.0 | | 4.0 | 1.0 | 3.0 |
| | 0.0625 | 9.0 | 7.0 | 1.0 | 9.0 | 0.0 | 5.0 | | 1.0 | 6.0 | 1.0 | | 1.0 | 1.0 | 1.0 |
| | 0.0313 | 7.0 | 5.0 | 0.0 | 9.0 | 0.0 | 3.0 | | 0.0 | 0.0 | 0.0 | | 0.0 | | 1.0 |
| | 0.0156 | 4.0 | 2.0 | 0.0 | 7.0 | 0.0 | 0.0 | | 0.0 | 0.0 | 0.0 | | 0.0 | 0.0 | 0.0 |
| 63 | 0.2500 | 9.0 | 9.0 | 7.0 | 9.0 | 9.0 | 9.0 | | 9.0 | 9.0 | 7.0 | | 7.0 | 7.0 | 7.0 |
| | 0.1250 | 9.0 | 9.0 | 2.0 | 9.0 | 9.0 | 7.0 | | 4.0 | 9.0 | 6.0 | | 7.0 | 6.0 | 6.0 |
| | 0.0625 | 9.0 | 6.0 | 2.0 | 9.0 | 0.0 | 6.0 | | 1.0 | 1.0 | 4.0 | | 5.0 | 1.0 | 2.0 |
| | 0.0313 | 6.0 | 0.0 | 2.0 | 7.0 | 0.0 | 1.0 | | 0.0 | 0.0 | 1.0 | | 0.0 | 0.0 | 1.0 |
| | 0.0156 | 1.0 | 0.0 | 0.0 | | 0.0 | 0.0 | | 0.0 | 0.0 | 0.0 | | 0.0 | 0.0 | 0.0 |
| 64 | 0.2500 | 9.0 | 9.0 | 4.0 | 9.0 | 7.0 | 9.0 | | 6.0 | 9.0 | 5.0 | | 5.0 | 3.0 | 7.0 |
| | 0.1250 | 9.0 | 9.0 | 5.0 | 9.0 | | 9.0 | | 3.0 | 7.0 | 3.0 | | 1.0 | 1.0 | 3.0 |
| | 0.0625 | 9.0 | 7.0 | 1.0 | 9.0 | 1.0 | 9.0 | | 1.0 | 9.0 | 2.0 | | 1.0 | 1.0 | 1.0 |
| | 0.0313 | 9.0 | 6.0 | 0.0 | 9.0 | 0.0 | 0.0 | | 0.0 | 0.0 | 0.0 | | 0.0 | 0.0 | 0.0 |
| | 0.0156 | 1.0 | 2.0 | 0.0 | 9.0 | 0.0 | 0.0 | | 0.0 | 0.0 | 0.0 | | 0.0 | 0.0 | 0.0 |
| 65 | 0.2500 | 9.0 | 9.0 | 2.0 | 9.0 | 9.0 | 7.0 | | 5.0 | 9.0 | 5.0 | | 6.0 | 3.0 | 4.0 |
| | 0.1250 | 9.0 | 9.0 | 1.0 | 9.0 | 1.0 | 9.0 | | 2.0 | 7.0 | 2.0 | | 1.0 | 1.0 | 2.0 |
| | 0.0625 | 9.0 | 4.0 | 1.0 | 9.0 | 0.0 | 1.0 | | 0.0 | 2.0 | 1.0 | | 1.0 | 1.0 | 1.0 |
| | 0.0313 | 9.0 | 2.0 | 0.0 | 9.0 | 0.0 | 0.0 | | 0.0 | 1.0 | 0.0 | | 0.0 | 0.0 | 0.0 |
| | 0.0156 | 2.0 | 1.0 | 0.0 | 9.0 | 0.0 | 0.0 | | 0.0 | 0.0 | 1.0 | | 0.0 | | 0.0 |
| 66 | 0.5000 | 9.0 | 9.0 | 3.0 | 9.0 | 9.0 | 9.0 | | 9.0 | 9.0 | 9.0 | | 8.0 | 4.0 | 7.0 |
| | 0.2500 | 9.0 | 9.0 | 0.5 | 9.0 | 8.0 | 6.0 | | 3.0 | 7.5 | 4.5 | | 2.5 | 1.0 | 2.5 |
| | 0.1250 | 9.0 | 9.0 | 0.5 | 9.0 | 3.5 | 3.0 | | 0.5 | 6.0 | 0.5 | | 0.5 | 0.5 | 1.0 |
| | 0.0625 | 9.0 | 3.0 | 0.0 | 9.0 | 0.0 | 0.5 | | 0.5 | 0.5 | 0.5 | | 0.5 | 0.5 | 0.5 |
| | 0.0313 | 8.0 | 1.0 | 0.0 | 9.0 | 0.0 | 0.0 | | 0.0 | 0.5 | 0.0 | | 0.0 | 0.0 | 0.0 |
| | 0.0156 | 5.0 | 0.5 | 0.0 | 4.0 | 0.0 | 0.0 | | 0.0 | 0.0 | 0.0 | | 0.0 | 0.0 | 0.5 |
| 67 | 0.2500 | 9.0 | 7.0 | 2.0 | 9.0 | 0.0 | 6.0 | | 1.0 | 7.0 | 2.0 | | 1.0 | 1.0 | 1.0 |
| | 0.1250 | 7.0 | 7.0 | 2.0 | 9.0 | 1.0 | 3.0 | | 1.0 | 6.0 | 2.0 | | 1.0 | 1.0 | 1.0 |
| | 0.0625 | 9.0 | 3.0 | 0.0 | 9.0 | 0.0 | 2.0 | | 0.0 | 0.0 | 2.0 | | 0.0 | 0.0 | 1.0 |
| | 0.0313 | 9.0 | 0.0 | 0.0 | 9.0 | 0.0 | 0.0 | | 0.0 | 0.0 | 1.0 | | 0.0 | 0.0 | 0.0 |
| | 0.0156 | 1.0 | 0.0 | 0.0 | 2.0 | 0.0 | 0.0 | | 0.0 | 0.0 | 0.0 | | 0.0 | 0.0 | 0.0 |
| 68 | 0.2500 | 9.0 | 7.0 | 1.0 | 9.0 | 0.0 | 6.0 | | 1.0 | 2.0 | 1.0 | | 1.0 | 1.0 | 1.0 |
| | 0.1250 | 5.0 | 1.0 | 0.0 | 9.0 | 0.0 | 0.0 | | 0.0 | 0.0 | 1.0 | | 0.0 | 0.0 | 1.0 |
| | 0.0625 | 1.0 | 0.0 | 0.0 | 9.0 | 0.0 | 0.0 | | 0.0 | 0.0 | 0.0 | | 0.0 | 0.0 | 0.0 |
| | 0.0313 | 1.0 | 0.0 | 0.0 | 9.0 | 0.0 | 0.0 | | 0.0 | 0.0 | 0.0 | | 0.0 | 0.0 | 0.0 |
| | 0.0156 | 0.0 | 0.0 | 0.0 | 2.0 | 0.0 | 0.0 | | 0.0 | 0.0 | 0.0 | | 0.0 | 0.0 | 0.0 |
| 69 | 0.2500 | 9.0 | 7.0 | 5.0 | 9.0 | 1.0 | 4.0 | | 3.0 | 7.0 | 2.0 | | 1.0 | 1.0 | 3.0 |
| | 0.1250 | 9.0 | 9.0 | 1.0 | 9.0 | 1.0 | 1.0 | | 1.0 | 4.0 | 1.0 | | 1.0 | 1.0 | 3.0 |
| | 0.0625 | 9.0 | 5.0 | 0.0 | 9.0 | 0.0 | 2.0 | | 0.0 | 0.0 | 0.0 | | 0.0 | 0.0 | 0.0 |
| | 0.0313 | 0.0 | 4.0 | 0.0 | 9.0 | 0.0 | 0.0 | | 0.0 | 0.0 | 0.0 | | 0.0 | 0.0 | 0.0 |
| | 0.0156 | 0.0 | 0.0 | 0.0 | 9.0 | 0.0 | | | 0.0 | 0.0 | 1.0 | | 0.0 | 0.0 | 0.0 |
| 70 | 0.2500 | 9.0 | 9.0 | 0.0 | 9.0 | 0.0 | 5.0 | | 1.0 | 9.0 | 2.0 | | 3.0 | 5.0 | 3.0 |
| | 0.1250 | 6.0 | 3.0 | 1.0 | 9.0 | 0.0 | 1.0 | | 1.0 | 9.0 | 0.0 | | 1.0 | 1.0 | 1.0 |
| | 0.0625 | | 0.0 | 0.0 | 9.0 | 0.0 | 0.0 | | 0.0 | 2.0 | 0.0 | | 0.0 | 0.0 | 0.0 |
| | 0.0313 | 0.0 | 0.0 | 0.0 | 9.0 | 0.0 | 0.0 | | 0.0 | 0.0 | 0.0 | | 0.0 | 0.0 | 0.0 |
| | 0.0156 | 0.0 | 0.0 | 0.0 | 2.0 | 0.0 | 0.0 | | 0.0 | 0.0 | 0.0 | | 0.0 | 0.0 | 0.0 |
| 71 | 0.2500 | 9.0 | 9.0 | 9.0 | 9.0 | 6.0 | 9.0 | | 4.0 | 9.0 | | | 3.0 | 3.0 | 3.0 |
| | 0.1250 | 9.0 | 9.0 | 7.0 | 9.0 | 9.0 | 9.0 | | 2.0 | 4.0 | 3.0 | | 1.0 | 1.0 | 3.0 |
| | 0.0625 | 9.0 | 7.0 | 0.0 | 9.0 | 0.0 | 0.0 | | 0.0 | 0.0 | 1.0 | | 0.0 | 0.0 | 0.0 |
| | 0.0313 | 9.0 | 2.0 | 0.0 | 9.0 | 0.0 | 0.0 | | 0.0 | 0.0 | 0.0 | | 0.0 | 0.0 | 0.0 |
| | 0.0156 | 1.0 | 1.0 | 0.0 | 3.0 | 0.0 | 0.0 | | 0.0 | 0.0 | 1.0 | | 0.0 | 0.0 | 0.0 |
| 72 | 0.2500 | 9.0 | 9.0 | 1.0 | 9.0 | 9.0 | 7.0 | | 3.0 | 9.0 | 3.0 | | 1.0 | 2.0 | 1.0 |
| | 0.1250 | 9.0 | 9.0 | 1.0 | 9.0 | 0.0 | 2.0 | | 0.0 | 9.0 | 1.0 | | 1.0 | 1.0 | 1.0 |
| | 0.0625 | 9.0 | 2.0 | 0.0 | 9.0 | 0.0 | 0.0 | | 0.0 | 0.0 | 0.0 | | 0.0 | 0.0 | 0.0 |
| | 0.0313 | 9.0 | | 0.0 | 9.0 | 0.0 | 0.0 | | 0.0 | 0.0 | 0.0 | | 0.0 | 0.0 | 0.0 |
| | 0.0156 | 2.0 | 0.0 | 0.0 | 9.0 | 0.0 | 0.0 | | 0.0 | 0.0 | 0.0 | | 0.0 | 0.0 | 0.0 |
| 73 | 0.2500 | 9.0 | 9.0 | 2.0 | 9.0 | 9.0 | 7.0 | | 4.0 | 9.0 | 9.0 | | 4.0 | 4.0 | 7.0 |
| | 0.1250 | 9.0 | 9.0 | 1.0 | 9.0 | 4.0 | 1.0 | | 0.0 | 9.0 | 1.0 | | 2.0 | 3.0 | 4.0 |
| | 0.0625 | 9.0 | 4.0 | 0.0 | 9.0 | 0.0 | 0.0 | | 0.0 | 0.0 | 1.0 | | 2.0 | 1.0 | 1.0 |
| | 0.0313 | 9.0 | 0.0 | 0.0 | 9.0 | 0.0 | 1.0 | | 0.0 | 1.0 | 1.0 | | 0.0 | 0.0 | 0.0 |
| | 0.0156 | 9.0 | 1.0 | | 9.0 | 0.0 | 0.0 | | 0.0 | 0.0 | 0.0 | | 0.0 | 0.0 | 0.0 |
| 74 | 0.2500 | 9.0 | 9.0 | 0.0 | 9.0 | 9.0 | 1.0 | | 1.0 | 9.0 | 1.0 | | 1.0 | 1.0 | 1.0 |
| | 0.1250 | 9.0 | 9.0 | 0.0 | 9.0 | 0.0 | 0.0 | | 0.0 | 4.0 | 1.0 | | 1.0 | 1.0 | 1.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0625 | 9.0 | 3.0 | 0.0 | 9.0 | 0.0 | 1.0 |  | 1.0 | 1.0 | 0.0 | 1.0 | 1.0 | 0.0 |
|  | 0.0313 | 4.0 | 1.0 | 0.0 | 9.0 | 0.0 |  |  | 0.0 | 0.0 | 1.0 | 0.0 | 0.0 | 0.0 |
|  | 0.0156 | 0.0 | 0.0 | 0.0 | 9.0 | 0.0 | 0.0 |  | 0.0 | 0.0 | 0.0 | 0.0 | 0.0 | 0.0 |
| 75 | 0.2500 | 9.0 | 7.0 | 1.0 | 9.0 | 0.0 | 2.0 |  | 2.0 | 9.0 | 2.0 | 2.0 | 2.0 | 3.0 |
|  | 0.1250 | 9.0 | 6.0 | 1.0 | 9.0 | 0.0 | 0.0 |  | 0.0 | 9.0 | 2.0 | 1.0 | 1.0 | 1.0 |
|  | 0.0625 | 9.0 | 1.0 | 0.0 | 9.0 | 0.0 | 0.0 |  | 0.0 | 0.0 | 0.0 | 0.0 | 0.0 | 0.0 |
|  | 0.0313 | 0.0 | 0.0 | 0.0 | 9.0 | 0.0 | 0.0 |  | 0.0 | 0.0 | 0.0 | 0.0 | 0.0 | 0.0 |
|  | 0.0156 | 0.0 | 0.0 | 0.0 | 9.0 | 0.0 | 0.0 |  | 0.0 | 0.0 | 0.0 | 0.0 | 0.0 | 0.0 |
| 76 | 0.2500 | 9.0 | 9.0 | 1.0 | 9.0 | 9.0 | 9.0 |  | 9.0 | 9.0 | 9.0 | 5.0 | 9.0 | 7.0 |
|  | 0.1250 | 9.0 | 9.0 | 0.0 | 9.0 | 1.0 | 9.0 |  | 7.0 | 9.0 | 6.0 | 4.0 | 7.0 | 7.0 |
|  | 0.0625 | 9.0 | 7.0 | 0.0 | 9.0 | 0.0 | 0.0 |  | 1.0 | 7.0 | 3.0 | 3.0 | 3.0 | 5.0 |
|  | 0.0313 | 1.0 | 0.0 | 0.0 | 9.0 | 0.0 | 0.0 |  | 0.0 | 6.0 | 0.0 | 0.0 | 0.0 | 1.0 |
|  | 0.0156 | 1.0 | 0.0 | 0.0 | 9.0 | 0.0 | 0.0 |  | 0.0 | 0.0 | 0.0 | 0.0 | 0.0 | 0.0 |
| 77 | 0.2500 | 9.0 | 7.0 | 0.0 | 9.0 | 1.0 | 2.0 |  | 0.0 | 9.0 | 1.0 | 0.0 | 0.0 | 1.0 |
|  | 0.1250 | 9.0 | 2.0 | 0.0 | 9.0 | 1.0 | 0.0 |  | 0.0 | 0.0 | 0.0 | 0.0 | 1.0 | 0.0 |
|  | 0.0625 | 9.0 | 1.0 | 0.0 | 9.0 | 0.0 | 0.0 |  | 0.0 | 0.0 | 0.0 | 0.0 | 0.0 | 0.0 |
|  | 0.0313 | 0.0 | 2.0 | 0.0 | 9.0 | 0.0 | 0.0 |  | 0.0 | 0.0 | 0.0 | 0.0 | 0.0 | 0.0 |
|  | 0.0156 | 1.0 | 0.0 | 0.0 | 2.0 | 0.0 | 1.0 |  | 0.0 | 0.0 | 0.0 | 0.0 | 0.0 | 2.0 |
| 78 | 0.2500 | 9.0 | 1.0 | 1.0 | 9.0 | 2.0 | 3.0 |  | 1.0 | 6.0 | 1.0 | 0.0 | 0.0 | 1.0 |
|  | 0.1250 | 2.0 | 1.0 | 0.0 | 9.0 | 3.0 | 0.0 |  | 0.0 | 0.0 | 0.0 | 0.0 | 0.0 | 0.0 |
|  | 0.0625 | 0.0 | 0.0 | 0.0 | 9.0 | 0.0 | 0.0 |  | 0.0 | 0.0 | 0.0 | 0.0 | 0.0 | 0.0 |
|  | 0.0313 | 0.0 | 0.0 | 0.0 | 9.0 | 0.0 | 0.0 |  | 0.0 | 0.0 | 0.0 | 0.0 | 0.0 | 0.0 |
|  | 0.0156 | 0.0 | 0.0 |  | 9.0 | 0.0 | 0.0 |  | 0.0 | 0.0 | 1.0 | 0.0 | 0.0 | 0.0 |
| 79 | 0.2500 | 9.0 | 6.0 | 1.0 | 9.0 | 0.0 | 1.0 |  | 0.0 | 4.0 | 2.0 | 1.0 | 1.0 | 2.0 |
|  | 0.1250 | 6.0 | 1.0 | 0.0 | 9.0 | 0.0 | 0.0 |  | 0.0 | 1.0 | 0.0 | 0.0 | 0.0 | 1.0 |
|  | 0.0625 | 2.0 | 3.0 | 0.0 | 9.0 | 0.0 | 0.0 |  | 0.0 | 1.0 | 1.0 | 1.0 | 1.0 | 1.0 |
|  | 0.0313 | 0.0 | 1.0 | 1.0 | 9.0 | 0.0 | 0.0 |  | 0.0 | 1.0 | 0.0 | 0.0 | 0.0 | 1.0 |
| 80 | 0.2500 | 9.0 | 7.0 | 9.0 | 9.0 | 4.0 | 9.0 |  | 0.0 | 7.0 | 1.0 | 1.0 | 1.0 | 3.0 |
|  | 0.1250 | 9.0 | 9.0 | 9.0 | 9.0 | 4.0 | 4.0 |  | 1.0 | 7.0 | 1.0 | 1.0 | 2.0 | 3.0 |
|  | 0.0625 | 9.0 | 2.0 | 0.0 | 9.0 | 0.0 | 0.0 |  | 0.0 | 1.0 | 1.0 | 0.0 | 0.0 | 1.0 |
|  | 0.0313 | 1.0 | 0.0 | 0.0 | 9.0 | 0.0 | 0.0 |  | 0.0 | 0.0 | 0.0 | 0.0 | 0.0 | 0.0 |
|  | 0.0156 | 0.0 |  | 1.0 | 7.0 | 0.0 | 0.0 |  | 0.0 | 0.0 | 0.0 | 0.0 | 0.0 | 0.0 |
| 81 | 0.2500 | 9.0 | 9.0 | 0.0 | 9.0 | 1.0 | 9.0 |  | 1.0 | 3.0 | 3.0 | 1.0 | 1.0 | 2.0 |
|  | 0.1250 | 9.0 | 9.0 | 0.0 | 9.0 | 0.0 | 1.0 |  | 0.0 | 0.0 | 1.0 | 1.0 | 1.0 | 2.0 |
|  | 0.0625 | 9.0 | 6.0 |  | 9.0 | 0.0 |  |  | 0.0 | 1.0 | 2.0 | 0.0 | 0.0 | 2.0 |
|  | 0.0313 | 9.0 | 6.0 | 0.0 | 7.0 | 0.0 | 0.0 |  | 0.0 | 0.0 | 0.0 | 0.0 | 0.0 | 0.0 |
| 82 | 0.2500 | 9.0 | 9.0 | 9.0 | 9.0 | 9.0 | 9.0 |  | 7.0 | 9.0 | 5.0 | 0.0 | 0.0 | 3.0 |
|  | 0.1250 | 9.0 | 9.0 | 9.0 | 9.0 | 9.0 | 9.0 |  | 3.0 | 9.0 | 0.0 | 0.0 | 0.0 | 0.0 |
|  | 0.0625 | 9.0 | 3.0 | 3.0 | 9.0 | 0.0 | 4.0 |  | 0.0 | 7.0 | 0.0 | 0.0 | 0.0 | 0.0 |
|  | 0.0313 | 9.0 | 2.0 | 0.0 | 9.0 | 0.0 | 0.0 |  | 0.0 | 0.0 | 0.0 | 0.0 | 0.0 | 0.0 |
|  | 0.0156 | 3.0 | 0.0 | 0.0 | 9.0 | 0.0 | 0.0 |  | 0.0 | 0.0 | 0.0 | 0.0 | 0.0 | 0.0 |
| 83 | 0.5000 | 9.0 | 9.0 | 3.0 | 9.0 | 9.0 | 9.0 |  | 4.0 | 9.0 | 7.0 | 5.0 | 5.0 | 7.0 |
|  | 0.2500 | 9.0 | 9.0 | 3.0 | 9.0 | 9.0 | 9.0 |  | 0.0 | 9.0 | 5.0 | 0.0 | 0.0 | 0.0 |
|  | 0.1250 | 9.0 | 9.0 | 0.0 | 9.0 | 0.0 | 3.0 |  | 0.0 | 2.0 | 0.0 | 0.0 | 0.0 | 0.0 |
|  | 0.0625 | 9.0 | 0.0 | 0.0 | 9.0 | 0.0 | 0.0 |  | 0.0 | 0.0 | 0.0 | 0.0 | 0.0 | 0.0 |
|  | 0.0313 | 6.0 | 0.0 | 0.0 | 9.0 | 0.0 | 0.0 |  | 0.0 | 0.0 | 0.0 | 0.0 | 0.0 | 0.0 |
|  | 0.0156 | 4.0 | 0.0 | 0.0 | 9.0 | 0.0 | 0.0 |  | 0.0 | 0.0 | 0.0 | 0.0 | 0.0 | 0.0 |
| 84 | 0.5000 | 9.0 | 9.0 | 9.0 | 9.0 | 5.0 | 9.0 |  | 9.0 | 9.0 | 7.0 | 9.0 | 9.0 | 9.0 |
|  | 0.2500 | 9.0 | 9.0 | 0.0 | 9.0 | 5.0 | 9.0 |  | 2.0 | 9.0 | 5.0 | 3.0 | 6.0 | 8.0 |
|  | 0.1250 | 9.0 | 9.0 | 0.0 | 9.0 | 0.0 | 1.0 |  | 0.0 | 3.0 | 3.0 | 0.0 | 4.0 | 5.0 |
|  | 0.0625 | 7.0 | 4.0 | 0.0 | 9.0 | 0.0 | 0.0 |  | 0.0 | 0.0 | 0.0 | 0.0 | 0.0 | 0.0 |
|  | 0.0313 | 2.0 | 3.0 | 0.0 | 9.0 | 0.0 | 0.0 |  | 0.0 | 0.0 | 0.0 | 0.0 | 0.0 | 0.0 |
|  | 0.0156 | 2.0 | 0.0 | 0.0 | 5.0 | 0.0 | 0.0 |  | 0.0 | 0.0 | 0.0 | 0.0 | 0.0 | 0.0 |
| 85 | 0.5000 | 9.0 | 9.0 | 9.0 | 9.0 | 9.0 | 9.0 |  | 4.0 | 9.0 | 9.0 | 3.0 | 8.0 | 9.0 |
|  | 0.2500 | 9.0 | 9.0 | 0.0 | 9.0 | 6.0 | 7.0 |  | 0.0 | 9.0 | 2.0 | 2.0 | 5.0 | 5.0 |
|  | 0.1250 | 9.0 | 7.0 | 0.0 | 9.0 | 4.0 | 5.0 |  | 0.0 | 0.0 | 2.0 | 0.0 | 3.0 | 2.0 |
|  | 0.0625 | 9.0 | 3.0 | 0.0 | 9.0 | 0.0 | 2.0 |  | 0.0 | 0.0 | 0.0 | 0.0 | 0.0 | 0.0 |
|  | 0.0313 | 9.0 | 0.0 | 0.0 | 9.0 | 0.0 | 0.0 |  | 0.0 | 0.0 | 0.0 | 0.0 | 0.0 | 0.0 |
|  | 0.0156 | 0.0 | 0.0 | 0.0 | 3.0 | 0.0 | 0.0 |  | 0.0 | 0.0 | 0.0 | 0.0 | 0.0 | 0.0 |
| 86 | 0.5000 | 9.0 | 9.0 | 3.0 | 9.0 | 9.0 | 9.0 |  | 4.0 | 9.0 | 8.0 | 6.0 | 6.0 | 9.0 |
|  | 0.2500 | 9.0 | 9.0 | 0.0 | 9.0 | 9.0 | 9.0 |  | 0.0 | 9.0 | 4.0 | 2.0 | 2.0 | 4.0 |
|  | 0.1250 | 9.0 | 9.0 | 0.0 | 9.0 | 0.0 | 9.0 |  | 0.0 | 8.0 | 0.0 | 0.0 | 0.0 | 0.0 |
|  | 0.0625 | 9.0 | 6.0 | 0.0 | 9.0 | 0.0 | 8.0 |  | 0.0 | 4.0 | 0.0 | 0.0 | 0.0 | 0.0 |
|  | 0.0313 | 9.0 | 0.0 | 0.0 | 4.0 | 0.0 | 0.0 |  | 0.0 | 0.0 | 0.0 | 0.0 | 0.0 | 0.0 |
|  | 0.0156 | 9.0 | 0.0 | 0.0 | 4.0 | 0.0 | 0.0 |  | 0.0 | 0.0 | 0.0 | 0.0 | 0.0 | 0.0 |
| 87 | 0.5000 | 9.0 | 9.0 | 2.0 | 9.0 | 7.0 | 6.0 |  | 0.0 | 9.0 | 5.0 | 0.0 | 1.0 | 1.0 |
|  | 0.2500 | 9.0 | 0.0 | 0.0 | 9.0 | 0.0 | 5.0 |  | 0.0 | 0.0 | 4.0 | 0.0 | 0.0 | 0.0 |
|  | 0.1250 | 3.0 | 0.0 | 0.0 | 4.0 | 0.0 | 1.0 |  | 0.0 | 0.0 | 0.0 | 0.0 | 0.0 | 0.0 |
| 88 | 0.2500 | 9.0 | 9.0 | 9.0 | 9.0 | 9.0 | 9.0 |  | 2.0 | 9.0 | 9.0 | 7.0 | 9.0 | 8.0 |
|  | 0.1250 | 9.0 | 9.0 | 3.0 | 9.0 | 3.0 | 9.0 |  | 0.0 | 7.0 | 4.0 | 2.0 | 3.0 | 6.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0625 | 9.0 | 7.0 | 0.0 | 9.0 | 3.0 | 0.0 | 0.0 | 3.0 | 0.0 | 0.0 | 0.0 | 0.0 |
|  | 0.0313 | 9.0 | 0.0 | 0.0 | 9.0 | 0.0 | 0.0 | 0.0 | 0.0 | 0.0 | 0.0 | 0.0 | 0.0 |
|  | 0.0156 | 9.0 | 0.0 | 0.0 | 7.0 | 0.0 | 0.0 | 0.0 | 0.0 | 0.0 | 0.0 | 0.0 | 0.0 |
| 89 | 0.5000 | 9.0 | 9.0 | 9.0 | 9.0 | 9.0 | 9.0 | 9.0 | 9.0 | 9.0 | 9.0 | 9.0 | 9.0 |
|  | 0.2500 | 9.0 | 6.5 | 6.0 | 9.0 | 8.5 | 9.0 | 5.5 | 9.0 | 8.5 | 8.0 | 6.5 | 7.5 |
|  | 0.1250 | 9.0 | 6.5 | 3.0 | 9.0 | 4.5 | 1.5 | 2.0 | 9.0 | 2.0 | 4.5 | 2.0 | 6.5 |
|  | 0.0625 | 9.0 | 2.0 | 0.0 | 9.0 | 0.0 | 0.5 | 0.0 | 1.5 | 1.0 | 2.0 | 0.5 | 1.0 |
|  | 0.0313 | 6.5 | 0.5 | 0.0 | 9.0 | 0.0 | 0.0 | 0.0 | 1.5 | 0.0 | 0.5 | 0.0 | 0.0 |
|  | 0.0156 | 1.5 | 0.0 | 0.0 | 8.0 | 0.0 | 0.0 | 0.0 | 0.0 | 0.0 | 0.0 | 0.0 | 0.0 |
| 90 | 0.2500 | 9.0 | 9.0 | 9.0 | 9.0 | 7.0 | 9.0 | 3.0 | 9.0 | 9.0 | 9.0 | 7.0 | 8.0 |
|  | 0.1250 | 9.0 | 9.0 | 9.0 | 9.0 | 3.0 | 9.0 | 0.0 | 9.0 | 7.0 | 2.0 | 2.0 | 7.0 |
|  | 0.0625 | 9.0 | 3.0 | 9.0 | 9.0 | 0.0 | 4.0 | 0.0 | 3.0 | 2.0 | 0.0 | 0.0 | 0.0 |
|  | 0.0313 | 9.0 | 0.0 | 3.0 | 7.0 | 0.0 | 1.0 | 0.0 | 0.0 | 0.0 | 0.0 | 0.0 | 0.0 |
| 91 | 0.2500 | 9.0 | 0.0 | 0.0 | 9.0 | 0.0 | 0.0 | 0.0 | 0.0 | 0.0 | 0.0 | 0.0 | 0.0 |
|  | 0.1250 | 4.0 | 0.0 | 0.0 | 4.0 | 0.0 | 0.0 | 0.0 | 0.0 | 0.0 | 0.0 | 0.0 | 0.0 |
| 92 | 0.2500 | 9.0 | 9.0 | 3.0 | 9.0 | 9.0 | 9.0 | 0.0 | 9.0 | 5.0 | 5.0 | 2.0 | 6.0 |
|  | 0.1250 | 9.0 | 5.0 |  | 9.0 | 9.0 | 9.0 | 0.0 | 0.0 | 1.0 | 0.0 | 0.0 | 0.0 |
|  | 0.0625 | 9.0 | 0.0 | 0.0 | 9.0 | 0.0 | 0.0 | 0.0 | 0.0 | 0.0 | 0.0 | 0.0 | 0.0 |
|  | 0.0313 | 3.0 | 0.0 | 0.0 | 9.0 | 0.0 | 0.0 | 0.0 | 0.0 | 0.0 | 0.0 | 0.0 | 0.0 |
|  | 0.0156 | 0.0 | 0.0 | 0.0 | 9.0 | 0.0 | 0.0 | 0.0 | 0.0 | 0.0 | 0.0 | 0.0 | 0.0 |
| 93 | 0.2500 | 9.0 | 9.0 | 9.0 | 9.0 | 9.0 | 9.0 | 0.0 | 9.0 | 8.0 | 4.0 | 7.0 | 6.0 |
|  | 0.1250 | 9.0 | 9.0 | 0.0 | 9.0 | 9.0 | 9.0 | 0.0 | 0.0 | 4.0 | 2.0 | 2.0 | 1.0 |
|  | 0.0625 | 9.0 | 0.0 | 0.0 | 9.0 | 0.0 | 2.0 | 0.0 | 0.0 | 0.0 | 0.0 | 0.0 | 0.0 |
|  | 0.0313 | 5.0 | 0.0 | 0.0 | 3.0 | 0.0 | 0.0 | 0.0 | 0.0 | 0.0 | 0.0 | 0.0 | 0.0 |
| 94 | 0.2500 | 9.0 | 9.0 | 0.0 | 9.0 | 9.0 | 9.0 | 0.0 | 9.0 | 4.0 | 3.0 | 0.0 | 6.0 |
|  | 0.1250 | 9.0 | 9.0 | 0.0 | 9.0 | 3.0 | 9.0 | 0.0 | 4.0 | 0.0 | 0.0 | 0.0 | 0.0 |
|  | 0.0625 | 9.0 | 4.0 | 0.0 | 9.0 | 0.0 | 0.0 | 0.0 | 0.0 | 0.0 | 0.0 | 0.0 | 0.0 |
|  | 0.0313 | 9.0 | 0.0 | 0.0 | 9.0 | 0.0 | 0.0 | 0.0 | 0.0 | 0.0 | 0.0 | 0.0 | 0.0 |
|  | 0.0156 | 0.0 | 0.0 | 0.0 | 9.0 | 0.0 | 0.0 | 0.0 | 0.0 | 0.0 | 0.0 | 0.0 | 0.0 |
| 95 | 0.5000 | 9.0 | 9.0 | 9.0 | 9.0 | 9.0 | 9.0 | 0.0 | 7.0 | 3.0 | 1.0 | 1.0 | 5.0 |
|  | 0.2500 | 9.0 | 6.0 | 7.0 | 9.0 | 7.0 | 2.0 | 0.0 | 4.0 | 2.0 | 1.0 | 0.0 | 1.0 |
|  | 0.1250 | 9.0 | 4.0 | 0.0 | 6.0 | 6.0 | 0.0 | 0.0 | 0.0 | 2.0 | 0.0 | 0.0 | 0.0 |
|  | 0.0625 | 9.0 | 1.0 | 0.0 |  | 4.0 | 0.0 | 0.0 | 0.0 | 0.0 | 0.0 | 0.0 | 0.0 |
| 96 | 0.5000 | 9.0 | 6.0 | 9.0 | 9.0 | 7.0 | 9.0 | 1.0 | 4.0 | 4.0 | 2.0 | 1.0 | 4.0 |
|  | 0.2500 | 9.0 | 4.0 | 4.0 | 9.0 | 6.0 | 9.0 | 1.0 | 1.0 | 3.0 | 1.0 | 1.0 | 2.0 |
|  | 0.1250 | 9.0 | 1.0 | 0.0 | 3.0 | 2.0 | 1.0 | 0.0 | 0.0 | 0.0 | 0.0 | 0.0 | 0.0 |
|  | 0.0625 | 9.0 | 0.0 | 0.0 | 2.0 | 2.0 | 0.0 | 0.0 | 1.0 | 0.0 | 0.0 | 0.0 | 1.0 |
|  | 0.0313 | 1.0 | 0.0 | 0.0 | 2.0 | 0.0 | 0.0 | 0.0 | 1.0 | 0.0 | 0.0 | 0.0 | 0.0 |
| 97 | 0.5000 | 9.0 | 4.0 | 3.0 | 9.0 | 5.0 | 9.0 | 0.0 | 7.0 | 3.0 | 1.0 | 2.0 | 4.0 |
|  | 0.2500 | 9.0 | 4.0 | 1.0 | 9.0 | 0.0 | 9.0 | 0.0 | 1.0 | 0.0 | 1.0 | 1.0 | 0.0 |
|  | 0.1250 | 4.0 | 0.0 | 0.0 | 7.0 | 1.0 | 1.0 | 0.0 | 0.0 | 0.0 | 0.0 | 0.0 | 0.0 |
| 98 | 0.5000 | 9.0 | 7.0 | 7.0 | 9.0 | 7.0 | 9.0 | 2.0 | 7.0 | 5.0 | 4.0 | 3.0 | 6.0 |
|  | 0.2500 | 6.0 | 5.0 | 2.0 | 9.0 | 7.0 | 4.0 | 1.0 | 3.0 | 4.0 | 1.0 | 1.0 | 4.0 |
|  | 0.1250 | 6.0 | 3.0 | 1.0 | 7.0 |  | 3.0 | 1.0 | 4.0 | 1.0 | 0.0 | 0.0 | 0.0 |
|  | 0.0625 | 2.0 | 2.0 | 0.0 | 5.0 | 6.0 | 1.0 | 0.0 | 0.0 | 1.0 | 0.0 | 0.0 | 0.0 |
|  | 0.0313 | 0.0 | 0.0 | 0.0 | 2.0 | 0.0 | 0.0 | 0.0 | 1.0 | 0.0 | 0.0 | 0.0 | 0.0 |
|  | 0.0156 | 0.0 | 0.0 | 0.0 | 0.0 | 1.0 | 0.0 | 0.0 | 0.0 | 0.0 | 0.0 | 0.0 | 0.0 |
| 99 | 0.5000 | 9.0 | 9.0 | 7.0 | 9.0 | 7.0 | 9.0 | 7.0 | 9.0 | 7.0 | 4.0 | 5.0 | 7.0 |
|  | 0.2500 | 9.0 | 9.0 | 3.0 | 9.0 | 9.0 | 9.0 | 1.0 | 7.0 | 7.0 | 4.0 | 4.0 | 6.0 |
|  | 0.1250 | 9.0 | 9.0 | 2.0 | 9.0 | 7.0 | 9.0 | 1.0 | 6.0 | 4.0 | 1.0 | 1.0 | 2.0 |
|  | 0.0625 | 9.0 | 4.0 | 1.0 | 9.0 | 1.0 | 9.0 | 0.0 | 1.0 | 3.0 | 1.0 | 1.0 | 1.0 |
|  | 0.0313 | 9.0 | 0.0 |  | 9.0 | 0.0 | 0.0 | 0.0 | 1.0 | 0.0 | 0.0 | 0.0 | 0.0 |
|  | 0.0156 | 9.0 | 0.0 | 0.0 | 9.0 | 0.0 | 0.0 | 0.0 | 0.0 | 0.0 | 0.0 | 0.0 | 0.0 |
| 100 | 0.5000 | 9.0 | 7.0 | 8.0 | 9.0 | 6.0 | 5.0 | 1.0 | 1.0 | 2.0 | 1.0 | 1.0 | 1.0 |
|  | 0.2500 | 9.0 | 1.0 | 0.0 | 9.0 | 6.0 | 2.0 | 1.0 | 1.0 | 0.0 | 0.0 | 0.0 | 0.0 |
|  | 0.1250 | 2.0 | 1.0 | 0.0 | 9.0 |  | 0.0 | 0.0 | 0.0 | 1.0 | 0.0 | 1.0 | 0.0 |
|  | 0.0625 | 0.0 | 0.0 | 0.0 | 9.0 | 1.0 | 0.0 | 0.0 | 1.0 | 1.0 | 0.0 | 0.0 | 0.0 |
|  | 0.0313 | 0.0 | 0.0 | 0.0 | 9.0 | 0.0 | 1.0 | 0.0 | 0.0 | 0.0 | 0.0 | 0.0 | 0.0 |
| 102 | 0.5000 | 9.0 | 7.0 | 4.0 | 9.0 | 4.0 | 9.0 | 0.0 | 1.0 | 4.0 | 1.0 | 1.0 | 1.0 |
|  | 0.2500 | 6.0 | 4.0 | 0.0 | 1.0 | 1.0 | 1.0 | 0.0 | 0.0 | 1.0 | 0.0 | 0.0 | 0.0 |
|  | 0.0625 | 9.0 | 0.0 | 0.0 | 5.0 | 0.0 | 0.0 | 0.0 | 0.0 | 0.0 | 0.0 | 0.0 | 0.0 |
|  | 0.0313 | 0.0 | 0.0 | 0.0 | 6.0 | 1.0 | 0.0 | 0.0 | 1.0 | 0.0 | 0.0 | 0.0 | 0.0 |
|  | 0.0156 | 0.0 | 0.0 | 0.0 |  | 0.0 | 0.0 | 0.0 | 1.0 | 0.0 | 0.0 | 0.0 | 0.0 |
| 103 | 0.5000 | 9.0 | 9.0 | 3.0 | 9.0 | 7.0 | 9.0 | 2.0 | 9.0 | 3.0 | 2.0 | 1.0 | 1.0 |
|  | 0.2500 | 9.0 | 4.0 | 3.0 | 9.0 | 0.0 | 5.0 | 0.0 | 3.0 | 0.0 | 0.0 | 0.0 | 0.0 |
|  | 0.1250 | 9.0 | 0.0 | 0.0 | 9.0 | 0.0 | 3.0 | 0.0 | 3.0 | 0.0 | 0.0 | 0.0 | 0.0 |
|  | 0.0625 | 9.0 | 0.0 | 0.0 | 4.0 | 0.0 | 0.0 | 0.0 | 0.0 | 0.0 | 0.0 | 0.0 | 0.0 |
|  | 0.0313 | 9.0 | 0.0 | 0.0 | 0.0 | 0.0 | 0.0 | 0.0 | 0.0 | 0.0 | 0.0 | 0.0 | 0.0 |
| 104 | 0.5000 | 9.0 | 9.0 | 0.0 | 9.0 | 6.0 | 9.0 | 1.0 | 6.0 | 3.0 | 0.0 | 1.0 | 2.0 |
|  | 0.2500 | 9.0 | 3.0 | 0.0 | 9.0 | 0.0 | 3.0 | 1.0 | 0.0 | 0.0 | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.1250 | 8.0 | 0.0 | 0.0 | 9.0 | 0.0 | 0.0 | 0.0 | 0.0 | 0.0 | 0.0 | 0.0 | 0.0 | 0.0 | |
| | 0.0625 | 3.0 | 0.0 | 0.0 | 0.0 | 0.0 | 0.0 | 0.0 | 0.0 | 0.0 | 0.0 | 0.0 | 0.0 | 0.0 | |
| 105 | 0.5000 | 9.0 | 4.0 | 0.0 | 9.0 | 7.0 | 4.0 | 1.0 | 3.0 | 0.0 | 0.0 | 0.0 | 2.0 | | |
| | 0.2500 | 9.0 | 3.0 | 0.0 | 9.0 | 3.0 | 3.0 | 0.0 | 3.0 | 0.0 | 0.0 | 0.0 | 1.0 | | |
| | 0.1250 | 7.0 | 1.0 | 0.0 | 9.0 | | 0.0 | 0.0 | 0.0 | 0.0 | 0.0 | 0.0 | 0.0 | | |
| 106 | 0.2500 | 9.0 | 9.0 | 6.0 | 9.0 | 7.0 | 9.0 | 7.0 | 9.0 | 5.0 | 5.0 | 5.0 | 5.0 | | |
| | 0.1250 | 9.0 | 7.0 | 4.0 | 9.0 | 6.0 | 7.5 | 2.0 | 9.0 | 3.5 | 2.5 | 3.0 | 4.0 | | |
| | 0.0625 | 8.0 | 5.0 | 2.0 | 9.0 | 3.0 | 7.0 | 1.5 | 4.5 | 2.0 | 2.0 | 2.0 | 2.5 | | |
| | 0.0313 | 6.5 | 1.5 | 1.5 | 9.0 | 2.0 | 2.5 | 1.0 | 0.5 | 1.5 | 1.0 | 0.0 | 1.0 | | |
| | 0.0156 | 5.0 | 1.5 | 0.0 | 8.0 | 1.0 | 2.0 | 0.0 | 0.0 | 1.0 | 1.5 | 0.0 | 0.0 | | |
| 107 | 0.2500 | 9.0 | 2.0 | 1.0 | 9.0 | 7.0 | 7.0 | 1.0 | 7.0 | 3.0 | 2.0 | 4.0 | 4.0 | | |
| | 0.1250 | 9.0 | 0.0 | 0.0 | 9.0 | 7.0 | 1.0 | 0.0 | 0.0 | 2.0 | 0.0 | 0.0 | 1.0 | | |
| | 0.0625 | 1.0 | 0.0 | 0.0 | 6.0 | 1.0 | 0.0 | 0.0 | 1.0 | 1.0 | 0.0 | 0.0 | 0.0 | | |
| | 0.0313 | 0.0 | 0.0 | 0.0 | | 1.0 | 0.0 | 0.0 | 0.0 | 0.0 | 0.0 | 0.0 | 0.0 | | |
| 108 | 0.2500 | 9.0 | 1.0 | 9.0 | 9.0 | 9.0 | 9.0 | 1.0 | 9.0 | 2.0 | 5.0 | 5.0 | 2.0 | | |
| | 0.1250 | 8.0 | 0.0 | 0.0 | 9.0 | 7.0 | 4.0 | 0.0 | 7.0 | 2.0 | 1.0 | 2.0 | 1.0 | | |
| | 0.0625 | 4.0 | 0.0 | 0.0 | 9.0 | 6.0 | 0.0 | 0.0 | 1.0 | 2.0 | 0.0 | 0.0 | 0.0 | | |
| | 0.0313 | 0.0 | 0.0 | 0.0 | 0.0 | 2.0 | 0.0 | 0.0 | 0.0 | | 0.0 | 0.0 | 0.0 | | |
| | 0.0156 | 0.0 | 0.0 | 0.0 | | 1.0 | 0.0 | 0.0 | 0.0 | 0.0 | 0.0 | 0.0 | 0.0 | | |
| 109 | 0.5000 | 9.0 | 9.0 | 9.0 | 9.0 | | 9.0 | 9.0 | 9.0 | 9.0 | 6.0 | | 7.0 | | |
| | 0.2500 | 9.0 | 9.0 | 9.0 | 9.0 | 4.0 | 8.0 | 8.5 | 9.0 | 9.0 | 5.0 | 4.0 | 6.5 | | |
| | 0.1250 | 9.0 | 9.0 | 6.5 | 9.0 | 4.0 | 8.0 | 7.0 | 9.0 | 7.5 | 4.0 | 6.0 | 6.0 | | |
| | 0.0625 | 9.0 | 8.0 | 5.5 | 9.0 | 3.0 | 5.0 | 4.0 | 9.0 | 5.0 | 2.0 | 1.0 | 4.0 | | |
| | 0.0313 | 9.0 | 3.0 | 4.0 | 9.0 | 3.0 | 2.0 | 2.5 | 6.0 | 2.0 | 1.0 | 1.0 | 3.5 | | |
| | 0.0156 | 6.5 | 3.0 | 6.5 | 9.0 | 3.0 | 2.0 | 1.5 | 5.5 | 1.5 | 0.0 | 0.0 | 3.0 | | |
| 110 | 0.5000 | 9.0 | 9.0 | 9.0 | 9.0 | | 9.0 | 4.0 | 9.0 | 7.0 | 3.0 | | 4.0 | | |
| | 0.2500 | 9.0 | 6.5 | 5.0 | 9.0 | 2.0 | 9.0 | 3.0 | 9.0 | 5.5 | 5.0 | 1.0 | 3.5 | | |
| | 0.1250 | 9.0 | 4.5 | 2.0 | 9.0 | 0.0 | 9.0 | 2.0 | 8.0 | 4.0 | 1.5 | 1.0 | 2.5 | | |
| | 0.0625 | 9.0 | 3.5 | 0.0 | 9.0 | 0.0 | 5.5 | 0.5 | 5.0 | 2.5 | 0.5 | 1.0 | 1.0 | | |
| | 0.0313 | 9.0 | 2.5 | 0.0 | 9.0 | 0.0 | 4.5 | 0.0 | 2.5 | 0.5 | 0.5 | 1.0 | 0.5 | | |
| | 0.0156 | 5.5 | 1.0 | 0.0 | 8.0 | 0.0 | 3.5 | 0.0 | 1.5 | 0.5 | 0.0 | 0.0 | 0.0 | | |
| 111 | 0.2500 | 9.0 | 7.0 | 9.0 | 9.0 | 7.0 | 7.0 | 4.0 | 7.0 | 4.0 | 5.0 | 4.0 | 4.0 | | |
| | 0.1250 | 9.0 | 6.0 | 1.0 | 9.0 | 6.0 | 9.0 | 0.0 | 7.0 | 3.0 | 1.0 | 1.0 | 4.0 | | |
| | 0.0625 | 2.0 | 0.0 | 1.0 | 9.0 | 0.0 | 0.0 | 0.0 | 1.0 | 1.0 | 0.0 | 0.0 | 0.0 | | |
| | 0.0313 | 0.0 | 0.0 | 0.0 | 0.0 | 0.0 | 0.0 | 0.0 | 0.0 | 1.0 | 0.0 | 0.0 | 0.0 | | |
| | 0.0156 | 1.0 | 0.0 | 0.0 | | 0.0 | 0.0 | 0.0 | 0.0 | 1.0 | 0.0 | 0.0 | 0.0 | | |
| 112 | 0.2500 | 1.0 | 0.0 | 0.0 | 1.0 | 0.0 | 0.0 | 0.0 | 0.0 | 3.0 | 2.0 | 1.0 | 4.0 | | |
| | 0.1250 | | 0.0 | 0.0 | | 0.0 | 0.0 | 0.0 | 0.0 | 3.0 | 0.0 | 0.0 | 1.0 | | |
| | 0.0625 | 0.0 | 0.0 | 0.0 | | 0.0 | 0.0 | 0.0 | 0.0 | 1.0 | 0.0 | 0.0 | 0.0 | | |
| | 0.0313 | 0.0 | 0.0 | 0.0 | | 0.0 | 0.0 | 0.0 | 1.0 | 0.0 | 0.0 | 0.0 | 0.0 | | |
| 113 | 0.2500 | 9.0 | 2.0 | 0.0 | 9.0 | 3.0 | 1.0 | 0.0 | 1.0 | 2.0 | 0.0 | 0.0 | 1.0 | | |
| | 0.1250 | 9.0 | 0.0 | 0.0 | 9.0 | 1.0 | 0.0 | 0.0 | 0.0 | 0.0 | 0.0 | 0.0 | 0.0 | | |
| | 0.0625 | 1.0 | 0.0 | 0.0 | 0.0 | 0.0 | 0.0 | 0.0 | 0.0 | 0.0 | 0.0 | 0.0 | 0.0 | | |
| | 0.0313 | 1.0 | 0.0 | 0.0 | 7.0 | 0.0 | 0.0 | 0.0 | 0.0 | 1.0 | 0.0 | 0.0 | 1.0 | | |
| | 0.0156 | 0.0 | 0.0 | 0.0 | 6.0 | 0.0 | 0.0 | 0.0 | 0.0 | 0.0 | 0.0 | 0.0 | 0.0 | | |
| 114 | 0.2500 | 9.0 | 7.0 | 9.0 | 9.0 | 9.0 | 7.0 | 4.0 | 9.0 | 3.0 | 2.0 | 3.0 | 2.0 | | |
| | 0.1250 | 9.0 | 5.0 | 3.0 | 9.0 | 7.0 | 9.0 | 2.0 | 7.0 | 2.0 | 2.0 | 1.0 | 1.0 | | |
| | 0.0625 | 6.0 | 0.0 | 1.0 | 7.0 | 3.0 | 0.0 | 0.0 | 2.0 | 0.0 | 0.0 | 0.0 | 1.0 | | |
| | 0.0313 | 1.0 | 0.0 | 0.0 | 9.0 | 0.0 | 0.0 | 0.0 | 0.0 | 1.0 | 0.0 | 0.0 | 1.0 | | |
| | 0.0156 | 0.0 | 0.0 | 0.0 | 9.0 | 0.0 | 0.0 | 0.0 | 0.0 | 0.0 | 0.0 | 0.0 | 0.0 | | |
| 115 | 0.2500 | 9.0 | 1.0 | 2.0 | 9.0 | 9.0 | 7.0 | 0.0 | 4.0 | 4.0 | 3.0 | 4.0 | 2.0 | | |
| | 0.1250 | 9.0 | 0.0 | 4.0 | 9.0 | 7.0 | 2.0 | 0.0 | 0.0 | 3.0 | 1.0 | 0.0 | 1.0 | | |
| | 0.0625 | 0.0 | 0.0 | 0.0 | 7.0 | 3.0 | 0.0 | 0.0 | 0.0 | 1.0 | 0.0 | 0.0 | 0.0 | | |
| | 0.0313 | 0.0 | 0.0 | | 5.0 | 3.0 | 0.0 | 0.0 | 0.0 | 0.0 | 0.0 | 0.0 | 0.0 | | |
| | 0.0156 | 0.0 | 0.0 | 2.0 | | 1.0 | 0.0 | 0.0 | 1.0 | 0.0 | 0.0 | 0.0 | 0.0 | | |
| 116 | 0.2500 | 9.0 | 1.0 | 2.0 | 9.0 | 7.0 | 3.0 | 0.0 | 3.0 | 2.0 | 1.0 | 1.0 | 0.0 | | |
| | 0.1250 | 9.0 | 2.0 | 0.0 | 7.0 | 0.0 | 1.0 | 0.0 | 0.0 | 1.0 | 0.0 | 0.0 | 0.0 | | |
| | 0.0625 | 4.0 | 2.0 | 0.0 | 4.0 | 0.0 | 0.0 | 0.0 | 0.0 | 0.0 | 0.0 | 0.0 | 0.0 | | |
| | 0.0313 | 0.0 | 0.0 | 0.0 | 9.0 | 0.0 | 0.0 | 0.0 | 0.0 | 1.0 | 0.0 | 0.0 | 0.0 | | |
| | 0.0156 | 0.0 | 0.0 | 0.0 | 9.0 | 0.0 | 0.0 | 0.0 | 0.0 | 1.0 | 0.0 | 0.0 | 0.0 | | |
| 117 | 0.2500 | 9.0 | 7.0 | 1.0 | 9.0 | 7.0 | 9.0 | 0.0 | 0.0 | 1.0 | 0.0 | 0.0 | 0.0 | | |
| | 0.1250 | 1.0 | 0.0 | 1.0 | 6.0 | 3.0 | 0.0 | 0.0 | 0.0 | 1.0 | 0.0 | 0.0 | 1.0 | | |
| | 0.0625 | 0.0 | 0.0 | 0.0 | 9.0 | 0.0 | 0.0 | 0.0 | 1.0 | 1.0 | 0.0 | 0.0 | 0.0 | | |
| | 0.0313 | 0.0 | 0.0 | 0.0 | 9.0 | 0.0 | 0.0 | 0.0 | 0.0 | 0.0 | 0.0 | 0.0 | 0.0 | | |
| | 0.0156 | 0.0 | 0.0 | 0.0 | 9.0 | 0.0 | 0.0 | 0.0 | 0.0 | 1.0 | 0.0 | 0.0 | 0.0 | | |
| 118 | 0.2500 | 7.0 | 6.0 | 4.0 | 9.0 | 7.0 | 6.0 | 0.0 | 2.0 | 3.0 | 0.0 | 0.0 | 0.0 | | |
| | 0.1250 | 9.0 | 0.0 | | 9.0 | 6.0 | 1.0 | 0.0 | 0.0 | 0.0 | 0.0 | 0.0 | 0.0 | | |
| | 0.0625 | 9.0 | 0.0 | 0.0 | 6.0 | 1.0 | 0.0 | 0.0 | 0.0 | 1.0 | 0.0 | 0.0 | 0.0 | | |
| 119 | 0.2500 | 9.0 | 4.0 | 3.0 | 9.0 | 4.0 | 9.0 | 2.0 | 7.0 | 2.0 | 0.0 | 0.0 | 1.0 | | |
| | 0.1250 | 9.0 | 4.0 | | 9.0 | 0.0 | 9.0 | 2.0 | 7.0 | 1.0 | 0.0 | 0.0 | 0.0 | | |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
|  | 0.0625 | 4.0 | 0.0 | 0.0 | 9.0 | 0.0 | 0.0 |  | 0.0 | 2.0 | 0.0 |  | 0.0 | 0.0 | 0.0 |
|  | 0.0313 | 3.0 | 0.0 | 0.0 | 9.0 | 0.0 | 0.0 |  | 0.0 | 0.0 | 0.0 |  | 0.0 | 0.0 | 0.0 |
|  | 0.0156 | 0.0 | 0.0 | 0.0 | 9.0 | 0.0 | 0.0 |  | 0.0 | 0.0 | 0.0 |  | 0.0 | 0.0 | 0.0 |
| 120 | 0.2500 | 9.0 | 4.0 | 4.0 | 9.0 | 0.0 | 9.0 |  | 2.0 | 9.0 | 3.0 |  | 0.0 | 4.0 | 3.0 |
|  | 0.1250 | 9.0 | 4.0 | 4.0 | 9.0 | 0.0 | 4.0 |  | 0.0 | 9.0 | 0.0 |  | 0.0 | 0.0 | 0.0 |
|  | 0.0625 | 9.0 | 3.0 | 3.0 | 9.0 | 0.0 | 0.0 |  | 0.0 | 9.0 | 0.0 |  | 0.0 | 0.0 | 0.0 |
|  | 0.0313 | 9.0 | 0.0 | 0.0 | 9.0 | 0.0 | 0.0 |  | 0.0 | 0.0 | 0.0 |  | 0.0 | 0.0 | 0.0 |
|  | 0.0156 | 0.0 | 0.0 | 0.0 | 9.0 | 0.0 | 0.0 |  | 0.0 | 0.0 | 0.0 |  | 0.0 | 0.0 | 0.0 |
| 121 | 0.2500 | 9.0 | 8.0 | 9.0 | 9.0 | 9.0 | 9.0 |  | 9.0 | 9.0 | 2.0 |  | 5.0 | 8.0 | 8.0 |
|  | 0.1250 | 9.0 | 4.0 | 9.0 | 9.0 | 5.0 | 4.0 |  | 7.0 | 9.0 | 1.0 |  | 4.0 | 7.0 | 7.0 |
|  | 0.0625 | 9.0 | 3.0 | 0.0 | 9.0 | 0.0 | 3.0 |  | 4.0 | 7.0 | 0.0 |  | 0.0 | 3.0 | 6.0 |
|  | 0.0313 | 9.0 | 2.0 | 0.0 | 9.0 | 0.0 | 0.0 |  | 0.0 | 3.0 | 0.0 |  | 0.0 | 2.0 | 4.0 |
|  | 0.0156 | 9.0 | 0.0 | 0.0 | 9.0 | 0.0 | 0.0 |  | 0.0 | 0.0 | 0.0 |  | 0.0 | 0.0 | 0.0 |
| 122 | 0.5000 | 9.0 | 3.0 | 3.0 | 9.0 | 6.0 | 1.0 |  | 1.0 | 9.0 | 0.0 |  | 1.0 | 1.0 | 1.0 |
|  | 0.2500 | 9.0 | 2.0 | 0.0 | 9.0 | 4.0 | 1.0 |  | 0.0 | 1.0 | 0.0 |  | 0.0 | 0.0 | 0.0 |
|  | 0.1250 | 9.0 | 2.0 | 0.0 | 9.0 | 4.0 | 2.0 |  | 0.0 | 1.0 | 0.0 |  | 0.0 | 0.0 | 0.0 |
|  | 0.0625 | 4.0 | 0.0 | 0.0 | 7.0 | 3.0 | 0.0 |  | 0.0 | 0.0 | 1.0 |  | 0.0 | 0.0 | 0.0 |
|  | 0.0313 | 0.0 | 0.0 | 0.0 | 9.0 | 2.0 | 0.0 |  | 0.0 | 0.0 | 0.0 |  | 0.0 | 0.0 | 0.0 |
|  | 0.0156 | 0.0 | 0.0 | 0.0 | 9.0 | 3.0 | 0.0 |  | 0.0 | 0.0 | 0.0 |  | 0.0 | 0.0 | 0.0 |
| 123 | 0.5000 | 9.0 | 9.0 | 3.0 | 9.0 | 9.0 | 9.0 |  | 7.0 | 9.0 | 6.0 |  | 5.0 | 1.0 | 7.0 |
|  | 0.2500 | 9.0 | 9.0 |  | 9.0 | 6.0 | 9.0 |  | 4.0 | 9.0 | 9.0 |  | 3.0 | 1.0 | 7.0 |
|  | 0.1250 | 9.0 | 4.0 | 0.0 | 9.0 | 7.0 | 7.0 |  | 1.0 | 9.0 | 4.0 |  | 1.0 | 1.0 | 5.0 |
|  | 0.0625 | 9.0 | 3.0 | 0.0 | 9.0 | 3.0 | 0.0 |  | 0.0 | 7.0 | 1.0 |  | 0.0 | 0.0 | 1.0 |
|  | 0.0313 | 9.0 | 1.0 | 0.0 | 9.0 | 3.0 | 0.0 |  | 0.0 | 7.0 | 0.0 |  | 0.0 | 0.0 | 1.0 |
|  | 0.0156 | 9.0 | 2.0 | 0.0 | 9.0 | 2.0 | 0.0 |  | 0.0 | 7.0 | 0.0 |  | 0.0 | 0.0 | 0.0 |
| 124 | 0.5000 | 7.0 | 9.0 | 0.0 | 9.0 | 7.0 | 6.0 |  | 1.0 | 9.0 | 3.0 |  | 2.0 | 0.0 | 1.0 |
|  | 0.2500 | 4.0 | 9.0 | 3.0 | 9.0 | 6.0 | 1.0 |  | 0.0 | 4.0 | 0.0 |  | 0.0 | 0.0 | 0.0 |
|  | 0.1250 | 2.0 | 9.0 | 0.0 | 9.0 | 0.0 | 0.0 |  | 0.0 | 0.0 | 0.0 |  | 0.0 | 0.0 | 0.0 |
|  | 0.0625 | 0.0 | 4.0 | 1.0 | 9.0 | 0.0 | 0.0 |  | 0.0 | 0.0 | 0.0 |  | 0.0 | 0.0 | 0.0 |
|  | 0.0313 | 0.0 | 0.0 | 0.0 | 9.0 | 0.0 | 0.0 |  | 0.0 | 0.0 | 0.0 |  | 0.0 | 0.0 | 0.0 |
|  | 0.0156 | 0.0 | 0.0 | 0.0 | 9.0 | 0.0 | 0.0 |  | 0.0 | 0.0 | 0.0 |  | 0.0 | 0.0 | 0.0 |
| 125 | 0.5000 | 9.0 | 9.0 | 9.0 | 9.0 | 9.0 | 9.0 |  | 9.0 | 9.0 | 7.0 |  | 4.0 | 5.0 | 7.0 |
|  | 0.2500 | 9.0 | 9.0 | 9.0 | 9.0 | 7.0 | 9.0 |  | 7.0 | 9.0 | 4.0 |  | 4.0 | 4.0 | 7.0 |
|  | 0.1250 | 6.0 | 9.0 | 2.0 | 9.0 | 1.0 | 4.0 |  | 3.0 | 9.0 | 3.0 |  | 1.0 | 1.0 | 6.0 |
|  | 0.0625 | 4.0 | 9.0 | 3.0 | 9.0 | 0.0 | 4.0 |  | 0.0 | 5.0 | 0.0 |  | 1.0 | 1.0 | 3.0 |
|  | 0.0313 | 2.0 | 6.0 | 1.0 | 9.0 | 0.0 | 0.0 |  | 0.0 | 0.0 | 0.0 |  | 0.0 | 0.0 | 0.0 |
|  | 0.0156 | 0.0 | 0.0 | 0.0 | 9.0 | 0.0 | 0.0 |  | 0.0 | 0.0 | 0.0 |  | 0.0 | 0.0 | 0.0 |
| 126 | 0.5000 | 9.0 | 5.0 | 3.0 | 9.0 | 9.0 | 9.0 |  | 2.0 | 9.0 | 7.0 |  | 3.0 | 0.0 | 8.0 |
|  | 0.2500 | 9.0 | 4.0 | 0.0 | 9.0 | 9.0 | 1.0 |  | 0.0 | 3.0 | 3.0 |  | 0.0 | 0.0 | 4.0 |
|  | 0.1250 | 5.0 | 0.0 | 0.0 | 9.0 | 0.0 | 1.0 |  | 0.0 | 0.0 | 2.0 |  | 0.0 | 0.0 | 2.0 |
|  | 0.0625 | 5.0 | 0.0 | 0.0 | 9.0 | 0.0 | 0.0 |  | 0.0 | 0.0 | 0.0 |  | 0.0 | 0.0 | 0.0 |
| 127 | 0.5000 | 9.0 | 9.0 | 6.0 | 9.0 | 9.0 | 9.0 |  | 0.0 | 9.0 | 4.0 |  | 3.0 | 7.0 | 8.0 |
|  | 0.2500 | 9.0 | 5.0 | 2.0 | 9.0 | 7.0 | 9.0 |  | 0.0 | 9.0 | 4.0 |  | 0.0 | 0.0 | 4.0 |
|  | 0.1250 | 9.0 |  | 0.0 | 9.0 | 3.0 | 1.0 |  | 0.0 | 9.0 | 0.0 |  | 0.0 | 0.0 | 0.0 |
|  | 0.0625 | 7.0 | 0.0 | 0.0 | 9.0 | 3.0 | 0.0 |  | 0.0 | 0.0 | 0.0 |  | 0.0 | 0.0 | 0.0 |
|  | 0.0313 | 7.0 | 0.0 | 0.0 | 9.0 | 0.0 | 0.0 |  | 0.0 | 0.0 | 0.0 |  | 0.0 | 0.0 | 0.0 |
| 128 | 0.2500 | 9.0 | 3.0 | 0.0 | 9.0 | 1.0 | 7.0 |  | 2.0 | 7.0 | 0.0 |  | 0.0 | 0.0 | 0.0 |
|  | 0.1250 | 3.0 | 2.0 |  | 9.0 | 1.0 | 9.0 |  | 0.0 | 1.0 | 0.0 |  | 0.0 | 0.0 | 0.0 |
|  | 0.0625 | 1.0 | 0.0 | 1.0 | 9.0 | 0.0 | 4.0 |  | 0.0 |  | 0.0 |  | 0.0 | 0.0 | 0.0 |
|  | 0.0313 | 0.0 | 0.0 | 1.0 | 7.0 | 0.0 | 0.0 |  | 0.0 | 1.0 | 0.0 |  | 0.0 | 0.0 | 0.0 |
|  | 0.0156 | 0.0 | 0.0 | 0.0 | 9.0 | 0.0 | 0.0 |  | 0.0 | 0.0 | 0.0 |  | 0.0 | 0.0 | 0.0 |
| 129 | 0.2500 | 9.0 | 7.0 | 8.0 | 9.0 | 0.0 | 9.0 |  | 0.0 | 7.0 | 4.0 |  | 3.0 | 1.0 | 1.0 |
|  | 0.1250 | 9.0 | 7.0 | 7.0 | 9.0 | 0.0 | 9.0 |  | 1.0 | 6.0 | 2.0 |  | 1.0 | 1.0 | 1.0 |
|  | 0.0625 | 9.0 | 0.0 | 1.0 | 9.0 | 1.0 | 0.0 |  | 0.0 | 1.0 | 2.0 |  | 1.0 | 0.0 | 0.0 |
|  | 0.0313 | 1.0 | 0.0 | 1.0 | 3.0 | 1.0 | 0.0 |  | 0.0 | 1.0 | 0.0 |  | 0.0 | 0.0 | 0.0 |
|  | 0.0156 | 0.0 | 0.0 | 1.0 | 4.0 | 1.0 | 0.0 |  | 0.0 | 1.0 | 0.0 |  | 0.0 | 0.0 | 0.0 |
| 130 | 0.2500 | 9.0 | 9.0 | 3.0 | 9.0 | 2.0 | 7.0 |  | 7.0 | 9.0 | 5.0 |  | 6.0 | 6.0 | 9.0 |
|  | 0.1250 | 9.0 | 9.0 |  | 9.0 | 2.0 | 9.0 |  | 4.0 | 7.0 | 3.0 |  | 3.0 | 3.0 | 7.0 |
|  | 0.0625 | 9.0 | 7.0 | 2.0 | 9.0 | 0.0 | 2.0 |  | 1.0 | 7.0 | 2.0 |  | 1.0 | 1.0 | 4.0 |
|  | 0.0313 | 9.0 | 1.0 | 1.0 | 9.0 |  | 0.0 |  | 0.0 | 6.0 | 0.0 |  | 0.0 | 0.0 | 1.0 |
|  | 0.0156 | 1.0 | 0.0 | 0.0 | 9.0 | 0.0 | 0.0 |  | 0.0 | 0.0 | 0.0 |  | 0.0 | 0.0 | 0.0 |
| 131 | 0.2500 | 9.0 | 0.0 | 2.0 | 9.0 | 9.0 | 0.0 |  | 2.0 | 3.0 | 1.0 |  | 0.0 | 0.0 | 0.0 |
|  | 0.1250 | 2.0 | 0.0 | 0.0 | 9.0 | 2.0 | 0.0 |  | 0.0 | 0.0 | 1.0 |  | 0.0 | 0.0 | 0.0 |
|  | 0.0625 | 0.0 | 0.0 | 0.0 | 9.0 | 3.0 | 0.0 |  | 0.0 | 0.0 | 1.0 |  | 0.0 | 0.0 | 0.0 |
|  | 0.0313 | 0.0 | 0.0 | 0.0 | 9.0 | 4.0 | 0.0 |  | 0.0 | 0.0 | 0.0 |  | 0.0 | 0.0 | 0.0 |
| 132 | 0.2500 | 9.0 | 7.0 | 0.0 | 9.0 | 5.0 | 2.0 |  | 7.0 | 9.0 | 2.0 |  | 1.0 | 1.0 | 2.0 |
|  | 0.1250 | 9.0 | 4.0 |  | 9.0 | 4.0 | 0.0 |  | 0.0 | 3.0 | 0.0 |  | 0.0 | 0.0 | 0.0 |
|  | 0.0625 | 9.0 | 0.0 | 0.0 | 9.0 | 4.0 | 0.0 |  | 0.0 | 0.0 | 0.0 |  | 0.0 | 0.0 | 0.0 |
| 133 | 0.2500 | 5.0 | 1.0 | 9.0 | 9.0 | 0.0 | 1.0 |  | 0.0 | 0.0 | 0.0 |  | 0.0 | 0.0 | 0.0 |
|  | 0.1250 | 1.0 | 0.0 | 0.0 | 9.0 | 0.0 | 0.0 |  | 0.0 | 0.0 | 0.0 |  | 0.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| | 0.0625 | 0.0 | 0.0 | 0.0 | 9.0 | 0.0 | 0.0 | 0.0 | 0.0 | 0.0 | 0.0 | 0.0 | 0.0 | 0.0 |
| | 0.0313 | 0.0 | 0.0 | 0.0 | 9.0 | 0.0 | 0.0 | 0.0 | 0.0 | 0.0 | 0.0 | 0.0 | 0.0 | 0.0 |
| 134 | 0.2500 | 7.0 | 3.0 | 1.0 | 9.0 | 0.0 | 0.0 | 0.0 | 0.0 | 2.0 | 0.0 | 0.0 | 0.0 | 0.0 |
| | 0.1250 | 0.0 | 0.0 | 0.0 | 9.0 | 1.0 | 0.0 | 0.0 | 0.0 | 0.0 | 0.0 | 0.0 | 0.0 | 0.0 |
| 135 | 0.2500 | 8.0 | 7.0 | 5.0 | 9.0 | 1.0 | 9.0 | 1.0 | 7.0 | 3.0 | 7.0 | 1.0 | 1.0 |
| | 0.1250 | 6.0 | 4.0 | 1.0 | 9.0 | 0.0 | 9.0 | 0.0 | 4.0 | 1.0 | 1.0 | 0.0 | 2.0 |
| | 0.0625 | 3.0 | 0.0 | 1.0 | 9.0 | 0.0 | 1.0 | 0.0 | 2.0 | 0.0 | 1.0 | 0.0 | 0.0 |
| | 0.0313 | 0.0 | 0.0 | 1.0 | 7.0 | 0.0 | 0.0 | 0.0 | 0.0 | 0.0 | 1.0 | 0.0 | 1.0 |
| | 0.0156 | 0.0 | 0.0 | 0.0 | 7.0 | 0.0 | 0.0 | 0.0 | 0.0 | 0.0 | 1.0 | 0.0 | 1.0 |
| 136 | 0.2500 | 9.0 | 5.0 | 0.0 | 9.0 | 3.0 | 0.0 | 0.0 | 7.0 | 2.0 | 1.0 | 1.0 | 3.0 |
| | 0.1250 | 9.0 | 2.0 | 0.0 | 9.0 | 2.0 | 0.0 | 0.0 | 4.0 | 1.0 | 1.0 | 1.0 | 1.0 |
| | 0.0625 | 9.0 | 1.0 | 0.0 | 9.0 | 1.0 | 0.0 | 0.0 | 2.0 | 0.0 | 0.0 | 0.0 | 0.0 |
| | 0.0313 | 9.0 | 0.0 | 0.0 | 9.0 | 0.0 | 0.0 | 0.0 | 0.0 | 0.0 | 0.0 | 0.0 | 0.0 |
| | 0.0156 | 4.0 | 0.0 | 0.0 | 2.0 | 0.0 | 0.0 | 0.0 | 0.0 | 0.0 | 0.0 | 0.0 | 0.0 |
| 137 | 0.2500 | 9.0 | 7.0 | 0.0 | 9.0 | 0.0 | 1.0 | 0.0 | 2.0 | 1.0 | 0.0 | 0.0 | 0.0 |
| | 0.1250 | 0.0 | 0.0 | 0.0 | 9.0 | 0.0 | 0.0 | 0.0 | 0.0 | 0.0 | 0.0 | 0.0 | 0.0 |
| | 0.0625 | 0.0 | 0.0 | 0.0 | 9.0 | 0.0 | 0.0 | 0.0 | 0.0 | 0.0 | 0.0 | 0.0 | 0.0 |
| 138 | 0.2500 | 9.0 | 2.0 | 0.0 | 9.0 | 4.0 | 0.0 | 0.0 | 2.0 | 1.0 | 0.0 | 0.0 | 0.0 |
| | 0.1250 | 9.0 | 1.0 | 0.0 | 9.0 | 0.0 | 0.0 | 0.0 | 3.0 | 0.0 | 0.0 | 0.0 | 0.0 |
| | 0.0625 | 0.0 | 0.0 | 0.0 | 7.0 | 0.0 | 0.0 | 0.0 | 0.0 | 0.0 | 0.0 | 0.0 | 0.0 |
| | 0.0313 | 0.0 | 0.0 | 0.0 | 9.0 | 0.0 | 0.0 | 0.0 | 0.0 | 0.0 | 0.0 | 0.0 | 0.0 |
| | 0.0156 | 0.0 | 0.0 | 0.0 | 1.0 | 0.0 | 0.0 | 0.0 | 0.0 | 0.0 | 0.0 | 0.0 | 0.0 |
| 139 | 0.2500 | 9.0 | 4.0 | 1.0 | 9.0 | 0.0 | 2.0 | 1.0 | 7.0 | 1.0 | 2.0 | 1.0 | 1.0 |
| | 0.1250 | 9.0 | 3.0 | 2.0 | 9.0 | 0.0 | | 1.0 | 1.0 | 0.0 | 1.0 | 0.0 | 0.0 |
| | 0.0625 | 0.0 | 0.0 | 1.0 | 9.0 | 0.0 | 2.0 | 0.0 | 0.0 | 0.0 | 0.0 | 0.0 | 0.0 |
| | 0.0313 | 0.0 | 1.0 | 0.0 | 7.0 | 0.0 | 0.0 | 0.0 | 0.0 | 1.0 | 0.0 | 0.0 | 0.0 |
| | 0.0156 | 0.0 | 0.0 | 0.0 | 0.0 | 0.0 | 0.0 | 1.0 | 0.0 | 0.0 | 0.0 | 0.0 | 0.0 |
| 140 | 0.2500 | 7.0 | 0.0 | 0.0 | 9.0 | 0.0 | 3.0 | 0.0 | 0.0 | 0.0 | 0.0 | 0.0 | 0.0 |
| | 0.1250 | 3.0 | 0.0 | 0.0 | 9.0 | 0.0 | 3.0 | 0.0 | 0.0 | 0.0 | 0.0 | 0.0 | 0.0 |
| | 0.0625 | 0.0 | 0.0 | 0.0 | 9.0 | 0.0 | 0.0 | 0.0 | 0.0 | 0.0 | 0.0 | 0.0 | 0.0 |
| 141 | 0.2500 | 9.0 | 4.0 | 3.0 | 9.0 | 0.0 | 3.0 | 2.0 | 4.0 | 3.0 | 0.0 | 0.0 | 2.0 |
| | 0.1250 | 4.0 | 0.0 | 0.0 | 9.0 | 0.0 | 0.0 | 0.0 | 0.0 | 0.0 | 0.0 | 0.0 | 0.0 |
| | 0.0625 | 0.0 | 0.0 | 0.0 | 9.0 | 0.0 | 0.0 | 0.0 | 0.0 | 0.0 | 0.0 | 0.0 | 0.0 |
| | 0.0313 | 0.0 | 0.0 | 0.0 | 9.0 | 0.0 | 0.0 | 0.0 | 0.0 | 0.0 | 0.0 | 0.0 | 0.0 |
| | 0.0156 | 0.0 | 0.0 | 0.0 | 3.0 | 0.0 | 0.0 | 0.0 | 0.0 | 0.0 | 0.0 | 0.0 | 0.0 |
| 142 | 0.2500 | 9.0 | 1.0 | 0.0 | 9.0 | 9.0 | 2.0 | 0.0 | 7.0 | 1.0 | 0.0 | 0.0 | 2.0 |
| | 0.1250 | 4.0 | 2.0 | 1.0 | 9.0 | 0.0 | 1.0 | 0.0 | 2.0 | 0.0 | 1.0 | 0.0 | 2.0 |
| | 0.0625 | 1.0 | 4.0 | 2.0 | 9.0 | 0.0 | 0.0 | 0.0 | 0.0 | 0.0 | 0.0 | 0.0 | 0.0 |
| | 0.0313 | 1.0 | 0.0 | 0.0 | 3.0 | 0.0 | 0.0 | 0.0 | 1.0 | 0.0 | 0.0 | 0.0 | 0.0 |
| | 0.0156 | 0.0 | 0.0 | 1.0 | 4.0 | 0.0 | 0.0 | 0.0 | 0.0 | 1.0 | 0.0 | 0.0 | 0.0 |
| 143 | 0.2500 | 9.0 | 3.0 | 1.0 | 9.0 | 0.0 | 3.0 | 1.0 | 3.0 | 1.0 | 1.0 | 1.0 | 0.0 |
| | 0.1250 | 6.0 | 2.0 | 0.0 | 9.0 | 1.0 | 1.0 | 1.0 | 3.0 | 0.0 | 0.0 | 0.0 | 0.0 |
| | 0.0625 | 1.0 | 0.0 | 0.0 | 7.0 | 0.0 | 0.0 | 0.0 | 0.0 | 0.0 | 0.0 | 0.0 | 0.0 |
| | 0.0313 | 1.0 | 0.0 | 0.0 | 7.0 | 0.0 | 0.0 | 0.0 | 0.0 | 0.0 | 0.0 | 0.0 | 0.0 |
| 144 | 0.2500 | 9.0 | 7.0 | 2.0 | 9.0 | 2.0 | 1.0 | 1.0 | 9.0 | 0.0 | 0.0 | 0.0 | 0.0 |
| | 0.1250 | 9.0 | 4.0 | 1.0 | 9.0 | 2.0 | 0.0 | 0.0 | 9.0 | 0.0 | 0.0 | 0.0 | 0.0 |
| | 0.0625 | 0.0 | 0.0 | 0.0 | 9.0 | 1.0 | 0.0 | 0.0 | 2.0 | 0.0 | 0.0 | 0.0 | 0.0 |
| | 0.0313 | 0.0 | 0.0 | 0.0 | 7.0 | 1.0 | 0.0 | 0.0 | 0.0 | 0.0 | 0.0 | 0.0 | 0.0 |
| | 0.0156 | 0.0 | 0.0 | 0.0 | 6.0 | 1.0 | 0.0 | 0.0 | 0.0 | 0.0 | 0.0 | 0.0 | 0.0 |
| 145 | 0.2500 | 6.0 | 7.0 | 7.0 | 9.0 | 3.0 | 5.0 | 1.0 | 7.0 | 2.0 | 1.0 | 1.0 | 2.0 |
| | 0.1250 | 9.0 | 5.0 | 1.0 | 9.0 | 1.0 | 7.0 | 1.0 | 3.0 | 1.0 | 3.0 | 0.0 | 1.0 |
| | 0.0625 | 3.0 | 2.0 | 6.0 | 7.0 | 0.0 | 0.0 | 1.0 | 7.0 | 0.0 | 2.0 | 1.0 | 0.0 |
| | 0.0313 | 2.0 | 0.0 | 1.0 | 9.0 | 0.0 | 0.0 | 0.0 | 0.0 | 0.0 | 1.0 | 1.0 | 0.0 |
| | 0.0156 | 0.0 | 0.0 | 1.0 | 7.0 | 0.0 | 0.0 | 0.0 | 1.0 | 0.0 | 1.0 | 0.0 | 0.0 |
| 146 | 0.2500 | 9.0 | 3.0 | 1.0 | 9.0 | 2.0 | 0.0 | 0.0 | 5.0 | 1.0 | 1.0 | 1.0 | 0.0 |
| | 0.1250 | 9.0 | 0.0 | 1.0 | 9.0 | 2.0 | 0.0 | 0.0 | 3.0 | 0.0 | 0.0 | 0.0 | 0.0 |
| | 0.0625 | 1.0 | 0.0 | 0.0 | 9.0 | 0.0 | 0.0 | 0.0 | 0.0 | 0.0 | 0.0 | 0.0 | 0.0 |
| | 0.0313 | | 0.0 | 0.0 | 9.0 | 0.0 | 0.0 | 0.0 | 0.0 | 0.0 | 0.0 | 0.0 | 0.0 |
| | 0.0156 | 0.0 | 0.0 | 0.0 | 0.0 | 1.0 | 0.0 | 0.0 | 0.0 | 0.0 | 0.0 | 0.0 | 0.0 |
| 147 | 0.2500 | 7.0 | 4.0 | 5.0 | 9.0 | 1.0 | 0.0 | 0.0 | 4.0 | 1.0 | 0.0 | 0.0 | 2.0 |
| | 0.1250 | 4.0 | 1.0 | 0.0 | 9.0 | 1.0 | 0.0 | 0.0 | 1.0 | 0.0 | 0.0 | 0.0 | 1.0 |
| | 0.0625 | 0.0 | 0.0 | 0.0 | 6.0 | 0.0 | 0.0 | 0.0 | 0.0 | 0.0 | 0.0 | 0.0 | 0.0 |
| | 0.0313 | 0.0 | 0.0 | 0.0 | 0.0 | 0.0 | 0.0 | 0.0 | 0.0 | 0.0 | 0.0 | 0.0 | 1.0 |
| | 0.0156 | 0.0 | 0.0 | 0.0 | 0.0 | 0.0 | 0.0 | 0.0 | 1.0 | 1.0 | 0.0 | 0.0 | 1.0 |
| 148 | 0.2500 | 4.0 | 4.0 | 0.0 | 9.0 | 0.0 | 0.0 | 0.0 | 5.0 | 0.0 | 0.0 | 0.0 | 1.0 |
| | 0.1250 | 4.0 | 0.0 | 0.0 | 9.0 | 0.0 | 0.0 | 0.0 | 0.0 | 0.0 | 0.0 | 0.0 | 0.0 |
| | 0.0625 | 1.0 | 0.0 | 0.0 | 9.0 | 0.0 | 0.0 | 0.0 | 0.0 | 0.0 | 0.0 | 0.0 | 0.0 |
| | 0.0313 | 0.0 | 0.0 | 0.0 | 6.0 | 0.0 | 0.0 | 0.0 | 1.0 | 0.0 | 0.0 | 0.0 | 0.0 |
| 149 | 0.2500 | 7.0 | 0.0 | 0.0 | 9.0 | 0.0 | 2.0 | 0.0 | 0.0 | 7.0 | 2.0 | 2.0 | 2.0 |
| | 0.1250 | 3.0 | 0.0 | 0.0 | 3.0 | 0.0 | 0.0 | 0.0 | 0.0 | 3.0 | 2.0 | 0.0 | 0.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | IPOSS | ECHCG | SETVI | GLXMAW | GLXMA | ORYSAT | TRZAWR | ZEAMX |
|---|---|---|---|---|---|---|---|---|---|---|---|---|---|---|---|
| 150 | 0.2500 | 9.0 | 7.0 | 2.0 | 9.0 | 2.0 | 9.0 | | 4.0 | 9.0 | 2.0 | | 1.0 | 1.0 | 1.0 |
| | 0.1250 | 9.0 | 3.0 | 1.0 | 9.0 | 0.0 | 9.0 | | 2.0 | 4.0 | 0.0 | | 2.0 | 1.0 | 2.0 |
| | 0.0625 | 4.0 | 0.0 | 2.0 | 9.0 | 0.0 | 0.0 | | 0.0 | 0.0 | 0.0 | | 1.0 | 0.0 | 1.0 |
| | 0.0313 | 0.0 | 0.0 | 0.0 | 9.0 | 0.0 | 0.0 | | 0.0 | 0.0 | 0.0 | | 0.0 | 0.0 | 0.0 |
| 151 | 0.2500 | 9.0 | 9.0 | 9.0 | 9.0 | 9.0 | 9.0 | | 9.0 | 9.0 | 7.0 | | 9.0 | 9.0 | 9.0 |
| | 0.1250 | 9.0 | 9.0 | 9.0 | 9.0 | 9.0 | 9.0 | | 9.0 | 9.0 | 7.0 | | 9.0 | 8.0 | 9.0 |
| | 0.0625 | 9.0 | 9.0 | 2.0 | 9.0 | 4.0 | 9.0 | | 7.0 | 9.0 | 4.0 | | 5.0 | 5.0 | 7.0 |
| | 0.0313 | 9.0 | 7.0 | 2.0 | 9.0 | 4.0 | 9.0 | | 9.0 | 9.0 | 5.0 | | 5.0 | 6.0 | 7.0 |
| | 0.0156 | 9.0 | 1.0 | 0.0 | 9.0 | 2.0 | 4.0 | | 2.0 | 9.0 | 2.0 | | 2.0 | 2.0 | 7.0 |
| 152 | 0.2500 | 9.0 | 6.0 | 3.0 | 9.0 | 6.0 | 7.0 | | 1.0 | 9.0 | 2.0 | | 1.0 | 1.0 | 2.0 |
| | 0.1250 | 9.0 | 2.0 | 0.0 | 9.0 | 1.0 | 4.0 | | 1.0 | 1.0 | 2.0 | | 1.0 | 1.0 | 1.0 |
| | 0.0625 | 0.0 | 0.0 | 1.0 | 9.0 | 0.0 | 1.0 | | 0.0 | 1.0 | 2.0 | | 1.0 | 1.0 | 1.0 |
| | 0.0313 | 0.0 | 0.0 | 0.0 | 2.0 | 0.0 | 0.0 | | 0.0 | 0.0 | 0.0 | | 0.0 | 0.0 | 0.0 |
| 153 | 0.2500 | 2.0 | 1.0 | 0.0 | 7.0 | 1.0 | 0.0 | | 0.0 | 0.0 | 1.0 | | 0.0 | 0.0 | 0.0 |
| | 0.1250 | 0.0 | 0.0 | 0.0 | 1.0 | 0.0 | 1.0 | | 0.0 | 1.0 | 0.0 | | 0.0 | 0.0 | 0.0 |
| 154 | 0.2500 | 9.0 | 9.0 | 9.0 | 9.0 | 9.0 | 9.0 | | 9.0 | 9.0 | 8.0 | | 9.0 | 9.0 | 9.0 |
| | 0.1250 | 9.0 | 9.0 | 9.0 | 9.0 | 9.0 | 9.0 | | 9.0 | 9.0 | | | 9.0 | 8.0 | 9.0 |
| | 0.0625 | 9.0 | 9.0 | 9.0 | 9.0 | 4.0 | 9.0 | | 9.0 | 9.0 | 5.0 | | 8.0 | 8.0 | 8.0 |
| | 0.0313 | 9.0 | 5.0 | 0.0 | 9.0 | 0.0 | 9.0 | | 4.0 | 7.0 | 2.0 | | 4.0 | 2.0 | 7.0 |
| | 0.0156 | 9.0 | 3.0 | 0.0 | 9.0 | 0.0 | 0.0 | | 0.0 | 2.0 | 0.0 | | 3.0 | 0.0 | 5.0 |
| 155 | 0.2500 | 7.0 | 4.0 | 0.0 | 9.0 | 4.0 | 2.0 | | 0.0 | 0.0 | 4.0 | | 2.0 | 0.0 | 2.0 |
| | 0.1250 | 4.0 | 2.0 | 0.0 | 9.0 | 4.0 | 0.0 | | 0.0 | 0.0 | 0.0 | | 0.0 | 0.0 | 0.0 |
| | 0.0625 | 2.0 | 0.0 | 0.0 | 0.0 | 4.0 | 0.0 | | 0.0 | 0.0 | 0.0 | | 0.0 | 0.0 | 0.0 |
| 156 | 0.2500 | 9.0 | 9.0 | 0.0 | 9.0 | 9.0 | 9.0 | | 0.0 | 9.0 | 7.0 | | 3.0 | 3.0 | 5.0 |
| | 0.1250 | 9.0 | 5.0 | | 9.0 | 4.0 | 9.0 | | 0.0 | 2.0 | 0.0 | | 0.0 | 0.0 | 2.0 |
| | 0.0625 | 9.0 | 0.0 | 0.0 | 9.0 | 4.0 | 3.0 | | 0.0 | 2.0 | 0.0 | | 0.0 | 0.0 | 1.0 |
| | 0.0313 | 4.0 | 0.0 | 0.0 | 9.0 | 0.0 | 0.0 | | 0.0 | 0.0 | 0.0 | | 0.0 | 0.0 | 0.0 |
| 157 | 0.2500 | 6.0 | 1.0 | 5.0 | 9.0 | 4.0 | 2.0 | | 0.0 | 1.0 | 4.0 | | 0.0 | 0.0 | 1.0 |
| | 0.1250 | 4.0 | 0.0 | 1.0 | 9.0 | 0.0 | 1.0 | | 1.0 | 2.0 | 2.0 | | 0.0 | 0.0 | 1.0 |
| | 0.0625 | 0.0 | 0.0 | 0.0 | 0.0 | 0.0 | 0.0 | | 0.0 | 0.0 | 0.0 | | 0.0 | 0.0 | 0.0 |
| | 0.0313 | 0.0 | 0.0 | 1.0 | 1.0 | 0.0 | 0.0 | | 0.0 | 0.0 | 1.0 | | 0.0 | 0.0 | 0.0 |
| 158 | 0.2500 | 9.0 | 9.0 | 5.0 | 9.0 | 6.0 | 9.0 | | 9.0 | 9.0 | 9.0 | | 8.0 | 7.0 | 9.0 |
| | 0.1250 | 9.0 | 9.0 | 9.0 | 9.0 | 7.0 | 9.0 | | 9.0 | 9.0 | 7.0 | | 7.0 | 7.0 | 9.0 |
| | 0.0625 | 9.0 | 7.0 | 4.0 | 9.0 | 5.0 | 7.0 | | 9.0 | 9.0 | 6.0 | | 7.0 | 5.0 | 8.0 |
| | 0.0313 | 9.0 | 3.0 | 3.0 | 9.0 | 0.0 | 4.0 | | 7.0 | 9.0 | 4.0 | | 4.0 | 4.0 | 7.0 |
| | 0.0156 | 9.0 | 1.0 | 1.0 | 9.0 | 0.0 | 1.0 | | 2.0 | 7.0 | 1.0 | | 3.0 | 1.0 | 5.0 |
| 159 | 0.2500 | 9.0 | 8.0 | 7.0 | 9.0 | 5.0 | 9.0 | | 3.0 | 7.0 | 3.0 | | 2.0 | 3.0 | 7.0 |
| | 0.1250 | 9.0 | 6.0 | 3.0 | 9.0 | 5.0 | 7.0 | | 2.0 | 9.0 | 2.0 | | 1.0 | 1.0 | 2.0 |
| | 0.0625 | 9.0 | 4.0 | 3.0 | 8.0 | 1.0 | 9.0 | | 0.0 | 7.0 | 1.0 | | 0.0 | 0.0 | 1.0 |
| | 0.0313 | 9.0 | 3.0 | 1.0 | 9.0 | 0.0 | 2.0 | | 1.0 | 8.0 | 0.0 | | 0.0 | 0.0 | 0.0 |
| | 0.0156 | 2.0 | 1.0 | 0.0 | 7.0 | 0.0 | 0.0 | | 0.0 | 1.0 | 1.0 | | 0.0 | 0.0 | 0.0 |
| 160 | 0.5000 | 9.0 | 9.0 | 9.0 | 9.0 | 7.0 | 9.0 | | 9.0 | 9.0 | 9.0 | | 8.0 | 7.0 | 8.0 |
| | 0.2500 | 9.0 | 9.0 | 7.0 | 9.0 | 7.0 | 8.0 | | 9.0 | 7.0 | 9.0 | | 7.0 | 4.0 | 5.0 |
| | 0.1250 | 9.0 | 9.0 | 1.0 | 9.0 | 0.0 | 9.0 | | 2.0 | 7.0 | 2.0 | | 1.0 | 1.0 | 2.0 |
| | 0.0625 | 9.0 | 9.0 | 2.0 | 9.0 | 0.0 | 9.0 | | 1.0 | 7.0 | 1.0 | | 1.0 | 1.0 | 1.0 |
| | 0.0313 | 9.0 | 6.0 | 0.0 | 9.0 | 0.0 | 6.0 | | 0.0 | 1.0 | 1.0 | | 0.0 | 0.0 | 0.0 |
| | 0.0156 | 5.0 | 7.0 | 0.0 | 2.0 | 0.0 | 3.0 | | 0.0 | 0.0 | 1.0 | | 0.0 | 0.0 | 0.0 |
| 161 | 0.5000 | 9.0 | 9.0 | 9.0 | 9.0 | 9.0 | 9.0 | | 9.0 | 9.0 | 9.0 | | 9.0 | 9.0 | 9.0 |
| | 0.2500 | 9.0 | 9.0 | 9.0 | 9.0 | 7.0 | 9.0 | | 7.0 | 9.0 | 9.0 | | 9.0 | 7.0 | 6.0 |
| | 0.1250 | 9.0 | 9.0 | 9.0 | 9.0 | 7.0 | 9.0 | | 4.0 | 9.0 | 7.0 | | 7.0 | 4.0 | 5.0 |
| | 0.0625 | 2.0 | 5.0 | 1.0 | 9.0 | 3.0 | 7.0 | | 0.0 | 7.0 | 1.0 | | 7.0 | 1.0 | 1.0 |
| | 0.0313 | 1.0 | 3.0 | 0.0 | 7.0 | 0.0 | 2.0 | | 0.0 | 0.0 | 1.0 | | 1.0 | 0.0 | 0.0 |
| | 0.0156 | 0.0 | 0.0 | 0.0 | 6.0 | 0.0 | | | 0.0 | 0.0 | 0.0 | | 0.0 | 0.0 | 0.0 |
| 162 | 0.2500 | 9.0 | 9.0 | 4.0 | 9.0 | 3.0 | 9.0 | | 9.0 | 9.0 | 9.0 | | 8.0 | 9.0 | 9.0 |
| | 0.1250 | 9.0 | 9.0 | 0.0 | 9.0 | 3.0 | 9.0 | | 9.0 | 9.0 | 5.0 | | 6.0 | 7.0 | 9.0 |
| | 0.0625 | 9.0 | 5.0 | 0.0 | 9.0 | 0.0 | 4.0 | | 8.0 | 9.0 | 2.0 | | 5.0 | 7.0 | 9.0 |
| | 0.0313 | 9.0 | 3.0 | | 9.0 | 0.0 | 0.0 | | 4.0 | 9.0 | 2.0 | | 3.0 | 3.0 | 7.0 |
| | 0.0156 | 9.0 | 0.0 | 0.0 | 9.0 | 0.0 | 0.0 | | 1.0 | 9.0 | 2.0 | | 2.0 | 0.0 | 6.0 |
| 163 | 0.2500 | 9.0 | 9.0 | 5.0 | 9.0 | 3.0 | 9.0 | | 9.0 | 9.0 | 5.0 | | 8.0 | 7.0 | 8.0 |
| | 0.1250 | 9.0 | 9.0 | 0.0 | 9.0 | 0.0 | 9.0 | | 8.0 | 9.0 | 3.0 | | 7.0 | 7.0 | 7.0 |
| | 0.0625 | 9.0 | 9.0 | 0.0 | 9.0 | 0.0 | 3.0 | | 7.0 | 9.0 | 3.0 | | 5.0 | 3.0 | 7.0 |
| | 0.0313 | 9.0 | 3.0 | 0.0 | 9.0 | 0.0 | 0.0 | | 4.0 | 9.0 | 2.0 | | 3.0 | 0.0 | 5.0 |
| | 0.0156 | 9.0 | 0.0 | 0.0 | 9.0 | 0.0 | 0.0 | | 2.0 | 9.0 | 0.0 | | 1.0 | 0.0 | 5.0 |
| 164 | 0.5000 | 9.0 | 9.0 | 5.0 | 9.0 | 9.0 | 9.0 | | 9.0 | 9.0 | 7.0 | | 9.0 | 9.0 | 9.0 |
| | 0.2500 | 9.0 | 9.0 | 9.0 | 9.0 | 7.0 | 9.0 | | 9.0 | 9.0 | 7.0 | | 7.0 | 7.0 | 8.0 |
| | 0.1250 | 9.0 | 7.0 | 7.0 | 9.0 | 9.0 | 9.0 | | 9.0 | 9.0 | 7.0 | | 5.0 | 6.0 | 7.0 |
| | 0.0625 | 9.0 | 7.0 | 7.0 | 9.0 | 4.0 | 9.0 | | 7.0 | 9.0 | 5.0 | | 3.0 | 4.0 | 6.0 |
| | 0.0313 | 9.0 | 7.0 | 0.0 | 9.0 | 4.0 | 9.0 | | 7.0 | 9.0 | 2.0 | | 1.0 | 1.0 | 3.0 |
| | 0.0156 | 6.0 | 6.0 | 1.0 | 9.0 | 3.0 | 4.0 | | 0.0 | 4.0 | 1.0 | | 1.0 | 1.0 | 2.0 |

TABLE II-continued

Preemergence Herbicidal Evaluations of Test Compounds

| Compound Number | Rate (kg/ha) | ABUTH | AMBEL | CASOB | CHEAL | GALAP | IPOHE | ECHCG | SETVI | GLXMAW | ORYSAT | TRZAWR | ZEAMX |
|---|---|---|---|---|---|---|---|---|---|---|---|---|---|
| 165 | 0.5000 | 9.0 | 9.0 | 7.0 | 9.0 | 8.0 | 9.0 | 7.0 | 9.0 | 6.0 | 5.0 | 4.0 | 7.0 |
|  | 0.2500 | 9.0 | 7.0 | 7.0 | 9.0 | 7.0 | 9.0 | 6.0 | 9.0 | 5.0 | 3.0 | 2.0 | 4.0 |
|  | 0.1250 | 9.0 | 7.0 | 1.0 | 9.0 | 4.0 | 2.0 | 3.0 | 9.0 | 4.0 | 1.0 | 1.0 | 1.0 |
|  | 0.0625 | 0.0 | 0.0 | 0.0 | 9.0 | 0.0 |  | 0.0 | 6.0 | 4.0 | 0.0 | 0.0 | 1.0 |
|  | 0.0313 | 0.0 | 1.0 | 0.0 | 9.0 | 0.0 | 0.0 | 0.0 | 6.0 | 0.0 | 0.0 | 0.0 | 0.0 |
|  | 0.0156 | 0.0 | 0.0 |  | 4.0 | 0.0 | 0.0 | 0.0 | 0.0 | 0.0 | 0.0 | 0.0 | 0.0 |
| 166 | 0.5000 | 9.0 | 7.0 | 6.0 | 9.0 | 8.0 | 8.0 | 4.0 | 9.0 | 6.0 | 5.0 | 3.0 | 6.0 |
|  | 0.2500 | 9.0 | 7.0 | 4.0 | 9.0 | 7.0 | 6.0 | 0.0 | 6.0 | 6.0 | 1.0 | 1.0 | 3.0 |
|  | 0.1250 | 7.0 | 6.0 | 0.0 | 9.0 | 5.0 | 2.0 | 0.0 | 6.0 | 2.0 | 1.0 | 1.0 | 1.0 |
|  | 0.0625 | 1.0 | 3.0 | 2.0 | 3.0 | 2.0 |  | 1.0 | 1.0 | 2.0 | 1.0 | 1.0 | 1.0 |
|  | 0.0313 | 2.0 | 0.0 | 0.0 | 0.0 | 0.0 | 3.0 | 0.0 | 0.0 | 2.0 | 0.0 | 0.0 | 0.0 |
|  | 0.0156 | 0.0 | 1.0 | 0.0 | 1.0 | 0.0 | 0.0 | 0.0 | 0.0 | 0.0 | 0.0 | 0.0 | 0.0 |
| 167 | 0.5000 | 9.0 | 8.0 | 9.0 | 9.0 | 7.0 | 9.0 | 8.0 | 9.0 | 7.0 | 6.0 | 5.0 | 7.0 |
|  | 0.2500 | 9.0 | 7.0 | 4.0 | 9.0 | 6.0 | 9.0 | 9.0 | 9.0 | 4.0 | 5.0 | 4.0 | 6.0 |
|  | 0.1250 | 9.0 | 6.0 | 1.0 | 9.0 | 9.0 | 3.0 | 9.0 | 9.0 | 4.0 | 4.0 | 3.0 | 3.0 |
|  | 0.0625 | 9.0 | 7.0 | 1.0 | 9.0 | 7.0 | 2.0 | 6.0 | 9.0 | 0.0 | 1.0 | 1.0 | 3.0 |
|  | 0.0313 | 0.0 | 0.0 | 0.0 | 7.0 | 5.0 | 0.0 | 0.0 | 7.0 | 0.0 | 0.0 | 0.0 | 0.0 |
|  | 0.0156 |  | 1.0 | 0.0 | 7.0 | 1.0 | 0.0 | 0.0 | 5.0 | 1.0 | 0.0 | 0.0 | 0.0 |
| 168 | 0.2500 | 9.0 | 5.0 | 0.0 | 9.0 | 3.0 | 4.0 | 0.0 | 5.0 | 0.0 | 0.0 | 0.0 | 0.0 |
|  | 0.1250 | 9.0 | 0.0 | 0.0 | 9.0 | 0.0 | 3.0 | 0.0 | 0.0 | 0.0 | 0.0 | 0.0 | 0.0 |
|  | 0.0625 | 4.0 | 0.0 | 0.0 | 9.0 | 0.0 | 0.0 | 0.0 | 0.0 | 0.0 | 0.0 | 0.0 | 0.0 |
|  | 0.0313 | 0.0 | 0.0 | 0.0 | 9.0 | 0.0 | 0.0 | 0.0 | 0.0 | 0.0 | 0.0 | 0.0 | 0.0 |
|  | 0.0156 | 0.0 | 0.0 | 0.0 | 3.0 | 0.0 | 0.0 | 0.0 | 0.0 | 0.0 | 0.0 | 0.0 | 0.0 |
| 169 | 0.2500 | 5.0 | 3.0 | 0.0 | 4.0 | 0.0 | 3.0 | 0.0 | 0.0 | 3.0 | 0.0 | 0.0 | 0.0 |
| 170 | 0.2500 | 9.0 | 9.0 | 3.0 | 9.0 | 3.0 | 9.0 | 9.0 | 9.0 | 8.0 | 9.0 | 9.0 | 9.0 |
|  | 0.1250 | 9.0 | 9.0 | 3.0 | 9.0 | 0.0 | 7.0 | 9.0 | 9.0 | 5.0 | 7.0 | 8.0 | 9.0 |
|  | 0.0625 | 9.0 | 4.0 | 0.0 | 9.0 | 0.0 |  | 9.0 | 9.0 | 4.0 | 6.0 | 7.0 | 8.0 |
|  | 0.0313 | 6.0 | 0.0 | 0.0 | 9.0 | 0.0 | 7.0 | 9.0 | 9.0 | 4.0 | 0.0 | 6.0 | 7.0 |
|  | 0.0156 | 0.0 | 0.0 | 0.0 | 9.0 | 0.0 | 3.0 | 3.0 | 9.0 | 1.0 | 0.0 | 0.0 | 5.0 |
| 171 | 0.2500 | 9.0 | 9.0 | 9.0 | 9.0 | 6.0 | 9.0 | 9.0 | 9.0 | 8.0 | 8.0 | 8.0 | 9.0 |
|  | 0.1250 | 9.0 | 9.0 | 4.0 | 9.0 | 5.0 | 9.0 | 9.0 | 9.0 | 7.0 | 6.0 | 6.0 | 8.0 |
|  | 0.0625 | 9.0 | 9.0 | 2.0 | 9.0 |  | 9.0 | 8.0 | 9.0 | 6.0 | 5.0 | 6.0 | 8.0 |
|  | 0.0313 | 9.0 | 4.0 | 5.0 | 9.0 | 0.0 | 3.0 | 4.0 | 9.0 | 2.0 | 4.0 | 3.0 | 6.0 |
|  | 0.0156 | 9.0 | 3.0 | 4.0 | 9.0 | 0.0 | 2.0 | 0.0 | 7.0 | 1.0 | 2.0 | 2.0 | 2.0 |
| 172 | 0.2500 | 9.0 | 9.0 | 9.0 | 9.0 | 9.0 | 9.0 | 9.0 | 9.0 | 9.0 | 8.0 | 9.0 | 9.0 |
|  | 0.1250 | 9.0 | 9.0 | 9.0 | 9.0 | 7.0 | 9.0 | 8.0 | 9.0 | 9.0 | 7.0 | 7.0 | 9.0 |
|  | 0.0625 | 9.0 | 9.0 | 7.0 | 9.0 | 5.0 | 7.0 | 8.0 | 9.0 | 7.0 | 7.0 | 7.0 | 8.0 |
|  | 0.0313 | 9.0 | 7.0 | 3.0 | 9.0 | 0.0 | 7.0 | 6.0 | 7.0 | 2.0 | 5.0 | 3.0 | 7.0 |
|  | 0.0156 | 9.0 | 5.0 | 1.0 | 9.0 | 0.0 | 2.0 | 4.0 | 5.0 | 1.0 | 2.0 | 2.0 | 4.0 |

EXAMPLE 39

Rice Tolerance to Post-transplant Applications and Preemergence Weed Control Under Flooded Paddy Conditions The tolerance of transplanted rice to post-transplanted herbicide applications is determined as follows: two ten-day-old rice seedlings (cv. Tebonnet) are transplanted into silt loam soil in 32 oz. plastic containers with a diameter of 10.5 cm and no drainage holes. After transplanting, the containers are flooded and the water level is maintained at 1.5 to 3 cm above the soil surface. Three days after transplanting, the flooded soil surface of the containers is treated with the selected aqueous/acetone 50/50 v/v mixture containing the test compounds to provide the equivalent of about 0.0313 to 0.500 kg/ha of active ingredient. The treated containers are placed on greenhouse benches, watered such that the water level is maintained as stated above, and cared for in accordance with conventional greenhouse procedures. Three to four weeks after treatment, the test is terminated and each container is examined and herbicidal effect rated according to the rating system provided in Example 37. The data obtained are reported in Table III. The compounds evaluated are reported by compound number given in Example 37.

Preemergence herbicidal activity under flooded paddy conditions is determined as follows: plant seeds or propagating organs are planted in the top 0.5 cm of silt loam soil in 32 oz. plastic containers with a diameter of 10.5 cm and no drainage holes. Water is added to these containers and maintained at 1.5 to 3 cm above the soil surface for the duration of the experiment. The test compounds are applied as aqueous/acetone mixtures 50/50 v/v pipetted directly into the flood water to give the equivalent of about 0.0313 to 0.500 kg/ha of active ingredient. The treated containers are placed on greenhouse benches and cared for in accordance with conventional greenhouse procedures. Three to four weeks after treatment, the test is terminated and each container is examined and herbicidal effect rated according to the rating system provided in Example 37. The data obtained are reported in Table III. The compounds evaluated are reported by compound number given in Example 37.

PLANT SPECIES EMPLOYED IN RICE TOLERANCE/PREEMERGENCE WEED CONTROL EVALUATIONS

| Header Abbr. | Common Name | Scientific Name |
|---|---|---|
| ECHORC | Watergrass (Calif.) | *Echinochloa oryzoides* (Ard.) Fritsch. |
| CYPIR | Rice Flatsedge | *Cyperus iria* |
| CYPSE | Flatsedge | *Cyperus serotinus*, Rottb. |
| MOOVA | Monochoria | *Monochoria vaginalis*, Presl. |
| SAGPY | Arrowhead (Pygmaea) | *Sagittaria pygmaea*, L. |
| ORYSAT | Rice, Tebonnet | *Oryza sativa*, (L.) Tebonnet |

TABLE III

Paddy Conditions - Post-Transplant Rice Preemergence Weeds

| Compound Number | Rate (kg/ha) | ECHORC | CYPIR | CYPSE | MOOVA | SAGPY | ORYSAT |
|---|---|---|---|---|---|---|---|
| 1 | 0.5000 | 9.0 | 9.0 | 8.0 | 9.0 | 0.0 | 4.0 |
|   | 0.2500 | 7.0 | 9.0 | 2.0 | 9.0 | 0.0 | 3.0 |
|   | 0.1250 | 6.0 | 9.0 | 0.0 | 9.0 | 0.0 | 2.0 |
|   | 0.0625 | 4.0 | 7.0 | 0.0 | 9.0 | 0.0 | 2.0 |
|   | 0.0313 | 2.0 | 2.0 | 0.0 | 8.0 | 0.0 | 1.0 |
| 2 | 0.5000 | 9.0 | 1.0 | 0.0 | 9.0 | 0.0 | 3.0 |
|   | 0.2500 | 8.0 | 0.0 | 0.0 | 9.0 | 0.0 | 2.0 |
|   | 0.1250 | 7.0 | 0.0 | 0.0 | 9.0 | 0.0 | 1.0 |
|   | 0.0625 | 2.0 | 0.0 | 0.0 | 9.0 | 0.0 | 0.0 |
|   | 0.0313 | 2.0 | 0.0 | 0.0 | 4.0 | 0.0 | 0.0 |
| 3 | 0.5000 | 4.0 | 0.0 | 0.0 | 9.0 | 0.0 | 3.0 |
|   | 0.2500 | 2.0 | 0.0 | 0.0 | 9.0 | 0.0 | 2.0 |
|   | 0.1250 | 0.0 | 0.0 | 0.0 | 9.0 | 0.0 | 2.0 |
|   | 0.0625 | 0.0 | 0.0 | 0.0 | 2.0 | 0.0 | 0.0 |
| 4 | 0.5000 | 9.0 | 9.0 | 0.0 | 9.0 | 0.0 | 3.0 |
|   | 0.2500 | 8.0 | 9.0 | 0.0 | 9.0 | 0.0 | 3.0 |
|   | 0.1250 | 7.0 | 8.0 | 0.0 | 8.0 | 0.0 | 2.0 |
|   | 0.0625 | 4.0 | 4.0 | 0.0 | 7.0 | 0.0 | 2.0 |
|   | 0.0313 | 2.0 | 0.0 | 0.0 | 2.0 | 0.0 | 0.0 |
| 5 | 0.5000 | 4.0 | 0.0 | 1.0 | 8.0 | 0.0 | 2.0 |
|   | 0.2500 | 2.0 | 0.0 | 0.0 | 4.0 | 0.0 | 1.0 |
|   | 0.1250 | 1.0 | 0.0 | 0.0 | 2.0 | 0.0 | 1.0 |
| 6 | 0.5000 | 7.0 | 7.0 | 0.0 | 9.0 | 0.0 | 0.0 |
|   | 0.2500 | 7.0 | 6.0 | 0.0 | 9.0 | 0.0 | 0.0 |
|   | 0.1250 | 2.0 | 4.0 | 0.0 | 8.0 | 0.0 | 0.0 |
|   | 0.0625 | 0.0 | 2.0 | 0.0 | 8.0 | 0.0 | 0.0 |
|   | 0.0313 | 0.0 | 0.0 | 0.0 | 2.0 | 0.0 | 0.0 |
| 7 | 0.2500 | 9.0 | 9.0 | 9.0 | 9.0 | 9.0 | 9.0 |
|   | 0.1250 | 9.0 | 9.0 | 7.0 | 9.0 | 8.0 | 8.0 |
|   | 0.0625 | 9.0 | 9.0 | 7.0 | 9.0 | 4.0 | 7.0 |
|   | 0.0313 | 8.0 | 8.0 | 4.0 | 9.0 | 2.0 | 7.0 |
| 8 | 0.2500 | 8.5 | 4.0 | 0.0 | 9.0 | 0.0 | 6.0 |
|   | 0.1250 | 7.5 | 0.0 | 0.0 | 9.0 | 0.0 | 5.0 |
|   | 0.0625 | 6.5 | 0.0 | 0.0 | 9.0 | 0.0 | 3.5 |
|   | 0.0313 | 6.5 | 0.0 | 0.0 | 9.0 | 0.0 | 2.5 |
| 9 | 0.2500 | 7.0 | 6.0 | 7.0 | 9.0 | 2.0 | 9.0 |
|   | 0.1250 | 4.0 | 4.0 | 2.0 | 9.0 | 1.0 | 9.0 |
|   | 0.0625 | 2.0 | 2.0 | 0.0 | 9.0 | 0.0 | 8.0 |
|   | 0.0313 | 0.0 | 0.0 | 0.0 | 9.0 | 0.0 | 7.0 |
| 10 | 0.2500 | 2.0 | 4.0 | 0.0 | 9.0 | 0.0 | 7.0 |
|   | 0.1250 | 2.0 | 2.0 | 0.0 | 9.0 | 0.0 | 6.0 |
|   | 0.0625 | 1.0 | 0.0 | 0.0 | 9.0 | 0.0 | 4.0 |
|   | 0.0313 | 0.0 | 0.0 | 0.0 | 9.0 | 0.0 | 3.0 |
| 11 | 0.2500 | 3.0 | 0.0 | 0.0 | 7.0 | 0.0 | 3.0 |
|   | 0.1250 | 2.0 | 0.0 | 0.0 | 4.0 | 0.0 | 3.0 |
|   | 0.0625 | 2.0 | 0.0 | 0.0 | 1.0 | 0.0 | 2.0 |
|   | 0.0313 | 1.0 | 0.0 | 0.0 | 0.0 | 0.0 | 2.0 |
| 12 | 0.2500 | 9.0 | 0.0 | 6.0 | 9.0 | 0.0 | 7.0 |
|   | 0.1250 | 8.5 | 1.0 | 1.0 | 9.0 | 4.0 | 5.5 |
|   | 0.0625 | 9.0 | 0.0 | 3.0 | 9.0 | 1.0 | 3.5 |
|   | 0.0313 | 5.0 | 0.0 | 1.0 | 9.0 | 0.0 | 3.0 |
| 13 | 0.2500 | 9.0 | 1.0 | 0.0 | 9.0 | 0.0 | 5.0 |
|   | 0.1250 | 8.0 | 0.5 | 0.0 | 9.0 | 0.0 | 3.0 |
|   | 0.0625 | 7.0 | 0.0 | 0.0 | 9.0 | 0.0 | 2.5 |
|   | 0.0313 | 5.5 | 0.0 | 0.0 | 9.0 | 0.0 | 1.5 |
|   | 0.0156 | 3.5 | 0.0 | 0.0 | 7.5 | 0.0 | 1.0 |
| 14 | 0.2500 | 9.0 | 0.0 | 0.0 | 0.0 | 0.0 | 0.0 |
|   | 0.1250 | 7.5 | 4.5 | 3.0 | 4.5 | 0.0 | 1.0 |
|   | 0.0625 | 4.5 | 2.5 | 0.0 | 4.5 | 0.0 | 0.5 |
|   | 0.0313 | 1.5 | 2.0 | 0.0 | 4.5 | 0.0 | 0.0 |
| 15 | 0.2500 | 9.0 | 7.0 | 0.0 | 9.0 | 0.0 | 3.0 |
|   | 0.1250 | 9.0 | 6.0 | 0.0 | 9.0 | 0.0 | 3.0 |
|   | 0.0625 | 9.0 | 2.0 | 0.0 | 9.0 | 0.0 | 2.0 |
|   | 0.0313 | 6.0 | 2.0 | 0.0 | 9.0 | 0.0 | 0.0 |
| 16 | 0.2500 | 0.0 | 9.0 | 0.0 | 3.0 | 0.0 | 0.0 |
|   | 0.1250 | 0.0 | 4.0 | 0.0 | 9.0 | 0.0 | 0.0 |
|   | 0.0625 | 0.0 | 0.0 | 0.0 | 9.0 | 0.0 | 0.0 |
|   | 0.0313 | 0.0 | 0.0 | 0.0 | 9.0 | 0.0 | 0.0 |
| 17 | 0.2500 | 9.0 | 9.0 | 9.0 | 9.0 | 4.0 | 9.0 |
|   | 0.1250 | 9.0 | 6.0 | 9.0 | 9.0 | 4.0 | 9.0 |
|   | 0.0625 | 9.0 | 0.0 | 9.0 | 9.0 | 0.0 | 6.0 |
|   | 0.0313 | 4.0 | 0.0 | 9.0 | 9.0 | 0.0 | 4.0 |
| 18 | 0.4630 | 7.0 | 0.0 | 4.0 | 9.0 | 6.0 | 3.0 |
|   | 0.2310 | 7.0 | 0.0 | 0.0 | 9.0 | 0.0 | 3.0 |
|   | 0.1160 | 7.0 | 0.0 | 0.0 | 9.0 | 0.0 | 3.0 |
| 19 | 0.4630 | 9.0 | 0.0 | 4.0 | 9.0 | 3.0 | 3.0 |
|   | 0.2310 | 7.0 | 0.0 | 4.0 | 9.0 | 3.0 | 3.0 |
|   | 0.1160 | 7.0 | 0.0 | 4.0 | 9.0 | 0.0 | 3.0 |
| 20 | 0.4630 | 7.0 | 0.0 | 5.0 | 9.0 | 3.0 | 2.0 |
|   | 0.2310 | 7.0 | 0.0 | 5.0 | 9.0 | 0.0 | 2.0 |
|   | 0.1160 | 7.0 | 0.0 | 5.0 | 9.0 | 0.0 | 2.0 |
| 21 | 0.4630 | 5.0 | 0.0 | 0.0 | 0.0 | 0.0 | 0.0 |
|   | 0.2310 | 4.0 | 0.0 | 0.0 | 0.0 | 0.0 | 0.0 |
|   | 0.1160 | 2.0 | 0.0 | 0.0 | 0.0 | 0.0 | 0.0 |
| 22 | 0.4630 | 9.0 | 5.0 | 4.0 | 9.0 | 5.0 | 7.0 |
|   | 0.2310 | 9.0 | 0.0 | 4.0 | 9.0 | 4.0 | 6.0 |
|   | 0.1160 | 6.0 | 0.0 | 4.0 | 9.0 | 4.0 | 3.0 |
| 23 | 0.4630 | 4.0 | 0.0 | 0.0 | 9.0 | 3.0 | 5.0 |
|   | 0.2310 | 4.0 | 0.0 | 0.0 | 9.0 | 0.0 | 4.0 |
|   | 0.1160 | 4.0 | 0.0 | 0.0 | 9.0 | 0.0 | 4.0 |
| 24 | 0.2500 | 9.0 | 0.0 |  | 9.0 | 0.0 | 0.0 |
|   | 0.1250 | 9.0 | 0.0 |  | 9.0 | 0.0 | 0.0 |
|   | 0.0625 | 9.0 | 0.0 |  | 9.0 | 0.0 | 0.0 |
|   | 0.0313 | 4.0 | 0.0 |  | 0.0 | 0.0 | 0.0 |
| 25 | 0.2500 | 9.0 | 0.0 |  | 9.0 | 5.0 | 5.0 |
|   | 0.1250 | 7.0 | 0.0 |  | 9.0 | 5.0 | 4.0 |
|   | 0.0625 | 6.0 | 0.0 |  | 9.0 | 0.0 | 4.0 |
|   | 0.0313 | 4.0 | 0.0 |  | 9.0 | 0.0 | 3.0 |
| 26 | 0.2500 | 9.0 | 9.0 |  | 9.0 | 7.0 | 2.0 |
|   | 0.1250 | 9.0 | 7.0 |  | 9.0 | 5.0 | 1.0 |
|   | 0.0625 | 9.0 | 4.0 |  | 9.0 | 4.0 | 0.0 |
|   | 0.0313 | 7.0 | 2.0 |  | 9.0 | 0.0 | 0.0 |
| 27 | 0.2500 | 9.0 | 9.0 | 9.0 | 9.0 | 4.0 | 4.0 |
|   | 0.1250 | 9.0 | 6.0 | 0.0 | 9.0 | 4.0 | 4.0 |
|   | 0.0625 | 7.0 | 4.0 | 0.0 | 9.0 | 0.0 | 2.0 |
|   | 0.0313 | 6.0 | 3.0 | 0.0 | 9.0 | 0.0 | 1.0 |
| 28 | 0.2500 | 9.0 | 9.0 | 0.0 | 9.0 | 0.0 | 1.0 |
|   | 0.1250 | 7.0 | 9.0 | 0.0 | 9.0 | 0.0 | 0.0 |
|   | 0.0625 | 4.0 | 9.0 | 0.0 | 9.0 | 0.0 | 0.0 |
|   | 0.0313 | 0.0 | 9.0 | 0.0 | 9.0 | 0.0 | 0.0 |
| 29 | 0.2500 | 7.0 | 0.0 | 0.0 | 0.0 | 0.0 | 3.0 |
|   | 0.1250 | 7.0 | 0.0 | 0.0 | 0.0 | 0.0 | 2.0 |
|   | 0.0625 | 7.0 | 0.0 | 0.0 | 0.0 | 0.0 | 1.0 |
|   | 0.0313 | 4.0 | 0.0 | 0.0 | 0.0 | 0.0 | 0.0 |
| 30 | 0.2500 | 0.0 | 4.5 | 0.0 | 4.5 | 2.0 | 0.0 |
|   | 0.1250 | 0.0 | 2.0 | 0.0 | 1.5 | 0.0 | 0.0 |

TABLE III-continued

Paddy Conditions - Post-Transplant Rice Preemergence Weeds

| Compound Number | Rate (kg/ha) | ECHORC | CYPIR | CYPSE | MOGVA | SAPY | ORYSAT |
|---|---|---|---|---|---|---|---|
| 31 | 0.2500 | 5.0 | 2.5 | 0.0 | 2.5 | 0.0 | 0.0 |
|  | 0.1250 | 2.0 | 0.0 | 0.0 | 0.0 | 0.0 | 0.0 |
|  | 0.0625 | 1.0 | 0.0 | 0.0 | 0.0 | 0.0 | 0.0 |
| 32 | 0.2500 | 6.0 | 0.0 | 0.0 |  | 0.0 | 0.0 |
|  | 0.1250 | 3.0 | 0.0 | 0.0 |  | 0.0 | 0.0 |
| 33 | 0.2500 | 0.0 | 0.0 | 0.0 |  | 0.0 | 0.0 |
| 34 | 0.2500 | 9.0 | 0.0 | 0.0 |  | 0.0 | 6.0 |
|  | 0.1250 | 4.0 | 0.0 | 0.0 |  | 0.0 | 4.0 |
|  | 0.0625 | 4.0 | 0.0 | 0.0 |  | 0.0 | 3.0 |
|  | 0.0313 | 3.0 | 0.0 | 0.0 |  | 0.0 | 3.0 |
| 35 | 0.2500 | 6.0 | 0.0 | 0.0 |  | 3.0 | 3.0 |
|  | 0.1250 | 3.0 | 0.0 | 0.0 |  | 0.0 | 2.0 |
| 36 | 0.2500 | 9.0 | 9.0 | 4.0 |  | 9.0 | 5.0 |
|  | 0.1250 | 7.0 | 5.0 | 2.0 |  | 3.0 | 3.0 |
|  | 0.0625 | 6.0 | 5.0 | 0.0 |  | 0.0 | 3.0 |
|  | 0.0313 | 4.0 | 0.0 | 0.0 |  | 0.0 | 3.0 |
| 37 | 0.2500 | 7.0 | 0.0 | 0.0 |  | 3.0 | 3.0 |
|  | 0.1250 | 7.0 | 0.0 | 0.0 |  | 0.0 | 0.0 |
|  | 0.0625 | 6.0 | 0.0 | 0.0 |  | 0.0 | 0.0 |
|  | 0.0313 | 4.0 | 0.0 | 0.0 |  | 0.0 | 0.0 |
| 38 | 0.2500 | 7.0 | 5.0 | 3.0 | 9.0 | 9.0 | 7.0 |
|  | 0.1250 | 4.0 | 5.0 | 0.0 | 9.0 | 4.0 | 5.0 |
|  | 0.0625 | 2.0 | 3.0 | 0.0 | 9.0 | 3.0 | 5.0 |
|  | 0.0313 | 0.0 | 3.0 | 0.0 | 9.0 | 0.0 | 2.0 |
| 39 | 0.2500 | 3.0 | 0.0 | 0.0 | 9.0 | 4.0 | 3.0 |
|  | 0.1250 | 2.0 | 0.0 | 0.0 | 9.0 | 0.0 | 2.0 |
|  | 0.0625 | 0.0 | 0.0 | 0.0 | 9.0 | 0.0 | 0.0 |
|  | 0.0313 | 0.0 | 0.0 | 0.0 | 9.0 | 0.0 | 0.0 |
| 40 | 0.2500 | 9.0 | 0.0 | 6.0 | 9.0 | 0.0 | 3.0 |
|  | 0.1250 | 5.0 | 0.0 | 0.0 | 9.0 | 0.0 | 3.0 |
|  | 0.0625 | 5.0 | 0.0 | 0.0 | 9.0 | 0.0 | 3.0 |
|  | 0.0313 | 5.0 | 0.0 | 0.0 | 9.0 | 0.0 | 2.0 |
| 41 | 0.2500 | 7.0 | 4.0 | 7.0 | 9.0 | 6.0 | 5.0 |
|  | 0.1250 | 6.0 | 0.0 | 2.0 | 9.0 | 0.0 | 5.0 |
|  | 0.0625 | 4.0 | 0.0 | 0.0 | 9.0 | 0.0 | 5.0 |
|  | 0.0313 | 3.0 | 0.0 | 0.0 | 6.0 | 0.0 | 4.0 |
| 42 | 0.2500 | 6.0 | 0.0 | 0.0 | 9.0 | 3.0 | 0.0 |
|  | 0.1250 | 5.0 | 0.0 | 0.0 | 9.0 | 0.0 | 0.0 |
|  | 0.0625 | 5.0 | 0.0 | 0.0 | 9.0 | 0.0 | 0.0 |
|  | 0.0313 | 5.0 | 0.0 | 0.0 | 7.0 | 0.0 | 0.0 |
| 43 | 0.2500 | 9.0 | 5.0 | 9.0 | 9.0 | 9.0 | 6.0 |
|  | 0.1250 | 7.0 | 4.0 | 8.0 | 9.0 | 7.0 | 4.0 |
|  | 0.0625 | 6.0 | 2.0 | 5.0 | 9.0 | 7.0 | 3.0 |
|  | 0.0313 | 5.0 | 0.0 | 5.0 | 9.0 | 7.0 | 2.0 |
| 44 | 0.2500 | 8.0 | 9.0 | 0.0 | 9.0 |  | 5.0 |
|  | 0.1250 | 7.0 | 6.0 | 0.0 | 7.0 |  | 3.0 |
|  | 0.0625 | 6.0 | 6.0 | 0.0 | 4.0 |  | 3.0 |
|  | 0.0313 | 6.0 | 5.0 | 0.0 | 4.0 |  | 0.0 |
| 45 | 0.2500 | 7.0 | 7.0 | 0.0 | 9.0 | 4.0 | 3.0 |
|  | 0.1250 | 7.0 | 7.0 |  | 9.0 | 0.0 | 2.0 |
|  | 0.0625 | 4.0 | 3.0 | 0.0 | 7.0 | 0.0 | 2.0 |
|  | 0.0313 | 3.0 | 0.0 | 0.0 | 7.0 | 0.0 | 3.0 |
| 46 | 0.2500 | 4.0 | 0.0 | 6.0 | 7.0 | 3.0 | 3.0 |
|  | 0.1250 | 0.0 | 0.0 | 0.0 | 6.0 | 0.0 | 2.0 |
|  | 0.0625 | 0.0 | 0.0 | 0.0 | 4.0 | 0.0 | 2.0 |
|  | 0.0313 | 0.0 | 0.0 | 0.0 | 3.0 | 0.0 | 0.0 |
| 47 | 0.2500 | 7.0 | 6.0 | 0.0 | 9.0 | 7.0 | 3.0 |
|  | 0.1250 | 4.0 | 4.0 | 0.0 | 9.0 | 4.0 | 0.0 |
|  | 0.0625 | 2.0 | 0.0 | 0.0 | 6.0 | 0.0 | 0.0 |
|  | 0.0313 | 0.0 | 0.0 | 0.0 | 5.0 | 0.0 | 0.0 |
| 48 | 0.2500 | 6.0 | 5.0 | 0.0 | 6.0 | 6.0 | 6.0 |
|  | 0.1250 | 3.0 | 2.0 | 0.0 | 3.0 | 3.0 | 4.0 |
| 49 | 0.2500 | 7.0 | 7.0 | 4.0 | 9.0 | 7.0 | 7.0 |
|  | 0.1250 | 5.0 | 2.0 |  | 9.0 | 6.0 | 7.0 |
|  | 0.0625 | 2.0 | 0.0 | 3.0 | 9.0 | 4.0 | 5.0 |
|  | 0.0313 | 0.0 | 0.0 | 2.0 | 9.0 | 2.0 | 5.0 |
| 50 | 0.2500 | 7.0 | 0.0 | 0.0 | 7.0 | 3.0 | 1.0 |
|  | 0.1250 | 7.0 | 0.0 | 0.0 | 3.0 | 3.0 | 0.0 |
|  | 0.0625 | 7.0 | 0.0 | 0.0 | 0.0 | 2.0 | 0.0 |
|  | 0.0313 | 4.0 | 0.0 | 0.0 | 0.0 | 2.0 | 0.0 |
| 51 | 0.2500 | 0.0 | 6.0 | 0.0 | 4.0 | 0.0 | 0.0 |
|  | 0.1250 | 0.0 | 3.0 | 0.0 | 4.0 | 0.0 | 0.0 |
|  | 0.0625 | 0.0 | 2.0 | 0.0 | 3.0 | 0.0 | 0.0 |
| 52 | 0.2500 | 0.0 | 2.0 | 0.0 | 4.0 | 0.0 | 0.0 |
| 53 | 0.2500 | 3.0 | 9.0 | 0.0 | 9.0 | 0.0 | 3.0 |
|  | 0.1250 | 2.0 | 9.0 | 0.0 | 9.0 | 0.0 | 2.0 |
|  | 0.0625 | 0.0 | 2.0 | 0.0 | 2.0 | 0.0 | 0.0 |
|  | 0.0313 | 0.0 | 2.0 | 0.0 | 2.0 | 0.0 | 0.0 |
| 54 | 0.2500 | 9.0 | 4.0 | 4.0 | 6.0 | 2.0 | 4.0 |
|  | 0.1250 | 7.0 | 4.0 | 0.0 | 6.0 | 0.0 | 3.0 |
|  | 0.0625 | 5.0 | 4.0 | 0.0 | 0.0 | 0.0 | 2.0 |
|  | 0.0313 | 5.0 | 0.0 | 0.0 | 0.0 | 0.0 | 0.0 |
| 55 | 0.2500 | 7.0 | 9.0 | 0.0 | 9.0 | 0.0 | 4.0 |
|  | 0.1250 | 7.0 | 9.0 | 0.0 | 9.0 | 0.0 | 1.0 |
|  | 0.0625 | 7.0 | 9.0 | 0.0 | 9.0 | 0.0 | 1.0 |
|  | 0.0313 | 7.0 | 9.0 | 0.0 | 9.0 | 0.0 | 0.0 |
| 56 | 0.2500 | 5.0 | 0.0 | 0.0 | 9.0 | 0.0 | 2.0 |
|  | 0.1250 | 3.0 | 0.0 | 0.0 | 9.0 | 0.0 | 0.0 |
|  | 0.0625 | 0.0 | 0.0 | 0.0 | 6.0 | 0.0 | 0.0 |
|  | 0.0313 | 0.0 | 0.0 | 0.0 | 6.0 | 0.0 | 0.0 |
| 57 | 0.2500 | 5.0 | 9.0 | 3.0 | 9.0 | 6.0 | 4.0 |
|  | 0.1250 | 2.0 | 9.0 | 0.0 | 9.0 | 0.0 | 0.0 |
|  | 0.0625 | 2.0 | 9.0 | 0.0 | 9.0 | 0.0 | 0.0 |
|  | 0.0313 | 0.0 | 0.0 | 0.0 | 9.0 | 0.0 | 0.0 |
| 58 | 0.2500 | 9.0 | 3.0 | 5.0 | 9.0 | 4.0 | 5.0 |
|  | 0.1250 | 7.0 | 2.0 | 5.0 | 3.0 | 0.0 | 4.0 |
|  | 0.0625 | 7.0 | 0.0 | 5.0 | 0.0 | 0.0 | 4.0 |
|  | 0.0313 | 7.0 | 0.0 | 5.0 | 0.0 | 0.0 | 4.0 |
| 59 | 0.2500 | 7.0 | 9.0 | 7.0 | 9.0 | 3.0 | 2.0 |
|  | 0.1250 | 5.0 | 0.0 | 0.0 | 0.0 | 0.0 | 2.0 |
|  | 0.0625 | 4.0 | 0.0 | 0.0 | 0.0 | 0.0 | 0.0 |
| 60 | 0.2500 | 9.0 | 6.0 | 4.0 | 9.0 | 9.0 | 5.0 |
|  | 0.1250 | 9.0 | 6.0 | 4.0 | 9.0 | 9.0 | 5.0 |
|  | 0.0625 | 9.0 | 3.0 | 2.0 | 9.0 | 4.0 | 4.0 |
|  | 0.0313 | 7.0 | 3.0 | 2.0 | 9.0 | 3.0 | 4.0 |
| 61 | 0.2500 | 0.0 | 0.0 | 0.0 | 0.0 | 0.0 | 0.0 |
| 62 | 0.2500 | 5.0 | 9.0 | 0.0 | 9.0 | 6.0 | 4.0 |
|  | 0.1250 | 2.0 | 9.0 | 0.0 | 9.0 | 3.0 | 3.0 |
|  | 0.0625 | 0.0 | 2.0 | 0.0 | 9.0 | 0.0 | 3.0 |
|  | 0.0313 | 0.0 | 0.0 | 0.0 | 4.0 | 0.0 | 2.0 |
| 63 | 0.2500 | 5.0 | 7.0 | 0.0 | 9.0 | 9.0 | 3.0 |
|  | 0.1250 | 5.0 | 7.0 | 0.0 | 9.0 | 9.0 | 3.0 |
|  | 0.0625 | 0.0 | 6.0 | 0.0 | 9.0 | 7.0 | 3.0 |
|  | 0.0313 | 0.0 | 2.0 | 0.0 | 9.0 | 4.0 | 3.0 |
| 64 | 0.2500 | 9.0 | 7.0 | 0.0 | 9.0 | 8.0 | 5.0 |
|  | 0.1250 | 6.0 | 2.0 | 0.0 | 9.0 | 5.0 | 5.0 |
|  | 0.0625 | 6.0 | 2.0 | 0.0 | 9.0 | 3.0 | 4.0 |
|  | 0.0313 | 5.0 | 0.0 | 0.0 | 7.0 | 0.0 | 3.0 |
| 65 | 0.2500 | 7.0 | 8.0 | 0.0 | 9.0 | 7.0 | 6.0 |
|  | 0.1250 | 6.0 | 7.0 | 0.0 | 9.0 | 5.0 | 6.0 |
|  | 0.0625 | 5.0 | 7.0 | 0.0 | 9.0 | 4.0 | 3.0 |
|  | 0.0313 | 5.0 | 6.0 | 0.0 | 9.0 | 2.0 | 2.0 |
| 66 | 0.2500 | 9.0 | 7.0 | 4.0 | 9.0 | 4.0 | 3.0 |
|  | 0.1250 | 9.0 | 7.0 | 4.0 | 9.0 | 4.0 | 3.0 |
|  | 0.0625 | 7.0 | 6.0 | 0.0 | 9.0 | 4.0 | 2.0 |
|  | 0.0313 | 7.0 | 6.0 | 0.0 | 9.0 | 3.0 | 2.0 |
| 67 | 0.2500 | 5.0 | 8.0 | 3.0 | 9.0 | 6.0 | 6.0 |
|  | 0.1250 | 5.0 | 5.0 | 3.0 | 9.0 | 4.0 | 4.0 |
|  | 0.0625 | 4.0 | 5.0 | 3.0 | 9.0 | 4.0 | 3.0 |
|  | 0.0313 | 0.0 | 5.0 | 0.0 | 9.0 | 0.0 | 2.0 |
| 68 | 0.2500 | 7.0 | 8.0 | 0.0 | 9.0 | 3.0 | 4.0 |
|  | 0.1250 | 7.0 | 5.0 | 0.0 | 9.0 | 0.0 | 2.0 |
|  | 0.0625 | 5.0 | 0.0 | 0.0 | 9.0 | 0.0 | 0.0 |
|  | 0.0313 | 0.0 | 0.0 | 0.0 | 3.0 | 0.0 | 0.0 |
| 69 | 0.2500 | 7.0 | 3.0 | 9.0 |  | 3.0 | 3.0 |
|  | 0.1250 | 5.0 | 3.0 | 9.0 |  | 3.0 | 2.0 |

TABLE III-continued

Paddy Conditions - Post-Transplant Rice Preemergence Weeds

| Compound Number | Rate (kg/ha) | ECHROC | CYPIR | CYPSE | MOGVA | SAPY | ORYSAT |
|---|---|---|---|---|---|---|---|
|  | 0.0625 | 4.0 | 3.0 | 3.0 |  | 0.0 | 2.0 |
|  | 0.0313 | 0.0 | 3.0 | 3.0 |  | 0.0 | 0.0 |
| 70 | 0.2500 | 0.0 | 2.0 | 3.0 | 4.0 | 0.0 | 2.0 |
|  | 0.1250 | 0.0 | 2.0 | 0.0 | 4.0 | 2.0 |  |
|  | 0.0625 | 0.0 | 2.0 | 0.0 | 4.0 | 0.0 |  |
|  | 0.0313 | 0.0 | 0.0 | 0.0 | 4.0 | 0.0 |  |
| 71 | 0.2500 | 7.0 | 7.0 | 3.0 | 0.0 | 4.0 |  |
|  | 0.1250 | 0.0 | 3.0 | 3.0 | 0.0 | 4.0 |  |
| 72 | 0.2500 | 9.0 | 9.0 | 9.0 | 4.0 | 3.0 |  |
|  | 0.1250 | 9.0 | 7.0 | 9.0 | 4.0 | 3.0 |  |
|  | 0.0625 | 9.0 | 6.0 | 0.0 | 4.0 | 2.0 |  |
|  | 0.0313 | 9.0 | 6.0 | 0.0 | 4.0 | 1.0 |  |
| 73 | 0.2500 | 7.0 | 6.0 | 4.0 | 4.0 | 6.0 |  |
|  | 0.1250 | 3.0 | 0.0 | 2.0 | 3.0 | 5.0 |  |
| 74 | 0.2500 | 9.0 | 0.0 | 9.0 | 9.0 | 3.0 |  |
|  | 0.1250 | 9.0 | 0.0 | 5.0 | 3.0 | 2.0 |  |
|  | 0.0625 | 9.0 | 0.0 | 5.0 | 3.0 | 0.0 |  |
|  | 0.0313 | 7.0 | 0.0 | 0.0 | 3.0 | 0.0 |  |
| 75 | 0.2500 | 9.0 | 6.0 | 3.0 | 3.0 | 2.0 |  |
|  | 0.1250 | 9.0 | 6.0 | 3.0 | 0.0 | 1.0 |  |
|  | 0.0625 | 6.0 | 0.0 | 3.0 | 0.0 | 0.0 |  |
|  | 0.0313 | 6.0 | 0.0 | 2.0 | 0.0 | 0.0 |  |
| 76 | 0.2500 | 9.0 | 6.0 | 3.0 | 4.0 | 4.0 |  |
|  | 0.1250 | 9.0 | 0.0 | 2.0 | 4.0 | 3.0 |  |
|  | 0.0625 | 7.0 | 0.0 | 2.0 | 0.0 | 2.0 |  |
|  | 0.0313 | 4.0 | 0.0 | 2.0 | 0.0 | 2.0 |  |
| 77 | 0.2500 | 9.0 | 0.0 | 4.0 | 0.0 | 3.0 |  |
|  | 0.1250 | 9.0 | 0.0 | 0.0 | 0.0 | 3.0 |  |
|  | 0.0625 | 9.0 | 0.0 | 0.0 | 0.0 | 2.0 |  |
|  | 0.0313 | 9.0 | 0.0 | 0.0 | 0.0 | 2.0 |  |
| 78 | 0.2500 | 9.0 | 9.0 | 9.0 | 4.0 | 1.0 |  |
|  | 0.1250 | 9.0 | 6.0 | 7.0 | 2.0 | 0.0 |  |
|  | 0.0625 | 7.0 | 5.0 | 6.0 | 0.0 | 0.0 |  |
|  | 0.0313 | 7.0 | 5.0 | 6.0 | 0.0 | 0.0 |  |
| 79 | 0.2500 | 8.0 | 6.0 | 9.0 | 4.0 | 3.0 |  |
|  | 0.1250 | 7.0 | 2.0 | 0.0 | 4.0 | 3.0 |  |
|  | 0.0625 | 6.0 | 0.0 | 0.0 | 0.0 | 2.0 |  |
|  | 0.0313 | 5.0 | 0.0 | 0.0 | 0.0 | 0.0 |  |
| 80 | 0.2500 | 9.0 | 7.0 | 4.0 | 0.0 | 2.0 |  |
|  | 0.1250 | 9.0 | 7.0 | 3.0 | 0.0 | 0.0 |  |
|  | 0.0625 | 9.0 | 7.0 | 3.0 | 0.0 | 0.0 |  |
|  | 0.0313 | 9.0 | 5.0 | 3.0 | 0.0 | 0.0 |  |
| 81 | 0.2500 | 3.0 | 5.0 | 0.0 | 0.0 | 0.0 |  |
|  | 0.1250 | 3.0 | 5.0 | 0.0 | 0.0 | 0.0 |  |
|  | 0.0625 | 0.0 | 4.0 | 0.0 | 0.0 | 0.0 |  |
| 82 | 0.2500 | 9.0 | 3.0 | 4.0 | 7.0 | 3.0 |  |
|  | 0.1250 | 6.0 | 3.0 | 2.0 | 4.0 | 3.0 |  |
|  | 0.0625 | 4.0 | 0.0 | 0.0 | 4.0 | 0.0 |  |
|  | 0.0313 | 4.0 | 0.0 | 0.0 | 4.0 | 0.0 |  |
| 83 | 0.2500 | 7.0 | 7.0 | 5.0 | 9.0 | 9.0 | 6.0 |
|  | 0.1250 | 7.0 | 6.0 | 3.0 | 9.0 | 7.0 | 5.0 |
|  | 0.0625 | 6.0 | 6.0 |  | 9.0 | 7.0 | 3.0 |
|  | 0.0313 | 5.0 | 5.0 | 0.0 | 9.0 | 7.0 | 3.0 |
| 84 | 0.2500 | 9.0 | 9.0 | 9.0 | 9.0 | 9.0 | 7.0 |
|  | 0.1250 | 7.0 | 9.0 | 9.0 | 9.0 | 7.0 | 6.0 |
|  | 0.0625 | 5.0 | 7.0 | 3.0 | 9.0 | 6.0 | 4.0 |
|  | 0.0313 | 4.0 | 3.0 | 0.0 | 9.0 | 2.0 | 3.0 |
| 85 | 0.2500 | 9.0 | 9.0 | 9.0 | 9.0 | 9.0 | 5.0 |
|  | 0.1250 | 7.0 | 9.0 | 2.0 | 9.0 | 9.0 | 4.0 |
|  | 0.0625 | 5.0 | 7.0 | 2.0 | 9.0 | 3.0 | 4.0 |
|  | 0.0313 | 4.0 | 3.0 | 0.0 | 9.0 | 3.0 | 3.0 |
| 86 | 0.2500 | 9.0 | 9.0 | 9.0 | 9.0 | 9.0 | 5.0 |
|  | 0.1250 | 9.0 | 8.0 | 3.0 | 9.0 | 9.0 | 4.0 |
|  | 0.0625 | 6.0 | 7.0 | 0.0 | 9.0 | 9.0 | 4.0 |
|  | 0.0313 | 5.0 | 3.0 | 0.0 | 9.0 | 5.0 | 3.0 |
| 87 | 0.5000 | 3.0 | 7.0 | 5.0 | 9.0 | 7.0 | 6.0 |
|  | 0.2500 | 3.0 | 5.0 | 5.0 | 9.0 | 5.0 | 4.0 |
|  | 0.1250 | 2.0 | 5.0 | 5.0 | 9.0 | 4.0 | 3.0 |

TABLE III-continued

Paddy Conditions - Post-Transplant Rice Preemergence Weeds

| Compound Number | Rate (kg/ha) | ECHROC | CYPIR | CYPSE | MOGVA | SAPY | ORYSAT |
|---|---|---|---|---|---|---|---|
|  | 0.0625 | 0.0 | 5.0 | 0.0 | 9.0 | 4.0 | 3.0 |
|  | 0.0313 | 0.0 | 5.0 | 0.0 | 9.0 | 0.0 | 2.0 |
| 88 | 0.2500 | 7.0 | 0.0 | 7.0 | 9.0 | 9.0 | 4.0 |
|  | 0.1250 | 6.0 | 0.0 | 7.0 | 9.0 | 9.0 | 4.0 |
|  | 0.0625 | 6.0 | 0.0 | 5.0 | 9.0 | 9.0 | 3.0 |
|  | 0.0313 | 6.0 | 0.0 | 3.0 | 9.0 | 6.0 | 2.0 |
| 89 | 0.2500 | 6.0 | 4.0 | 6.0 | 9.0 | 9.0 | 6.0 |
|  | 0.1250 | 5.0 | 2.0 | 4.0 | 9.0 | 9.0 | 5.0 |
|  | 0.0625 | 4.0 | 0.0 | 0.0 | 9.0 | 5.0 | 4.0 |
|  | 0.0313 | 3.0 | 0.0 | 0.0 | 9.0 | 4.0 | 2.0 |
| 90 | 0.2500 | 3.0 | 3.0 | 3.0 | 9.0 | 9.0 | 3.0 |
|  | 0.1250 | 0.0 | 1.0 | 0.0 | 9.0 | 9.0 | 1.0 |
|  | 0.0625 | 0.0 | 0.0 | 0.0 | 9.0 | 6.0 | 0.0 |
|  | 0.0313 | 0.0 | 0.0 | 0.0 | 9.0 | 4.0 | 0.0 |
| 91 | 0.2500 | 4.0 | 0.0 | 0.0 | 9.0 | 0.0 | 2.0 |
|  | 0.1250 | 2.0 | 0.0 | 0.0 | 9.0 | 0.0 | 0.0 |
|  | 0.0625 | 0.0 | 0.0 | 0.0 | 9.0 | 0.0 | 0.0 |
|  | 0.0313 | 0.0 | 0.0 | 0.0 | 9.0 | 0.0 | 0.0 |
| 92 | 0.2500 | 3.0 | 7.0 | 9.0 | 9.0 | 9.0 | 3.0 |
|  | 0.1250 | 2.0 | 5.0 | 9.0 | 9.0 | 4.0 | 3.0 |
|  | 0.0625 | 0.0 | 3.0 | 9.0 | 9.0 | 0.0 | 2.0 |
|  | 0.0313 | 0.0 | 3.0 | 9.0 | 9.0 | 0.0 | 1.0 |
| 93 | 0.2500 | 7.0 | 0.0 | 9.0 | 9.0 | 9.0 | 3.0 |
|  | 0.1250 | 4.0 | 0.0 | 5.0 | 9.0 | 3.0 | 0.0 |
|  | 0.0625 | 3.0 | 0.0 | 0.0 | 9.0 | 0.0 | 0.0 |
|  | 0.0313 | 0.0 | 0.0 | 0.0 | 9.0 | 0.0 | 0.0 |
| 94 | 0.2500 | 7.0 | 4.0 | 9.0 | 9.0 | 9.0 | 3.0 |
|  | 0.1250 | 2.0 | 4.0 | 6.0 | 9.0 | 5.0 | 3.0 |
|  | 0.0625 | 0.0 | 3.0 |  | 9.0 | 0.0 | 2.0 |
|  | 0.0313 | 0.0 | 0.0 |  | 9.0 | 0.0 | 0.0 |
| 95 | 0.2500 | 3.0 | 7.0 | 3.0 | 9.0 |  | 8.0 |
|  | 0.1250 | 3.0 | 7.0 | 0.0 | 9.0 |  | 8.0 |
|  | 0.0625 | 0.0 | 4.0 | 0.0 | 5.0 |  | 4.0 |
|  | 0.0313 | 0.0 | 4.0 | 0.0 | 5.0 |  | 3.0 |
| 96 | 0.2500 | 3.0 | 6.0 | 0.0 | 3.0 |  | 5.0 |
|  | 0.1250 | 0.0 | 6.0 | 0.0 | 3.0 |  | 4.0 |
|  | 0.0625 | 0.0 | 5.0 | 0.0 | 2.0 |  | 4.0 |
|  | 0.0313 | 0.0 | 0.0 | 0.0 | 2.0 |  | 3.0 |
| 97 | 0.2500 | 3.0 | 4.0 | 3.0 | 9.0 |  | 5.0 |
|  | 0.1250 | 2.0 | 3.0 | 0.0 | 9.0 |  | 5.0 |
|  | 0.0625 | 0.0 | 0.0 | 0.0 | 9.0 |  | 4.0 |
|  | 0.0313 | 0.0 | 0.0 | 0.0 | 9.0 |  | 1.0 |
| 98 | 0.2500 | 3.0 | 9.0 | 4.0 | 9.0 |  | 7.0 |
|  | 0.1250 | 1.0 | 9.0 | 4.0 | 9.0 |  | 7.0 |
|  | 0.0625 | 0.0 | 9.0 | 3.0 | 9.0 |  | 6.0 |
|  | 0.0313 | 0.0 | 9.0 | 2.0 | 9.0 |  | 2.0 |
| 99 | 0.5000 | 4.0 | 0.0 | 0.0 | 9.0 | 4.0 | 4.0 |
|  | 0.2500 | 0.0 | 0.0 | 0.0 | 9.0 | 4.0 | 4.0 |
|  | 0.1250 | 0.0 | 0.0 | 0.0 | 9.0 | 3.0 | 4.0 |
|  | 0.0625 | 0.0 | 0.0 | 0.0 | 9.0 | 0.0 | 2.0 |
|  | 0.0313 | 0.0 | 0.0 | 0.0 | 9.0 | 0.0 | 2.0 |
| 100 | 0.5000 | 4.0 | 9.0 |  | 9.0 | 6.0 | 4.0 |
|  | 0.2500 | 3.0 | 4.0 | 0.0 | 9.0 | 4.0 | 3.0 |
|  | 0.1250 | 0.0 | 0.0 | 0.0 | 9.0 | 0.0 | 3.0 |
|  | 0.0625 | 0.0 | 0.0 | 0.0 | 9.0 | 0.0 | 3.0 |
|  | 0.0313 | 0.0 | 0.0 | 0.0 | 9.0 | 0.0 | 3.0 |
| 101 | 0.5000 | 0.0 | 4.0 | 0.0 | 9.0 | 4.0 | 3.0 |
|  | 0.2500 | 0.0 | 3.0 | 0.0 | 9.0 | 2.0 | 0.0 |
|  | 0.1250 | 0.0 | 0.0 | 0.0 | 7.0 | 0.0 | 0.0 |
|  | 0.0625 | 0.0 | 0.0 | 0.0 | 5.0 | 0.0 | 0.0 |
|  | 0.0313 | 0.0 | 0.0 | 0.0 | 5.0 | 0.0 | 0.0 |
| 102 | 0.5000 | 2.0 | 6.0 | 0.0 | 4.0 | 0.0 | 4.0 |
|  | 0.2500 | 0.0 | 2.0 | 0.0 | 9.0 | 0.0 | 2.0 |
| 103 | 0.2500 | 6.0 | 9.0 | 6.0 | 9.0 | 9.0 | 6.0 |
|  | 0.1250 | 5.0 | 9.0 | 6.0 | 9.0 | 9.0 | 5.0 |
|  | 0.0625 | 4.0 | 6.0 | 5.0 | 7.0 | 9.0 | 5.0 |
|  | 0.0313 | 4.0 | 4.0 | 5.0 | 5.0 | 7.0 | 4.0 |
| 104 | 0.2500 | 6.0 | 9.0 | 0.0 | 9.0 | 9.0 | 6.0 |
|  | 0.1250 | 6.0 | 9.0 | 0.0 | 9.0 | 9.0 | 7.0 |

TABLE III-continued

Paddy Conditions - Post-Transplant Rice Preemergence Weeds

| Compound Number | Rate (kg/ha) | ECHORC | CYPIR | CYPSE | MOGVA | SAPY | ORYSAT |
|---|---|---|---|---|---|---|---|
|  | 0.0625 | 5.0 | 9.0 |  | 9.0 | 9.0 | 5.0 |
|  | 0.0313 | 4.0 | 5.0 | 0.0 | 7.0 | 6.0 | 3.0 |
| 105 | 0.2500 | 5.0 | 9.0 | 9.0 | 9.0 | 7.0 | 6.0 |
|  | 0.1250 | 4.0 | 7.0 | 7.0 | 7.0 | 5.0 | 3.0 |
|  | 0.0625 | 3.0 | 7.0 | 5.0 | 7.0 | 5.0 | 5.0 |
|  | 0.0313 | 0.0 | 5.0 | 2.0 | 6.0 | 3.0 | 5.0 |
| 106 | 0.2500 | 7.0 | 9.0 | 6.0 | 9.0 | 7.0 | 5.0 |
|  | 0.1250 | 5.0 | 6.0 | 2.0 | 9.0 | 5.0 | 3.0 |
|  | 0.0625 | 4.0 | 6.0 | 0.0 | 9.0 | 4.0 | 2.0 |
|  | 0.0313 | 2.0 | 5.0 | 0.0 | 9.0 | 3.0 | 2.0 |
| 107 | 0.2500 | 4.0 | 7.0 |  | 9.0 | 3.0 | 3.0 |
|  | 0.1250 | 4.0 | 4.0 | 0.0 | 7.0 | 0.0 | 0.0 |
|  | 0.0625 | 4.0 | 0.0 | 0.0 | 6.0 | 0.0 | 0.0 |
|  | 0.0313 | 0.0 | 0.0 | 0.0 | 4.0 | 0.0 | 0.0 |
| 108 | 0.2500 | 0.0 | 7.0 |  | 9.0 | 6.0 | 3.0 |
|  | 0.1250 | 0.0 | 7.0 | 0.0 | 9.0 | 3.0 | 2.0 |
|  | 0.0625 | 0.0 | 6.0 | 0.0 | 9.0 | 0.0 | 2.0 |
|  | 0.0313 | 0.0 | 4.0 | 0.0 | 9.0 | 0.0 | 0.0 |
| 109 | 0.2500 | 9.0 | 9.0 | 6.5 | 9.0 | 9.0 | 7.5 |
|  | 0.1250 | 9.0 | 9.0 | 9.0 | 9.0 | 9.0 | 7.0 |
|  | 0.0625 | 9.0 | 7.0 | 5.5 | 9.0 | 7.5 | 8.0 |
|  | 0.0313 | 9.0 | 5.0 | 4.5 | 7.0 | 4.5 | 5.0 |
| 110 | 0.2500 | 9.0 | 8.0 | 0.0 | 9.0 | 8.0 | 4.0 |
|  | 0.1250 | 7.0 | 7.0 | 0.0 | 9.0 | 7.0 | 2.0 |
|  | 0.0625 | 7.0 | 4.0 | 0.0 | 9.0 | 7.0 | 0.0 |
|  | 0.0313 | 7.0 | 3.0 | 0.0 | 9.0 | 6.0 | 0.0 |
| 111 | 0.2500 | 7.0 | 5.0 | 9.0 | 4.0 | 6.0 | 3.0 |
|  | 0.1250 | 6.0 | 4.0 | 9.0 | 4.0 | 5.0 | 4.0 |
|  | 0.0625 | 3.0 | 3.0 | 4.0 | 4.0 | 4.0 | 3.0 |
|  | 0.0313 | 0.0 | 0.0 |  | 3.0 | 3.0 | 0.0 |
| 112 | 0.2500 | 3.0 | 7.0 |  | 9.0 | 7.0 | 5.0 |
|  | 0.1250 | 3.0 | 6.0 |  | 9.0 | 7.0 | 3.0 |
|  | 0.0625 | 3.0 | 3.0 |  | 9.0 | 7.0 | 0.0 |
|  | 0.0313 | 0.0 | 0.0 | 0.0 | 9.0 | 6.0 | 0.0 |
| 113 | 0.2500 | 7.0 | 6.0 | 0.0 | 9.0 | 9.0 | 0.0 |
|  | 0.1250 | 5.0 | 5.0 | 0.0 | 9.0 | 9.0 | 0.0 |
|  | 0.0625 | 4.0 | 5.0 | 0.0 | 9.0 | 6.0 | 0.0 |
|  | 0.0313 | 4.0 | 3.0 | 0.0 | 9.0 | 4.0 | 0.0 |
| 114 | 0.2500 | 8.0 | 9.0 | 4.5 | 9.0 | 4.5 | 4.5 |
|  | 0.1250 | 7.0 | 8.5 | 3.5 | 9.0 | 3.5 | 4.5 |
|  | 0.0625 | 7.0 | 6.5 | 4.5 | 9.0 | 3.5 | 4.5 |
|  | 0.0313 | 6.0 | 4.5 | 3.5 | 9.0 | 3.5 | 2.0 |
| 115 | 0.2500 | 5.0 | 9.0 | 6.0 | 9.0 | 6.0 | 4.0 |
|  | 0.1250 | 5.0 | 9.0 |  | 9.0 | 5.0 | 4.0 |
|  | 0.0625 | 4.0 | 6.0 | 0.0 | 9.0 | 3.0 | 3.0 |
|  | 0.0313 | 4.0 | 5.0 | 0.0 | 7.0 | 2.0 | 3.0 |
| 116 | 0.2500 | 5.0 | 7.0 | 8.0 | 9.0 | 6.0 | 4.0 |
|  | 0.1250 | 6.0 | 7.0 | 7.0 | 9.0 | 5.0 | 4.0 |
|  | 0.0625 | 5.0 | 6.0 | 6.0 | 9.0 | 3.0 | 2.0 |
|  | 0.0313 | 0.0 | 3.0 | 6.0 | 7.0 | 2.0 | 2.0 |
| 117 | 0.2500 | 0.0 | 6.0 | 9.0 | 9.0 | 0.0 | 3.0 |
|  | 0.1250 | 0.0 | 5.0 | 9.0 | 9.0 | 0.0 | 3.0 |
|  | 0.0625 | 0.0 | 2.0 | 7.0 | 7.0 | 0.0 | 0.0 |
|  | 0.0313 | 0.0 | 0.0 |  | 6.0 | 0.0 | 2.0 |
| 118 | 0.2500 | 6.0 | 0.0 | 0.0 | 7.0 | 3.0 | 3.0 |
|  | 0.1250 | 4.0 | 0.0 | 0.0 | 6.0 | 3.0 | 3.0 |
|  | 0.0625 | 0.0 | 0.0 | 0.0 | 4.0 | 0.0 | 1.0 |
|  | 0.0313 | 0.0 | 0.0 | 0.0 | 4.0 | 0.0 | 0.0 |
| 119 | 0.2500 | 9.0 | 8.0 | 1.0 | 9.0 | 4.5 | 5.5 |
|  | 0.1250 | 9.0 | 8.5 | 0.0 | 9.0 | 3.5 | 3.0 |
|  | 0.0625 | 9.0 | 7.0 | 0.0 | 8.0 | 3.0 | 2.0 |
|  | 0.0313 | 8.0 | 4.5 | 0.0 | 7.s | 2.5 | 1.0 |
| 120 | 0.2500 | 9.0 | 9.0 | 3.5 | 9.0 | 7.5 | 4.0 |
|  | 0.1250 | 9.0 | 3.5 | 0.0 | 9.0 | 2.0 | 3.0 |
|  | 0.0625 | 8.0 | 2.5 | 0.0 | 9.0 | 0.0 | 1.0 |
|  | 0.0313 | 7.0 | 2.0 | 0.0 | 8.5 | 0.0 | 2.0 |
| 121 | 0.2500 | 6.0 | 8.0 | 5.0 | 9.0 | 6.0 | 7.0 |
|  | 0.1250 | 6.0 | 8.0 | 5.0 | 9.0 | 4.0 | 6.0 |
|  | 0.0625 | 5.0 | 4.0 |  | 9.0 | 4.0 | 4.0 |
|  | 0.0313 | 4.0 | 4.0 | 2.0 | 9.0 | 0.0 | 3.0 |
| 122 | 0.2500 | 7.0 | 8.0 | 3.0 | 9.0 | 6.0 | 3.0 |
|  | 0.1250 | 7.0 | 7.0 |  | 9.0 | 5.0 | 3.0 |
|  | 0.0625 | 7.0 | 7.0 |  | 9.0 | 3.0 | 2.0 |
|  | 0.0313 | 6.0 | 4.0 |  | 8.0 | 2.0 | 2.0 |
| 123 | 0.2500 | 9.0 | 9.0 | 9.0 | 9.0 | 8.0 | 3.0 |
|  | 0.1250 | 9.0 | 9.0 | 9.0 | 9.0 | 6.0 | 3.0 |
|  | 0.0625 | 9.0 | 5.0 | 9.0 | 7.0 | 6.0 | 2.0 |
|  | 0.0313 | 7.0 | 6.0 | 5.0 | 6.0 | 5.0 | 2.0 |
| 124 | 0.2500 | 8.0 | 6.0 | 3.0 | 7.0 | 5.0 | 5.0 |
|  | 0.1250 | 9.0 | 0.0 | 2.0 | 0.0 | 4.0 | 2.0 |
|  | 0.0625 | 5.0 | 0.0 | 0.0 | 0.0 | 0.0 | 0.0 |
|  | 0.0313 | 5.0 | 0.0 | 0.0 | 0.0 | 0.0 | 0.0 |
| 125 | 0.2500 | 7.0 | 9.0 | 9.0 | 9.0 | 9.0 | 7.0 |
|  | 0.1250 | 7.0 | 7.0 | 9.0 | 7.0 | 4.0 | 3.0 |
|  | 0.0625 | 4.0 | 6.0 | 4.0 | 7.0 | 4.0 | 2.0 |
|  | 0.0313 | 2.0 | 3.0 | 2.0 | 5.0 | 3.0 | 0.0 |
| 126 | 0.2500 | 7.0 | 2.0 | 0.0 | 7.0 | 3.0 | 4.0 |
|  | 0.1250 | 6.0 | 0.0 | 0.0 | 6.0 | 3.0 | 3.0 |
|  | 0.0625 | 3.0 | 0.0 | 0.0 | 4.0 | 0.0 | 3.0 |
|  | 0.0313 | 0.0 | 0.0 | 0.0 | 3.0 | 0.0 | 0.0 |
| 127 | 0.2500 | 9.0 | 4.0 | 0.0 | 7.0 | 3.0 | 4.0 |
|  | 0.1250 | 9.0 | 4.0 | 0.0 | 5.0 | 0.0 | 4.0 |
|  | 0.0625 | 7.0 | 2.0 | 0.0 | 3.0 | 0.0 | 2.0 |
|  | 0.0313 | 4.0 | 2.0 | 0.0 | 3.0 | 0.0 | 0.0 |
| 128 | 0.2500 | 9.0 | 4.0 | 3.0 | 9.0 | 6.0 | 3.0 |
|  | 0.1250 | 7.0 | 4.0 |  | 9.0 | 4.0 | 0.0 |
|  | 0.0625 | 7.0 | 4.0 | 0.0 | 7.0 | 3.0 | 0.0 |
|  | 0.0313 | 5.0 | 0.0 |  | 6.0 | 0.0 | 0.0 |
| 129 | 0.2500 | 9.0 | 9.0 | 9.0 | 9.0 | 7.0 | 2.0 |
|  | 0.1250 | 9.0 | 7.0 | 7.0 | 9.0 | 2.0 | 0.0 |
|  | 0.0625 | 9.0 | 5.0 |  | 7.0 | 0.0 | 0.0 |
|  | 0.0313 | 9.0 | 4.0 |  | 6.0 | 0.0 | 0.0 |
| 130 | 0.2500 | 4.0 | 6.0 | 7.0 | 6.0 | 3.0 | 6.0 |
|  | 0.1250 | 3.0 | 4.0 | 0.0 | 6.0 | 0.0 | 4.0 |
|  | 0.0625 | 2.0 | 2.0 |  | 5.0 | 0.0 | 4.0 |
|  | 0.0313 | 0.0 | 0.0 |  | 5.0 | 0.0 | 4.0 |
| 131 | 0.2500 | 4.0 | 4.0 | 0.0 | 2.0 | 2.0 | 5.0 |
|  | 0.1250 | 2.0 | 0.0 | 0.0 | 0.0 | 0.0 | 2.0 |
| 132 | 0.2500 | 6.0 | 3.0 | 0.0 | 9.0 | 0.0 | 4.0 |
|  | 0.1250 | 4.0 | 0.0 | 0.0 | 9.0 | 0.0 | 4.0 |
|  | 0.0625 | 4.0 | 0.0 | 0.0 | 9.0 | 0.0 | 2.0 |
|  | 0.0313 | 3.0 | 0.0 | 0.0 | 6.0 | 0.0 | 0.0 |
| 133 | 0.2500 | 9.0 | 3.0 | 1.0 | 6.0 | 3.0 | 4.0 |
|  | 0.1250 | 9.0 | 2.0 | 0.0 | 4.0 | 3.0 | 4.0 |
|  | 0.0625 | 6.0 | 0.0 | 0.0 | 4.0 | 3.0 | 2.0 |
|  | 0.0313 | 6.0 | 0.0 | 0.0 | 3.0 | 0.0 | 2.0 |
| 134 | 0.2500 | 2.0 | 3.0 |  | 2.0 | 0.0 | 2.0 |
| 135 | 0.2500 | 9.0 | 7.0 | 0.0 | 8.0 | 6.0 | 0.0 |
|  | 0.1250 | 7.0 | 7.0 | 0.0 | 9.0 | 5.0 | 0.0 |
|  | 0.0625 | 7.0 | 6.0 |  | 9.0 | 3.0 | 0.0 |
|  | 0.0313 | 7.0 | 5.0 |  | 6.0 | 0.0 | 0.0 |
| 136 | 0.2500 | 9.0 | 7.0 | 0.0 | 9.0 | 3.0 | 3.0 |
|  | 0.1250 | 7.0 | 6.0 | 0.0 | 9.0 | 3.0 | 3.0 |
|  | 0.0625 | 7.0 | 5.0 | 0.0 | 4.0 | 0.0 | 2.0 |
|  | 0.0313 | 7.0 | 0.0 | 0.0 | 3.0 | 0.0 | 2.0 |
| 137 | 0.2500 | 5.0 | 4.0 | 0.0 | 8.0 | 3.0 | 4.0 |
|  | 0.1250 | 3.0 | 2.0 | 0.0 | 5.0 | 0.0 | 1.0 |
|  | 0.0625 | 3.0 | 2.0 | 0.0 | 5.0 | 0.0 | 0.0 |
|  | 0.0313 | 3.0 | 3.0 | 0.0 | 4.0 | 0.0 | 0.0 |
| 138 | 0.2500 | 9.0 | 5.0 | 0.0 | 7.0 | 3.0 | 3.0 |
|  | 0.1250 | 9.0 | 3.0 | 0.0 | 6.0 | 0.0 | 3.0 |
|  | 0.0625 | 9.0 | 0.0 | 0.0 | 6.0 | 0.0 | 3.0 |
|  | 0.0313 | 7.0 | 2.0 | 0.0 | 5.0 | 0.0 | 3.0 |
| 139 | 0.2500 | 7.0 | 6.0 | 0.0 | 7.0 | 0.0 | 2.0 |
|  | 0.1250 | 7.0 | 5.0 | 0.0 | 7.0 | 0.0 | 0.0 |
|  | 0.0625 | 7.0 | 4.0 |  | 5.0 | 0.0 | 0.0 |
|  | 0.0313 | 6.0 | 2.0 |  | 4.0 | 0.0 | 0.0 |

TABLE III-continued

Paddy Conditions - Post-Transplant Rice Preemergence Weeds

| Compound Number | Rate (kg/ha) | ECHORC | CYPIR | CYPSE | MOGVA | SAPY | ORYSAT |
|---|---|---|---|---|---|---|---|
| 140 | 0.2500 | 7.0 | 7.0 | 0.0 | 9.0 | 4.0 | 2.0 |
|  | 0.1250 | 7.0 | 9.0 | 0.0 | 9.0 | 4.0 | 0.0 |
|  | 0.0625 | 5.0 | 7.0 | 0.0 | 7.0 | 3.0 | 0.0 |
|  | 0.0313 | 5.0 | 4.0 | 0.0 | 4.0 | 2.0 | 0.0 |
| 141 | 0.2500 | 7.0 | 6.0 | 0.0 | 9.0 | 6.0 | 0.0 |
|  | 0.1250 | 7.0 | 6.0 | 0.9 | 8.0 | 5.0 | 0.0 |
|  | 0.0625 | 5.0 | 5.0 | 0.0 | 8.0 | 5.0 | 0.0 |
|  | 0.0313 | 5.0 | 4.0 | 0.0 | 7.0 | 4.0 | 0.0 |
| 142 | 0.2500 | 7.0 | 7.0 | 0.0 | 8.0 | 2.0 | 1.0 |
|  | 0.1250 | 7.0 | 6.0 |  | 9.0 | 0.0 | 0.0 |
|  | 0.0625 | 5.0 | 2.0 |  | 7.0 | 0.0 | 0.0 |
|  | 0.0313 | 4.0 | 0.0 |  | 6.0 | 0.0 | 0.0 |
| 143 | 0.2500 | 9.0 | 4.0 | 0.0 | 6.0 | 5.0 | 3.0 |
|  | 0.1250 | 9.0 | 4.0 | 0.0 | 6.0 | 0.0 | 3.0 |
|  | 0.0625 | 7.0 | 3.0 | 0.0 | 6.0 | 0.0 | 3.0 |
|  | 0.0313 | 5.0 | 0.0 | 0.0 | 5.0 | 0.0 | 1.0 |
| 144 | 0.2500 | 3.0 | 9.0 | 9.0 | 9.0 | 4.0 | 3.0 |
|  | 0.1250 | 1.0 | 9.0 | 9.0 | 9.0 | 2.0 | 3.0 |
|  | 0.0625 | 0.0 | 3.0 | 7.0 | 9.0 | 0.0 | 0.0 |
|  | 0.0313 | 0.0 | 3.0 | 7.0 | 6.0 | 0.0 | 0.0 |
| 145 | 0.2500 | 7.0 | 9.0 | 9.0 | 9.0 | 5.0 | 2.0 |
|  | 0.1250 | 7.0 | 7.0 | 9.0 | 9.0 | 5.0 | 0.0 |
|  | 0.0625 | 6.0 | 5.0 |  | 6.0 | 2.0 | 0.0 |
|  | 0.0313 | 6.0 | 4.0 |  | 4.0 | 0.0 | 0.0 |
| 146 | 0.2500 | 9.0 | 7.0 | 0.0 | 9.0 | 4.0 | 2.0 |
|  | 0.1250 | 9.0 | 6.0 | 0.0 | 6.0 | 3.0 | 0.0 |
|  | 0.0625 | 9.0 | 6.0 | 0.0 | 6.0 | 0.0 | 0.0 |
|  | 0.0313 | 9.0 | 4.0 | 0.0 | 4.0 | 0.0 | 0.0 |
| 147 | 0.2500 | 9.0 | 7.0 | 0.0 | 9.0 | 2.0 | 5.0 |
|  | 0.1250 | 9.0 | 7.0 |  | 9.0 | 0.0 | 4.0 |
|  | 0.0625 | 7.0 | 4.0 |  | 9.0 | 0.0 | 3.0 |
|  | 0.0313 | 5.0 | 4.0 | 7.0 | 0.0 | 2.0 |  |
| 148 | 0.2500 | 9.0 | 7.0 | 5.0 | 9.0 | 4.0 | 0.0 |
|  | 0.1250 | 9.0 | 6.0 | 0.0 | 9.0 | 4.0 | 0.0 |
|  | 0.0625 | 7.0 | 4.0 |  | 7.0 | 3.0 | 0.0 |
|  | 0.0313 | 6.0 | 4.0 | 0.0 | 7.0 | 0.0 | 0.0 |
| 149 | 0.2500 | 7.0 | 4.0 | 0.0 | 7.0 | 3.0 | 0.0 |
|  | 0.1250 | 6.0 | 7.0 | 0.0 | 7.0 | 3.0 | 0.0 |
|  | 0.0625 | 3.0 | 4.0 | 0.0 | 7.0 | 2.0 | 0.0 |
|  | 0.0313 | 2.0 | 3.0 | 0.0 | 5.0 | 0.0 | 0.0 |
| 150 | 0.2500 | 9.0 | 9.0 | 9.0 | 9.0 | 2.0 | 5.0 |
|  | 0.1250 | 9.0 | 9.0 | 9.0 | 9.0 | 2.0 | 3.0 |
|  | 0.0625 | 7.0 | 9.0 |  | 9.0 | 2.0 | 2.0 |
|  | 0.0313 | 6.0 | 9.0 |  | 6.0 | 0.0 | 0.0 |
| 151 | 0.2500 | 9.0 | 8.0 | 7.0 | 9.0 | 6.0 | 9.0 |
|  | 0.1250 | 9.0 | 6.0 |  | 9.0 | 8.0 | 8.0 |
|  | 0.0625 | 5.0 | 2.0 | 7.0 | 9.0 | 2.0 | 9.0 |
|  | 0.0313 | 3.0 | 0.0 |  | 6.0 | 0.0 | 6.0 |
| 152 | 0.2500 | 0.0 | 0.0 | 0.0 | 3.0 | 0.0 | 3.0 |
|  | 0.1250 | 0.0 | 0.0 | 0.0 | 3.0 | 0.0 | 2.0 |
|  | 0.0625 | 0.0 | 0.0 | 0.0 | 3.0 | 0.0 | 0.0 |
| 153 | 0.2500 | 0.0 | 3.0 | 0.0 | 5.0 | 0.0 | 4.0 |
|  | 0.1250 | 0.0 | 0.0 | 0.0 | 4.0 | 0.0 | 2.0 |
|  | 0.0625 | 0.0 | 0.0 | 0.0 | 3.0 | 0.0 | 2.0 |
| 154 | 0.2500 | 7.0 | 6.0 | 9.0 | 9.0 | 6.0 | 8.0 |
|  | 0.1250 | 7.0 | 4.0 | 9.0 | 8.0 | 5.0 | 9.0 |
|  | 0.0625 | 4.0 | 3.0 | 6.0 | 7.0 | 4.0 | 8.0 |
|  | 0.0313 | 3.0 | 2.0 | 4.0 | 6.0 | 2.0 | 9.0 |
| 155 | 0.2500 | 4.0 | 0.0 |  | 0.0 | 0.0 | 3.0 |
|  | 0.1250 | 4.0 | 0.0 | 0.0 | 0.0 | 0.0 | 1.0 |
|  | 0.0625 | 4.0 | 0.0 | 0.0 | 0.0 | 0.0 | 0.0 |
|  | 0.0313 | 4.0 | 0.0 | 0.0 | 0.0 | 0.0 | 0.0 |
| 156 | 0.2500 | 0.0 | 0.0 | 0.0 | 0.0 | 0.0 | 3.0 |
| 157 | 0.2500 | 0.0 | 0.0 |  | 0.0 | 0.0 | 0.0 |
| 158 | 0.2500 | 9.0 | 9.0 | 9.0 | 9.0 | 9.0 | 7.0 |
|  | 0.1250 | 9.0 | 9.0 | 9.0 | 9.0 | 6.0 | 9.0 |
|  | 0.0625 | 9.0 | 9.0 | 9.0 | 9.0 | 5.0 | 6.0 |
|  | 0.0313 | 9.0 | 9.0 | 5.0 | 9.0 | 4.0 | 6.0 |
| 159 | 0.2500 | 7.0 | 4.0 |  | 9.0 | 6.0 | 8.0 |
|  | 0.1250 | 5.0 | 3.0 | 0.0 | 6.0 | 3.0 | 2.0 |
|  | 0.0625 | 4.0 | 0.0 | 0.0 | 3.0 | 3.0 | 0.0 |
|  | 0.0313 | 2.0 | 0.0 |  | 0.0 | 0.0 | 0.0 |
| 160 | 0.2500 | 4.0 | 9.0 | 3.0 | 7.0 | 8.0 | 6.0 |
|  | 0.1250 | 2.0 | 6.0 | 3.0 | 6.0 | 5.0 | 5.0 |
|  | 0.0625 | 0.0 | 3.0 | 3.0 | 6.0 | 2.0 | 3.0 |
|  | 0.0313 | 0.0 | 0.0 | 3.0 | 5.0 | 0.0 | 3.0 |
| 161 | 0.2500 | 4.0 | 6.0 | 3.0 | 9.0 | 9.0 | 4.0 |
|  | 0.1250 | 2.0 | 5.0 | 0.0 | 7.0 | 6.0 | 3.0 |
|  | 0.0625 | 0.0 | 4.0 | 0.0 | 7.0 |  | 2.0 |
|  | 0.0313 | 0.0 | 3.0 | 0.0 | 7.0 | 2.0 | 0.0 |
| 162 | 0.2500 | 8.0 | 9.0 | 9.0 | 9.0 | 3.0 | 7.0 |
|  | 0.1250 | 8.0 | 6.0 | 9.0 | 7.0 | 3.0 | 6.0 |
|  | 0.0625 | 7.0 | 6.0 |  | 7.0 | 3.0 | 3.0 |
|  | 0.0313 | 6.0 | 5.0 |  | 7.0 | 0.0 | 2.0 |
| 163 | 0.2500 | 9.0 | 9.0 | 9.0 | 9.0 | 7.0 | 7.0 |
|  | 0.1250 | 9.0 | 9.0 | 9.0 | 9.0 | 6.0 | 6.0 |
|  | 0.0625 | 9.0 | 7.0 |  | 9.0 | 3.0 | 3.0 |
|  | 0.0313 | 9.0 | 6.0 |  | 9.0 | 2.0 | 2.0 |
| 164 | 0.2500 | 9.0 | 9.0 | 7.0 | 9.0 | 6.0 | 6.0 |
|  | 0.1250 | 9.0 | 6.0 | 3.0 | 9.0 | 5.0 | 3.0 |
|  | 0.0625 | 7.0 | 5.0 | 0.0 | 9.0 | 4.0 | 2.0 |
|  | 0.0313 | 6.0 | 3.0 | 0.0 | 8.0 | 4.0 | 2.0 |
| 165 | 0.2500 | 9.0 | 9.0 | 3.0 | 9.0 | 7.0 | 3.0 |
|  | 0.1250 | 9.0 | 9.0 | 0.0 | 9.0 | 4.0 | 1.0 |
|  | 0.0625 | 9.0 | 7.0 |  | 9.0 | 5.0 | 1.0 |
|  | 0.0313 | 9.0 | 6.0 | 0.0 | 9.0 | 4.0 | 0.0 |
| 166 | 0.2500 | 4.0 | 9.0 | 0.0 | 9.0 | 6.0 | 3.0 |
|  | 0.1250 | 2.0 | 6.0 | 0.0 | 9.0 | 5.0 | 3.0 |
|  | 0.0625 | 2.0 | 2.0 | 0.0 | 9.0 | 4.0 | 0.0 |
|  | 0.0313 | 2.0 | 2.0 | 0.0 | 9.0 | 2.0 | 0.0 |
| 167 | 0.2500 | 9.0 | 9.0 | 5.0 | 9.0 | 7.0 | 4.0 |
|  | 0.1250 | 9.0 | 9.0 | 3.0 | 9.0 | 6.0 | 4.0 |
|  | 0.0625 | 9.0 | 9.0 | 0.0 | 9.0 | 5.0 | 4.0 |
|  | 0.0313 | 9.0 | 7.0 | 0.0 | 9.0 | 4.0 | 4.0 |
| 168 | 0.2500 | 0.0 | 0.0 |  | 7.0 | 2.0 | 2.0 |
|  | 0.1250 | 0.0 | 0.0 | 0.0 | 6.0 | 0.0 | 0.0 |
|  | 0.0625 | 0.0 | 0.0 | 0.0 | 6.0 | 0.0 | 0.0 |
|  | 0.0313 | 0.0 | 0.0 | 0.0 | 6.0 | 0.0 | 0.0 |
| 169 | 0.2500 | 2.0 | 2.0 |  | 7.0 | 3.0 | 2.0 |
|  | 0.1250 | 0.0 | 0.0 | 0.0 | 6.0 | 0.0 | 0.0 |
|  | 0.0625 | 0.0 | 0.0 |  | 6.0 | 0.0 | 0.0 |
|  | 0.0313 | 0.0 | 0.0 | 0.0 | 5.0 | 0.0 | 0.0 |
| 170 | 0.2500 | 9.0 | 9.0 |  | 9.0 | 9.0 | 9.0 |
|  | 0.1250 | 9.0 | 9.0 |  | 9.0 | 8.0 | 6.0 |
|  | 0.0625 | 9.0 | 9.0 |  | 9.0 | 9.0 | 8.0 |
|  | 0.0313 | 9.0 | 9.0 |  | 9.0 | 5.0 | 4.0 |
| 171 | 0.2500 | 9.0 | 9.0 | 9.0 | 9.0 | 9.0 | 7.0 |
|  | 0.1250 | 9.0 | 9.0 | 9.0 | 9.0 | 8.0 | 6.0 |
|  | 0.0625 | 9.0 | 9.0 | 9.0 | 9.0 | 7.0 | 6.0 |
|  | 0.0313 | 8.0 | 3.0 | 0.0 | 9.0 | 6.0 | 5.0 |
| 172 | 0.2500 | 9.0 | 9.0 | 9.0 | 9.0 | 9.0 | 9.0 |
|  | 0.1250 | 9.0 | 8.0 | 9.0 | 9.0 | 9.0 | 9.0 |
|  | 0.0625 | 9.0 | 7.0 | 6.0 | 9.0 | 6.0 | 7.0 |
|  | 0.0313 | 6.0 | 5.0 |  | 9.0 | 6.0 | 6.0 |

EXAMPLE 40

Rice Tolerance to Post-transplant Applications and Postemergence Weed Control Under Flooded Paddy Conditions Plastic containers containing weeds which are 3 to 5 cm tall and rice seedlings at the 1.5 to 2.5 leaf stage are flooded with water. The water is maintained at 1.5 to 3 cm above the soil surface for the duration of the experiment. Test compounds are applied as aqueous/acetone mixtures 50/50 v/v directly into the flood water to provide the equivalent of about 0.0313 to 0.500 kg/ha of active ingredient. The treated containers are placed on greenhouse benches and cared for in accordance with conventional greenhouse procedures. Three to four weeks after treatment, the test is terminated and each container is examined and herbicidal effect rated according to the rating system provided in Example 37. The results are summarized in Table IV. The compounds evaluated are reported by compound number given in Example 37.

TABLE IV

Paddy Conditions - Post Transplant Rice Postemergence Weeds

| Compound Number | Rate (kg/ha) | ECHORC | CYPIR | CYPSE | MOVA | SAGPY | ORYSAT |
|---|---|---|---|---|---|---|---|
| 1 | 0.5000 | 5.5 | 8.5 | 4.0 | 5.5 | 0.0 | 4.0 |
|   | 0.2500 | 3.5 | 6.5 | 1.0 | 5.0 | 0.0 | 3.0 |
|   | 0.1250 | 3.0 | 5.5 | 0.0 | 4.s | 0.0 | 2.5 |
|   | 0.0625 | 2.0 | 3.5 | 0.0 | 4.s | 0.0 | 2.5 |
|   | 0.0313 | 1.0 | 1.0 | 0.0 | 4.0 | 0.0 | 1.5 |
| 2 | 0.5000 | 4.5 | 4.0 | 0.0 | 9.0 | 1.0 | 2.5 |
|   | 0.2500 | 4.0 | 1.0 | 0.0 | 9.0 | 0.0 | 1.5 |
|   | 0.1250 | 3.5 | 0.0 | 0.0 | 5.5 | 0.0 | 0.5 |
|   | 0.0625 | 1.0 | 0.0 | 0.0 | 4.5 | 0.0 | 0.0 |
|   | 0.0313 | 1.0 | 0.0 | 0.0 | 2.0 | 0.0 | 0.0 |
| 3 | 0.5000 | 2.0 | 0.5 | 0.0 | 5.5 | 0.0 | 2.0 |
|   | 0.2500 | 1.0 | 0.0 | 0.0 | 4.5 | 0.0 | 1.0 |
|   | 0.1250 | 0.0 | 0.0 | 0.0 | 4.5 | 0.0 | 1.0 |
|   | 0.0625 | 0.0 | 0.0 | 0.0 | 1.0 | 0.0 | 0.0 |
| 4 | 0.5000 | 5.0 | 9.0 | 0.0 | 8.0 | 0.0 | 3.0 |
|   | 0.2500 | 4.0 | 6.5 | 0.0 | 5.5 | 0.0 | 2.5 |
|   | 0.1250 | 3.5 | 4.5 | 0.0 | 4.0 | 0.0 | 2.0 |
|   | 0.0625 | 2.0 | 2.0 | 0.0 | 3.5 | 0.0 | 1.5 |
|   | 0.0313 | 1.0 | 0.0 | 0.0 | 1.0 | 0.0 | 0.0 |
| 5 | 0.5000 | 2.0 | 0.0 | 0.5 | 4.0 | 0.0 | 1.0 |
|   | 0.2500 | 1.0 | 0.0 | 0.0 | 2.0 | 0.0 | 0.5 |
|   | 0.1250 | 0.5 | 0.0 | 0.0 | 1.0 | 0.0 | 0.5 |
| 6 | 0.5000 | 3.5 | 3.5 | 0.0 | 4.5 | 0.0 | 0.0 |
|   | 0.2500 | 3.5 | 3.0 | 0.0 | 4.5 | 0.0 | 0.0 |
|   | 0.1250 | 1.0 | 2.0 | 0.0 | 4.0 | 0.0 | 0.0 |
|   | 0.0625 | 0.0 | 1.0 | 0.0 | 4.0 | 0.0 | 0.0 |
|   | 0.0313 | 0.0 | 0.0 | 0.0 | 1.0 | 0.0 | 0.0 |
| 7 | 0.2500 | 9.0 | 9.0 | 8.0 | 9.0 | 8.5 | 9.0 |
|   | 0.1250 | 9.0 | 9.0 | 7.5 | 9.0 | 7.5 | 7.0 |
|   | 0.0625 | 8.5 | 9.0 | 7.0 | 9.0 | 5.5 | 6.5 |
|   | 0.0313 | 7.0 | 8.5 | 3.0 | 9.0 | 3.0 | 5.0 |
| 8 | 0.2500 | 8.5 | 4.0 | 0.0 | 9.0 | 0.0 | 6.0 |
|   | 0.1250 | 7.5 | 0.0 | 0.0 | 9.0 | 0.0 | 5.0 |
|   | 0.0625 | 6.5 | 0.0 | 0.0 | 9.0 | 0.0 | 3.5 |
|   | 0.0313 | 6.5 | 0.0 | 0.0 | 9.0 | 0.0 | 2.5 |
| 9 | 0.2500 | 7.0 | 6.0 | 7.0 | 9.0 | 2.0 | 9.0 |
|   | 0.1250 | 4.0 | 4.0 | 2.0 | 9.0 | 1.0 | 9.0 |
|   | 0.0625 | 2.0 | 2.0 | 0.0 | 9.0 | 0.0 | 8.0 |
|   | 0.0313 | 0.0 | 0.0 | 0.0 | 9.0 | 0.0 | 7.0 |
| 10 | 0.2500 | 2.0 | 4.0 | 0.0 | 9.0 | 0.0 | 7.0 |
|   | 0.1250 | 2.0 | 2.0 | 0.0 | 9.0 | 0.0 | 6.0 |
|   | 0.0625 | 1.0 | 0.0 | 0.0 | 9.0 | 0.0 | 4.0 |
|   | 0.0313 | 0.0 | 0.0 | 0.0 | 9.0 | 0.0 | 3.0 |
| 11 | 0.2500 | 3.0 | 0.0 | 0.0 | 7.0 | 0.0 | 3.0 |
|   | 0.1250 | 2.0 | 0.0 | 0.0 | 4.0 | 0.0 | 3.0 |
|   | 0.0625 | 2.0 | 0.0 | 0.0 | 1.0 | 0.0 | 2.0 |
|   | 0.0313 | 1.0 | 0.0 | 0.0 | 0.0 | 0.0 | 2.0 |
| 12 | 0.2500 | 9.0 | 0.0 | 6.0 | 9.0 | 0.0 | 7.0 |
|   | 0.1250 | 8.5 | 1.0 | 1.0 | 9.0 | 4.0 | 5.5 |
|   | 0.0625 | 9.0 | 0.0 | 3.0 | 9.0 | 1.0 | 3.5 |
|   | 0.0313 | 5.0 | 0.0 | 1.0 | 9.0 | 0.0 | 3.0 |
| 13 | 0.2500 | 9.0 | 1.0 | 0.0 | 9.0 | 0.0 | 5.0 |
|   | 0.1250 | 8.0 | 0.5 | 0.0 | 9.0 | 0.0 | 3.0 |
|   | 0.0625 | 7.0 | 0.0 | 0.0 | 9.0 | 0.0 | 2.5 |
|   | 0.0313 | 5.5 | 0.0 | 0.0 | 9.0 | 0.0 | 1.5 |

TABLE IV-continued

Paddy Conditions - Post Transplant Rice Postemergence Weeds

| Compound Number | Rate (kg/ha) | ECHORC | CYPIR | CYPSE | MOVA | SAGPY | ORYSAT |
|---|---|---|---|---|---|---|---|
| 14 | 0.2500 | 7.0 | 4.5 | 0.0 | 4.5 | 0.0 | 0.0 |
|   | 0.1250 | 3.8 | 6.8 | 1.5 | 6.8 | 0.0 | 0.5 |
|   | 0.0625 | 2.3 | 5.8 | 0.0 | 6.8 | 0.0 | 0.3 |
|   | 0.0313 | 0.8 | 4.0 | 0.0 | 6.8 | 0.0 | 0.0 |
| 15 | 0.2500 | 9.0 | 7.0 | 0.0 | 9.0 | 0.0 | 3.0 |
|   | 0.1250 | 9.0 | 6.0 | 0.0 | 9.0 | 0.0 | 3.0 |
|   | 0.0625 | 9.0 | 2.0 | 0.0 | 9.0 | 0.0 | 2.0 |
|   | 0.0313 | 6.0 | 2.0 | 0.0 | 9.0 | 0.0 | 0.0 |
| 16 | 0.2500 | 0.0 | 9.0 | 0.0 | 3.0 | 0.0 | 0.0 |
|   | 0.1250 | 0.0 | 4.0 | 0.0 | 9.0 | 0.0 | 0.0 |
|   | 0.0625 | 0.0 | 0.0 | 0.0 | 9.0 | 0.0 | 0.0 |
|   | 0.0313 | 0.0 | 0.0 | 0.0 | 9.0 | 0.0 | 0.0 |
| 17 | 0.2500 | 9.0 | 9.0 | 9.0 | 9.0 | 4.0 | 9.0 |
|   | 0.1250 | 9.0 | 6.0 | 9.0 | 9.0 | 4.0 | 9.0 |
|   | 0.0625 | 9.0 | 0.0 | 9.0 | 9.0 | 0.0 | 6.0 |
|   | 0.0313 | 4.0 | 0.0 | 9.0 | 9.0 | 0.0 | 4.0 |
| 18 | 0.4630 | 7.0 | 0.0 | 4.0 | 9.0 | 6.0 | 3.0 |
|   | 0.2310 | 7.0 | 0.0 | 0.0 | 9.0 | 0.0 | 3.0 |
|   | 0.1160 | 7.0 | 0.0 | 0.0 | 9.0 | 0.0 | 3.0 |
| 19 | 0.4630 | 9.0 | 0.0 | 4.0 | 9.0 | 3.0 | 3.0 |
|   | 0.2310 | 7.0 | 0.0 | 4.0 | 9.0 | 3.0 | 3.0 |
|   | 0.1160 | 7.0 | 0.0 | 4.0 | 9.0 | 0.0 | 3.0 |
| 20 | 0.4630 | 7.0 | 0.0 | 5.0 | 9.0 | 3.0 | 2.0 |
|   | 0.2310 | 7.0 | 0.0 | 5.0 | 9.0 | 0.0 | 2.0 |
|   | 0.1160 | 7.0 | 0.0 | 5.0 | 9.0 | 0.0 | 2.0 |
| 21 | 0.4630 | 5.0 | 0.0 | 0.0 | 0.0 | 0.0 | 0.0 |
|   | 0.2310 | 4.0 | 0.0 | 0.0 | 0.0 | 0.0 | 0.0 |
|   | 0.1160 | 2.0 | 0.0 | 0.0 | 0.0 | 0.0 | 0.0 |
| 22 | 0.4630 | 9.0 | 5.0 | 4.0 | 9.0 | 5.0 | 7.0 |
|   | 0.2310 | 9.0 | 0.0 | 4.0 | 9.0 | 4.0 | 6.0 |
|   | 0.1160 | 6.0 | 0.0 | 4.0 | 9.0 | 4.0 | 3.0 |
| 23 | 0.4630 | 4.0 | 0.0 | 0.0 | 9.0 | 3.0 | 5.0 |
|   | 0.2310 | 4.0 | 0.0 | 0.0 | 9.0 | 0.0 | 4.0 |
|   | 0.1160 | 4.0 | 0.0 | 0.0 | 9.0 | 0.0 | 4.0 |
| 24 | 0.2500 | 9.0 | 0.0 |  | 9.0 | 0.0 | 0.0 |
|   | 0.1250 | 9.0 | 0.0 |  | 9.0 | 0.0 | 0.0 |
|   | 0.0625 | 9.0 | 0.0 |  | 9.0 | 0.0 | 0.0 |
|   | 0.0313 | 4.0 | 0.0 |  | 0.0 | 0.0 | 0.0 |
| 25 | 0.2500 | 9.0 | 0.0 |  | 9.0 | 5.0 | 5.0 |
|   | 0.1250 | 7.0 | 0.0 |  | 9.0 | 5.0 | 4.0 |
|   | 0.0625 | 6.0 | 0.0 |  | 9.0 | 0.0 | 4.0 |
|   | 0.0313 | 4.0 | 0.0 |  | 9.0 | 0.0 | 3.0 |
| 26 | 0.2500 | 9.0 | 9.0 |  | 9.0 | 7.0 | 2.0 |
|   | 0.1250 | 9.0 | 7.0 |  | 9.0 | 5.0 | 1.0 |
|   | 0.0625 | 9.0 | 4.0 |  | 9.0 | 4.0 | 0.0 |
|   | 0.0313 | 7.0 | 2.0 |  | 9.0 | 0.0 | 0.0 |
| 27 | 0.2500 | 9.0 | 9.0 | 9.0 | 9.0 | 4.0 | 4.0 |
|   | 0.1250 | 9.0 | 6.0 | 0.0 | 9.0 | 4.0 | 4.0 |
|   | 0.0625 | 7.0 | 4.0 | 0.0 | 9.0 | 0.0 | 2.0 |
|   | 0.0313 | 6.0 | 3.0 | 0.0 | 9.0 | 0.0 | 1.0 |
| 28 | 0.2500 | 9.0 | 9.0 | 0.0 | 9.0 | 0.0 | 1.0 |
|   | 0.1250 | 7.0 | 9.0 | 0.0 | 9.0 | 0.0 | 0.0 |
|   | 0.0625 | 4.0 | 9.0 | 0.0 | 9.0 | 0.0 | 0.0 |
|   | 0.0313 | 0.0 | 9.0 | 0.0 | 9.0 | 0.0 | 0.0 |
| 29 | 0.2500 | 7.0 | 0.0 | 0.0 | 0.0 | 0.0 | 3.0 |
|   | 0.1250 | 7.0 | 0.0 | 0.0 | 0.0 | 0.0 | 2.0 |
|   | 0.0625 | 7.0 | 0.0 | 0.0 | 0.0 | 0.0 | 1.0 |
|   | 0.0313 | 4.0 | 0.0 | 0.0 | 0.0 | 0.0 | 0.0 |
| 30 | 0.2500 | 0.0 | 4.5 | 0.0 | 4.5 | 2.0 | 0.0 |
|   | 0.1250 | 0.0 | 2.0 | 0.0 | 1.5 | 0.0 | 0.0 |
| 31 | 0.2500 | 5.0 | 2.5 | 0.0 | 2.5 | 0.0 | 0.0 |
|   | 0.1250 | 2.0 | 0.0 | 0.0 | 0.0 | 0.0 | 0.0 |
|   | 0.0625 | 1.0 | 0.0 | 0.0 | 0.0 | 0.0 | 0.0 |
| 32 | 0.2500 | 6.0 | 0.0 | 0.0 |  | 0.0 | 0.0 |
|   | 0.1250 | 3.0 | 0.0 | 0.0 |  | 0.0 | 0.0 |
| 33 | 0.2500 | 0.0 | 0.0 | 0.0 |  | 0.0 | 0.0 |
| 34 | 0.2500 | 9.0 | 0.0 | 0.0 |  | 0.0 | 6.0 |
|   | 0.1250 | 4.0 | 0.0 | 0.0 |  | 0.0 | 4.0 |

TABLE IV-continued

Paddy Conditions - Post Transplant Rice
Postemergence Weeds

| Compound Number | Rate (kg/ha) | ECHORC | CYPIR | CYPSE | M0VA | SAGPY | ORYSAT |
|---|---|---|---|---|---|---|---|
|  | 0.0625 | 4.0 | 0.0 | 0.0 |  | 0.0 | 3.0 |
|  | 0.0313 | 3.0 | 0.0 | 0.0 |  | 0.0 | 3.0 |
| 35 | 0.2500 | 6.0 | 0.0 | 0.0 |  | 3.0 | 3.0 |
|  | 0.1250 | 3.0 | 0.0 | 0.0 |  | 0.0 | 2.0 |
| 36 | 0.2500 | 9.0 | 9.0 | 4.0 |  | 9.0 | 5.0 |
|  | 0.1250 | 7.0 | 5.0 | 2.0 |  | 3.0 | 3.0 |
|  | 0.0625 | 6.0 | 5.0 | 0.0 |  | 0.0 | 3.0 |
|  | 0.0313 | 4.0 | 0.0 | 0.0 |  | 0.0 | 3.0 |
| 37 | 0.2500 | 7.0 | 0.0 | 0.0 |  | 3.0 | 3.0 |
|  | 0.1250 | 7.0 | 0.0 | 0.0 |  | 0.0 | 0.0 |
|  | 0.0625 | 6.0 | 0.0 | 0.0 |  | 0.0 | 0.0 |
|  | 0.0313 | 4.0 | 0.0 | 0.0 |  | 0.0 | 0.0 |
| 38 | 0.2500 | 7.0 | 5.0 | 3.0 | 9.0 | 9.0 | 7.0 |
|  | 0.1250 | 4.0 | 5.0 | 0.0 | 9.0 | 4.0 | 5.0 |
|  | 0.0625 | 2.0 | 3.0 | 0.0 | 9.0 | 3.0 | 5.0 |
|  | 0.0313 | 0.0 | 3.0 | 0.0 | 9.0 | 0.0 | 2.0 |
| 39 | 0.2500 | 3.0 | 0.0 | 0.0 | 9.0 | 4.0 | 3.0 |
|  | 0.1250 | 2.0 | 0.0 | 0.0 | 9.0 | 0.0 | 2.0 |
|  | 0.0625 | 0.0 | 0.0 | 0.0 | 9.0 | 0.0 | 0.0 |
|  | 0.0313 | 0.0 | 0.0 | 0.0 | 9.0 | 0.0 | 0.0 |
| 40 | 0.2500 | 9.0 | 0.0 | 6.0 | 9.0 | 0.0 | 3.0 |
|  | 0.1250 | 5.0 | 0.0 | 0.0 | 9.0 | 0.0 | 3.0 |
|  | 0.0625 | 5.0 | 0.0 | 0.0 | 9.0 | 0.0 | 3.0 |
|  | 0.0313 | 5.0 | 0.0 | 0.0 | 9.0 | 0.0 | 2.0 |
| 41 | 0.2500 | 7.0 | 4.0 | 7.0 | 9.0 | 6.0 | 5.0 |
|  | 0.1250 | 6.0 | 0.0 | 2.0 | 9.0 | 0.0 | 5.0 |
|  | 0.0625 | 4.0 | 0.0 | 0.0 | 9.0 | 0.0 | 5.0 |
|  | 0.0313 | 3.0 | 0.0 | 0.0 | 6.0 | 0.0 | 4.0 |
| 42 | 0.2500 | 6.0 | 0.0 | 0.0 | 9.0 | 3.0 | 0.0 |
|  | 0.1250 | 5.0 | 0.0 | 0.0 | 9.0 | 0.0 | 0.0 |
|  | 0.0625 | 5.0 | 0.0 | 0.0 | 9.0 | 0.0 | 0.0 |
|  | 0.0313 | 5.0 | 0.0 | 0.0 | 7.0 | 0.0 | 0.0 |
| 43 | 0.2500 | 9.0 | 5.0 | 9.0 | 9.0 | 9.0 | 6.0 |
|  | 0.1250 | 7.0 | 4.0 | 8.0 | 9.0 | 7.0 | 4.0 |
|  | 0.0625 | 6.0 | 2.0 | 5.0 | 9.0 | 7.0 | 3.0 |
|  | 0.0313 | 5.0 | 0.0 | 5.0 | 9.0 | 7.0 | 2.0 |
| 44 | 0.2500 | 8.0 | 9.0 | 0.0 | 9.0 |  | 5.0 |
|  | 0.1250 | 7.0 | 6.0 | 0.0 | 7.0 |  | 3.0 |
|  | 0.0625 | 6.0 | 6.0 | 0.0 | 4.0 |  | 3.0 |
|  | 0.0313 | 6.0 | 5.0 | 0.0 | 4.0 |  | 0.0 |
| 45 | 0.2500 | 7.0 | 7.0 | 0.0 | 9.0 | 4.0 | 3.0 |
|  | 0.1250 | 7.0 | 7.0 |  | 9.0 | 0.0 | 2.0 |
|  | 0.0625 | 4.0 | 3.0 | 0.0 | 7.0 | 0.0 | 2.0 |
|  | 0.0313 | 3.0 | 0.0 | 0.0 | 7.0 | 0.0 | 3.0 |
| 46 | 0.2500 | 4.0 | 0.0 | 6.0 | 7.0 | 3.0 | 3.0 |
|  | 0.1250 | 0.0 | 0.0 | 0.0 | 6.0 | 0.0 | 2.0 |
|  | 0.0625 | 0.0 | 0.0 | 0.0 | 4.0 | 0.0 | 2.0 |
|  | 0.0313 | 0.0 | 0.0 | 0.0 | 3.0 | 0.0 | 0.0 |
| 47 | 0.2500 | 7.0 | 6.0 | 0.0 | 9.0 | 7.0 | 3.0 |
|  | 0.1250 | 4.0 | 4.0 | 0.0 | 9.0 | 4.0 | 0.0 |
|  | 0.0625 | 2.0 | 0.0 | 0.0 | 6.0 | 0.0 | 0.0 |
|  | 0.0313 | 0.0 | 0.0 | 0.0 | 5.0 | 0.0 | 0.0 |
| 48 | 0.2500 | 6.0 | 5.0 | 0.0 | 6.0 | 6.0 | 6.0 |
|  | 0.1250 | 3.0 | 2.0 | 0.0 | 3.0 | 3.0 | 4.0 |
| 49 | 0.2500 | 7.0 | 7.0 | 4.0 | 9.0 | 7.0 | 7.0 |
|  | 0.1250 | 5.0 | 2.0 |  | 9.0 | 6.0 | 7.0 |
|  | 0.0625 | 2.0 | 0.0 | 3.0 | 9.0 | 4.0 | 5.0 |
|  | 0.0313 | 0.0 | 0.0 | 2.0 | 9.0 | 2.0 | 5.0 |
| 50 | 0.2500 | 7.0 | 0.0 | 0.0 | 7.0 | 3.0 | 1.0 |
|  | 0.1250 | 7.0 | 0.0 | 0.0 | 3.0 | 3.0 | 0.0 |
|  | 0.0625 | 7.0 | 0.0 | 0.0 | 0.0 | 2.0 | 0.0 |
|  | 0.0313 | 4.0 | 0.0 | 0.0 | 0.0 | 2.0 | 0.0 |
| 51 | 0.2500 | 0.0 | 6.0 | 0.0 | 4.0 | 0.0 | 0.0 |
|  | 0.1250 | 0.0 | 3.0 | 0.0 | 4.0 | 0.0 | 0.0 |
|  | 0.0625 | 0.0 | 2.0 | 0.0 | 3.0 | 0.0 | 0.0 |
| 52 | 0.2500 | 0.0 | 2.0 | 0.0 | 4.0 | 0.0 | 0.0 |
| 53 | 0.2500 | 3.0 | 9.0 | 0.0 | 9.0 | 0.0 | 3.0 |
|  | 0.1250 | 2.0 | 9.0 | 0.0 | 9.0 | 0.0 | 2.0 |
|  | 0.0625 | 0.0 | 2.0 | 0.0 | 2.0 | 0.0 | 0.0 |
|  | 0.0313 | 0.0 | 2.0 | 0.0 | 2.0 | 0.0 | 0.0 |
| 54 | 0.2500 | 9.0 | 4.0 | 4.0 | 6.0 | 2.0 | 4.0 |
|  | 0.1250 | 7.0 | 4.0 | 0.0 | 6.0 | 0.0 | 3.0 |
|  | 0.0625 | 5.0 | 4.0 | 0.0 | 0.0 | 0.0 | 2.0 |
|  | 0.0313 | 5.0 | 0.0 | 0.0 | 0.0 | 0.0 | 0.0 |
| 55 | 0.2500 | 7.0 | 9.0 | 0.0 | 9.0 | 0.0 | 4.0 |
|  | 0.1250 | 7.0 | 9.0 | 0.0 | 9.0 | 0.0 | 1.0 |
|  | 0.0625 | 7.0 | 9.0 | 0.0 | 9.0 | 0.0 | 1.0 |
|  | 0.0313 | 7.0 | 9.0 | 0.0 | 9.0 | 0.0 | 0.0 |
| 56 | 0.2500 | 5.0 | 0.0 | 0.0 | 9.0 | 0.0 | 2.0 |
|  | 0.1250 | 3.0 | 0.0 | 0.0 | 9.0 | 0.0 | 0.0 |
|  | 0.0625 | 0.0 | 0.0 | 0.0 | 6.0 | 0.0 | 0.0 |
|  | 0.0313 | 0.0 | 0.0 | 0.0 | 6.0 | 0.0 | 0.0 |
| 57 | 0.2500 | 5.0 | 9.0 | 3.0 | 9.0 | 6.0 | 4.0 |
|  | 0.1250 | 2.0 | 9.0 | 0.0 | 9.0 | 0.0 | 0.0 |
|  | 0.0625 | 2.0 | 9.0 | 0.0 | 9.0 | 0.0 | 0.0 |
|  | 0.0313 | 0.0 | 0.0 | 0.0 | 9.0 | 0.0 | 0.0 |
| 58 | 0.2500 | 9.0 | 3.0 | 5.0 | 9.0 | 4.0 | 5.0 |
|  | 0.1250 | 7.0 | 2.0 | 5.0 | 3.0 | 0.0 | 4.0 |
|  | 0.0625 | 7.0 | 0.0 | 5.0 | 0.0 | 0.0 | 4.0 |
|  | 0.0313 | 7.0 | 0.0 | 5.0 | 0.0 | 0.0 | 4.0 |
| 59 | 0.2500 | 7.0 | 9.0 | 7.0 | 9.0 | 3.0 | 2.0 |
|  | 0.1250 | 5.0 | 0.0 | 0.0 | 0.0 | 0.0 | 2.0 |
|  | 0.0625 | 4.0 | 0.0 | 0.0 | 0.0 | 0.0 | 0.0 |
| 60 | 0.2500 | 9.0 | 6.0 | 4.0 | 9.0 | 9.0 | 5.0 |
|  | 0.1250 | 9.0 | 6.0 | 4.0 | 9.0 | 9.0 | 5.0 |
|  | 0.0625 | 9.0 | 3.0 | 2.0 | 9.0 | 4.0 | 4.0 |
|  | 0.0313 | 7.0 | 3.0 | 2.0 | 9.0 | 3.0 | 4.0 |
| 61 | 0.2500 | 0.0 | 0.0 | 0.0 | 0.0 | 0.0 | 0.0 |
| 62 | 0.2500 | 5.0 | 9.0 | 0.0 | 9.0 | 6.0 | 4.0 |
|  | 0.1250 | 2.0 | 9.0 | 0.0 | 9.0 | 3.0 | 3.0 |
|  | 0.0625 | 0.0 | 2.0 | 0.0 | 9.0 | 0.0 | 3.0 |
|  | 0.0313 | 0.0 | 0.0 | 0.0 | 4.0 | 0.0 | 2.0 |
| 63 | 0.2500 | 5.0 | 7.0 | 0.0 | 9.0 | 9.0 | 3.0 |
|  | 0.1250 | 5.0 | 7.0 | 0.0 | 9.0 | 9.0 | 3.0 |
|  | 0.0625 | 0.0 | 6.0 | 0.0 | 9.0 | 7.0 | 3.0 |
|  | 0.0313 | 0.0 | 2.0 | 0.0 | 9.0 | 4.0 | 3.0 |
| 64 | 0.2500 | 9.0 | 7.0 | 0.0 | 9.0 | 8.0 | 6.0 |
|  | 0.1250 | 6.0 | 2.0 | 0.0 | 9.0 | 5.0 | 5.0 |
|  | 0.0625 | 6.0 | 2.0 | 0.0 | 9.0 | 3.0 | 4.0 |
|  | 0.0313 | 5.0 | 0.0 | 0.0 | 7.0 | 0.0 | 3.0 |
| 65 | 0.2500 | 7.0 | 8.0 | 0.0 | 9.0 | 7.0 | 6.0 |
|  | 0.1250 | 6.0 | 7.0 | 0.0 | 9.0 | 5.0 | 6.0 |
|  | 0.0625 | 5.0 | 7.0 | 0.0 | 9.0 | 4.0 | 3.0 |
|  | 0.0313 | 5.0 | 6.0 | 0.0 | 9.0 | 2.0 | 2.0 |
| 66 | 0.2500 | 9.0 | 7.0 | 4.0 | 9.0 | 4.0 | 3.0 |
|  | 0.1250 | 9.0 | 7.0 | 4.0 | 9.0 | 4.0 | 3.0 |
|  | 0.0625 | 7.0 | 6.0 | 0.0 | 9.0 | 4.0 | 2.0 |
|  | 0.0313 | 7.0 | 6.0 | 0.0 | 9.0 | 3.0 | 2.0 |
| 67 | 0.2500 | 5.0 | 8.0 | 3.0 | 9.0 | 6.0 | 6.0 |
|  | 0.1250 | 5.0 | 5.0 | 3.0 | 9.0 | 4.0 | 4.0 |
|  | 0.0625 | 4.0 | 5.0 | 3.0 | 9.0 | 4.0 | 3.0 |
|  | 0.0313 | 0.0 | 5.0 | 0.0 | 9.0 | 0.0 | 2.0 |
| 68 | 0.2500 | 7.0 | 8.0 | 0.0 | 9.0 | 3.0 | 4.0 |
|  | 0.1250 | 7.0 | 5.0 | 0.0 | 9.0 | 0.0 | 2.0 |
|  | 0.0625 | 5.0 | 0.0 | 0.0 | 9.0 | 0.0 | 0.0 |
|  | 0.0313 | 0.0 | 0.0 | 0.0 | 3.0 | 0.0 | 0.0 |
| 69 | 0.2500 | 7.0 | 3.0 | 9.0 |  | 3.0 | 3.0 |
|  | 0.1250 | 5.0 | 3.0 | 9.0 |  | 3.0 | 2.0 |
|  | 0.0625 | 4.0 | 3.0 | 3.0 |  | 0.0 | 0.0 |
|  | 0.0313 | 0.0 | 3.0 | 3.0 |  | 0.0 | 0.0 |
| 70 | 0.2500 | 0.0 | 2.0 | 3.0 |  | 4.0 | 2.0 |
|  | 0.1250 | 0.0 | 2.0 | 0.0 |  | 4.0 | 2.0 |
|  | 0.0625 | 0.0 | 2.0 | 0.0 |  | 4.0 | 0.0 |
|  | 0.0313 | 0.0 | 0.0 | 0.0 |  | 4.0 | 0.0 |
| 71 | 0.2500 | 7.0 | 7.0 | 3.0 |  | 0.0 | 4.0 |
|  | 0.1250 | 0.0 | 3.0 | 3.0 |  | 0.0 | 4.0 |
| 72 | 0.2500 | 9.0 | 9.0 | 9.0 |  | 4.0 | 3.0 |
|  | 0.1250 | 9.0 | 7.0 | 9.0 |  | 4.0 | 3.0 |

TABLE IV-continued

Paddy Conditions - Post Transplant Rice Postemergence Weeds

| Compound Number | Rate (kg/ha) | ECHOCRC | CYPIR | CYPSE | M0VA | SAPY | ORYSAT |
|---|---|---|---|---|---|---|---|
| | 0.0625 | 9.0 | 6.0 | 0.0 | | 4.0 | 2.0 |
| | 0.0313 | 9.0 | 6.0 | 0.0 | | 4.0 | 1.0 |
| 73 | 0.2500 | 7.0 | 6.0 | 4.0 | | 4.0 | 6.0 |
| | 0.1250 | 3.0 | 0.0 | 2.0 | | 3.0 | 5.0 |
| 74 | 0.2500 | 9.0 | 0.0 | 9.0 | | 9.0 | 3.0 |
| | 0.1250 | 9.0 | 0.0 | 5.0 | | 3.0 | 2.0 |
| | 0.0625 | 9.0 | 0.0 | 5.0 | | 3.0 | 0.0 |
| | 0.0313 | 7.0 | 0.0 | 0.0 | | 3.0 | 0.0 |
| 75 | 0.2500 | 9.0 | 6.0 | 3.0 | | 3.0 | 2.0 |
| | 0.1250 | 9.0 | 6.0 | 3.0 | | 0.0 | 1.0 |
| | 0.0625 | 6.0 | 0.0 | 3.0 | | 0.0 | 0.0 |
| | 0.0313 | 6.0 | 0.0 | 2.0 | | 0.0 | 0.0 |
| 76 | 0.2500 | 9.0 | 6.0 | 3.0 | | 4.0 | 4.0 |
| | 0.1250 | 9.0 | 0.0 | 2.0 | | 4.0 | 3.0 |
| | 0.0625 | 7.0 | 0.0 | 2.0 | | 0.0 | 2.0 |
| | 0.0313 | 4.0 | 0.0 | 2.0 | | 0.0 | 2.0 |
| 77 | 0.2500 | 9.0 | 0.0 | 4.0 | | 0.0 | 3.0 |
| | 0.1250 | 9.0 | 0.0 | 0.0 | | 0.0 | 3.0 |
| | 0.0625 | 9.0 | 0.0 | 0.0 | | 0.0 | 2.0 |
| | 0.0313 | 9.0 | 0.0 | 0.0 | | 0.0 | 2.0 |
| 78 | 0.2500 | 9.0 | 9.0 | 9.0 | | 4.0 | 1.0 |
| | 0.1250 | 9.0 | 6.0 | 7.0 | | 2.0 | 0.0 |
| | 0.0625 | 7.0 | 5.0 | 6.0 | | 0.0 | 0.0 |
| | 0.0313 | 7.0 | 5.0 | 6.0 | | 0.0 | 0.0 |
| 79 | 0.2500 | 8.0 | 6.0 | 9.0 | | 4.0 | 3.0 |
| | 0.1250 | 7.0 | 2.0 | 0.0 | | 4.0 | 3.0 |
| | 0.0625 | 6.0 | 0.0 | 0.0 | | 0.0 | 2.0 |
| | 0.0313 | 5.0 | 0.0 | 0.0 | | 0.0 | 0.0 |
| 80 | 0.2500 | 9.0 | 7.0 | 4.0 | | 0.0 | 2.0 |
| | 0.1250 | 9.0 | 7.0 | 3.0 | | 0.0 | 0.0 |
| | 0.0625 | 9.0 | 7.0 | 3.0 | | 0.0 | 0.0 |
| | 0.0313 | 9.0 | 5.0 | 3.0 | | 0.0 | 0.0 |
| 81 | 0.2500 | 3.0 | 5.0 | 0.0 | | 0.0 | 0.0 |
| | 0.1250 | 3.0 | 5.0 | 0.0 | | 0.0 | 0.0 |
| | 0.0625 | 0.0 | 4.0 | 0.0 | | 0.0 | 0.0 |
| 82 | 0.2500 | 9.0 | 3.0 | 4.0 | | 7.0 | 3.0 |
| | 0.1250 | 6.0 | 3.0 | 2.0 | | 4.0 | 3.0 |
| | 0.0625 | 4.0 | 0.0 | 0.0 | | 4.0 | 0.0 |
| | 0.0313 | 4.0 | 0.0 | 0.0 | | 4.0 | 0.0 |
| 83 | 0.2500 | 7.0 | 7.0 | 5.0 | 9.0 | 9.0 | 6.0 |
| | 0.1250 | 7.0 | 6.0 | 3.0 | 9.0 | 7.0 | 5.0 |
| | 0.0625 | 6.0 | 6.0 | | 9.0 | 7.0 | 3.0 |
| | 0.0313 | 5.0 | 5.0 | 0.0 | 9.0 | 7.0 | 3.0 |
| 84 | 0.2500 | 9.0 | 9.0 | 9.0 | 9.0 | 9.0 | 7.0 |
| | 0.1250 | 7.0 | 9.0 | 9.0 | 9.0 | 7.0 | 6.0 |
| | 0.0625 | 5.0 | 7.0 | 3.0 | 9.0 | 6.0 | 4.0 |
| | 0.0313 | 4.0 | 3.0 | 0.0 | 9.0 | 2.0 | 3.0 |
| 85 | 0.2500 | 9.0 | 9.0 | 9.0 | 9.0 | 9.0 | 5.0 |
| | 0.1250 | 7.0 | 9.0 | 2.0 | 9.0 | 9.0 | 4.0 |
| | 0.0625 | 5.0 | 7.0 | 2.0 | 9.0 | 3.0 | 4.0 |
| | 0.0313 | 4.0 | 3.0 | 0.0 | 9.0 | 3.0 | 3.0 |
| 86 | 0.2500 | 9.0 | 9.0 | 9.0 | 9.0 | 9.0 | 5.0 |
| | 0.1250 | 9.0 | 8.0 | 3.0 | 9.0 | 9.0 | 4.0 |
| | 0.0625 | 6.0 | 7.0 | 0.0 | 9.0 | 9.0 | 4.0 |
| | 0.0313 | 5.0 | 3.0 | 0.0 | 9.0 | 5.0 | 3.0 |
| 87 | 0.5000 | 3.0 | 7.0 | 5.0 | 9.0 | 7.0 | 6.0 |
| | 0.2500 | 3.0 | 5.0 | 5.0 | 9.0 | 5.0 | 4.0 |
| | 0.1250 | 2.0 | 5.0 | 5.0 | 9.0 | 4.0 | 3.0 |
| | 0.0625 | 0.0 | 5.0 | 0.0 | 9.0 | 4.0 | 3.0 |
| | 0.0313 | 0.0 | 5.0 | 0.0 | 9.0 | 0.0 | 2.0 |
| 88 | 0.2500 | 7.0 | 0.0 | 7.0 | 9.0 | 9.0 | 4.0 |
| | 0.1250 | 6.0 | 0.0 | 7.0 | 9.0 | 9.0 | 4.0 |
| | 0.0625 | 6.0 | 0.0 | 5.0 | 9.0 | 9.0 | 3.0 |
| | 0.0313 | 6.0 | 0.0 | 3.0 | 9.0 | 6.0 | 2.0 |
| 89 | 0.2500 | 6.0 | 4.0 | 6.0 | 9.0 | 9.0 | 6.0 |
| | 0.1250 | 5.0 | 2.0 | 4.0 | 9.0 | 9.0 | 5.0 |
| | 0.0625 | 4.0 | 0.0 | 0.0 | 9.0 | 5.0 | 4.0 |
| | 0.0313 | 3.0 | 0.0 | 0.0 | 9.0 | 4.0 | 2.0 |
| 90 | 0.2500 | 3.0 | 3.0 | 3.0 | 9.0 | 9.0 | 3.0 |
| | 0.1250 | 0.0 | 1.0 | 0.0 | 9.0 | 9.0 | 1.0 |
| | 0.0625 | 0.0 | 0.0 | 0.0 | 9.0 | 6.0 | 0.0 |
| | 0.0313 | 0.0 | 0.0 | 0.0 | 9.0 | 4.0 | 0.0 |
| 91 | 0.2500 | 4.0 | 0.0 | 0.0 | 9.0 | 0.0 | 2.0 |
| | 0.1250 | 2.0 | 0.0 | 0.0 | 9.0 | 0.0 | 0.0 |
| | 0.0625 | 0.0 | 0.0 | 0.0 | 9.0 | 0.0 | 0.0 |
| | 0.0313 | 0.0 | 0.0 | 0.0 | 9.0 | 0.0 | 0.0 |
| 92 | 0.2500 | 3.0 | 7.0 | 9.0 | 9.0 | 9.0 | 3.0 |
| | 0.1250 | 2.0 | 5.0 | 9.0 | 9.0 | 4.0 | 3.0 |
| | 0.0625 | 0.0 | 3.0 | 9.0 | 9.0 | 0.0 | 2.0 |
| | 0.0313 | 0.0 | 3.0 | 9.0 | 9.0 | 0.0 | 1.0 |
| 93 | 0.2500 | 7.0 | 0.0 | 9.0 | 9.0 | 9.0 | 3.0 |
| | 0.1250 | 4.0 | 0.0 | 5.0 | 9.0 | 3.0 | 0.0 |
| | 0.0625 | 3.0 | 0.0 | 0.0 | 9.0 | 0.0 | 0.0 |
| | 0.0313 | 0.0 | 0.0 | 0.0 | 9.0 | 0.0 | 0.0 |
| 94 | 0.2500 | 7.0 | 4.0 | 9.0 | 9.0 | 9.0 | 3.0 |
| | 0.1250 | 2.0 | 4.0 | 6.0 | 9.0 | 5.0 | 3.0 |
| | 0.0625 | 0.0 | 3.0 | | 9.0 | 0.0 | 2.0 |
| | 0.0313 | 0.0 | 0.0 | | 9.0 | 0.0 | 0.0 |
| 95 | 0.2500 | 3.0 | 7.0 | 3.0 | 9.0 | | 8.0 |
| | 0.1250 | 3.0 | 7.0 | 0.0 | 9.0 | | 8.0 |
| | 0.0625 | 0.0 | 4.0 | 0.0 | 5.0 | | 4.0 |
| | 0.0313 | 0.0 | 4.0 | 0.0 | 5.0 | | 3.0 |
| 96 | 0.2500 | 3.0 | 6.0 | 0.0 | 3.0 | | 5.0 |
| | 0.1250 | 0.0 | 6.0 | 0.0 | 3.0 | | 4.0 |
| | 0.0625 | 0.0 | 5.0 | 0.0 | 2.0 | | 4.0 |
| | 0.0313 | 0.0 | 0.0 | 0.0 | 2.0 | | 3.0 |
| 97 | 0.2500 | 3.0 | 4.0 | 3.0 | 9.0 | | 5.0 |
| | 0.1250 | 2.0 | 3.0 | 0.0 | 9.0 | | 5.0 |
| | 0.0625 | 0.0 | 0.0 | 0.0 | 9.0 | | 4.0 |
| | 0.0313 | 0.0 | 0.0 | 0.0 | 9.0 | | 1.0 |
| 98 | 0.2500 | 3.0 | 9.0 | 4.0 | 9.0 | | 7.0 |
| | 0.1250 | 1.0 | 9.0 | 4.0 | 9.0 | | 7.0 |
| | 0.0625 | 0.0 | 9.0 | 3.0 | 9.0 | | 6.0 |
| | 0.0313 | 0.0 | 9.0 | 2.0 | 9.0 | | 2.0 |
| 99 | 0.5000 | 4.0 | 0.0 | 0.0 | 9.0 | 4.0 | 4.0 |
| | 0.2500 | 0.0 | 0.0 | 0.0 | 9.0 | 4.0 | 4.0 |
| | 0.1250 | 0.0 | 0.0 | 0.0 | 9.0 | 3.0 | 4.0 |
| | 0.0625 | 0.0 | 0.0 | 0.0 | 9.0 | 0.0 | 2.0 |
| | 0.0313 | 0.0 | 0.0 | 0.0 | 9.0 | 0.0 | 2.0 |
| 100 | 0.5000 | 4.0 | 9.0 | | 9.0 | 6.0 | 4.0 |
| | 0.2500 | 3.0 | 4.0 | 0.0 | 9.0 | 4.0 | 3.0 |
| | 0.1250 | 0.0 | 0.0 | 0.0 | 9.0 | 0.0 | 3.0 |
| | 0.0625 | 0.0 | 0.0 | 0.0 | 9.0 | 0.0 | 3.0 |
| | 0.0313 | 0.0 | 0.0 | 0.0 | 9.0 | 0.0 | 3.0 |
| 101 | 0.5000 | 0.0 | 4.0 | 0.0 | 9.0 | 4.0 | 3.0 |
| | 0.2500 | 0.0 | 3.0 | 0.0 | 9.0 | 2.0 | 0.0 |
| | 0.1250 | 0.0 | 0.0 | 0.0 | 7.0 | 0.0 | 0.0 |
| | 0.0625 | 0.0 | 0.0 | 0.0 | 5.0 | 0.0 | 0.0 |
| | 0.0313 | 0.0 | 0.0 | 0.0 | 5.0 | 0.0 | 0.0 |
| 102 | 0.5000 | 2.0 | 6.0 | 0.0 | 4.0 | 0.0 | 4.0 |
| | 0.2500 | 0.0 | 2.0 | 0.0 | 0.0 | 0.0 | 2.0 |
| 103 | 0.2500 | 6.0 | 9.0 | 6.0 | 9.0 | 9.0 | 6.0 |
| | 0.1250 | 5.0 | 9.0 | 6.0 | 9.0 | 9.0 | 5.0 |
| | 0.0625 | 4.0 | 6.0 | 5.0 | 7.0 | 9.0 | 5.0 |
| | 0.0313 | 4.0 | 4.0 | 5.0 | 5.0 | 7.0 | 4.0 |
| 104 | 0.2500 | 6.0 | 9.0 | 0.0 | 9.0 | 9.0 | 6.0 |
| | 0.1250 | 6.0 | 9.0 | 0.0 | 9.0 | 9.0 | 7.0 |
| | 0.0625 | 5.0 | 9.0 | | 9.0 | 9.0 | 5.0 |
| | 0.0313 | 4.0 | 5.0 | 0.0 | 7.0 | 6.0 | 3.0 |
| 105 | 0.2500 | 5.0 | 9.0 | 9.0 | 9.0 | 7.0 | 6.0 |
| | 0.1250 | 4.0 | 7.0 | 7.0 | 7.0 | 5.0 | 3.0 |
| | 0.0625 | 3.0 | 5.0 | 5.0 | 7.0 | 5.0 | 5.0 |
| | 0.0313 | 0.0 | 5.0 | 2.0 | 6.0 | 3.0 | 5.0 |
| 109 | 0.2500 | 9.0 | 7.0 | 7.0 | 9.0 | 0.0 | 8.0 |
| | 0.1250 | 7.0 | 4.0 | | 9.0 | 0.0 | 4.0 |
| | 0.0625 | 2.0 | 2.0 | 0.0 | 4.0 | 0.0 | 2.0 |
| | 0.0313 | 2.0 | 0.0 | 0.0 | 2.0 | 0.0 | 2.0 |

TABLE IV-continued

Paddy Conditions - Post Transplant Rice Postemergence Weeds

| Compound Number | Rate (kg/ha) | ECHROC | CYPIR | CYPSE | MOVA | SAPY | ORYSAT |
|---|---|---|---|---|---|---|---|
| 114 | 0.2500 | 0.0 | 7.0 | 0.0 | 9.0 | 0.0 | 4.0 |
|  | 0.1250 | 0.0 | 4.0 | 0.0 | 9.0 | 0.0 | 4.0 |
|  | 0.0625 | 0.0 | 0.0 | 0.0 | 8.0 | 0.0 | 1.0 |
|  | 0.0313 | 0.0 | 0.0 | 0.0 | 6.0 | 0.0 | 1.0 |
| 119 | 0.2500 | 4.0 | 9.0 |  | 9.0 | 0.0 | 3.0 |
|  | 0.1250 | 4.0 | 6.0 | 0.0 | 8.0 | 0.0 | 2.0 |
|  | 0.0625 | 2.0 |  | 0.0 | 7.0 | 0.0 | 2.0 |
|  | 0.0313 | 0.0 | 2.0 | 0.0 | 4.0 | 0.0 | 2.0 |

What is claimed is:

1. A compound having the structural formula I

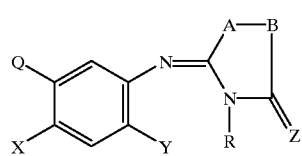

(I)

wherein

X and Y are each independently hydrogen, halogen, nitro, cyano, $C_1$–$C_4$alkyl, $C_1$–$C_4$haloalkyl or $S(O)_m R_1$;

R is hydrogen, a $C_1$–$C_8$alkyl, $C_3$–$C_7$cycloalkyl, $C_3$–$C_8$alkenyl, $C_5$–$C_7$cycloalkenyl or $C_3$–$C_8$alkynyl group, wherein each group is optionally substituted with any combination of one to six halogen atoms, one or two cyano groups, one or two nitro groups, one or two $C(W)R_2$ groups, one or two $C(W)OR_3$ groups, one or two $C(W)NR_4R_5$ groups, one or two $P(V)(OR_6)_2$ groups, one or two $OR_7$ groups, one or two $SR_8$ groups, one or two $NR_9R_{10}$ groups, one or two $OC(W)R_{11}$, groups, one or two $NR_{12}S(O)_n R_{13}$ groups, one or two $C(W)NR_{12}S(O)_n R_{13}$ groups, one 4- to 10-membered heterocyclic ring optionally substituted with any combination of one or two oxo groups, one or two thioxo groups, one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups, one or two $NR_{15}S(O)_p R_{16}$ groups or one or two $C(W)NR_{15}S(O)_p R_{16}$ groups, or one phenyl group optionally substituted with any combination of one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups one or two $NR_{15}S(O)_p R_{16}$ groups or one or two $C(W)NR_{15}S(O)_p R_{16}$ groups, a 4- to 10-membered heterocyclic ring optionally substituted with any combination of one or two oxo groups, one or two thioxo groups, one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups, one or two $NR_{15}S(O)_p R_{16}$ groups or one or two $C(W)NR_{15}S(O)_p R_{16}$ groups, phenyl optionally substituted with any combination of one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups, one or two $NR_{15}S(O)_p R_{16}$ groups or one or two $C(W)NR_{15}S(O)_p R_{16}$ groups, $OR_{17}$,
$NR_{18}R_{19}$,
$NR_{20}S(O)_q R_{21}$,
$NR_{22}C(V)R_{23}$,
$NR_{24}P(V)(OR_{25})_2$,
$C(V)NR_{20}S(O)_q R_{21}$,
cyano,
$S(O)_q R_{26}$,
$P(V)(OR_{27})_2$,
$C(V)R_{28}$ or
$C(V)OR_{29}$;

W is O, S, $NR_{30}$, $NOR_{31}$ or $NNR_{32}R_{33}$;

V and Z are each independently O or S;

$R_1$ and $R_{14}$ are each independently $C_1$–$C_4$alkyl or $C_1$–$C_4$haloalkyl;

$R_2$ is hydrogen, $C_1$–$C_6$alkyl, $C_3$–$C_7$cycloalkyl, $C_1$–$C_6$haloalkyl, $C_3$–$C_6$alkenyl, $C_3$–$C_6$alkynyl, $C_2$–$C_6$alkoxyalkyl, $C_2$–$C_6$haloalkoxyalkyl, $C_3$–$C_6$alkoxycarbonylalkyl, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two nitro groups, one or two cyano groups, one $NR_{15}S(O)_pR_{16}$ group, one $C_2$–$C_6$alkoxycarbonyl group, one $C_2$–$C_6$haloalkoxycarbonyl group, one $C_2$–$C_6$alkylcarbonyl group, one $C_2$–$C_6$haloalkylcarbonyl group, one $C_3$–$C_6$alkoxycarbonylalkyl group, one $C_3$–$C_6$haloalkoxycarbonylalkyl group, one $C_3$–$C_6$alkylcarbonylalkyl group or one $C_3$–$C_6$haloalkylcarbonylalkyl group, a 4- to 10-membered heterocyclic ring optionally substituted with any combination of one or two oxo groups, one or two thioxo groups, one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two nitro groups, one or two cyano groups, one $NR_{15}S(O)_pR_{16}$ group, one $C_2$–$C_6$alkoxycarbonyl group, one $C_2$–$C_6$haloalkoxycarbonyl group, one $C_2$–$C_6$alkylcarbonyl group, one $C_2$–$C_6$haloalkylcarbonyl group, one $C_3$–$C_6$alkoxycarbonylalkyl group, one $C_3$–$C_6$haloalkoxycarbonylalkyl group, one $C_3$–$C_6$alkylcarbonylalkyl group or one $C_3$–$C_6$haloalkylcarbonylalkyl group, $C_1$–$C_4$alkyl substituted with one phenyl group wherein the phenyl group is optionally substituted with any combination of one to three halogen atoms, one or two nitro groups, one or two cyano groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or $C_1$–$C_4$alkyl substituted with one 4- to 10-membered heterocyclic ring wherein the heterocyclic ring is optionally substituted with any combination of one to three halogen atoms, one or two nitro groups, one or two cyano groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_3$ is hydrogen, $C_1$–$C_6$alkyl, $C_1$–$C_6$haloalkyl, $C_3$–$C_7$cycloalkyl, $C_3$–$C_6$alkenyl $C_3$–$C_6$alkynyl, $C_2$–$C_6$alkoxyalkyl, $C_2$–$C_6$haloalkoxyalkyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or an alkali metal, alkaline earth metal, manganese, copper, zinc, cobalt, silver, nickel, ammonium or organic ammonium cation;

$R_4$ and $R_5$ are each independently hydrogen, $C_1$–$C_6$alkyl, $C_1$–$C_6$haloalkyl, $C_3$–$C_7$cycloalkyl, $C_1$–$C_6$alkoxy, hydroxy, $C_3$–$C_6$alkenyl, $C_3$–$C_6$haloalkenyl, $C_3$–$C_6$alkynyl, $C_3$–$C_6$haloalkynyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, $C_2$–$C_6$hydroxycarbonylalkyl, $C_2$–$C_6$alkylsulfonylalkyl, $C_2$–$C_6$haloalkylsulfonylalkyl, $S(O)_pR_{16}$, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, provided that only one of $R_4$ and $R_5$ can be hydroxy or $C_1$–$C_6$alkoxy, and when $R_4$ and $R_5$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_6$, $R_{25}$ and $R_{27}$ are each independently hydrogen, $C_1$–$C_6$alkyl, $C_1$–$C_6$haloalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_7$, $R_8$ and $R_{17}$ are each independently hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $C_2$–$C_6$haloalkoxyalkyl, $C_2$–$C_6$alkylcarbonylalkyl, $C_2$–$C_6$haloalkylcarbonylalkyl, $C_2$–$C_6$alkoxycarbonylalkyl, $C_2$–$C_6$haloalkoxycarbonylalkyl, $C_2$–$C_6$alkylsulfonylalkyl, $C_2$–$C_6$haloalkylsulfonylalkyl, $C_2$–$C_6$hydroxycarbonylalkyl, $C(V)NR_{12}S(O)_nR_{13}$, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_9$, $R_{10}$, $R_{18}$, $R_{19}$, $R_{32}$ and $R_{33}$ are each independently hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, $C_2$–$C_6$hydroxycarbonylalkyl, $C_2$–$C_6$alkylsulfonylalkyl, $C_2$–$C_6$haloalkylsulfonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_9$ and $R_{10}$ or $R_{18}$ and $R_{19}$ or $R_{32}$ and $R_{33}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{11}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $C_2$–$C_6$haloalkoxyalkyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, $C_2$–$C_6$hydroxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{12}$, $R_{15}$, $R_{20}$ and $R_{24}$ are each independently hydrogen, $C_1$–$C_6$alkyl, $C_1$–$C_6$haloalkyl, $C_3$–$C_6$alkenyl or $C_3$–$C_6$alkynyl; $R_{13}$, $R_{21}$, $R_{22}$, $R_{23}$, $R_{26}$, $R_{28}$ and $R_{29}$ are each independently hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two nitro groups, one or two cyano groups, one $C_3$–$C_6$alkoxycarbonylalkyl group, one $C_3$–$C_6$haloalkoxycarbonylalkyl group, one $C_3$–$C_6$alkylcarbonylalkyl group, one $C_3$–$C_6$haloalkylcarbonylalkyl group or one $C_2$–$C_6$hydroxycarbonylalkyl group, a 4- to 10-membered heterocyclic ring optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$ alkoxyalkyl groups, one or two $C_2$–$C_6$haloalkoxyalkyl groups, one or two nitro groups, one or two cyano groups, one $C_3$–$C_6$alkoxycarbonylalkyl group, one $C_3$–$C_6$haloalkoxycarbonylalkyl group, one $C_3$–$C_6$alkylcarbonylalkyl group, one $C_3$–$C_6$haloalkylcarbonylalkyl group or one $C_2$–$C_6$hydroxycarbonylalkyl group, benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{16}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, phenyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{30}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$alkynyl, $C_2$–$C_6$alkoxyalkyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $C_2$–$C_6$alkoxyalkyl group, one $C_2$–$C_6$haloalkoxyalkyl group, one $NR_{15}S(O)_nR_{16}$ group, one $C_2$–$C_6$alkoxycarbonyl group, one $C_2$–$C_6$alkylcarbonyl group, one $C_3$–$C_6$alkoxycarbonylalkyl group, one $C_3$–$C_6$alkylcarbonylalkyl group, one $C_3$–$C_6$haloalkoxycarbonylalkyl group or one $C_3$–$C_6$haloalkylcarbonylalkyl group, a 4- to 10-membered heterocyclic ring optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one $C_2$–$C_6$alkoxyalkyl group, one $C_2$–$C_6$haloalkoxyalkyl group, one $NR_{15}S(O)_nR_{16}$ group, one $C_2$–$C_6$alkoxycarbonyl group, one $C_2$–$C_6$alkylcarbonyl group, one $C_3$–$C_6$alkoxycarbonylalkyl group, one $C_3$–$C_6$alkylcarbonylalkyl group, one $C_3$–$C_6$haloalkoxycarbonylalkyl group or one $C_3$–$C_6$haloalkylcarbonylalkyl group, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{31}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkoxyalkyl, $C_2$–$C_6$haloalkoxyalkyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, $C_2$–$C_6$alkylsulfonylalkyl, $C_2$–$C_6$haloalkylsulfonylalkyl, $C_2$–$C_6$hydroxycarbonylalkyl, $C(V)NR_{12}S(O)_nR_{13}$, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, a 4- to 10-membered heterocyclic ring optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

A is —O—, —S(O)$_r$—, —NR$_{34}$— or —CR$_{35}$R$_{36}$—;

B is —CR$_{37}$R$_{38}$(CR$_{39}$R$_{40}$)$_s$—, —C(=T)— or —C(=CR$_{41}$R$_{42}$)—;

$R_{34}$, $R_{35}$, $R_{36}$, $R_{37}$, $R_{38}$, $R_{39}$ and $R_{40}$ are each independently hydrogen, halogen, $C_1$–$C_6$alkyl optionally substituted with one to three halogen atoms, one or two cyano groups, one or two nitro groups, one or two $C(W)R_2$ groups, one or two $C(W)OR_3$ groups, one or two $C(W)NR_4R_5$ groups, one or two $P(V)(OR_6)_2$ groups, one or two $OR_7$ groups, one or two $SR_8$ groups, one or two $NR_9R_{10}$ groups or one or two $OC(W)R_{11}$ groups, $C_3$–$C_7$cycloalkyl, $C_3$–$C_6$alkenyl, $C_3$–$C_6$haloalkenyl $C_3$–$C_6$alkynyl, $C_3$–$C_6$haloalkynyl, $C(V)NR_{12}S(O)_nR_{13}$, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two nitro groups, one or two cyano groups, one $NR_{15}S(O)_pR_{16}$ group, one $C_2$–$C_6$alkoxycarbonyl group, one $C_2$–$C_6$haloalkoxycarbonyl group, one $C_2$–$C_6$alkylcarbonyl group, one $C_2$–$C_6$haloalkylcarbonyl group, one $C_3$–$C_6$alkoxycarbonylalkyl group, one $C_3$–$C_6$haloalkoxycarbonylalkyl group, one $C_3$–$C_6$alkylcarbonylalkyl group or one $C_3$–$C_6$haloalkylcarbonylalkyl group, a 4- to 10-membered heterocyclic ring optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two nitro groups, one or two cyano groups, one $NR_{15}S(O)_pR_{16}$ group, one $C_2$–$C_6$alkoxycarbonyl group, one $C_2$–$C_6$haloalkoxycarbonyl group, one $C_2$–$C_6$alkylcarbonyl group, one $C_2$–$C_6$haloalkylcarbonyl group, one $C_3$–$C_6$alkoxycarbonylalkyl group, one $C_3$–$C_6$haloalkoxycarbonylalkyl group, one $C_3$–$C_6$alkylcarbonylalkyl group or one $C_3$–$C_6$haloalkylcarbonylalkyl group, $C_1$–$C_4$alkyl substituted with one phenyl group wherein the phenyl group is optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one $C_2$–$C_6$alkoxycarbonyl group, one $C_2$–$C_6$haloalkoxycarbonyl group, one $C_2$–$C_6$alkylcarbonyl group, one $C_2$–$C_6$haloalkylcarbonyl group, one $C_3$–$C_6$alkoxycarbonylalkyl group, one $C_3$–$C_6$haloalkoxycarbonylalkyl group, one $C_3$–$C_6$alkylcarbonylalkyl group, one $C_3$–$C_6$haloalkylcarbonylalkyl group, one $C_3$–$C_8$alkoxycarbonylalkoxy group or one $C_2$–$C_8$hydroxycarbonylalkoxy group, or $C_1$–$C_4$alkyl substituted with one 4- to 10-membered heterocyclic ring wherein the heterocyclic ring is optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one $C_2$–$C_6$alkoxycarbonyl group, one $C_2$–$C_6$haloalkoxycarbonyl group, one $C_2$–$C_6$alkylcarbonyl group, one $C_2$–$C_6$haloalkylcarbonyl group, one $C_3$–$C_6$alkoxycarbonylalkyl group, one $C_3$–$C_6$haloalkoxycarbonylalkyl group, one $C_3$–$C_6$alkylcarbonylalkyl group or one $C_3$–$C_6$haloalkylcarbonylalkyl group, and when $R_{35}$ and $R_{36}$ or $R_{37}$ and $R_{38}$ or $R_{39}$ and $R_{40}$ are taken together with the atom to which they are attached, they represent a ring in which $R_{35}R_{36}$ or $R_{37}R_{38}$ or $R_{39}R_{40}$ is a $C_2$–$C_6$alkylene group;

T is O, S, $NR_{30}$, $NOR_{31}$ or $NNR_{32}R_{33}$;

$R_{41}$ and $R_{42}$ are each independently hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, $C_2$–$C_6$alkylcarbonyl, $C_2$–$C_6$haloalkylcarbonyl, $C_2$–$C_6$alkoxycarbonyl, $C_2$–$C_6$haloalkoxycarbonyl, hydroxycarbonyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl, $C_2$–$C_6$hydroxycarbonylalkyl, $C_2$–$C_6$alkylsulfonylalkyl, $C_2$–$C_6$haloalkylsulfonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups or one $C_3$–$C_8$alkoxycarbonylalkoxy group, benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_{41}$ and $R_{42}$ are taken together with the atom to which they are attached, they represent a three- to seven-membered saturated or unsaturated ring optionally interrupted with one group selected from O, S(O)$_r$ or $NR_{31}$, and optionally substituted with one to three methyl groups or one or more halogen atoms;

m and r are each independently an integer of 0, 1 or 2;
n, p and q are each independently an integer of 1 or 2;
s is an integer of 0 or 1;
Q is

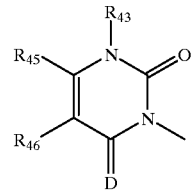

D is O or S;

$R_{43}$ is hydrogen, halogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, cyano, amino, hydroxy or benzyl, and when $R_{43}$ and $R_{44}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{45}$ and $R_{46}$ are each independently hydrogen, halogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $OR_{51}$, $S(O)_rR_{52}$ or $NR_{53}R_{54}$, and when $R_{45}$ and $R_{46}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{51}$ and $R_{52}$ are each independently hydrogen, $C_1$–$C_4$alkyl, $C_1$–$C_4$haloalkyl, $C_3$–$C_7$cycloalkyl, $C_1$–$C_4$cyanoalkyl, $C_3$–$C_6$alkenyl, $C_3$–$C_6$haloalkenyl, $C_3$–$C_6$alkynyl, benzyl or phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{53}$ is hydrogen, $C_1$–$C_4$alkyl, benzyl or phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{54}$ is hydrogen, $C_1$–$C_4$alkyl, $C_3$–$C_6$alkenyl, $C_3$–$C_7$cycloalkyl, benzyl, $S(O)_rR_{52}$ or phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups; and t is an integer of 0, 1 or 2; and
the agriculturally acceptable salts thereof.

2. The compound according to claim 1 wherein
X is hydrogen or halogen;
Y is hydrogen, halogen, nitro or cyano;
R is hydrogen,
- a $C_1$–$C_8$alkyl, $C_3$–$C_7$cycloalkyl, $C_3$–$C_8$alkenyl, $C_5$–$C_7$cycloalkenyl or $C_3$–$C_8$alkynyl group, wherein each group is optionally substituted with any combination of one to six halogen atoms, one or two cyano groups, one or two nitro groups, one or two $C(O)R_2$ groups, one or two $C(O)OR_3$ groups, one or two $C(O)NR_4R_5$ groups, one or two $P(O)(OR_6)_2$ groups, one or two $OR_7$ groups, one or two $SR_8$ groups, one or two $NR_9R_{10}$ groups, one or two $OC(O)R_{11}$ groups, one or two $NR_{12}S(O)_nR_{13}$ groups, one or two $C(O)NR_{12}S(O)_nR_{13}$ groups,
- one 4- to 10-membered heterocyclic ring optionally substituted with any combination of one or two oxo groups, one or two thioxo groups, one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups, one or two $NR_{15}S(O)_pR_{16}$ groups or one or two $C(O)NR_{15}S(O)_pR_{16}$ groups, or
- one phenyl group optionally substituted with any combination of one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups, one or two $NR_{15}S(O)_pR_{16}$ groups or one or two $C(O)NR_{15}S(O)_pR_{16}$ groups,
- phenyl optionally substituted with any combination of one to three halogen atoms, one to three nitro groups, one to three cyano groups, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two $C_2$–$C_6$haloalkoxyalkyl groups, one or two $C(O)OR_{14}$ groups, one or two $C(O)R_{14}$ groups, one to three $C_3$–$C_6$alkoxycarbonylalkyl groups, one to three $C_3$–$C_6$haloalkoxycarbonylalkyl groups, one to three $C_3$–$C_6$alkylcarbonylalkyl groups, one to three $C_3$–$C_6$haloalkylcarbonylalkyl groups or one or two $NR_{15}S(O)_pR_{16}$ groups,
- $OR_{17}$,
- $NR_{18}R_{19}$,
- $NR_{20}S(O)_qR_{21}$,
- $NR_{22}C(O)R_{23}$,
- $C(O)NR_{20}S(O)_qR_{21}$,
- $S(O)_qR_{26}$,
- $C(O)R_{28}$ or
- $C(O)OR_{29}$;

Z is O;

$R_{14}$ is $C_1$–$C_4$alkyl or $C_1$–$C_4$haloalkyl;

$R_2$ is hydrogen, $C_1$–$C_6$alkyl, $C_3$–$C_7$cycloalkyl, $C_1$–$C_6$-haloalkyl, $C_2$–$C_6$alkoxyalkyl, $C_3$–$C_6$alkoxycarbonylalkyl, or
- phenyl optionally substituted with any combination of one to three halogen atoms, one to three $C_1$–$C_4$alkyl groups, one to three $C_1$–$C_4$alkoxy groups, one or two $C_2$–$C_6$alkoxyalkyl groups, one $C_2$–$C_6$alkoxycarbonyl group, one $C_3$–$C_6$alkoxycarbonylalkyl group or one $C_3$–$C_6$haloalkoxycarbonylalkyl group;

$R_3$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$alkynyl, $C_2$–$C_6$alkoxyalkyl, $C_2$–$C_6$haloalkoxyalkyl, $C_3$–$C_6$alkoxycarbonylalkyl,
- phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
- benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
- furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
- an alkali metal, alkaline earth metal, manganese, copper, zinc, cobalt, silver, nickel, ammonium or organic ammonium cation;

$R_4$ and $R_5$ are each independently hydrogen, $C_1$–$C_6$alkyl, $C_3$–$C_7$cycloalkyl, $C_1$–$C_6$alkoxy, hydroxy, $C_3$–$C_6$alkenyl, $C_3$–$C_6$alkylcarbonylalkyl, $C_3$–$C_6$alkoxycarbonylalkyl, $C_2$–$C_6$alkylsulfonylalkyl, $C_2$–$C_6$haloalkylsulfonylalkyl, $S(O)_pR_{16}$,
- phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
- benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
- provided that only one of $R_4$ and $R_5$ can be hydroxy or $C_1$–$C_6$alkoxy, and
- when $R_4$ and $R_5$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_6$ is hydrogen, $C_1$–$C_6$alkyl, $C_1$–$C_6$haloalkyl,
phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_7$ and $R_8$ are each independently hydrogen, $C_1$–$C_6$alkyl, $C_2$–$C_6$alkoxycarbonylalkyl or $C_2$–$C_6$hydroxycarbonylalkyl;

$R_{17}$ is hydrogen, $C_1$–$C_6$alkyl, $C_3$–$C_7$cycloalkyl, $C_3$–$C_6$alkenyl, $C_3$–$C_6$alkynyl, $C_2$–$C_6$alkoxyalkyl, $C_2$–$C_6$haloalkoxyalkyl, $C_3$–$C_6$alkylcarbonylalkyl, $C_2$–$C_6$haloalkylcarbonylalkyl, $C_3$–$C_6$alkoxycarbonylalkyl, $C_2$–$C_6$hydroxycarbonylalkyl,
phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_9$ and $R_{10}$ are each independently hydrogen, $C_1$–$C_6$alkyl, $C_3$–$C_6$alkylcarbonylalkyl, $C_3$–$C_6$alkoxycarbonylalkyl, $C_2$–$C_6$hydroxycarbonylalkyl, or
phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and
when $R_9$ and $R_{10}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{18}$ and $R_{19}$ are each independently hydrogen, $C_1$–$C_6$alkyl, $C_3$–$C_6$alkoxycarbonylalkyl, $C_3$–$C_6$haloalkoxycarbonylalkyl, $C_2$–$C_6$hydroxycarbonylalkyl, $C_2$–$C_6$alkylsulfonylalkyl, $C_2$–$C_6$haloalkylsulfonylalkyl,
phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and
when $R_{18}$ and $R_{19}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms;

$R_{11}$ is hydrogen, $C_1$–$C_6$alkyl or $C_1$–$C_6$haloalkyl;

$R_{12}$, $R_{15}$ and $R_{20}$ are each independently hydrogen or $C_1$–$C_6$alkyl;

$R_{13}$, $R_{16}$, $R_{21}$ and $R_{26}$ are each independently $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, or
benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{22}$ is hydrogen or $C_1$–$C_6$alkyl;

$R_{23}$ is hydrogen, $C_1$–$C_6$alkyl, $C_1$–$C_6$haloalkyl, $C_3$–$C_7$cycloalkyl, $C_3$–$C_6$alkylcarbonylalkyl, $C_3$–$C_6$haloalkylcarbonylalkyl, $C_3$–$C_6$alkoxycarbonylalkyl, $C_3$–$C_6$haloalkoxycarbonylalkyl,
phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{28}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$alkynyl, $C_3$–$C_6$alkoxycarbonylalkyl, or
phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{29}$ is hydrogen, $C_1$–$C_6$alkyl or benzyl;

A is —O—, —S(O)$_r$—, or —NR$_{34}$—;

B is —CR$_{37}$R$_{38}$—, —C(O)— or —C(=CR$_{41}$R$_{42}$)—;

$R_{34}$ is hydrogen,
$C_1$–$C_6$alkyl optionally substituted with one to three halogen atoms, one or two cyano groups, one or two nitro groups, one or two C(O)R$_2$ groups, one or two C(O)OR$_3$ groups, one or two C(O)NR$_4$R$_5$ groups, one or two P(O)(OR$_6$)$_2$ groups, one or two OR$_7$ groups, one or two SR$_8$ groups, one or two NR$_9$R$_{10}$ groups or one or two OC(O)R$_{11}$ groups,
$C_3$–$C_7$cycloalkyl,
$C_3$–$C_6$alkenyl,
$C_3$–$C_6$alkynyl,
C(O)NR$_{12}$S(O)$_n$R$_{13}$,
phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two nitro groups, one or two cyano groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group, or $C_1$–$C_4$alkyl substituted with one phenyl group wherein the phenyl group is optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group;

$R_{37}$ and $R_{38}$ are each independently hydrogen, halogen,
  $C_1$–$C_6$alkyl optionally substituted with one to three halogen atoms, one or two cyano groups, one or two nitro groups, one or two $C(O)R_2$ groups, one or two $C(O)OR_3$ groups, one or two $C(O)NR_4R_5$ groups, one or two $P(O)(OR_6)_2$ groups, one or two $OR_7$ groups, one or two $SR_8$ groups, one or two $NR_9R_{10}$ groups or one or two $OC(O)R_{11}$ groups,
  $C_3$–$C_7$cycloalkyl,
  $C_3$–$C_6$alkenyl,
  $C_3$–$C_6$haloalkenyl
  $C_3$–$C_6$alkynyl,
  $C_3$–$C_6$haloalkynyl,
  $C(O)NR_{12}S(O)_nR_{13}$,
  phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two nitro groups, one or two cyano groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group, or
  $C_1$–$C_4$alkyl substituted with one phenyl group wherein the phenyl group is optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group, and
  when $R_{37}$ and $R_{38}$ are taken together with the atom to which they are attached, they represent a ring in which $R_{37}R_{38}$ is a $C_2$–$C_6$alkylene group;

$R_{41}$ and $R_{42}$ are each independently hydrogen, $C_1$–$C_6$alkyl, $C_2$–$C_6$alkylcarbonyl, $C_2$–$C_6$alkoxycarbonyl, hydroxycarbonyl, $C_3$–$C_6$alkylcarbonylalkyl, $C_3$–$C_6$alkoxycarbonylalkyl, $C_2$–$C_6$hydroxycarbonylalkyl,
  phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups,
  benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or
  furfural optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and
  when $R_{41}$, and $R_{42}$ are taken together with the atom to which they are attached, they represent a three- to seven-membered saturated or unsaturated ring optionally interrupted with one group selected from O, $S(O)_r$ or $NR_{31}$, and optionally substituted with one to three methyl groups or one or more halogen atoms;

r is an integer of 0, 1 or 2;

n, p and q are each independently an integer of 1 or 2;

Q is

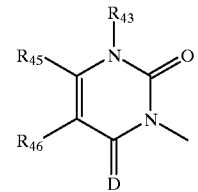

D is O or S;

$R_{43}$ is hydrogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, amino, or benzyl;

$R_{45}$ and $R_{46}$ are each independently hydrogen, halogen, $C_1$–$C_6$alkyl, $C_1$–$C_6$haloalkyl, $C_3$–$C_7$cycloalkyl, $C_3$–$C_6$alkenyl, $C_3$–$C_6$haloalkenyl or $C_3$–$C_6$alkynyl, and when $R_{45}$ and $R_{46}$ are taken together with the atom to which they are attached, they represent a three- to seven-membered saturated or unsaturated ring optionally interrupted by oxygen, sulfur or nitrogen, and optionally substituted with one to three methyl groups or one or more halogen atoms.

3. The compound according to claim 2 wherein

X is hydrogen, fluorine or chlorine;

Y is fluorine, chlorine, nitro or cyano;

R is hydrogen,
  $C_1$–$C_8$alkyl optionally substituted with any combination of one to six halogen atoms, one or two cyano groups, one or two nitro groups, one or two $C(O)R_2$ groups, one or two $C(O)OR_3$ groups, one or two $C(O)NR_4R_5$ groups, one or two $P(O)(OR_6)_2$ groups, one or two $OR_7$ groups, one or two $SR_8$ groups, one or two $NR_9R_{10}$ groups, one or two $C(O)NR_{12}S(O)_nR_{13}$ groups,
  one furyl group optionally substituted with any combination of one to three $C_1$–$C_4$alkyl groups, one to three $C_1$–$C_4$alkoxy groups, one or two $C(O)OR_{14}$ groups or one or two $C(O)R_{14}$ groups,
  one pyridyl group optionally substituted with any combination of one to three $C_1$–$C_4$alkyl groups, one to three $C_1$–$C_4$alkoxy groups, one or two $C(O)OR_{14}$ groups or one or two $C(O)R_{14}$ groups, or one phenyl group optionally substituted with any combination of one to three $C_1$–$C_4$alkyl groups, one to three $C_1$–$C_4$alkoxy groups, one or two $C(O)OR_{14}$ groups or one or two $C(O)R_{14}$ groups, phenyl optionally substituted with any combination of one to three $C_1$–$C_4$alkyl groups, one to three $C_1$–$C_4$alkoxy groups, one or two $C_2$–$C_6$alkoxyalkyl groups, one or two $C(O)OR_{14}$ groups, one or two $C(O)R_{14}$ groups, one to three $C_3$–$C_6$alkoxycarbonylalkyl groups or one or two $NR_{15}S(O)_pR_{16}$ groups, $C_3$–$C_7$cycloalkyl,
$C_3$–$C_8$alkenyl,
$C_3$–$C_8$alkynyl,
$OR_{17}$,
$NR_{18}R_{19}$,
$C(O)R_{28}$ or
$C(O)OR_{29}$;

Z is O;

$R_{14}$ is $C_1$–$C_4$alkyl;

$R_2$ is hydrogen, $C_1$–$C_6$alkyl, $C_2$–$C_6$alkoxyalkyl or $C_3$–$C_6$alkoxycarbonylalkyl;

$R_3$ is hydrogen, $C_1$–$C_6$alkyl, $C_1$–$C_6$haloalkyl, $C_3$–$C_6$alkenyl, $C_3$–$C_6$alkynyl, $C_2$–$C_6$alkoxyalkyl, $C_2$–$C_6$haloalkoxyalkyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_4$ and $R_5$ are each independently hydrogen, $C_1$–$C_6$alkyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_4$ and $R_5$ are taken together with the atom to which they are attached, they represent a ring in which $R_4R_5$ is a $C_2$–$C_6$alkylene group;

$R_6$ is hydrogen, $C_1$–$C_6$alkyl or benzyl;

$R_7$ and $R_8$ are each independently hydrogen, $C_1$–$C_6$alkyl, $C_2$–$C_6$alkoxycarbonylalkyl or $C_2$–$C_6$hydroxycarbonylalkyl;

$R_{17}$ is hydrogen, $C_1$–$C_6$alkyl, $C_3$–$C_6$alkenyl, $C_3$–$C_6$alkynyl, $C_2$–$C_6$alkoxyalkyl, $C_3$–$C_6$alkoxycarbonylalkyl, $C_2$–$C_6$hydroxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_9$ and $R_{10}$ are each independently hydrogen, $C_1$–$C_6$alkyl or $C_3$–$C_6$alkoxycarbonylalkyl, and when $R_9$ and $R_{10}$ are taken together with the atom to which they are attached, they represent a ring in which $R_9R_{10}$ is a $C_2$–$C_6$alkylene group;

$R_{18}$ and $R_{19}$ are each independently hydrogen, $C_1$–$C_6$alkyl, $C_3$–$C_6$alkoxycarbonylalkyl, $C_2$–$C_6$hydroxycarbonylalkyl, $C_2$–$C_6$alkylsulfonylalkyl, $C_2$–$C_6$haloalkylsulfonylalkyl, or phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, and when $R_{18}$ and $R_{19}$ are taken together with the atom to which they are attached, they represent a ring in which $R_{18}R_{19}$ is a $C_2$–$C_6$alkylene group;

$R_{12}$ and $R_{15}$ are each independently hydrogen or $C_1$–$C_6$alkyl;

$R_{13}$ and $R_{16}$ are each independently $C_1$–$C_6$alkyl, $C_1$–$C_6$haloalkyl, $C_3$–$C_7$cycloalkyl, $C_3$–$C_6$alkenyl, $C_3$–$C_6$haloalkenyl, $C_3$–$C_6$alkynyl, $C_3$–$C_6$haloalkynyl, or benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{28}$ is hydrogen, $C_1$–$C_6$alkyl, $C_1$–$C_6$haloalkyl, $C_3$–$C_6$alkenyl $C_3$–$C_6$alkynyl, $C_3$–$C_6$alkoxycarbonylalkyl, or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{29}$ is hydrogen, $C_1$–$C_6$alkyl or benzyl;

A is —O—, —S(O)$_r$—, or —NR$_{34}$—;

B is —CR$_{37}$R$_{38}$— or —C(=CR$_{41}$R$_{42}$)—;

$R_{34}$ is hydrogen,
$C_1$–$C_6$alkyl optionally substituted with one or two $C(O)OR_3$ groups or one or two $C(O)NR_4R_5$ groups,
$C_3$–$C_6$alkenyl,
$C_3$–$C_6$alkynyl, phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one or two nitro groups, one or two cyano groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group, or benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_{37}$ and $R_{38}$ are each independently hydrogen, halogen, $C_1$–$C_6$alkyl optionally substituted with one or two cyano groups, one or two $C(O)R_2$ groups, one or two $C(O)OR_3$ groups, one or two $C(O)NR_4R_5$ groups, one or two $P(O)(OR_6)_2$ groups, one or two $OR_7$ groups or one or two $NR_9R_{10}$ groups, $C_3$–$C_7$cycloalkyl,
$C_3$–$C_6$alkenyl,
$C_3$–$C_6$alkynyl,
$C(O)NR_{12}S(O)_nR_{13}$, or
benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one or two $C_2$–$C_6$alkoxyalkyl groups, one $C_2$–$C_6$alkoxycarbonyl group, one $C_2$–$C_6$alkylcarbonyl group, one $C_3$–$C_6$alkoxycarbonylalkyl group or one $C_3$–$C_6$alkylcarbonylalkyl group, and when $R_{37}$ and $R_{38}$ are taken together with the atom to which they are attached, they represent a ring in which $R_{37}R_{38}$ is a $C_2$–$C_6$alkylene group;

$R_{41}$ and $R_{42}$ are each independently hydrogen, $C_1$–$C_6$alkyl, $C_2$–$C_6$alkylcarbonyl, $C_2$–$C_6$alkoxycarbonyl, hydroxycarbonyl, or phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

r is an integer of 0, 1 or 2;

n and p are each independently an integer of 2; and

Q is

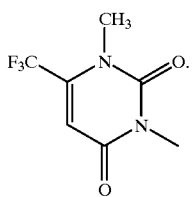

4. The compound according to claim 3 wherein

X is fluorine;

Y is chlorine;

R is $C_1$–$C_8$alkyl optionally substituted with any combination of one or two $C(O)OR_3$ groups, one or two $C(O)NR_4R_5$ groups, one or two $P(O)(OR_6)_2$ groups, one or two $OR_7$ groups, one or two $SR_8$ groups, one or two $NR_9R_{10}$ groups, one or two $C(O)NR_{12}S(O)_nR_{13}$ groups, one furyl group or one phenyl group optionally substituted with any combination of one to three halogen atoms, one to three $C_1$–$C_4$alkyl groups, one to three $C_1$–$C_4$alkoxy groups or one nitro group, phenyl optionally substituted with any combination of one to three $C_1$–$C_4$alkyl groups, one to three $C_1$–$C_4$alkoxy groups, one or two $C_2$–$C_6$alkoxyalkyl groups, one or two $C_3$–$C_6$alkoxycarbonylalkyl groups or one or two $NR_{15}S(O)_pR_{16}$ groups, $C_3$–$C_7$cycloalkyl,
$C_3$–$C_8$alkenyl or
$C_3$–$C_8$alkynyl;

Z is O;

$R_3$ is hydrogen, $C_1$–$C_6$alkyl, $C_1$–$C_6$haloalkyl, $C_3$–$C_6$alkenyl, $C_3$–$C_6$alkynyl, $C_3$–$C_6$alkoxycarbonylalkyl, phenyl optionally substituted with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups, or benzyl optionally substituted on the phenyl ring with any combination of one to three halogen atoms, one or two cyano groups, one or two nitro groups, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

$R_4$ and $R_5$ are each independently hydrogen or $C_1$–$C_6$alkyl, and when $R_4$ and $R_5$ are taken together with the atom to which they are attached, they represent a ring in which $R_4R_5$ is a $C_2$–$C_6$alkylene group;

$R_6$ is hydrogen or $C_1$–$C_6$alkyl;

$R_7$ and $R_8$ are each independently hydrogen, $C_1$–$C_6$alkyl $C_2$–$C_6$alkoxycarbonylalkyl or $C_2$–$C_6$hydroxycarbonylalkyl;

$R_9$ and $R_{10}$ are each independently hydrogen, $C_1$–$C_6$alkyl or $C_3$–$C_6$alkoxycarbonylalkyl, and when $R_9$ and $R_{10}$ are taken together with the atom to which they are attached, they represent a ring in which $R_9R_{10}$ is a $C_2$–$C_6$alkylene group;

$R_{12}$ and $R_{15}$ are hydrogen;

$R_{13}$ and $R_{16}$ are each independently $C_1$–$C_6$alkyl, $C_1$–$C_6$haloalkyl, $C_3$–$C_6$alkenyl, $C_3$–$C_6$alkynyl, or benzyl optionally substituted on the phenyl ring with any combination of one to three halogen atoms, one to three $C_1$–$C_4$alkyl groups, one to three $C_1$–$C_4$haloalkyl groups, one to three $C_1$–$C_4$alkoxy groups or one to three $C_1$–$C_4$haloalkoxy groups;

A is —O— or —S(O)$_r$—;

B is —$CR_{37}R_{38}$— or —C(=$CR_{41}R_{42}$)—;

$R_{37}$ and $R_{38}$ are each independently hydrogen, halogen, $C_1$–$C_6$alkyl optionally substituted with one or two $C(O)OR_3$ groups, one or two $C(O)NR_4R_5$ groups, one or two $OR_7$ groups or one or two $NR_9R_{10}$ groups, or benzyl optionally substituted on the phenyl ring with any combination of one to three $C_1$–$C_4$alkyl groups, one to three $C_1$–$C_4$alkoxy groups or one $C_3$–$C_6$alkoxycarbonylalkyl group, and when $R_{37}$ and $R_{38}$ are taken together with the atom to which they are attached, they represent a ring in which $R_{37}R_{38}$ is a $C_2$–$C_6$alkylene group;

$R_{41}$ and $R_{42}$ are each independently hydrogen, $C_1$–$C_6$alkyl, $C_2$–$C_6$alkylcarbonyl, $C_2$–$C_6$alkoxycarbonyl or hydroxycarbonyl;

r is an integer of 0, 1 or 2;

n and p are each independently an integer of 2; and

Q is selected from

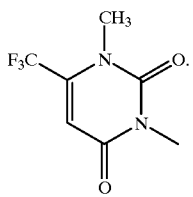

5. The compound according to claim 4 selected from the group consisting of

3-{4-chloro-2-fluoro-5-[3-methyl-4-oxo-2-thiazolidinylidene)amino]phenyl}-1-methyl-6-(trifluoromethyl)-2,4(1H,3H)-pyrimidinedione;

ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-(carboxymethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-delta5, alpha-thiazolidineacetic acid, diethyl ester;

ethyl 5-{{2-chloro-5-[3,6-dihydro-3-methyl-2,6-dioxo-4-(trifluoromethyl)-1(2H)-pyrimidinyl]-4-fluorophenyl}imino}-7-oxo-4-thia-6-azaspiro[2.4] heptane-6-acetate;

2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-oxazolidineacetate;

α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, L-;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl methyl ester;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl isopropyl ester;

ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

ethyl 2-{{2-chloro-5-[3,6-dihydro-3-methyl-2,6-dioxo-4-(trifluoromethyl)-1(2H)-pyrimidinyl]-4-fluorophenyl}imino}-5-[(methylcarbamoyl)methyl]-4-oxo-3-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl (2-propynyl) ester;

methyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

isopropyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl 2-fluoroethyl ester;

2-fluoroethyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-5-(hydroxyethyl)-4-oxo-3-thiazolidineacetate;

allyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

isopropyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{4-chloro-2-fluoro-5-[(3-furfuryl-4-oxo-2-thiazolidinylidene)amino]phenyl}-1-methyl-6-(trifluoromethyl)-2,4(1H,3H)-pyrimidinedione;

cyclopropylmethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

ethyl 5-chloro-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{4-chloro-5-[(3-cyclopropyl4-oxo-2-thiazolidinylidene)amino]-2-fluorophenyl}-1-methyl-6-(trifluoromethyl)-2,4(1H,3H)-pyrimidinedione;

3-{4-chloro-2-fluoro-5-{[3-(2-methoxyethyl)4-oxo-2-thiazolidinylidene]amino}phenyl}-1-methyl-6-(trifluoromethyl)-2,4(1H,3H)-pyrimidinedione;

3-{4-chloro-2-fluoro-5-{[3-(1-methyl-2-propynyl)-4-oxo-2-thiazolidinylidene]amino}phenyl}-1-methyl-6-(trifluoromethyl)-2,4(1H,3H)-pyrimidinedione;

ethyl 5-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{5-[(3-benzyl4-oxo-2-thiazolidinylidene)amino]-4-chloro-2-fluorophenyl}-1-methyl-6-(trifluoromethyl)-2,4(1H,3H)-pyrimidinedione;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinepropionate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, D-;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-α-(ρ-nitrobenzyl)-3-thiazolidineacetate, L-;

ethyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-; and methyl α-(ρ-chlorobenzyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, DL-.

6. A method for the control of undesirable plant species which comprises applying to the foliage of said plants or to the soil or water containing seeds or other propagating organs thereof, a herbicidally effective amount of a compound having the structural formula I

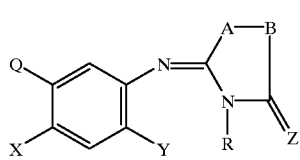

(I)

wherein A, B, Q, R, X, Y and Z are as described in claim 1.

7. The method according to claim 6 wherein A, B, Q, R, X, Y and Z are as described in claim 2.

8. The method according to claim 7 wherein A, B, Q. R, X, Y and Z are as described in claim 3.

9. The method according to claim 8 wherein A, B, Q. R, X, Y and Z are as described in claim 4.

10. The method according to claim 9 wherein the compound is selected from the group consisting of 3-{4-chloro-2-fluoro-5-[3-methyl4-oxo-2-thiazolidinylidene)amino]phenyl}-1-methyl-6-(trifluoromethyl)-2,4(1H,3H)-pyrimidinedione;

ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-(carboxymethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-delta5, alpha-thiazolidineacetic acid, diethyl ester;

ethyl 5-{{2-chloro-5-[3,6-dihydro-3-methyl-2,6-dioxo-4-(trifluoromethyl)-1(2H)-pyrimidinyl]-4-fluorophenyl}imino}-7-oxo4-thia-6-azaspiro[2.4]heptane-6-acetate;

2-{{2-chloro-5-[3,6-dihydro-3-methyl-2,6-dioxo-4-(trifluoromethyl)-1(2H)-pyrimidinyl]-4-fluorophenyl}4-oxo-3,5-thiazolidinediacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-oxazolidineacetate;

α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, L-;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl methyl ester;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl isopropyl ester;

ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

ethyl 2-{{2-chloro-5-[3,6-dihydro-3-methyl-2,6-dioxo-4-(trifluoromethyl)-1(2H)-pyrimidinyl]-4-fluorophenyl}imino}-5-[(methylcarbamoyl)methyl]-4-oxo-3-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl (2-propynyl) ester;

methyl 3-allyl-2-{{2-chloro-5-[3,6-dihydro-3-methyl-2,6-dioxo-4-(trifluoromethyl)-(2H)-pyrimidinyl]-4-fluorophenyl}imino}-4-oxo-5-thiazolidineacetate;

isopropyl 3-allyl-2-{{2-chloro-5-[3,6-dihydro-3-methyl-2,6-dioxo-4-(trifluoromethyly)-1(2H)-pyrimidinyl]-4-fluorophenyl}imino}-4-oxo-5-thiazolidineacetate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl 2-fluoroethyl ester;

2-fluoroethyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-5-(hydroxyethyl)-4-oxo-3-thiazolidineacetate;

allyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

isopropyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{4-chloro-2-fluoro-5-[(3-furfuryl4-oxo-2-thiazolidinylidene)amino]phenyl}-1-methyl-6-(trifluoromethyl)-2,4(1H,3H)-pyrimidinedione;

cyclopropylmethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

ethyl 5-chloro-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{4-chloro-5-[(3-cyclopropyl-4-oxo-2-thiazolidinylidene)amino]-2-fluorophenyl}-1-methyl-6-(trifluoromethyl)-2,4(1H,3H)-pyrimidinedione;

3-{4-chloro-2-fluoro-5-{[3-(2-methoxyethyl)-4-oxo-2-thiazolidinylidene]amino}phenyl}-1-methyl-6-(trifluoromethyl)-2,4(1H,3H)-pyrimidinedione;

3-(4-chloro-2-fluoro-5-{[3-(1-methyl-2-propynyl)4-oxo-2-thiazolidinylidene]amino}phenyl}-1-methyl-6-(trifluoromethyl)-2,4(1H,3H)-pyrimidinedione;

ethyl 5-benzyl-2-{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{5-[(3-benzyl4-oxo-2-thiazolidinylidene)amino]-4-chloro-2-fluorophenyl}-1-methyl-6-(trifluoromethyl)-2,4(1H,3H)-pyrimidinedione;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinepropionate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, D-;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-α-(p-nitrobenzyl)-3-thiazolidineacetate, L-;

ethyl (α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-; and methyl α-(p-chlorobenzyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, DL-.

11. The method according to claim 6 wherein the compound is applied to the foliage of the undesirable plant species or to the soil or water containing seeds or other propagating organs thereof in the presence of crop plants, crop seeds or other crop propagating organs.

12. The method according to claim 11 wherein the crop is a cereal crop.

13. The method according to claim 12 wherein the cereal crop is selected from the group consisting of corn, wheat and rice.

14. The method according to claim 13 wherein the cereal crop is corn and the compound is selected from the group consisting of ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

2-{{2-chloro-5-[3,6-dihydro-3-methyl-2,6-dioxo-4-(trifluoromethyl)-1(2H)-pyrimidinyl]-4-fluorophenyl}4-oxo-3,5-thiazolidinediacetic acid, 3-ethyl ester;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl methyl ester;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl isopropyl ester;

ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl (2-propynyl) ester;

isopropyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;

2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl 2-fluoroethyl ester;

2-fluoroethyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate; and 2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-oxazolidinediacetc acid, 3-ethyl ester.

15. The method according to claim 13 wherein the cereal crop is wheat and the compound is selected from the group consisting of 3-(carboxymethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-delta5,alpha-thiazolidineacetic acid, diethyl ester;

2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl methyl ester;

2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl isopropyl ester;

ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

ethyl 2-{{2-chloro-5-[3,6-dihydro-3-methyl-2,6-dioxo-4-(trifluoromethyl)-1(2H)-pyrimidinyl]-4-fluorophenyl}imino}-5-[(methylcarbamoyl)methyl]-4-oxo-3-thiazolidineacetate;

2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl (2-propynyl) ester;

isopropyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;

2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl 2-fluoroethyl ester;

2-fluoroethyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;

2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-oxazolidinediacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-5-(hydroxyethyl)-4-oxo-3-thiazolidineacetate; and cyclopropylmethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate.

16. The method according to claim 13 wherein the cereal crop is rice and the compound is selected from the group consisting of ethyl 5-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{5-[(3-benzyl-4-oxo-2-thiazolidinylidene)amino]-4-chloro-2-fluorophenyl}-1-methyl-6-(trifluoromethyl)-2,4(1H,3H)-pyrimidinedione;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinepropionate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;
methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, D-;
methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-α-(p-nitrobenzyl)-3-thiazolidineacetate, L-;
ethyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-; and
methyl α-(p-chlorobenzyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, DL-.

17. The method according to claim 11 wherein the crop is soybean.

18. The method according to claim 17 wherein the compound is selected from the group consisting of
ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-thiazolidinediacetic acid, 3-ethyl 2-fluoroethyl ester;
2-{{2-chloro-5-[3,6-dihydro-3-methyl-2,6-dioxo-4-(trifluoromethyl)-1(2H)-pyrimidinyl]-4-fluorophenyl}-imino}-4-oxo-3,5-oxazolidinediacetic acid, 3-ethyl ester;
allyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate; and
3-{4-chloro-2-fluoro-5-[(3-furfuryl-4-oxo-2-thiazolidinylidene)amino]phenyl}-1-methyl-6-(trifluoromethyl)-2,4(1H,3H)-pyrimidinedione.

19. The method according to claim 6 wherein the compound is applied to the foliage of the undesirable plant species or to the soil or water containing seeds or other propagating organs thereof at a rate of about 0.01 kg/ha to 1 kg/ha.

20. The method according to claim 6 wherein the compound is applied in combination with or in conjunction with one or more other biological compounds.

21. A herbicidal composition which comprises an inert solid or liquid carrier and a herbicidally effective amount of a compound having the structural formula I

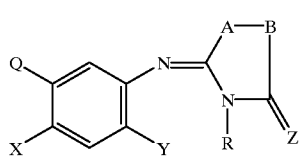

(I)

wherein A, B, Q, R, X, Y and Z are as described in claim 1.

22. The composition according to claim 21 wherein A, B, Q, R, X, Y and Z are as described in claim 2.

23. The composition according to claim 22 wherein A, B, Q, R, X, Y and Z are as described in claim 3.

24. The composition according to claim 23 wherein A, B, Q, R, X, Y and Z are as described in claim 4.

25. The composition according to claim 24 wherein the compound is selected from the group consisting of
3-{4-chloro-2-fluoro-5-[3-methyl4-oxo-2-thiazolidinylidene)amino]phenyl}-1-methyl-6-(trifluoromethyl)-2,4(1H,3H)-pyrimidinedione;
ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;
3-(carboxymethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-delta5,alpha-thiazolidineacetic acid, diethyl ester;
ethyl 5-{{2-chloro-5-[3,6-dihydro-3-methyl-2,6-dioxo-4-(trifluoromethyl)-1(2H)-pyrimidinyl]-4-fluorophenyl}imino}-7-oxo4-thia-6-azaspiro[2.4]heptane-6-acetate;
2-{{2-chloro-5-[3,6-dihydro-3-methyl-2,6-dioxo-4-(trifluoromethyl)-1(2H)-pyrimidinyl]-4-fluorophenyl}-4-oxo-3,5-thiazolidinediacetic acid, 3-ethyl ester;
ethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-oxazolidineacetate;
α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetic acid, L-;
2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl methyl ester;
2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl isopropyl ester;
ethyl 5-(carbamoylmethyl)-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;
ethyl 2-{{2-chloro-5-[3,6-dihydro-3-methyl-2,6-dioxo-4-(trifluoromethyl)-1(2H)-pyrimidinyl]-4-fluorophenyl}imino}-5-[(methylcarbamoyl)methyl]-4-oxo-3-thiazolidineacetate;
2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl (2-propynyl) ester;
methyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;
isopropyl 3-allyl-2-{{2-chloro-5-[3,6-dihydro-3-methyl-2,6-dioxo-4-(trifluoromethyl)-1(2H)-pyrimidinyl]-4-fluorophenyl}imino}-4-oxo-5-thiazolidineacetate;
methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-;
2-{{2-chloro-5-[3,6-dihydro-3-methyl-2,6-dioxo-4-(trifluoromethyl)-1(2H)-pyrimidinyl]-4-fluorophenyl}imino}-4-oxo-3,5-thiazolidinediacetic acid, 3-ethyl 2-fluoroethyl ester;
2-fluoroethyl 3-allyl-2-{{2-chloro-5-[3,6-dihydro-3-methyl-2,6-dioxo-4-(trifluoromethyl)1(2H)-pyrimidinyl]-4-fluorophenyl}imino}-4-oxo-5-thiazolidineacetate;

2-{{2-chloro-5-[3,6-dihydro-3-methyl-2,6-dioxo-4-(trifluoromethyl)-1(2H)-pyrimidinyl]-4-fluorophenyl}imino)4-oxo-3,5-oxazolidinediacetic acid, 3-ethyl ester;

ethyl 2-{{2-chloro-5-[3,6-dihydro-3-methyl-2,6-dioxo-4-(trifluoromethyl)-1(2H)-pyrimidinyl]-4-fluorophenyl}imino}-5-(hydroxyethyl)-4-oxo-3-thiazolidineacetate;

allyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

isopropyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{4-chloro-2-fluoro-5-[(3-furfuryl-4-oxo-2-thiazolidinylidene)amino]phenyl}-1-methyl-6-(trifluoromethyl)-2,4(1H,3H)-pyrimidinedione;

cyclopropylmethyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

ethyl 5-chloro-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{4-chloro-5-[(3-cyclopropyl-4-oxo-2-thiazolidinylidene)amino]-2-fluorophenyl}-1-methyl-6-(trifluoromethyl)-2,4(1H,3H)-pyrimidinedione;

3-{{4-chloro-2-fluoro-5-[3-(2-methoxyethyl)-4-oxo-2-thiazolidinylidene]amino}phenyl}-1-methyl-6-(trifluoromethyl)-2,4(1H,3H)-pyrimidinedione;

3-{4-chloro-2-fluoro-5-{[3-(1-methyl-2-propynyl)-4-oxo-2-thiazolidinylidene]amino}phenyl}-1-methyl-6-(trifluoromethyl)-2,4(1H,3H)-pyrimidinedione;

ethyl 5-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate;

3-{5-[(3-benzyl-4-oxo-2-thiazolidinylidene)amino]-4-chloro-2-fluorophenyl}-1-methyl-6-(trifluoromethyl)-2,4(1H,3H)-pyrimidinedione;

methyl 2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidinepropionate;

methyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, D-;

methyl 2-{{2-chloro-5-[3,6-dihydro-3-methyl-2,6-dioxo-4-((trifluoromethyl)-1(2H)-pyrimidinyl]-4-fluorophenyl}imino}-4-oxo-α-(p-nitrobenzyl)3-thiazolidineacetate, L-;

ethyl α-benzyl-2-{{2-chloro-5-[3,6-dihydro-3-methyl-2,6-dioxo-4-(trifluoromethyl)-1(2H)-pyrimidinyl]-4-fluorophenyl}imino}-4-oxo-3-thiazolidineacetate, L-; and methyl α-(p-chlorobenzyl)-2-{{2-chloro-5-[3,6-dihydro-3-methyl-2,6-dioxo-4-(trifluoromethylyl)-(2H)-pyrimidinyl]-4-fluorophenyl}imino}-4-oxo-3-thiazolidineacetate, DL-.

26. The composition according to claim 21 which further comprises one or more other biological compounds.

27. A compound having the structural formula

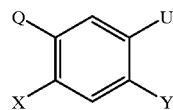

wherein
U is —N=C=NR, —N=C=S or

Q is

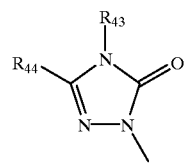 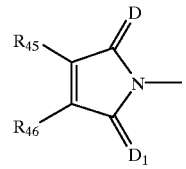

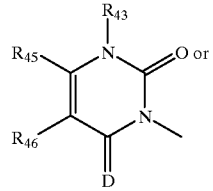 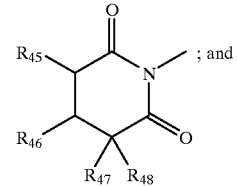; and

D, $D_1$, R, $R_{43}$, $R_{44}$, $R_{45}$, $R_{46}$, $R_{47}$, $R_{48}$, X and Y are as described in claim 1.

28. The compound according to claim 27 wherein
U is —N=C=NR, —N=C=S or

Q is

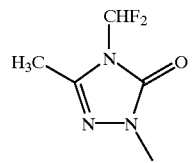 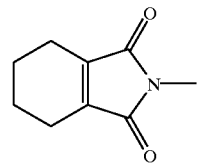

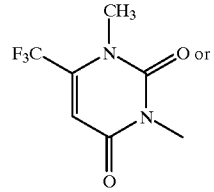 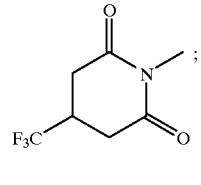;

X is hydrogen, fluorine or chlorine;
Y is fluorine, chlorine, nitro or cyano;
R is hydrogen,
$C_1$–$C_6$alkyl optionally substituted with one to three halogen atoms, one or two C(O)$OR_3$ groups, one cyano group, one $OR_7$ group, one $SR_8$ group, one P(O) $(OR_6)_2$ group, or a $C_3$–$C_6$alkenyl, $C_3$–$C_6$alkynyl, phenyl, benzyl or furfural group, wherein each group is optionally substituted with one to three halogen atoms, one $C_1$–$C_3$alkoxy group or one $C(O)OR_3$ group;

$R_3$ is hydrogen, $C_1$–$C_6$alkyl or $C_1$–$C_4$haloalkyl;

$R_6$ is hydrogen of $C_1$–$C_3$alkyl;

$R_7$ is hydrogen, $C_1$–$C_3$alkyl or $C_3$–$C_6$alkoxycarbonylalkyl; and $R_8$ is hydrogen, $C_1$–$C_3$alkyl or $C_3$–$C_6$alkoxycarbonyl.

29. A method for the preparation of a compound having the structural formula

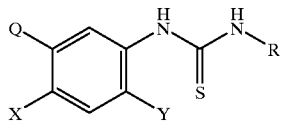

wherein

Q is

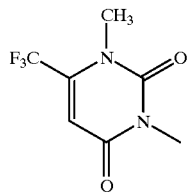

X is hydrogen, fluorine or chlorine;
Y is fluorine, chlorine, nitro or cyano;

R is hydrogen, $C_1$–$C_6$alkyl optionally substituted with one to three halogen atoms, one or two $C(O)OR_3$ groups, one cyano group, one $OR_7$ group, one $SR_8$ group, one $P(O)(OR_6)_2$ group, or a $C_3$–$C_6$alkenyl, $C_3$–$C_6$alkynyl, phenyl, benzyl or furfural group, wherein each group is optionally substituted with one to three halogen atoms, one $C_1$–$C_3$alkoxy group or one $C(O)OR_3$ group;

$R_3$ is hydrogen, $C_1$–$C_6$alkyl or $C_1$–$C_6$haloalkyl;

$R_6$ is hydrogen of $C_1$–$C_3$alkyl;

$R_7$ is hydrogen, $C_1$–$C_3$alkyl or $C_3$–$C_6$alkoxycarbonylalkyl; and $R_8$ is hydrogen, $C_1$–$C_3$alkyl or $C_3$–$C_6$alkoxycarbonyl which method comprises reacting a substituted aniline compound having the structural formula

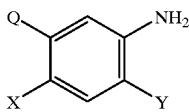

wherein Q, X and Y are as described above with an isothiocyanate compound having the structural formula

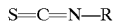

wherein R is as described above.

30. The method according to claim 29 wherein the reaction is conducted in the presence of a solvent.

* * * * *